(12) United States Patent
Andreacchi et al.

(10) Patent No.: US 8,003,157 B2
(45) Date of Patent: Aug. 23, 2011

(54) SYSTEM AND METHOD FOR COATING A STENT

(75) Inventors: Anthony S. Andreacchi, San Jose, CA (US); Yung-Ming Chen, Cupertino, CA (US); Arnoldo M. Currlin, San Diego, CA (US); Antonio Garcia, San Jose, CA (US); Jason Van Sciver, Los Gatos, CA (US); Bryan D. Glenn, Murrieta, CA (US)

(73) Assignees: Abbott Cardiovascular Systems Inc., Santa Clara, CA (US); ATS Automation Tooling Systems Inc., Cambridge (CA)

( * ) Notice: Subject to any disclaimer, the term of this patent is extended or adjusted under 35 U.S.C. 154(b) by 948 days.

(21) Appl. No.: 11/764,010

(22) Filed: Jun. 15, 2007

(65) Prior Publication Data
US 2008/0311281 A1 Dec. 18, 2008

(51) Int. Cl.
*A61L 33/00* (2006.01)
(52) U.S. Cl. ........ 427/2.24; 623/900; 424/423; 427/2.1; 427/2.12; 427/2.14; 427/2.25
(58) Field of Classification Search .................. 623/900; 424/423; 427/2.24
See application file for complete search history.

(56) References Cited

U.S. PATENT DOCUMENTS

| | | | |
|---|---|---|---|
| 3,419,062 A | 12/1968 | Petrus | |
| 4,162,126 A | 7/1979 | Nakagawa et al. | |
| 4,226,539 A | 10/1980 | Nakagawa et al. | |
| 4,410,278 A | 10/1983 | Makihira et al. | |
| 4,549,053 A | 10/1985 | Haugh | |
| 4,562,088 A | 12/1985 | Navarro | |
| 4,611,623 A | 9/1986 | Goodrich | |
| 4,878,841 A | 11/1989 | McCulloch et al. | |
| 4,915,713 A | 4/1990 | Buzza et al. | |
| 5,012,117 A | 4/1991 | Karafa et al. | |
| 5,090,355 A | 2/1992 | DiMaio et al. | |
| 5,141,494 A | 8/1992 | Danforth et al. | |
| 5,186,887 A | 2/1993 | Yaginuma | |
| 5,282,472 A | 2/1994 | Companion et al. | |
| 5,387,235 A | 2/1995 | Chuter | |
| 5,437,660 A | 8/1995 | Johnson et al. | |
| 5,439,446 A | 8/1995 | Barry | |
| 5,456,713 A | 10/1995 | Chuter | |
| 5,562,726 A | 10/1996 | Chuter | |
| 5,602,646 A | 2/1997 | Bernardin et al. | |
| 5,630,830 A | 5/1997 | Verbeek | |

(Continued)

FOREIGN PATENT DOCUMENTS
DE 100 32 398 2/2001
(Continued)

OTHER PUBLICATIONS

U.S. Appl. No. 10/255,913, filed Sep. 26, 2002, Tang et al.
(Continued)

*Primary Examiner* — Dah-Wei D Yuan
*Assistant Examiner* — Andrew Bowman
(74) *Attorney, Agent, or Firm* — Squire, Sanders & Dempsey (US) LLP

(57) ABSTRACT

A system for coating a stent includes a device for weighing a stent, a device for aligning the stent with a stent support, a device for coating the stent, a device for drying the stent, and a device for inspecting the stent.

6 Claims, 78 Drawing Sheets

U.S. PATENT DOCUMENTS

| | | |
|---|---|---|
| 5,642,571 A | 7/1997 | Park |
| 5,693,084 A | 12/1997 | Chuter |
| 5,720,776 A | 2/1998 | Chuter et al. |
| 5,755,777 A | 5/1998 | Chuter |
| 5,766,192 A | 6/1998 | Zacca |
| 5,817,101 A | 10/1998 | Fiedler |
| 5,857,998 A | 1/1999 | Barry |
| 5,879,697 A | 3/1999 | Ding et al. |
| 5,897,911 A | 4/1999 | Loeffler |
| 5,935,075 A | 8/1999 | Casscelis et al. |
| 5,947,977 A | 9/1999 | Slepian et al. |
| 6,056,759 A | 5/2000 | Fiedler |
| 6,056,998 A | 5/2000 | Fujimoto |
| 6,068,589 A | 5/2000 | Neukemans |
| 6,161,029 A | 12/2000 | Spreigl et al. |
| 6,174,323 B1 | 1/2001 | Biggs et al. |
| 6,214,115 B1 | 4/2001 | Taylor et al. |
| 6,231,516 B1 | 5/2001 | Keilman et al. |
| 6,322,847 B1 | 11/2001 | Zhong et al. |
| 6,344,028 B1 | 2/2002 | Barry |
| 6,413,273 B1 | 7/2002 | Baum et al. |
| 6,420,666 B1 | 7/2002 | Baumeler et al. |
| 6,475,159 B1 | 11/2002 | Casscells et al. |
| 6,491,720 B1 | 12/2002 | Vallana et al. |
| 6,527,734 B2 | 3/2003 | Cragg et al. |
| 6,527,863 B1 | 3/2003 | Pacetti et al. |
| 6,574,497 B1 | 6/2003 | Pacetti |
| 6,575,994 B1 | 6/2003 | Marin et al. |
| 6,599,311 B1 | 7/2003 | Biggs et al. |
| 6,605,109 B2 | 8/2003 | Fiedler |
| 6,606,403 B2 | 8/2003 | Freifeld |
| 6,610,026 B2 | 8/2003 | Cragg et al. |
| 6,626,902 B1 | 9/2003 | Kucharczyk et al. |
| 6,656,136 B1 | 12/2003 | Weng et al. |
| 6,673,022 B1 | 1/2004 | Bobo et al. |
| 6,676,595 B1 | 1/2004 | Delfino |
| 6,695,920 B1 | 2/2004 | Pacetti et al. |
| 6,699,179 B2 | 3/2004 | Wendlandt |
| 6,719,709 B2 | 4/2004 | Whalen et al. |
| 6,733,521 B2 | 5/2004 | Chobotov et al. |
| 6,761,733 B2 | 7/2004 | Chobotov et al. |
| 6,818,063 B1 | 11/2004 | Kerrigan |
| 6,979,348 B2 | 12/2005 | Sundar |
| 6,993,382 B2 | 1/2006 | Casscells et al. |
| 6,997,189 B2 | 2/2006 | Biggs et al. |
| 7,022,131 B1 | 4/2006 | Derowe et al. |
| 7,025,773 B2 | 4/2006 | Gittings et al. |
| 7,048,756 B2 | 5/2006 | Eggers et al. |
| 7,048,962 B2 | 5/2006 | Shekalim et al. |
| 7,090,655 B2 | 8/2006 | Barry |
| 7,160,299 B2 | 1/2007 | Bally |
| 7,172,552 B2 | 2/2007 | Wendlandt |
| 7,208,190 B2 | 4/2007 | Verlee et al. |
| 7,211,150 B1 | 5/2007 | Kokish et al. |
| 7,214,237 B2 | 5/2007 | Don Michael et al. |
| 7,223,280 B2 | 5/2007 | Anson et al. |
| 7,344,601 B2 | 3/2008 | Coye et al. |
| 7,390,524 B1 | 6/2008 | Chen |
| 7,402,329 B2 | 7/2008 | Pacetti et al. |
| 7,404,979 B1 | 7/2008 | Pacetti |
| 7,505,124 B2 | 3/2009 | Kreckel et al. |
| 7,718,213 B1 | 5/2010 | Scheer |
| 7,735,449 B1 | 6/2010 | Harold et al. |
| 7,776,381 B1 | 8/2010 | Tang et al. |
| 2002/0004663 A1 | 1/2002 | Gittings et al. |
| 2002/0032486 A1 | 3/2002 | Lazarovitz et al. |
| 2002/0041899 A1 | 4/2002 | Chudzik et al. |
| 2002/0058951 A1 | 5/2002 | Fiedler |
| 2002/0065476 A1 | 5/2002 | Whalen et al. |
| 2002/0107478 A1 | 8/2002 | Wendlandt |
| 2002/0143358 A1 | 10/2002 | Domingo et al. |
| 2002/0151953 A1 | 10/2002 | Chobotov et al. |
| 2003/0004430 A1 | 1/2003 | Casscells et al. |
| 2003/0015203 A1 | 1/2003 | Makower et al. |
| 2003/0018343 A1 | 1/2003 | Mathis |
| 2003/0055311 A1 | 3/2003 | Neukermans et al. |
| 2003/0060695 A1 | 3/2003 | Connelly |
| 2003/0153943 A1 | 8/2003 | Michael et al. |
| 2003/0215564 A1 | 11/2003 | Heller et al. |
| 2004/0078054 A1 | 4/2004 | Biggs et al. |
| 2004/0079354 A1 | 4/2004 | Takeda |
| 2004/0097988 A1 | 5/2004 | Gittings et al. |
| 2004/0143159 A1 | 7/2004 | Wendlandt |
| 2004/0181249 A1 | 9/2004 | Torrance et al. |
| 2004/0187775 A1 | 9/2004 | Kerrigan |
| 2004/0215347 A1* | 10/2004 | Hayes ........................... 623/900 |
| 2004/0220612 A1 | 11/2004 | Swainston et al. |
| 2004/0230213 A1 | 11/2004 | Wulfman et al. |
| 2004/0236170 A1 | 11/2004 | Kim |
| 2004/0243119 A1 | 12/2004 | Lane et al. |
| 2004/0243175 A1 | 12/2004 | Don Michael |
| 2004/0249437 A1 | 12/2004 | Sundar |
| 2004/0254419 A1 | 12/2004 | Wang et al. |
| 2005/0010282 A1 | 1/2005 | Thornton et al. |
| 2005/0021026 A1 | 1/2005 | Baily |
| 2005/0033343 A1 | 2/2005 | Cherrnoni |
| 2005/0038498 A1 | 2/2005 | Dubrow et al. |
| 2005/0079132 A1 | 4/2005 | Wang et al. |
| 2005/0113798 A1 | 5/2005 | Slater et al. |
| 2005/0119720 A1 | 6/2005 | Gale et al. |
| 2005/0144806 A1 | 7/2005 | Yoshida |
| 2005/0149002 A1 | 7/2005 | Wang et al. |
| 2005/0165317 A1 | 7/2005 | Turner et al. |
| 2005/0209627 A1 | 9/2005 | Kick et al. |
| 2005/0215871 A1 | 9/2005 | Feldman et al. |
| 2005/0240100 A1 | 10/2005 | Wang et al. |
| 2005/0251238 A1 | 11/2005 | Wallace et al. |
| 2005/0251239 A1 | 11/2005 | Wallace et al. |
| 2005/0273146 A1 | 12/2005 | DeSimone et al. |
| 2005/0288700 A1 | 12/2005 | Chermoni |
| 2006/0015136 A1 | 1/2006 | Besselink |
| 2006/0025800 A1 | 2/2006 | Suresh |
| 2006/0030912 A1 | 2/2006 | Eggers et al. |
| 2006/0030913 A1 | 2/2006 | Eggers et al. |
| 2006/0030914 A1 | 2/2006 | Eggers et al. |
| 2006/0035012 A1 | 2/2006 | Pacetti et al. |
| 2006/0041243 A1 | 2/2006 | Nayak et al. |
| 2006/0052821 A1 | 3/2006 | Abbott et al. |
| 2006/0094980 A1 | 5/2006 | Cassoells et al. |
| 2006/0155305 A1 | 7/2006 | Freudenthal et al. |
| 2006/0206002 A1 | 9/2006 | Frassica et al. |
| 2006/0206028 A1 | 9/2006 | Lee et al. |
| 2006/0212047 A1 | 9/2006 | Abbott et al. |
| 2006/0217763 A1 | 9/2006 | Abbott et al. |
| 2006/0217764 A1 | 9/2006 | Abbott et al. |
| 2006/0240061 A1 | 10/2006 | Atala et al. |
| 2006/0240401 A1 | 10/2006 | Clarke et al. |
| 2006/0241748 A1 | 10/2006 | Lee et al. |
| 2006/0247661 A1 | 11/2006 | Richards et al. |
| 2006/0252976 A1 | 11/2006 | Rosero |
| 2007/0003688 A1 | 1/2007 | Chen et al. |
| 2007/0005041 A1 | 1/2007 | Frassica et al. |
| 2007/0005094 A1 | 1/2007 | Eaton et al. |
| 2007/0010702 A1 | 1/2007 | Wang et al. |
| 2007/0016287 A1 | 1/2007 | Cartledge et al. |
| 2007/0043381 A1 | 2/2007 | Furst et al. |
| 2007/0049970 A1 | 3/2007 | Belef et al. |
| 2007/0073134 A1 | 3/2007 | Teichman et al. |
| 2007/0073337 A1 | 3/2007 | Abbott et al. |
| 2007/0093710 A1 | 4/2007 | Maschke |
| 2007/0112344 A1 | 5/2007 | Keilman |
| 2007/0112358 A1 | 5/2007 | Abbott et al. |
| 2007/0118015 A1 | 5/2007 | Wendlandt |
| 2007/0129755 A1 | 6/2007 | Abbott et al. |
| 2007/0129756 A1 | 6/2007 | Abbott et al. |
| 2007/0135803 A1 | 6/2007 | Belson |
| 2007/0219615 A1 | 9/2007 | Freifeld et al. |
| 2007/0259100 A1 | 11/2007 | Guerriero et al. |
| 2008/0037031 A1 | 2/2008 | Cole et al. |
| 2008/0042662 A1 | 2/2008 | Abraham |
| 2008/0087474 A1 | 4/2008 | Nufer et al. |
| 2008/0280025 A1 | 11/2008 | Scheer |
| 2008/0307668 A1 | 12/2008 | Van Sciver et al. |
| 2008/0311280 A1 | 12/2008 | Chen et al. |
| 2008/0311281 A1 | 12/2008 | Andreacchi et al. |
| 2008/0312747 A1 | 12/2008 | Van Sciver et al. |
| 2008/0312869 A1 | 12/2008 | Van Sciver et al. |

FOREIGN PATENT DOCUMENTS

| EP | 1 195 584 | 4/2002 |
|----|-----------|--------|
| EP | 1 518 570 | 3/2005 |
| GB | 2333476 | 1/1988 |
| JP | 06-031227 | 2/1994 |
| WO | WO 95/27878 | 10/1995 |
| WO | WO 2007/130257 | 11/2007 |

OTHER PUBLICATIONS

U.S. Appl. No. 10/750,312, filed Dec 30, 2003, Desnoyer et al.
U.S. Appl. No. 10/805,047, filed Mar. 2004, Yip et al.
U.S. Appl. No. 11/193,849, filed Jul. 28, 2005, Harold et al.
International Search Report and the Written Opinion, for PCT/US2008/061806, mailed Dec. 5, 2008, 19 pgs.
U.S. Appl. No. 10/750,312, filed Dec. 30, 2003, Desnoyer et al.
U.S. Appl. No. 10/805,047, filed Mar. 18, 2004, Yip et al.
Invitation to Pay Additional Fees for PCT/US2007/009115, filed Apr. 13, 2007, mailed Oct. 26, 2007, 10 pgs.
International Search Report and the Written Opinion, for PCT/US2008/061806, mailed Dec. 5, 2008, 19 pgs.
International Search Report and the Written Opinion, for PCT/US2009/032878, mailed Jun. 19, 2009, 19 pgs.
Invitation to pay additional fees, including communication relating to the results of the partial international search, for PCT/US2008/061806, mailed Aug. 27, 2008, 9 pgs.

\* cited by examiner

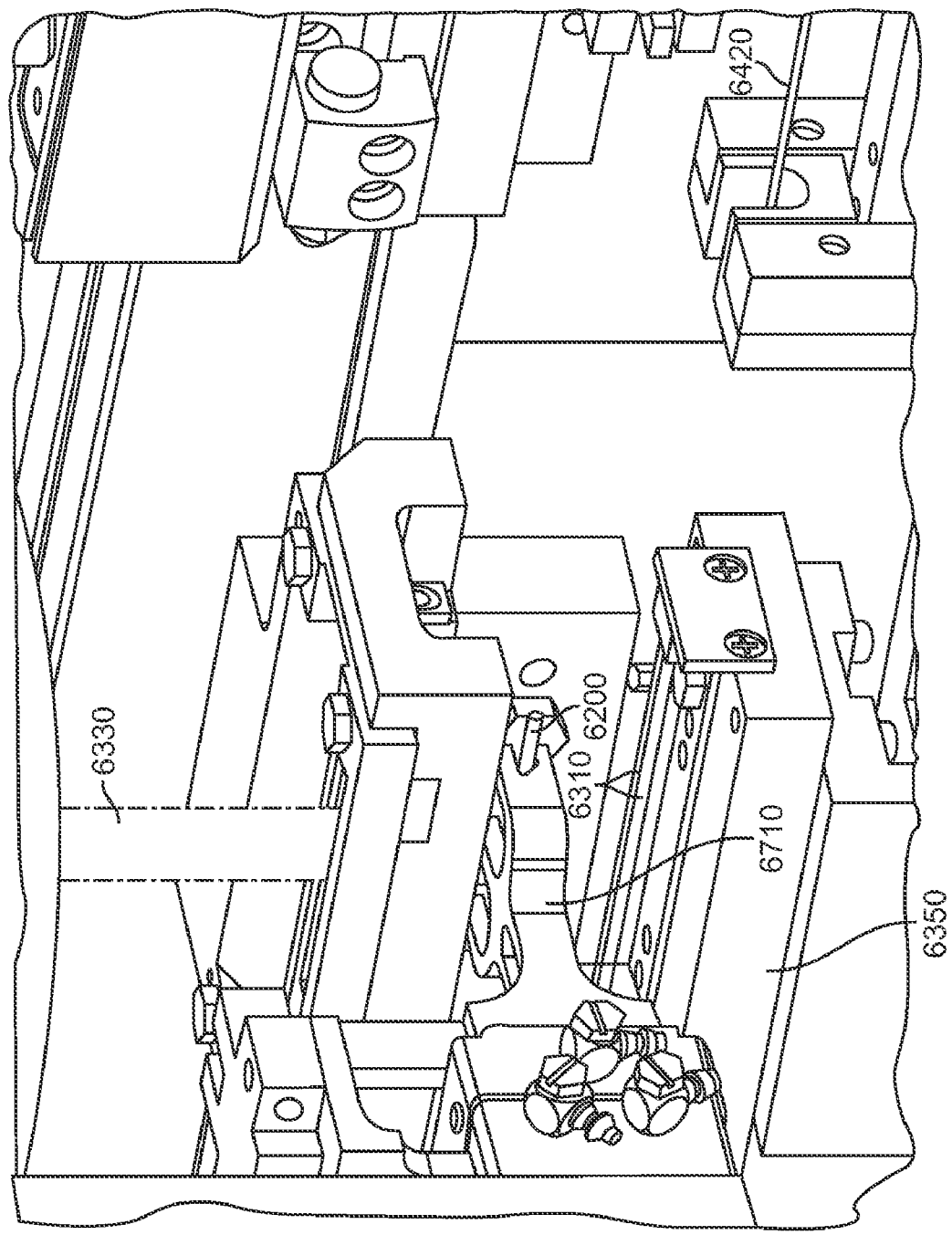

US 8,003,157 B2

SYSTEM AND METHOD FOR COATING A STENT

FIELD OF THE INVENTION

This invention relates to a system and method for coating a stent.

BACKGROUND

Minimally invasive surgical procedures, such as percutaneous transluminal coronary angioplasty (PTCA), have become increasingly common. A PTCA procedure involves the insertion of a catheter into a coronary artery to position an angioplasty balloon at the site of a stenotic lesion that is at least partially blocking the coronary artery. The balloon is then inflated to compress the stenosis and to widen the lumen in order to allow an efficient flow of blood through the coronary artery.

Following PTCA and other stenotic treatment procedures, a significant number of patients experience restenosis or other vascular blockage problems. These problems are prone to arise at the site of the former stenosis.

In order to help avoid restenosis and other similar problems, a stent may be implanted into the vessel at the site of the former stenosis with a stent delivery catheter. A stent is a tubular structure which is delivered to the site of the former stenosis or lesion and expanded to compress against vessel walls thereat, again with a balloon. The structure of the stent promotes maintenance of an open vessel lumen. The stent can be implanted in conjunction with the angioplasty.

A stent can also be used to provide for local delivery of a drug. For example, radiotherapy and drug delivery treatments applied to the site of the former stenosis following angioplasty have been found to aid in the healing process and to reduce significantly the risk of restenosis and other similar problems. Local delivery of drugs is often preferred over systemic delivery of drugs, particularly where high systemic doses are necessary to achieve an effect at a particular site. High systemic doses of drugs can often create adverse effects. One proposed method of local delivery is to coat the surface of a stent with a drug.

A stent is typically coated with a primer layer and a drug layer. The primer layer is applied between the stent and the drug layer to improve adhesion of the drug layer to the stent. In some cases, the drug layer may be applied directly to the stent.

Spray coating is commonly used to apply a layer of coating to a stent. A spray coating system typically includes a spray nozzle and a pump that supplies a coating substance from a reservoir to the spray nozzle. The coating substance is ejected through the nozzle and applied to the surface of the stent.

Current spray coating systems, however, are inefficient and unreliable, and produce a high defective rate. Additionally, it is difficult to keep track of the types of drugs coated on stents with current systems. Losing track of stent coating types may have grave consequences. Furthermore, some current systems may expose the operators to health risks due to extended exposure to drugs.

Therefore, there is a need for coating systems and methods that are efficient and reliable and reduce the operators' exposure to health risks.

SUMMARY

The present invention relates to a system and method for coating a stent, which is efficient and reliable and reduces the operators' exposure to health risks.

According to one aspect of the invention, a system for coating a stent includes a device for weighing a stent, a device for aligning the stent with a stent support, a device for coating the stent, a device for drying the stent, and a device for inspecting the stent.

According to one aspect of the invention, a method for coating a stent includes weighing a stent using a device for weighing a stent, aligning the stent using a stent support using a device for aligning a stent with a stent support, coating the stent using a device for coating the stent, drying the stent using a device for drying the stent, and inspecting the stent using a device for inspecting the stent.

BRIEF DESCRIPTION OF THE DRAWINGS

FIG. 66A is a three-dimensional design schematic depicting details of a system for stent inspection according to various aspects of the present invention.

DETAILED DESCRIPTION OF PREFERRED EMBODIMENTS

A stent used with the present invention may have any structural pattern that is compatible with a bodily lumen in which it is implanted. Typically, a stent is composed of a pattern or network of circumferential and longitudinally extending interconnecting structural elements or struts. In general, the struts are arranged in patterns, which are designed to contact the lumen walls of a vessel and to maintain vascular patency. A myriad of strut patterns are known in the art for achieving particular design goals. A few of the more important design characteristics of stents are radial or hoop strength, expansion ratio or coverage area, and longitudinal flexibility. Embodiments of the present invention are applicable to virtually any stent design and are, therefore, not limited to any particular stent design or pattern. One embodiment of a stent pattern may include cylindrical rings composed of struts. The cylindrical rings may be connected by connecting struts.

In some embodiments, a stent may be formed from a tube by laser cutting the pattern of struts in the tube. The stent may also be formed by laser cutting a metallic or polymeric sheet, rolling the pattern into the shape of the cylindrical stent, and providing a longitudinal weld to form the stent. Other methods of forming stents are well known and include chemically etching a metallic or polymeric sheet and rolling and then welding it to form the stent.

Figure 1:
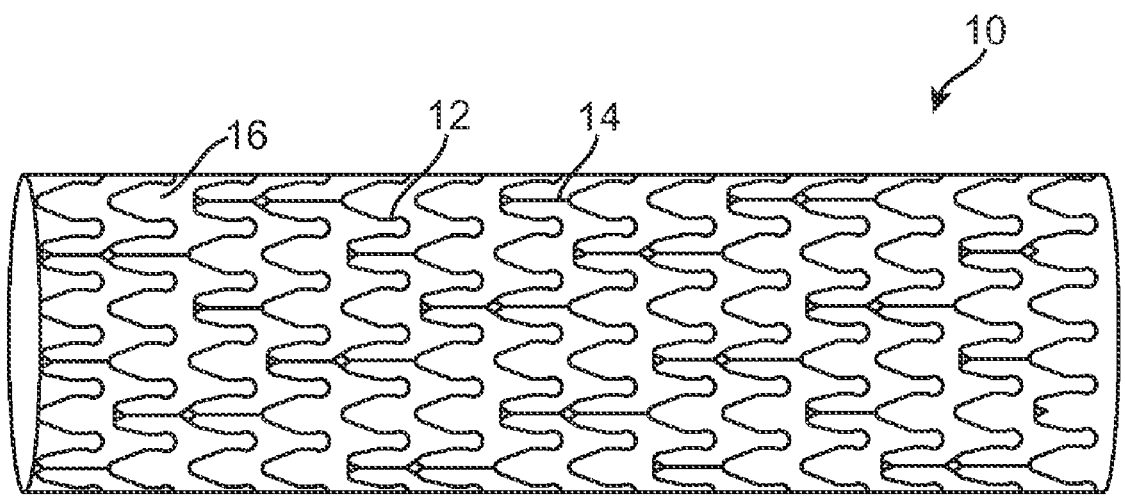
FIG. 1 is a perspective view of a cylindrically-shaped stent.

FIG. 1 illustrates a stent 10 formed from a plurality of struts 12. The plurality of struts 12 are radially expandable and interconnected by connecting elements 14 that are disposed between adjacent struts 12, leaving lateral openings or gaps 16 between adjacent struts 12. The struts 12 and connecting elements 14 define a tubular stent body having an outer, tissue-contacting surface and an inner surface.

The cross-section of the struts 12 in the stent 10 may be rectangular- or circular-shaped. The cross-section of struts is not limited to these, and therefore, other cross-sectional shapes are applicable with embodiments of the present invention. Furthermore, the pattern should not be limited to what has been illustrated as other stent patterns are easily applicable with embodiments of the present invention.

A stent may be coated with any number of layers. For example, the coating of a stent may comprise one or more of the following four types of layers:

(a) an agent layer, which may comprise a polymer and an agent or, alternatively, a polymer free agent;

(b) an optional primer layer including one or more polymers, which layer may improve adhesion of subsequent layers on the implantable substrate or on a previously formed layer;

(c) an optional topcoat layer, which may serve as a way of controlling the rate of release of an agent; and (d) an optional biocompatible finishing layer, which may improve the biocompatibility of the coating.

The agent layer may be applied directly to a stent as a pure agent. Alternatively, the agent can be combined with a biodegradable polymer as a matrix, wherein agent may or may not be bonded to the polymer. The optional primer layer may be applied between the implantable substrate and the agent layer to improve adhesion of the agent layer to the implantable substrate and can optionally comprise an agent. A pure agent layer can be sandwiched between layers comprising biodegradable polymer. The optional topcoat layer may serve as a membrane to control the rate of release of the bioactive agent and can optionally comprise agent. The biocompatible finishing layer may also be applied to increase the biocompatibility of the coating by, for example, increasing acute hemocompatibility and can also comprise an agent.

The polymers in the agent layer and optional primer layer can be biostable, bioabsorbable, biodegradable, or bioerodable. Biostable refers to polymers that are not biodegradable. The terms biodegradable, bioabsorbable, and bioerodable are used interchangeably and refer to polymers that are capable of being completely degraded and/or eroded when exposed to bodily fluids such as blood and can be gradually resorbed, absorbed, and/or eliminated by the body. The processes of breaking down and eventual absorption and elimination of the polymer can be caused by, for example, hydrolysis, metabolic processes, bulk or surface erosion, and the like.

The therapeutic agent can include any substance capable of exerting a therapeutic or prophylactic effect. Examples of therapeutic agents include antiproliferative substances such as actinomycin D, or derivatives and analogs thereof (manufactured by Sigma-Aldrich 1001 West Saint Paul Avenue, Milwaukee, Wis. 53233; or COSMEGEN available from Merck). Synonyms of actinomycin D include dactinomycin, actinomycin IV, actinomycin $I_1$, actinomycin $X_1$, and actinomycin $C_1$. The bioactive agent can also fall under the genus of antineoplastic, anti-inflammatory, antiplatelet, anticoagulant, antifibrin, antithrombin, antimitotic, antibiotic, antiallergic and antioxidant substances. Examples of such antineoplastics and/or antimitotics include paclitaxel, (e.g., TAXOL® by Bristol-Myers Squibb Co., Stamford, Conn.), docetaxel (e.g., Taxotere®, from Aventis S. A., Frankfurt, Germany), methotrexate, azathioprine, vincristine, vinblastine, fluorouracil, doxorubicin hydrochloride (e.g., Adriamycin® from Pharmacia & Upjohn, Peapack N.J.), and mitomycin (e.g., Mutamycin® from Bristol-Myers Squibb Co., Stamford, Conn.). Examples of such antiplatelets, anticoagulants, antifibrin, and antithrombins include aspirin, sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as Angiomax ä (Biogen, Inc., Cambridge, Mass.). Examples of such cytostatic or antiproliferative agents include angiopeptin, angiotensin converting enzyme inhibitors such as captopril (e.g., Capoten® and Capozide® from Bristol-Myers Squibb Co., Stamford, Conn.), cilazapril or lisinopril (e.g., Prinivil® and Prinzide® from Merck & Co., Inc., Whitehouse Station, N.J.), calcium channel blockers (such as nifedipine), colchicine, proteins, peptides, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents which may be appropriate agents include cisplatin, insulin sensitizers, receptor tyrosine kinase inhibitors, carboplatin, alpha-interferon, genetically engineered epithelial cells, steroidal anti-inflammatory agents, non-steroidal anti-inflammatory agents, antivirals, anticancer drugs, anticoagulant agents, free radical scavengers, estradiol, antibiotics, nitric oxide donors, super oxide dismutases, super oxide dismutases mimics, 4-amino-2,2,6,6-tetramethylpiperidine-1-oxyl (4-amino-TEMPO), tacrolimus, dexamethasone, ABT-578, clobetasol, cytostatic agents, prodrugs thereof, co-drugs thereof, and a combination thereof. Other therapeutic substances or agents may include rapamycin and structural derivatives or functional analogs thereof, such as 40-O-(2-hydroxy)ethyl-rapamycin (everolimus), 40-O-(3-hydroxy)propyl-rapamycin, 40-O-[2-(2-hydroxy)ethoxy]ethyl-rapamycin, and 40-O-tetrazole-rapamycin.

Figure 2:
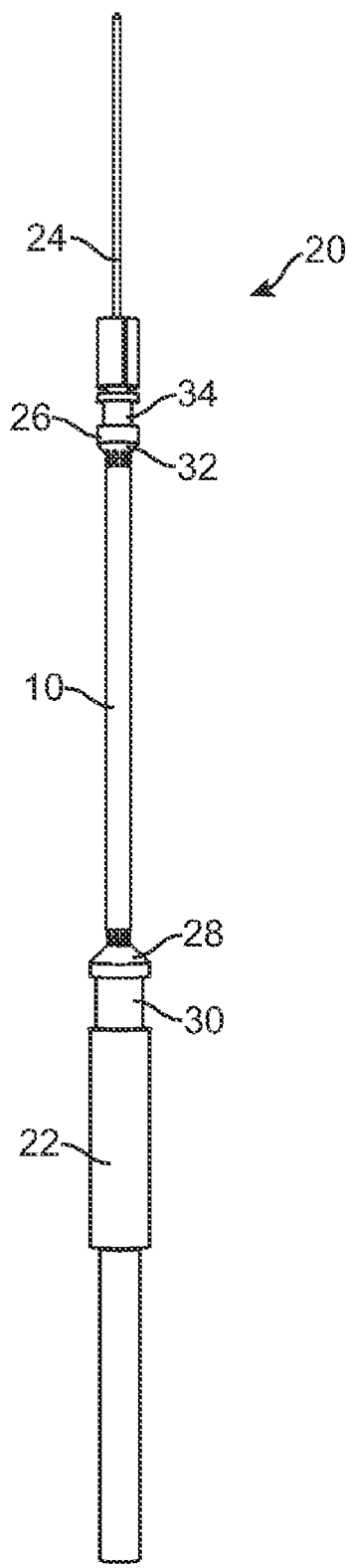
FIG. 2 is a perspective view of a stent support.

Typically, the stent is mounted on a stent support during stent coating operation. Referring to FIG. 2, a stent support 20 may include a first support element 22, a core element 24, and a second support element 26. The first support element of the stent support may be, for example, a shank. The second support element of the stent support may be, for example, a collet. The first support element 22 may be connected to a motor (not shown) to provide rotational motion about the longitudinal axis of the first support element 22 during coating.

The first support element 22 preferably includes a conical portion 28, tapering inwardly at an angle of, for example, about 15° to about 75°, more narrowly from about 30° to about 60°. In some cases, the angle can be about 45°. In the illustrated embodiment, a first end of the core element 24 is permanently affixed to the conical portion 28 of the first support element 22. Alternatively, the first support element may include a bore for receiving an end of the core element, and the end of the core element may be threaded to screw into the bore. The first support element 22 may also include a circumferential groove 30.

The second support element 26 also includes a conical portion 32 having an inwardly tapered angle which can be the same as or different from the tapered angle of the first support element's conical portion 28. The second support element 26 has a through bore. A second end (free end) of the core element 24 can extends into the through bore of the second support element 26 and can be press-fitted or friction-fitted within the bore to prevent the second support element 26 from freely moving on the core element 24. The second support element 26 may also include a circumferential groove 34.

Figure 3:
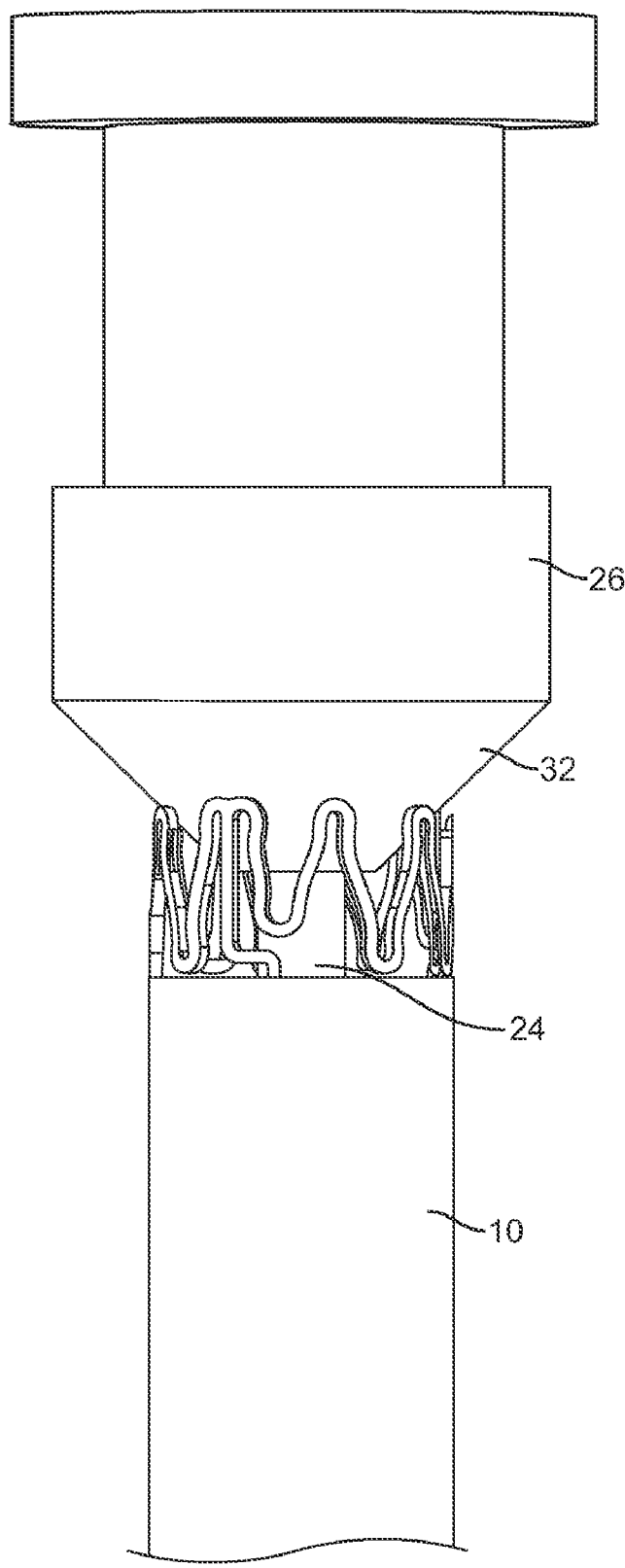
FIGS. 3 and 4 are perspective views showing the conical portions of the first and second support elements of a stent support supporting the ends of a stent.
Figure 4:
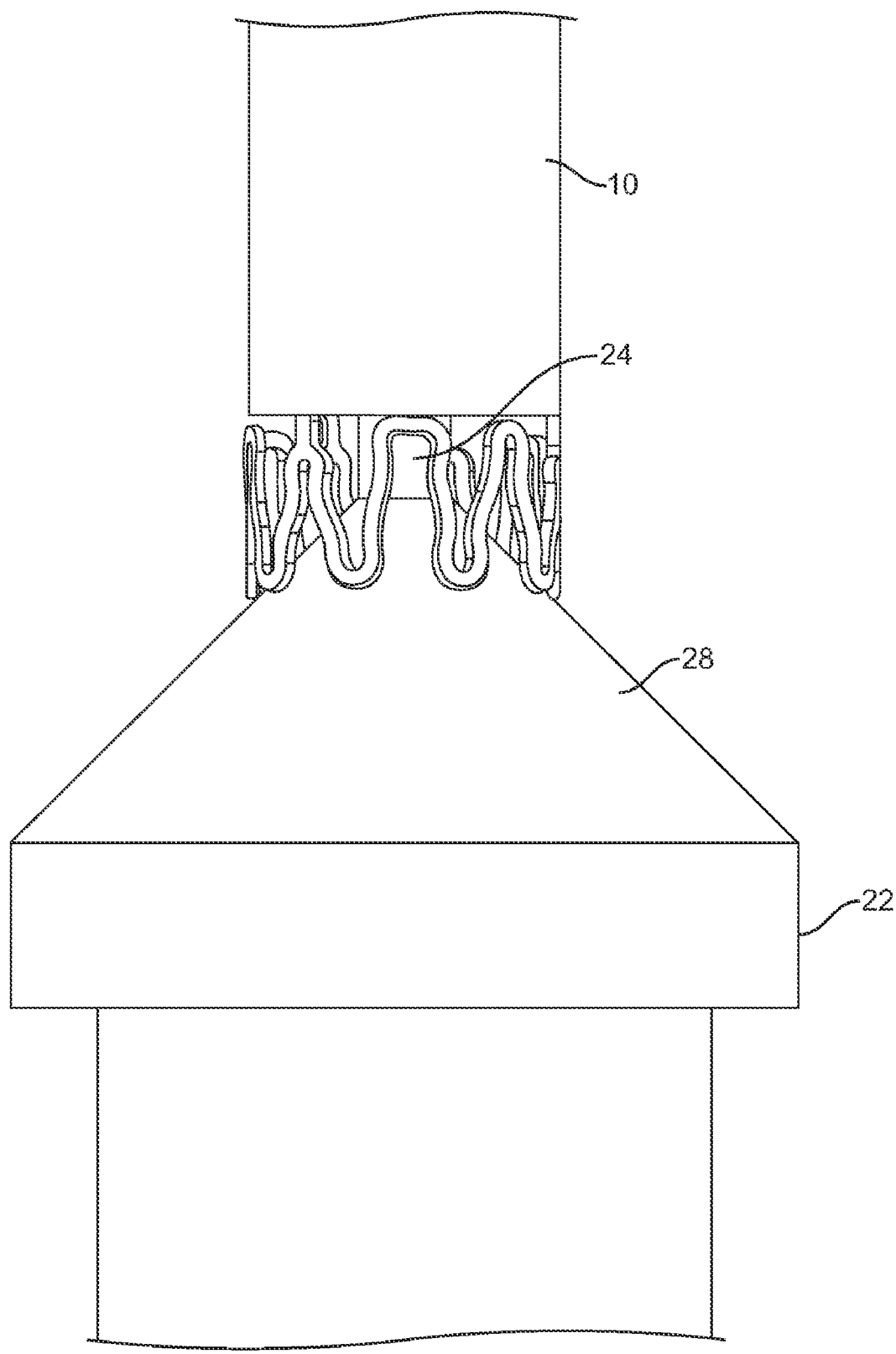

The stent support 20 supports the stent 24 via the conical portions 28, 30 of the first and second support elements 22, 26. FIG. 3 shows that the conical portion 28 of the first support element 22 supports one end of the stent 24, and FIG. 4 shows that the conical portion 32 of the second support element 26 supports the other end of the stent 24. In FIGS. 3 and 4 and in some of the subsequent Figures, only the struts in the end rings of the stent are shown, and the struts in the rest of the stent are not shown. As the conical portions 28, 30 of the first and second support elements 22, 26 are advanced towards each other, they automatically cause the stent 24 to become centered about the core element 24, and they also secure the stent 24 in the longitudinal direction of the stent support 20. The only contact between the stent 24 and the stent support 20 is at the interface between the conical portions 28, 30 and the inner rims at the ends of the stent 24.

According to one aspect of the present invention, stents, mounted on stent supports, arrive on a pallet at a coating system of the present invention. In some preferred embodiments, each pallet may hold 5 to 100, preferably 10 to 50, more preferably 15 to 40, mostly preferably 20 to 30, although each pallet may generally hold any number of stents and stent supports. Each stent support may include identification information, such as a two-dimensional matrix symbol, a barcode label or an RFID tag. The identification information may include, for example, the type of stent mounted on the stent support, the types of coating substances to be applied to the stent, the amount of each coating substance to be applied, and/or coating methods to be used. The pallet may also include identification information, such as a two-dimensional matrix symbol, a barcode label or an RFID tag, which identifies the types and locations of stents on the pallet.

The coating system may include a reader for reading the information provided by the stent supports and pallets. The reader may be, for example, an imaging device such as a camera, a barcode scanner, or an RFID reader.

The coating system may verify the information provided by the stent support and pallet. For example, the coating system may use an imaging device to determine the position of the second support element 26 of the stent support 20, which can be used to estimate the length of the stent. If the estimated stent length is inconsistent with the length of the stent provided by the stent support, the coating system will not proceed with the coating of the stent.

If the correct stent is mounted on the stent support, a robot arm of the coating system may remove the stent and stent support from the pallet and deliver them to a stent weighing apparatus of the coating system. In the stent weighing apparatus, the weight of the uncoated stent is measured. This weight may be used later to determine the amount of coating on the coated stent by comparing the weight of the uncoated and coated stent. Additionally, the weight of the uncoated stent may be compared with the weight of the stent identified by the reader for verification.

After the uncoated stent has been weighed, the same or a different robotic arm delivers the stent and stent support to an apparatus of the coating system for aligning the stent with the stent support. To increase the efficiency of coating operation, it is desirable for the axis of the stent to be aligned with the axis of the stent support. Misalignment between the stent axis and the stent support axis may cause inconsistent application of coating substance to the stent. This variation in the amount of stent coating may increase the number of stents having coating weights outside of the acceptable range, thereby increasing the stent defective rate.

If the stent needs a primer layer, the stent is delivered to a spray coating device to be coated with a primer layer. Then the stent primer may be dried in a drying device such as an oven. The primer layer may be inspected at an inspection station to determine whether there are any coating defects. If there are coating defects, the stent may be rejected as defective. Additionally, the amount of primer coating on the stent may be measured by weighing the coated stent at the same or a different stent weighing apparatus and comparing the weight of the uncoated and coated stent. If the amount of primer coating is outside of the acceptable range, the stent may also be rejected as defective.

After the stent has been weighed to measure the amount of primer coating, the stent is then mounted on the same or a different stent support and delivered to the apparatus for aligning the stent with the stent support.

The stent is then delivered to a spray coating device to be coated with an agent layer. Then the stent with the drug layer may be dried in the same or a different drying device. The agent layer may be inspected at an inspection station to determine whether there are any coating defects. If there are coating defects, the stent may be rejected as defective. Additionally, the amount of agent coating on the stent may be measured by weighing the coated stent at the stent weighing apparatus and comparing the weight of the stent coated with both primer and agent with the stent coated with only the primer. If the amount of agent coating is outside of the acceptable range, the stent may be rejected as defective.

The following is a detailed description of some components of a preferred stent coating system of the present invention.

Apparatus for Weighing Stent

Currently, the weighing of a stent requires manual manipulation of the stent and stent support. The operator must remove the stent from the stent support and place the stent on a scale to measure stent weight. The operator may need to put the stent support aside if she must manually operate the scale. After a successful measurement of stent weight, the operator picks up the stent support and mounts the stent on the stent support.

This manual procedure has several drawbacks. First, manual manipulation of the stent may damage the stent or stent coating. Additionally, the manual procedure is time-consuming. The dismounting of a stent from a stent support and mounting of a stent on a stent support are delicate and time-consuming tasks, and the operator must be careful to avoid damaging the stent or stent coating. Furthermore, if the operator needs to put the stent support aside to manually operate the scale, she may pick up a wrong stent support for mounting the stent. This may have grave consequences because the stent support usually has information identifying the type of stent mounted thereon and the drugs coated on the stent.

Therefore, there is a need for a method and apparatus for efficiently and automatically weighing a stent with minimum risk of damaging the stent or stent coating or mounting the stent on a wrong stent support.

Figure 5:
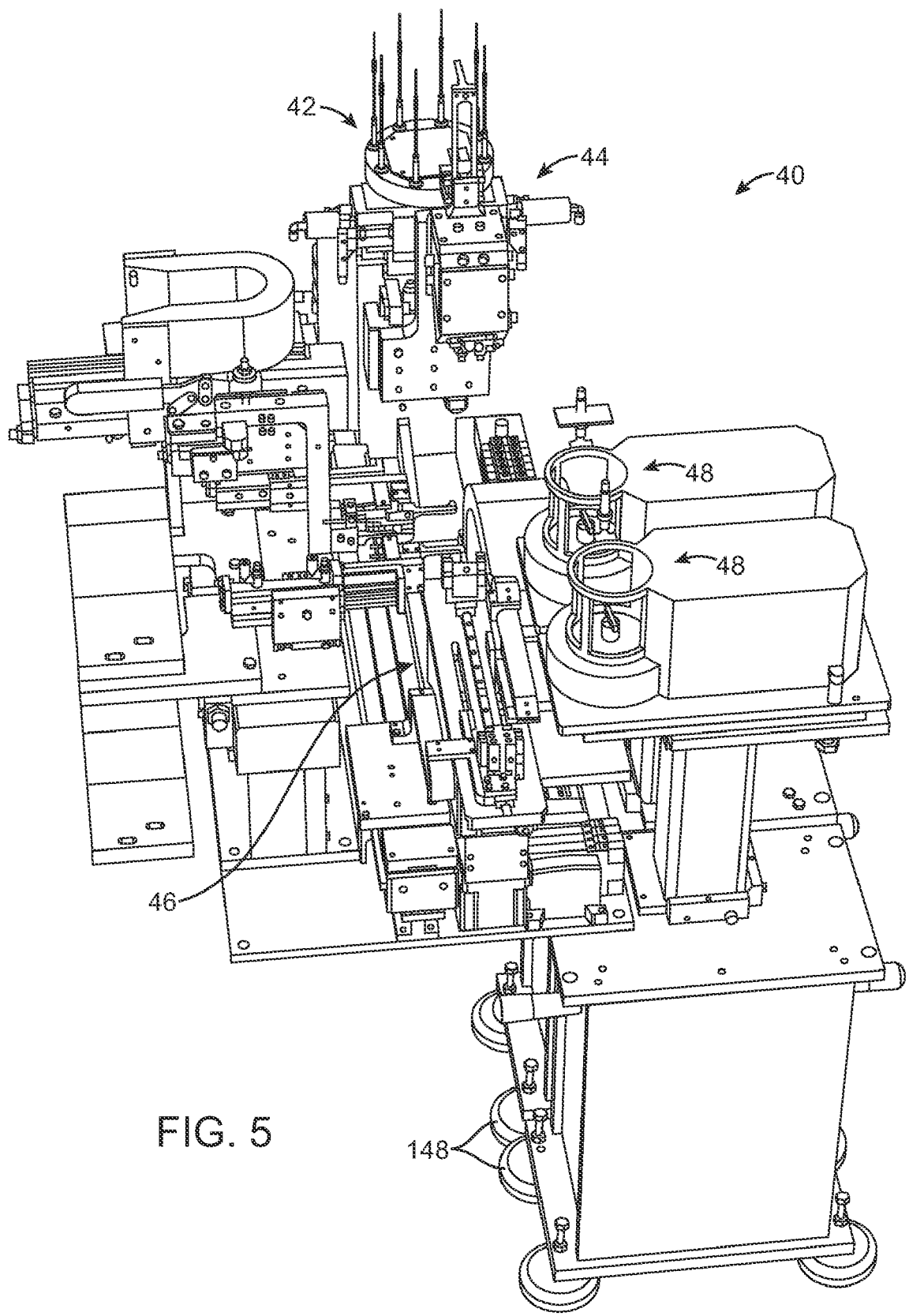
FIG. 5 is a perspective view of an apparatus for weighing a stent according to the present invention.

An apparatus for weighing a stent according to the present invention can overcome the above drawbacks associated with the current apparatus and methods for weighing a stent. FIG. 5 illustrates an example 40 of such an apparatus of the present invention. The apparatus 40 includes a buffer 42, a robotic arm 44, a stent mounting and dismounting assembly 46, and scale assemblies 48 each of which has a scale 50.

The buffer 42 is used to store stent supports 20 with stents 10 mounted thereon before and after the stents 10 have been weighed on the scales 50. The robotic arm 44 moves a stent support 20 from the buffer 42 to the stent mounting and dismounting assembly 46. The stent mounting and dismounting assembly 46 removes the stent 10 from the stent support 20 and places the stent 10 on a scale 50 to be weighed. After the stent 10 has been weighed, the stent mounting and dismounting assembly 46 removes the stent 10 from the scale 50 and mounts the stent 10 on the stent support 20. The robotic arm 44 moves the stent 10 and stent support 20 from the stent mounting and dismounting assembly 46 to the buffer 42.

The buffer 42 may be used to store stents 20 that are at various stages of the coating process. The weighing of a stent 10 may take place before the stent 10 is coated and after any one of various processes involved the coating of the stent, such as polymer coating, agent coating, drying, etc. These processes are not synchronized with the weighing of the stents. In some situations, several stents 20 to be weighed may be received in a short period of time at the weighing apparatus 40, while in other situations no stents may be received for a relatively long period of time at the weighing apparatus 40. If a buffer is not provided, a stent may have to be held at a coating station (or any other stage of the coating process) before it is weighed. As a result, the coating station lies idle until a scale 50 is available to weigh the stent. Alternatively, the scale 50 may lie idle when no stents are sent to the scale 50 to be weighed.

Figure 6:
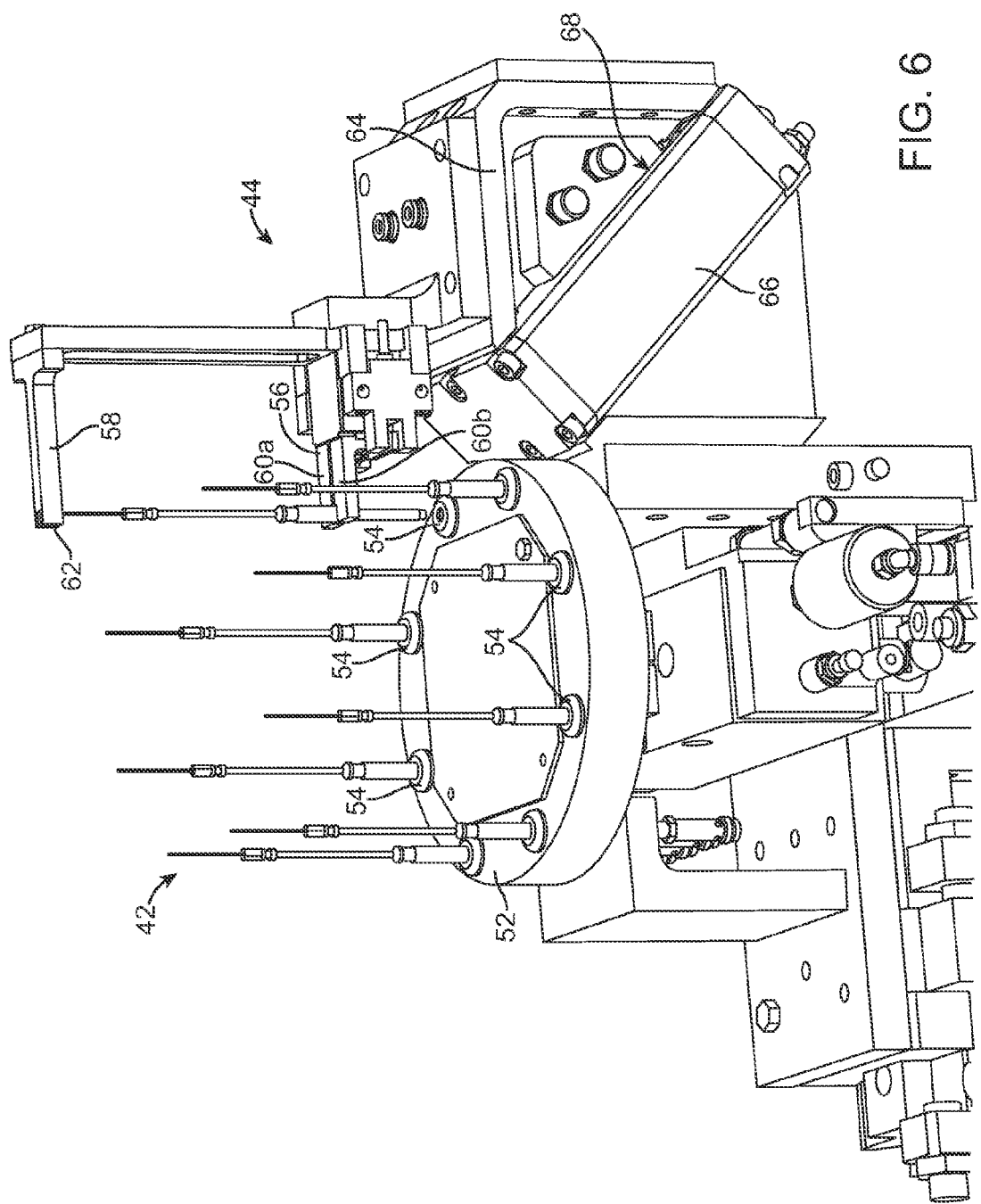
FIG. 6 is a perspective view of a buffer and a robotic arm of the apparatus shown in FIG. 5.

A buffer of the present invention may have any suitable configuration and structure. For example, as shown in FIG. 6, the buffer 42 may have a circular plate 52 and one or more receptacles 54 for receiving stent supports 20 that are arranged in a circle along the edge of the circular plate 52. Each receptacle 54 may hold the first support element 22 of a stent support 20, thereby placing the stent support 20 in a vertical position as shown in FIG. 6. The buffer 42 may include an electric or hydraulic motor (not shown) to rotate the buffer plate 52 and a controller (not shown) that can control the rotation of the buffer plate 52 to align a particular stent support 20 with the robotic arm 44 for pickup.

Alternatively, a buffer of the present invention may be similar to a conveyor belt and may include receptacles spaced at a fixed or variable interval on the convey belt. The movement of the conveyor belt may be controlled to align a particular stent support 20 with the robotic arm 44 for pickup.

A receptacle 54 of the buffer 42 may be designated to receive stents 10 that are at a particular stage of the coating process. As shown in FIG. 6, a receptacle 54 may be used to hold a stent that is clean (i.e., before it is coated) and needs to be weighed. Another receptacle 54 may be used to hold a stent that is clean and has been weighed. A further receptacle 54 may be used to hold a stent that has been baked (i.e., coated and dried in an oven) and has not be weighed. A still further receptacle 54 may be used to hold a stent that has been baked (i.e., coated and dried in an oven) and has been weighed.

The robotic arm 44 may be used to perform various functions. Preferably, the robotic arm 44 is able to grip and hold a stent support 20, to pick up a stent support 20 from and to place it in a receptacle 54 of the buffer 42, to pick up a stent support 20 from and to place it on the stent mounting and dismounting assembly 46, and/or to move a stent support 20 between the buffer 42 and the stent mounting and dismounting assembly 46.

The robotic arm 44 may have any suitable structural features that can be used to grip and hold a stent support 20. In the embodiment shown in FIG. 6, for example, the robotic arm 44 has a stent support griper 56 for gripping the first support element 22 of the stent support 20, and a holder 58 for holding the free end of the core element 24 of the stent support 20 to keep the stent support 20 straight. The stent support griper 56 may have two fingers 60a, 60b that can move away from each other to allow the first support element 22 to be placed between the fingers 60a, 60b and can move towards each other to grip the first support element 22. The core element holder 58 may have a groove 62 at its tip for receiving and holding the core element 24 of the stent support 20.

The robotic arm 44 may be moveable between two positions. The first position of the robotic arm 44 is shown in FIG. 6 where the robotic arm 44 is positioned next to the buffer 42 and can hold the stent support 20 in a vertical position. At the second position the robotic arm 44 is positioned next to the stent mounting and dismounting assembly 46 and holds the stent support 20 in a horizontal position. When the robotic arm 44 moves from the first position to the second position, it moves a stent support 20 from the buffer 42 to the stent mounting and dismounting assembly 46. When the robotic arm 44 moves from the second position to the first position, it moves a stent support 20 from the stent mounting and dismounting assembly 46 to the buffer 42.

To enable the robotic arm's movement between its first and second positions, the robotic arm 44 has first and second members 64, 66, each of which has a generally triangular configuration when viewed as shown in FIG. 6. The interface 68 between the two members 64, 66 is at a 45° from either the vertical or horizontal position. The first member 64 can rotate relative to the second member 66 at the interface 68. In other words, the first member 64 can rotate about an axis that is perpendicular to the interface 68. When the first member 64 is rotated 180° from the first position shown in FIG. 6, the stent support 20 is moved from the vertical position at the buffer 42 to a horizontal position just above the stent mounting and dismounting assembly 46. When the first member 64 is rotated back to the first position as shown in FIG. 6, the stent support 20 is moved from the horizontal position back to the vertical position shown in FIG. 6.

Additionally, the entire robotic arm 44 may move vertically between a first, lower position and a second, higher position shown in FIG. 6.

To move a stent support 20 from the buffer 42 to the stent mounting and dismounting assembly 46, the robotic arm 44 is first placed in its first position next to the buffer 42 and at the lower vertical position. The robotic arm 44 then grips the stent support 20 with its stent support griper 56 gripping the first support element 22 of the stent support 20 and the core element holder 58 holding the core element 24 of the stent support 20. At this point, the stent support 20 is still placed in a receptacle 54 of the buffer 42. Then the robotic arm 44 is raised to the higher vertical position, as shown in FIG. 6, to lift the stent support 20 out of the receptacle 54. The first member 64 of the robotic arm 44 is then rotated 180° relative to the second member 66 to move the stent support 20 from the vertical position shown in FIG. 6 to a horizontal position just above the stent mounting and dismounting assembly 46. Next the robotic arm 44 is lowered from its higher vertical position to its lower vertical position to place the stent support 20 on the stent mounting and dismounting assembly 46.

The stent mounting and dismounting assembly 46 is used to mount a stent 10 on a stent support 20 or dismount a stent 10 from a stent support 20. To that end, the assembly 46 may be equipped with a stent support gripper assembly 70 and a stent gripper assembly 72. The stent support gripper assembly 70 is used to hold a stent support 20 when a stent 10 is being mounted on or dismounted from the stent support 20. The stent gripper assembly 72 is used to holder the stent 10 when the stent 10 is being mounted on or dismounted from a stent support 20.

Figure 7:
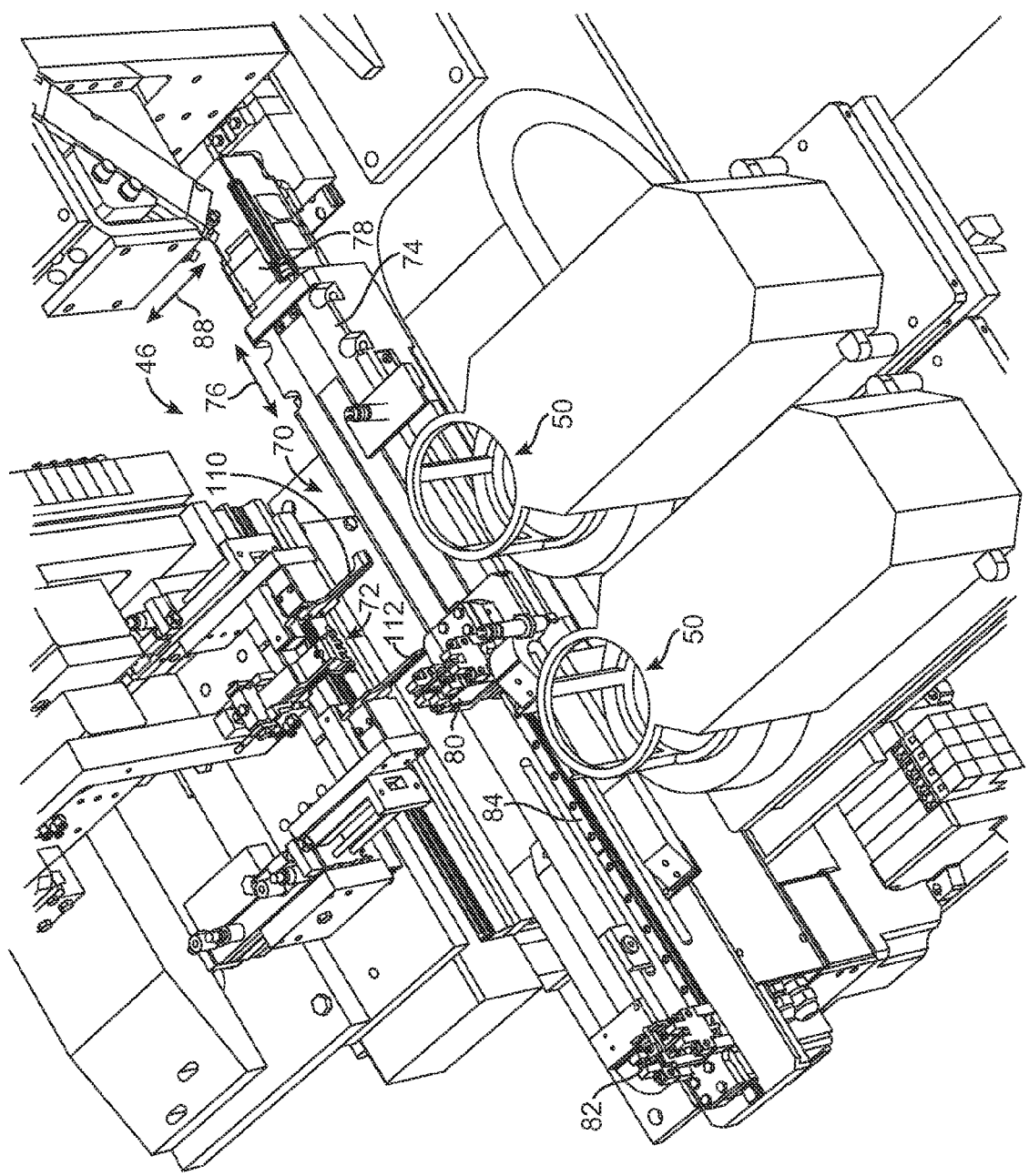
FIG. 7 is a perspective view of a stent mounting and dismounting assembly of the apparatus shown in FIG. 5, wherein the stent mounting and dismounting assembly includes a stent support gripper assembly, a stent gripper assembly, and first and second core element guides.

As shown in FIG. 7, the stent support gripper assembly 70 may include a platform 74 that is moveable in a longitudinal direction 76 along a longitudinal rail 78. The stent support gripper assembly 70 may further include a first support element gripper 80 and a second support element gripper 82. The first and second support element grippers 80, 82 are mounted on the platform 74 and are moveable independently of each other in the longitudinal direction 76 along a longitudinal platform rail 84 on the platform 74. In other words, the first and second support element grippers 80, 82 can move in the longitudinal direction 76 as part of the platform 74, or they can move in the longitudinal direction 76 relative to the platform 74. Alternatively, the stent support gripper assembly 70 may not include the platform 74. Instead the first and second support element grippers 80, 82 may be mounted directly on the rail 78 for longitudinal movement.

Figure 8:
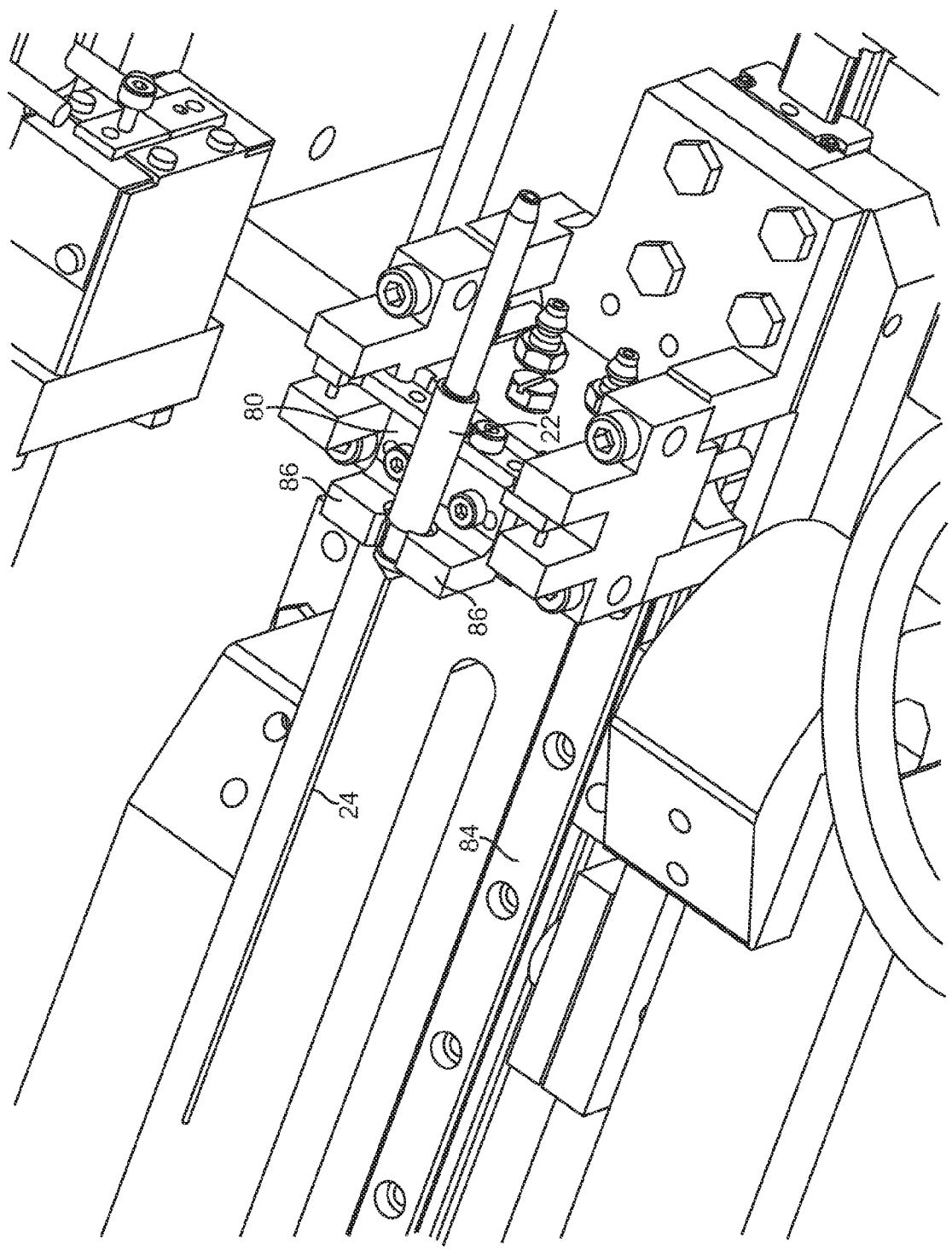
FIG. 8 is a perspective view of a first support element gripper of the stent support gripper assembly shown in FIG. 7, wherein a first support element is held in the first support element gripper.
Figure 9:
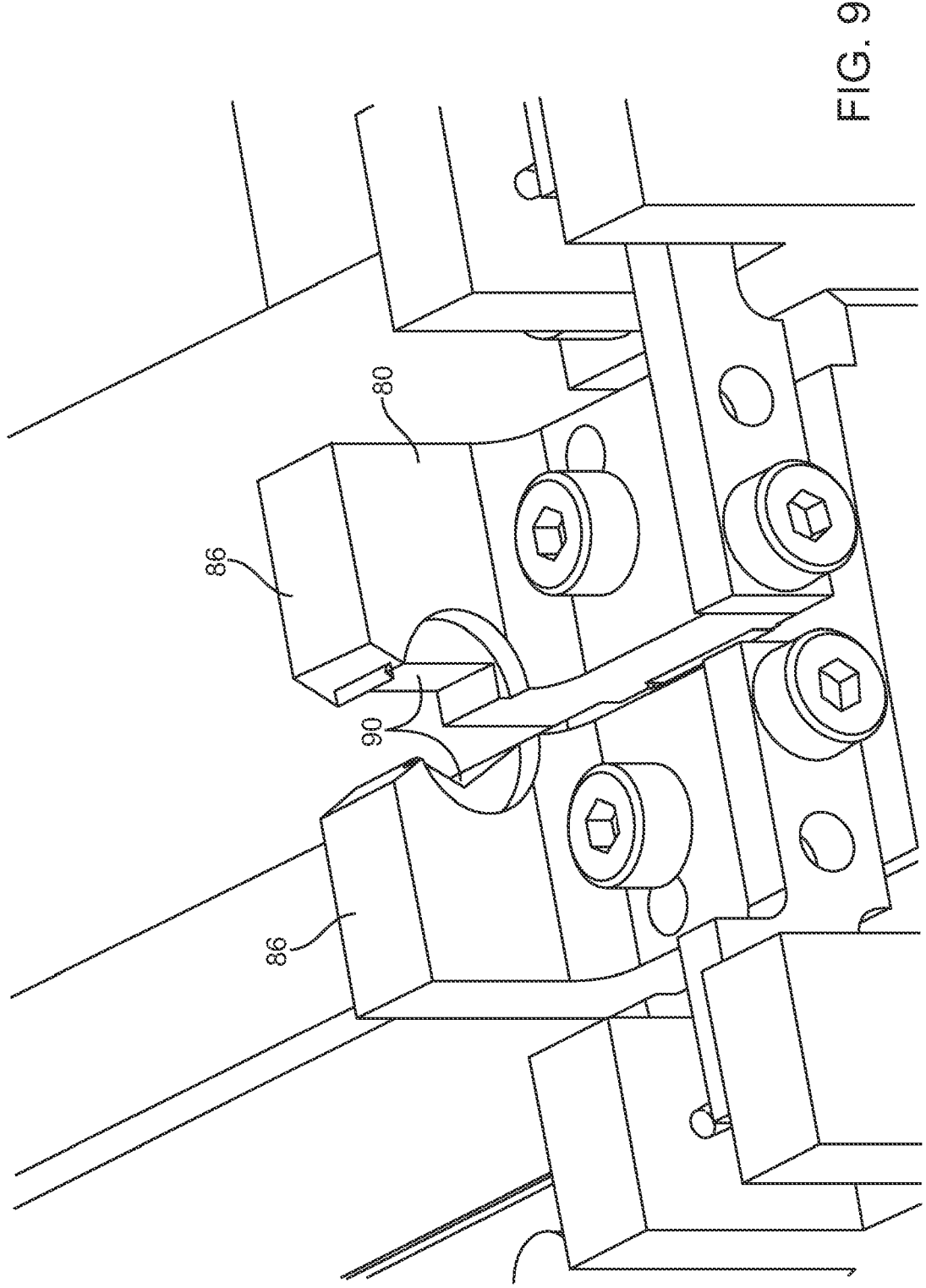
FIG. 9 is another perspective view of the first support element gripper shown in FIG. 8, wherein a first support element is not held in the first support element gripper.

As shown in FIG. 8, the first support element gripper 80 is used to grip and hold the first support element 22 of the stent support 20. The first support element gripper 80 may include two fingers 86 that extend upwards and can move in the lateral direction 88. The two fingers 86 can move away from each other so that the first support element 22 can be placed between the two fingers 86. And the two fingers 86 can move towards each other to grip the first support element 22. The two fingers 86 may grip the first support element 22 at its groove 30. In other words, when the two fingers 86 grip the first support element 22, they are placed within the groove 30 of the first support element 22. Preferably, the longitudinal dimension of the fingers 86 is substantially the same or slightly less than the width of the groove 30 so that the fingers 86, when placed in the groove 30, may limit the longitudinal movement of the first support element 22. Additionally, each of the fingers 86 may include a groove (or cut) 90 for receiving the first support element 22 (or the groove 30 of the first support element 22). The grooves 90 of the fingers 86 help ensure that the first support element 22 is securely held between the fingers 86. One or both of the grooves 90 may have a substantially semi-circular configuration, and the radius of the semi-circle may be substantially the same or slightly larger than the diameter of the first support element 22 (or the diameter of the groove 30 of the first support element 22). Alternatively, one or both of the grooves 90 may have a substantially triangular configuration. In the embodiment shown in FIG. 8, one of the grooves 90 has a triangular configuration (see FIG. 9) while the other groove 90 has a rectangular configuration.

Figure 10:
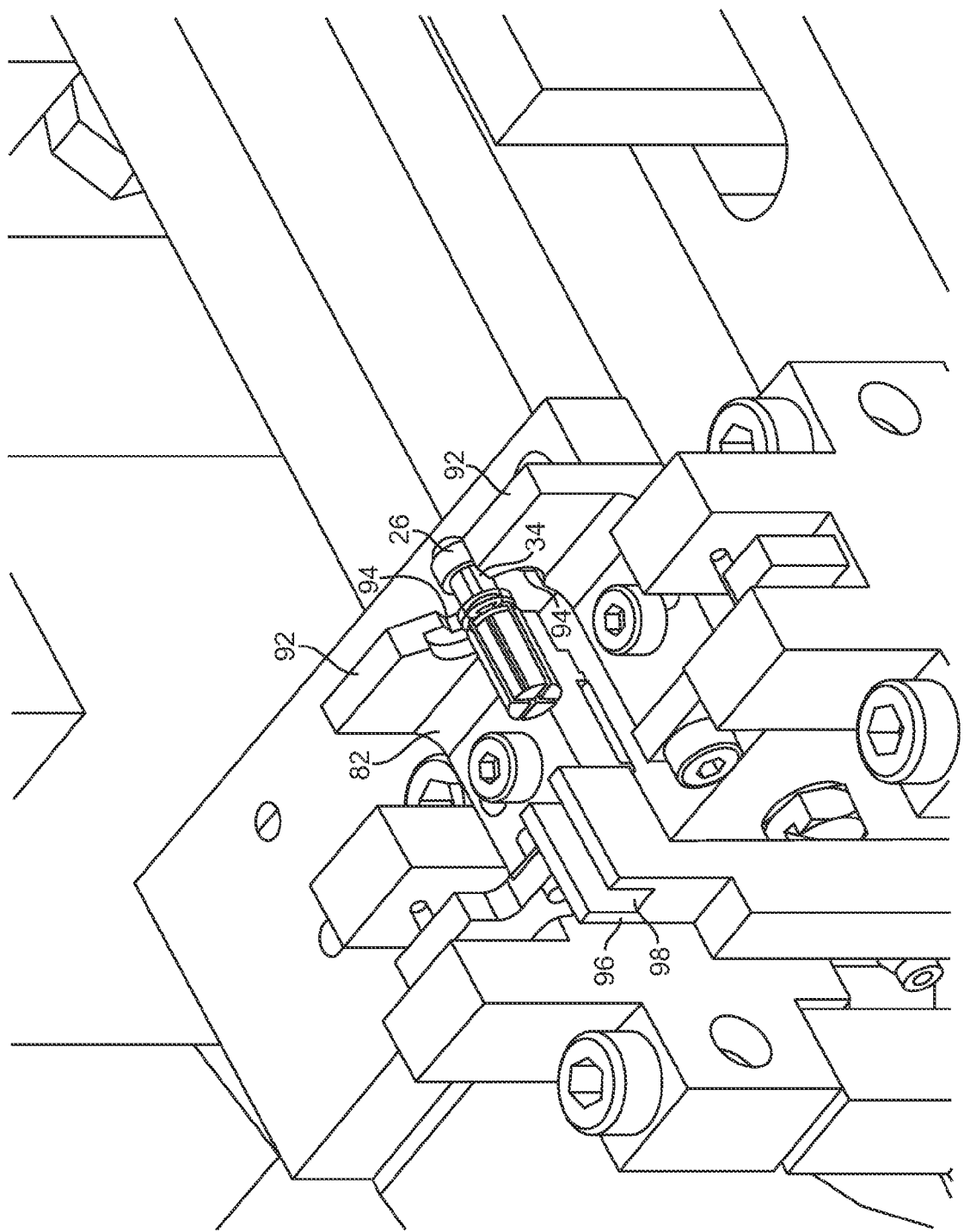
FIG. 10 is a perspective view of a second support element gripper of the stent support gripper assembly shown in FIG. 7, wherein a second support element is held in the second support element gripper.

As shown in FIG. 10, the second support element gripper 82 is used to grip and hold the second support element 26 of the stent support 20. The second support element gripper 82 may also include two fingers 92 that extend upwards and can move in the lateral direction 88. The two fingers 92 can move away from each other so that the second support element 26 can be placed between the two fingers 92. And the two fingers 92 can move towards each other to grip the second support element 26. Preferably, the two fingers 92 grip the second support element 26 at its groove 34. Preferably, the longitudinal dimension of the fingers 92 is substantially the same or slightly less than the width of the groove 34 so that the fingers 92, when placed in the groove 34, may limit the longitudinal movement of the second support element 26. Additionally, each of the fingers 92 may include a groove 94 for receiving the second support element 26 (or the groove 34 of the first support element 26). The grooves 94 of the fingers 92 help ensure that the second support element 26 is securely held between the fingers 92. One or both of the grooves 94 may have a substantially semi-circular configuration, and the radius of the semi-circle may be substantially the same or slightly larger than the diameter of the second support element 26 (or the diameter of the groove 34 of the second support element 26). Alternatively, one or both of the grooves 94 may have a substantially triangular configuration. In the embodiment shown in FIG. 10, one of the grooves 94 has a triangular configuration while the other groove 94 has a rectangular configuration.

Preferably, the second support element gripper 82 includes also a core element holder 96 for holding the free end of the core element 24 of the stent support 20. The core element holder 96 has a groove 98 for receiving and holding the free end of the core element 24.

During the dismounting of a stent 10 from a stent support 20, the stent gripper assembly 72 grips and holds the stent 10, and the first and second support element grippers 80, 82 grip and hold the first and second support elements 22, 26 of the stent support 20, respectively. At this point, the first and second support element grippers 80, 82 may move away from each other in the longitudinal direction 76 along the platform rail 84. This movement removes the second support element 26 of the stent support 20 from the core element 24 of the stent support 20. The movement of the first support element gripper 80 also extracts the core element 24 of the stent support 20 from the hollow center of the stent 10. As a result, the stent 10 is removed from the stent support 20.

During the mounting of a stent 10 on a stent support 20, the stent gripper assembly 72 places the stent 10 in a position where the stent 10 is substantially coaxial with the first and second support elements 22, 26 and core element 24 of the stent support 20 and where the stent is between the first and second support elements 22, 26. The first and second support element grippers 80, 82 move the first and second support elements 22, 26 of the stent support 20 towards each other in the longitudinal direction 76. This movement threads the core element 24 of the stent support 20 through the hollow center of the stent 10. The movement also mounts the second support element 26 on the core element 24 of the stent support 20. As a result, the stent 10 is mounted on the stent support 20.

Figure 11:
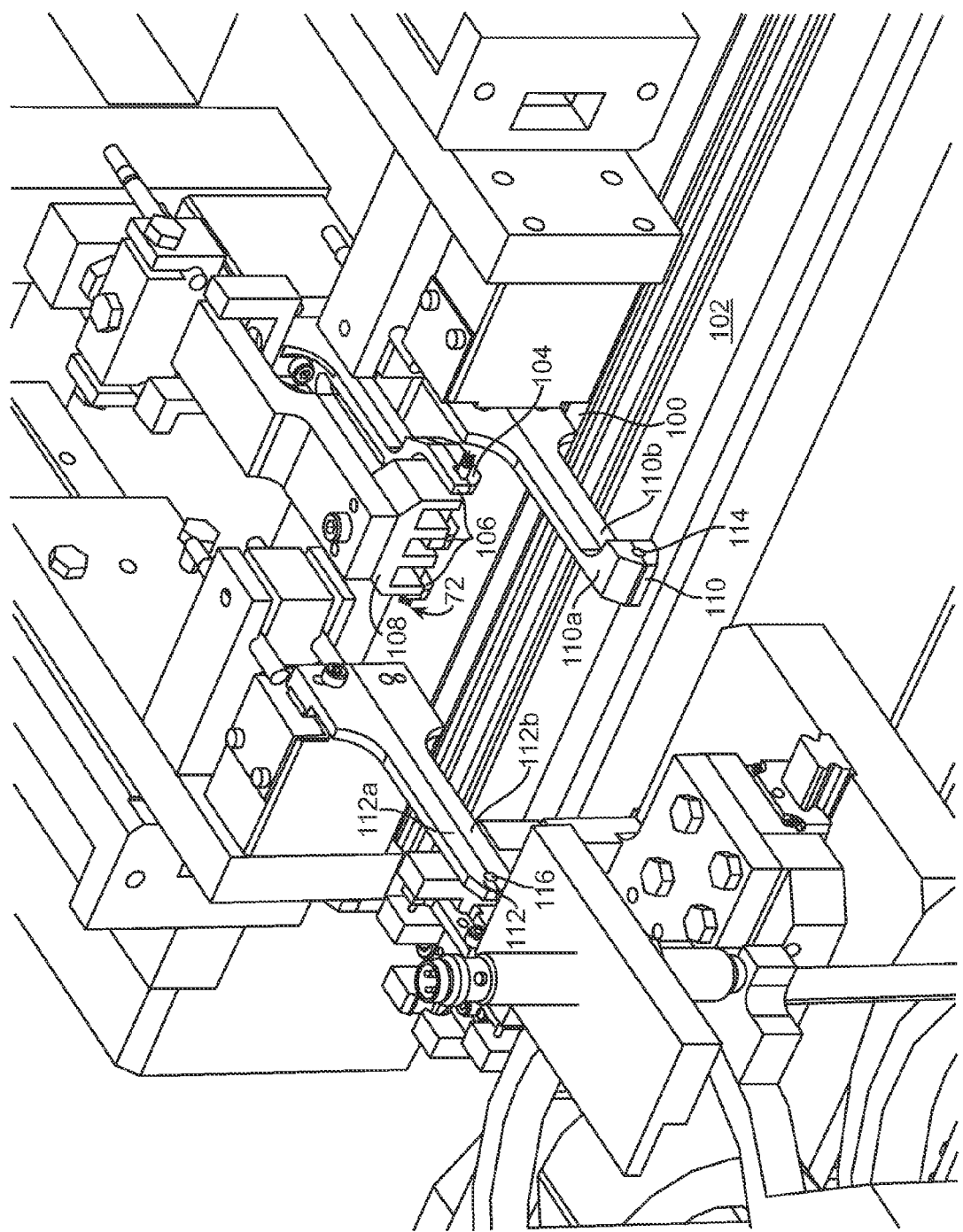
FIG. 11 is a detailed perspective view of the stent gripper assembly and first and second core element guides shown in FIG. 7.

As shown in FIG. 11, the stent gripper assembly 72 preferably includes a platform 100 that is moveable in a longitudinal direction 76 along a longitudinal rail 102. This longitudinal rail 102 is arranged side by side and in parallel with the longitudinal rail 78 on which the stent support gripper assembly 70 is moveably placed.

The stent gripper assembly 72 may include a stent gripper 104 that is mounted on and moveable with the platform 100 of the stent gripper assembly 72. Alternatively, the stent gripper assembly 72 may not include the platform 100. Instead the stent gripper 104 may be directly mounted on the rail 102 for longitudinal movement.

The stent gripper 104 may also be moveable in the lateral direction 88 and may have at least three lateral positions. The first lateral position (i.e., a middle position) is described above where the stent gripper 104 grips and holds the stent 10 when the stent 10 is being mounted on or dismounted from the stent support 20. At this position, as described above, the stent 10 is substantially coaxial with the first and second support elements 22, 26 and core element 24 of the stent support 20. The second lateral position of the stent gripper 104 is a retracted position, as shown in FIG. 11, where the stent gripper 104 is retracted from the first lateral position. The stent gripper 104 moves to the retracted position after the stent gripper 104 releases the stent 10 subsequent to a successful mounting of the stent 10 on the stent support 20. A retracted stent gripper 104 allows the robotic arm 44 to move the stent 10 from the second support element gripper 82 to the buffer 42. The third lateral position of the stent gripper 104 is an extended position where the stent gripper 104 extends into one of the scale assemblies 48 to place the stent 10 on or to remove the stent 10 from the scale 50.

Figure 12:
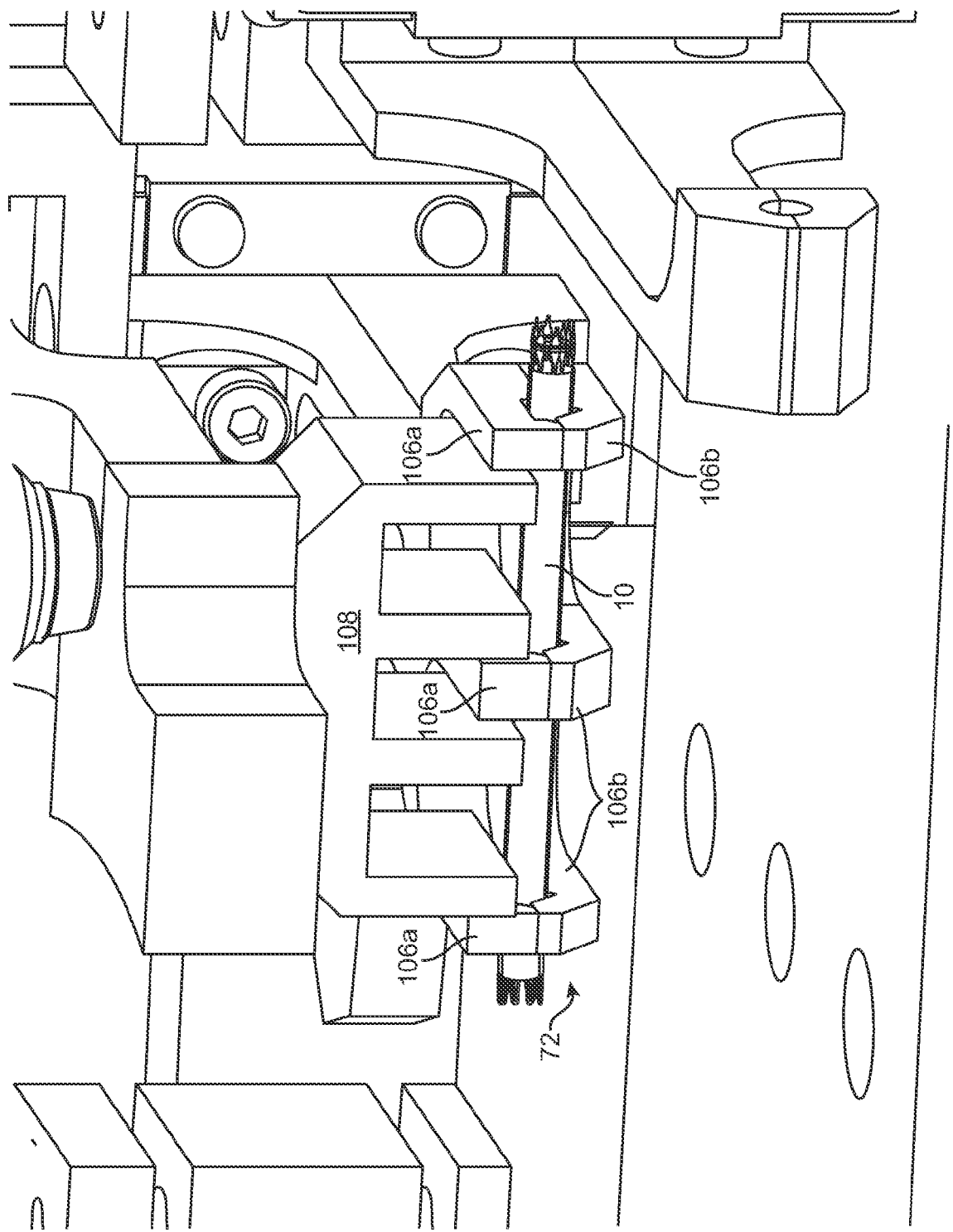
FIG. 12 is a perspective view of a stent gripper of the stent gripper assembly shown in FIGS. 7 and 11.

As shown in FIG. 12, the stent gripper 104 may have three pairs of fingers 106a, 106b, although the stent gripper may have any suitable number of finger pairs, including one, two or four pairs. In this embodiment, the three upper fingers 106a are integrally formed, and the three lower fingers 106b are also integrally formed. The fingers 106a, 106b of each pair can move away from each other to allow the stent 10 to be placed between the fingers 106a, 106b and can move towards each other to grip the stent 10 between the fingers 106a, 106b. Each pair of fingers 106a, 106b may also include grooves that are similar to or the same as the grooves 90 described above.

As shown in FIG. 12, the stent gripper 104 may also include a stripper block 108. The stripper block 108 may be used to hold the stent straight and keep it from moving during extraction and insertion of the core element 24.

As shown in FIG. 11, the apparatus 40 may also include first and second core element guides 110, 112 that are mounted on the stent gripper assembly 72, although the apparatus 40 may generally include any number of core element guides that are placed at any suitable locations. As will be described in detail below, each core element guide 110, 112 is used to guide and straighten the flexible core element 24 of the stent support 20 so that the core element 24 can be threaded through the stent 10 and the second support element 26 of the stent support 20 during stent mounting.

Figure 13:
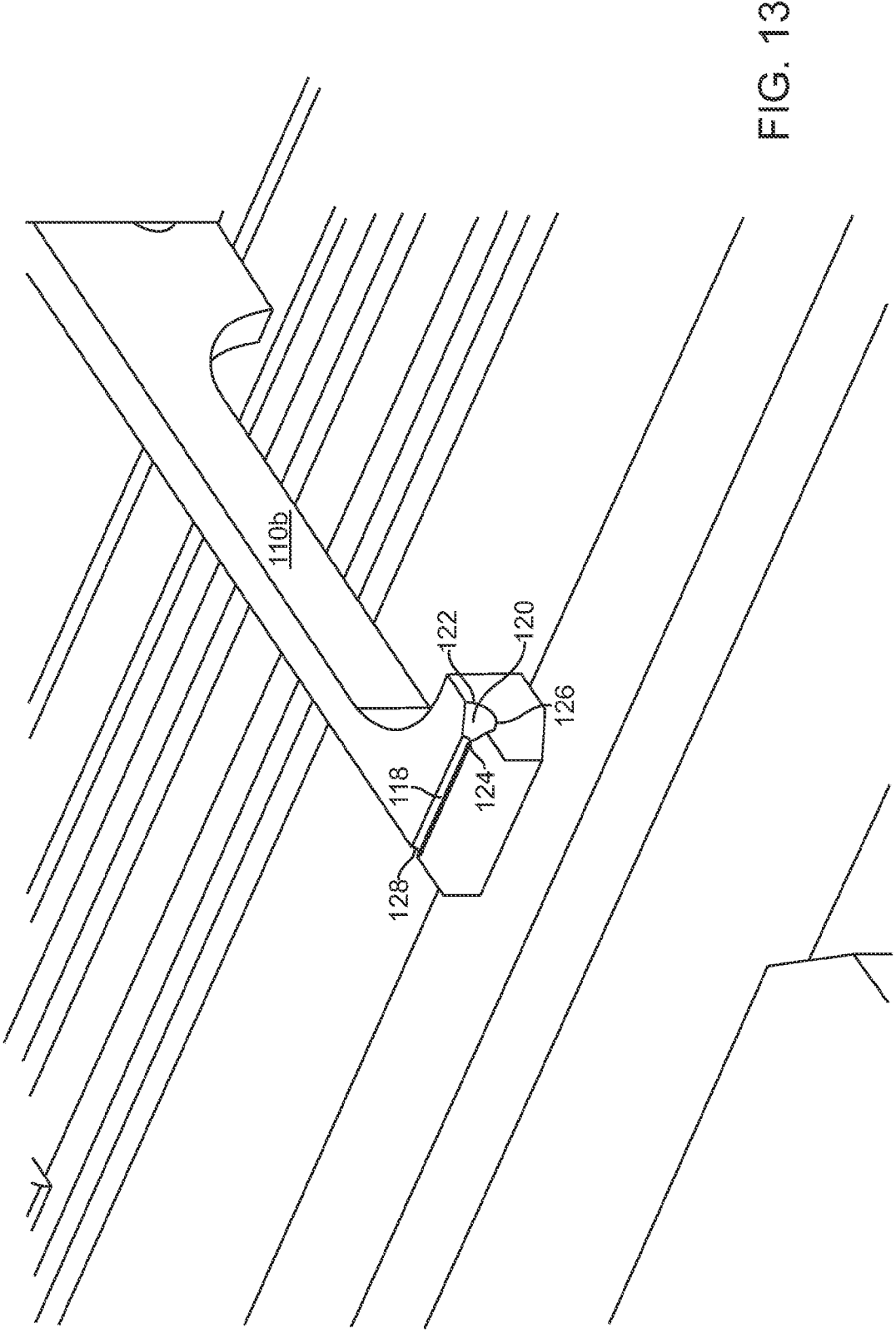
FIG. 13 is a perspective view of the lower finger of the first core element guide shown in FIGS. 7 and 11.

Preferably, each core element guide 110, 112 includes a bore 114, 116 for guiding the core element 24. The free end of the core element 24 enters from a first opening of the bore 114, 116 and exits the second opening of the bore 114, 116. The bore 114, 116 preferable has a large first opening to capture the free end of the core element 24 and a small second opening to guide and center the core element 24. As shown in FIG. 13, for example, the bore 114 of the first core element guide 110 has a cylindrical portion 118 and a conical portion 120 connected to the cylindrical portion 118. The conical portion 120 has a base 122 and an apex 124, wherein the base 74 defines the first opening 126 of the bore 114. The cylindrical portion 118 of the bore 114 defines the second opening 128 of the bore 114. During operation, as the free end of the core element 24 moves towards the first core element guide 110, the free end of the core element 24 is captured by the first opening 126 of the bore 114. As the movement of the core element 24 continues, the conical portion 120 guides the free end of the core element 24 into the small cylindrical portion 118 of the bore 114.

Figure 14:
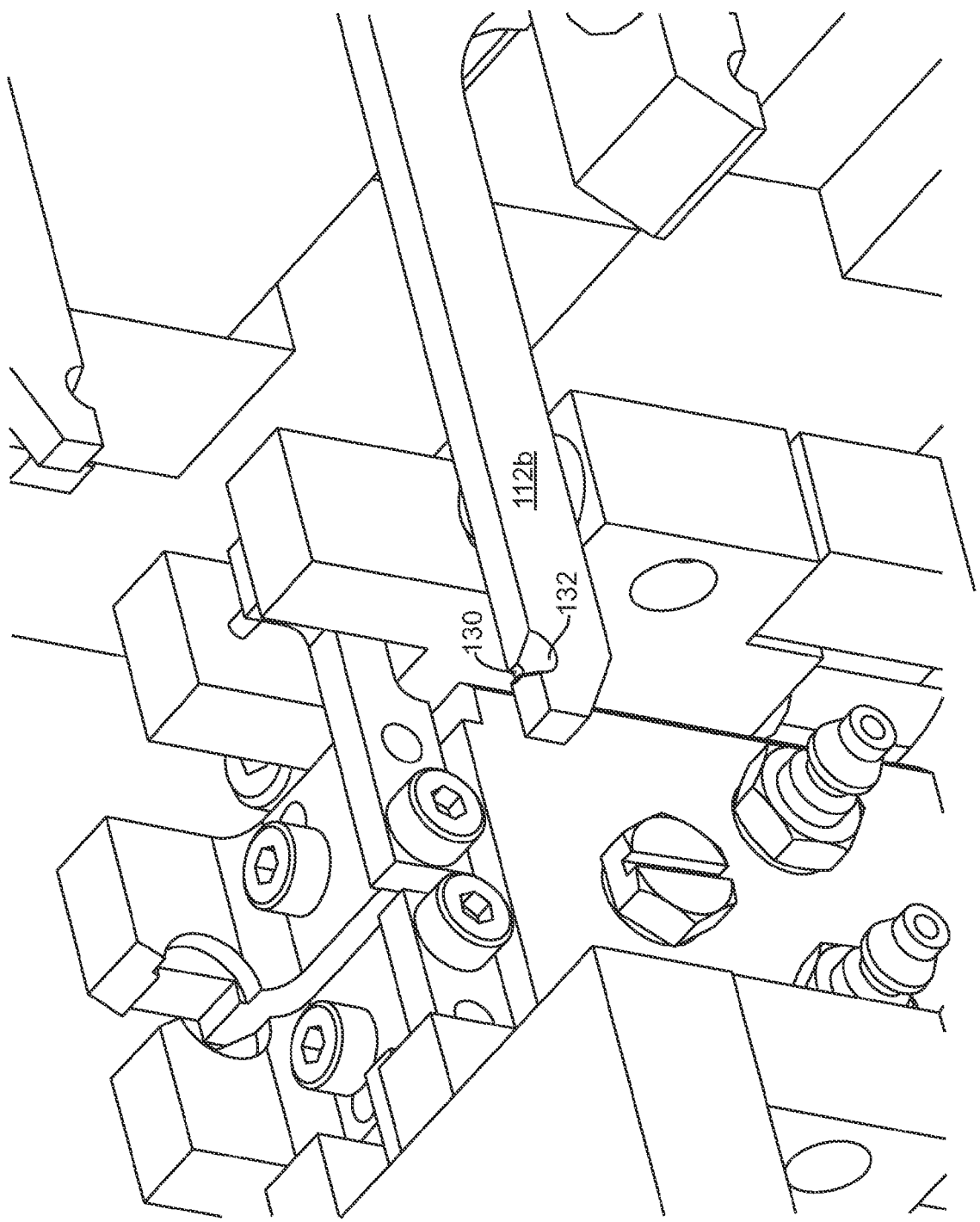
FIG. 14 is a perspective view of the lower finger of the second core element guide shown in FIGS. 7 and 11.

Similarly, as shown in FIG. 14, the bore 116 of the second core element guide 112 may also have a cylindrical portion 130 and a conical portion 132 connected with the cylindrical portion 130.

As shown in FIG. 11, the first core element guide 110 includes a pair of fingers 110a, 110b, such as an upper finger 110a and a lower finger 110b, which are moveable between an open position where the fingers 110a, 110b are apart and a closed position where the fingers 110a, 110b are next to each other. The two fingers 110a, 110b, when closed, define the bore 114 of the first core element guide 110. Preferably, the interface between the fingers 110a, 110b divides the bore 114 into an upper half and a lower half. Similarly, the second core element guide 112 may also include a pair of fingers 112a, 112b that are moveable between an open position and a closed position. The two fingers 112a, 112b, when closed, preferably define the bore 116 of the second core element guide 112. The interface between the fingers 112a, 112b preferably divides the bore 116 into an upper half and a lower half.

Each core element guide 110, 112 is moveable between two positions. The first position of each core element guide 110, 112 is the same as the first position (the middle position) of the stent gripper 104. When each core element guide 110, 112 is at its first position, its bore 114, 116 is substantially axially aligned with the stent 10 and with the first and second support elements 22, 26 of the stent support 20 to perform its function of guiding the core element 24 of the stent support 20. The second position of the each core element guide 110, 112 is a retracted position which is similar to the retracted position of the stent gripper 104.

The core element guides 110, 112 may be used in any suitable manner during stent mounting. For example, after the stent gripper 104 moves the stent 10 to the first position for stent mounting, the first and second core element guides 110, 112 may also move into their first positions to guide the core element 24 of the stent support. At this point, the stent 10 and the bores 114, 116 of the core element guides 110, 112 are substantially coaxially arranged. The first support element gripper 80 may then move the first support element 22 and core element 24 towards the stent 10 and the second support element 26. This movement causes the core element 24 to be threaded in sequence through the bore 114 of the first core element guide 110, the stent 10, the bore 116 of the second core element guide 112, and the second support element 26. As the first support element gripper 80 moves the first support element 22 and core element 24 towards the second support element 26, the second support element gripper 82 may also move the second support element 26 toward the first support element 22 and core element 24. After the stent 10 and second support element 26 have been mounted on the core element 24, the fingers 110a, 110b, 112a, 112b of each core element guide 110, 112 are opened to disengage the core element guides 110, 112 from the core element 24 of the stent support 20.

As shown in FIG. 5, the apparatus 40 may include two scale assemblies 48 for weighing a stent 10, although it may include any number of scale assemblies, such as one, three, or four scale assemblies. In the illustrated embodiment, the scale assemblies 48 and the stent gripper assembly 72 are placed on the opposite sides of the stent support gripper assembly 70, although they can be placed on the same side. To place a stent 10 in one of the scale assemblies 48, the stent gripper assembly 72 and the stent support gripper assembly 70 can be positioned longitudinally so that they are aligned with this scale assembly 48.

Figure 15:
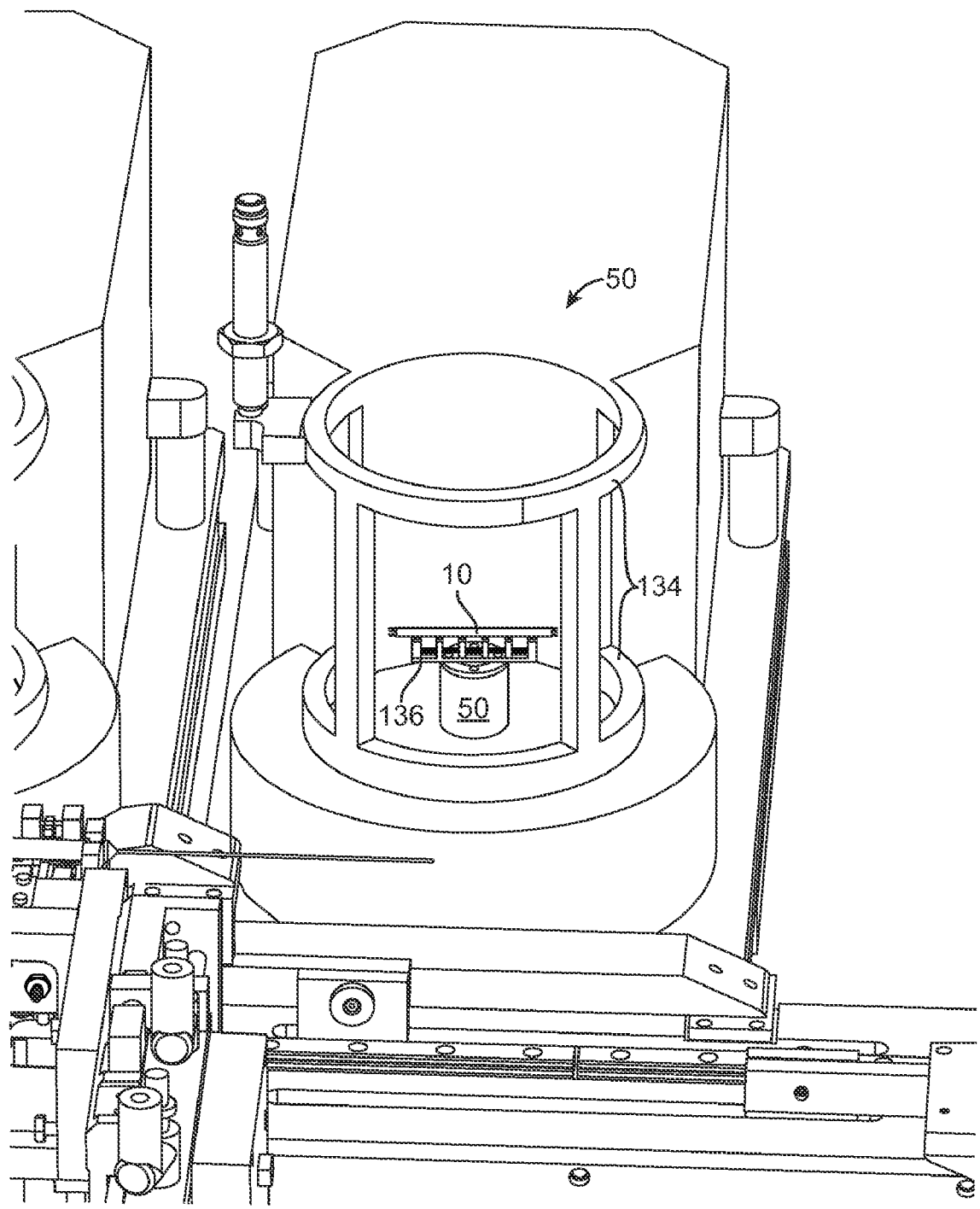
FIG. 15 is a perspective view of a scale assembly of the apparatus shown in FIG. 5.

As shown in FIG. 15, each scale assembly 48 includes a housing 134, a scale 50 disposed in the housing 134, and a stent nest 136 resting on the scale 50. In the illustrated embodiment, the housing 134 preferably has a door (not shown) that opens to allow the stent gripper 104 to place a stent 10 on the scale 50 or to remove a stent 10 from the scale 50. The door can be closed to isolate the scale 50 from the effects of air disturbance and noise. Air disturbance and noise may affect the accuracy of the scale 50 due to the scale's sensitivity.

The scale 50 may be any scale suitable for measuring stent weight, such as a scale that is commercially available. For example, the scale 50 may be a microbalance, such as the UMX5 Microbalance from Mettler-Toledo, Inc. of Columbus, Ohio. The maximum capacity of the UMX5 Microbalance including a weighing pan is 2.1 g. The weight of a coated stent that this scale can measure may be approximately 0.4 g.

Figure 16:
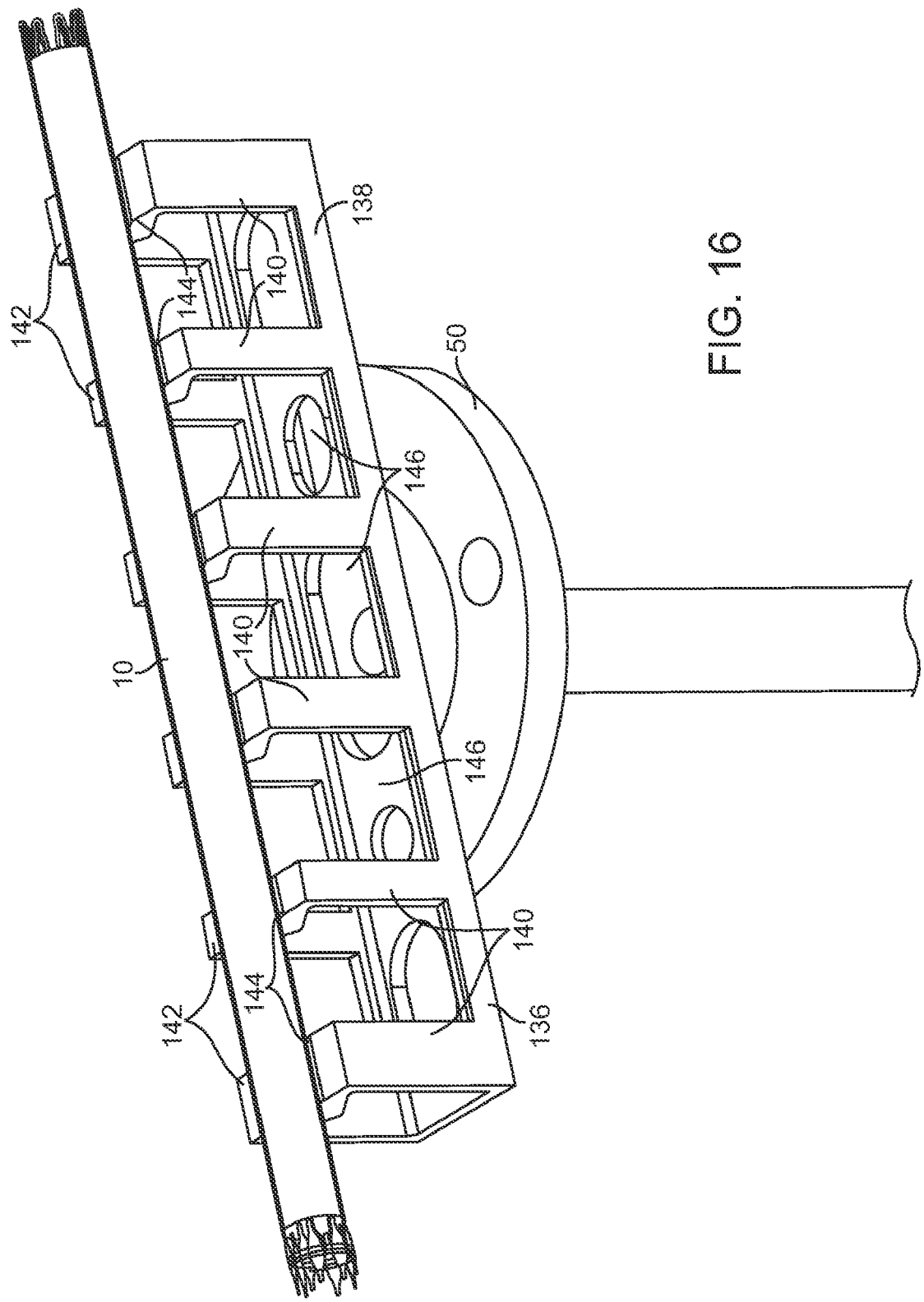
FIG. 16 is a perspective view of a stent nest of the scale assembly shown in FIG. 15.
Figure 17:
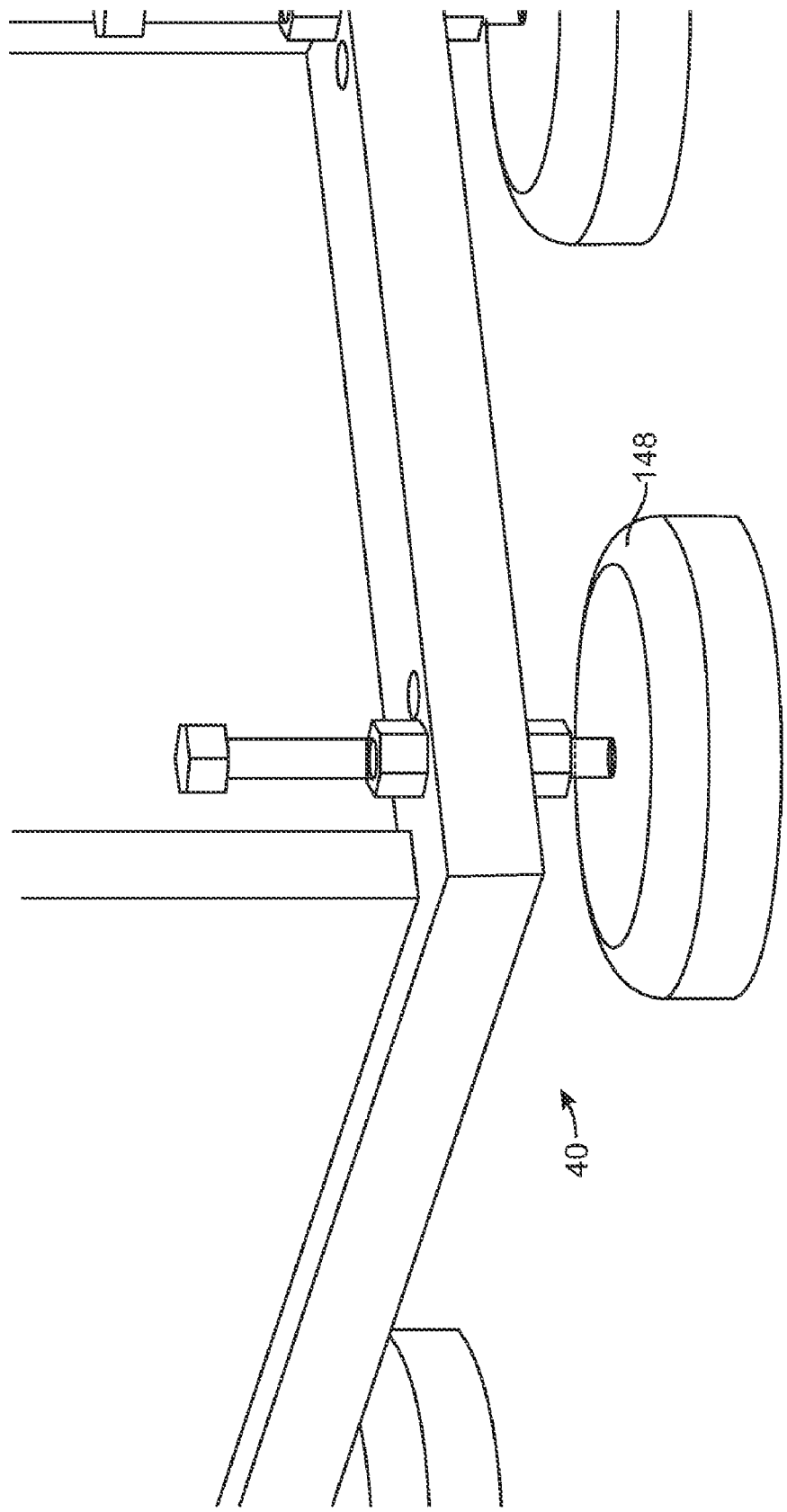
FIG. 17 is a perspective view of a mount of the apparatus shown in FIG. 5.

As shown in FIG. 16, the stent nest 136 has a horizontal member 138 and a plurality of vertical members 140 that extend upwards from the horizontal member 138. The horizontal member 138 of the stent nest 136 rests on the scale 50, and the stent 10 rests on top of the vertical members 140. The top surface 142 of each vertical member 140 may include a notch 144, in which the stent 10 may rest. In order for the stent gripper 104 to place a stent 10 into the notches 144 of the vertical members 140, each of its lower fingers 106b may need to extend into the space 146 between two adjacent vertical members 140 of the stent nest 136. Therefore, the space 146 between two adjacent vertical members 140 preferably is sufficiently wide and sufficiently high to accommodate a lower finger 106b of the stent gripper 104.

After the stent 10 has been placed on the stent nest 136, the scale 50 begins to measure stent weight. The weight signal measured by the scale 50 generally includes a constant stent weight and disturbances that vary with time. Because the stent weight is small, the disturbances may sometimes constitute a significant portion of the measured signal. To minimize the effects of disturbances, the scale 50 does not measure stent weight until the disturbances (oscillations) in the measured signal is below a certain value for a given period of time.

Preferably, the stent nest 136 is not attached or joined to the scale 50. Instead, the stent nest 136 merely rests on top of the scale 50 under the gravity of the stent nest 136. This may be desirable because if the stent gripper 104 collides with the stent nest 136, it would not damage the scale 50; it would just knock the stent nest 136 off the scale 50.

As shown in FIG. 5, the apparatus 40 for weighing a stent may further include a plurality of mounts 148 that reduce the amount of ground vibration transmitted to the scales 50. The inventors discovered that a substantial portion of disturbances experienced by the scales 50 is transmitted to the scales 50 from the ground and that the ground vibration generally has predictable frequency content. The inventors further discovered that the amount of ground vibration transmitted to the scales 50 can be significantly reduced by carefully selecting the elasticity and damping characteristics of the mount material in consideration of the mass of the apparatus 40. Preferably, ground vibration is first measured and its frequency content is determined. Then the system natural frequency, which is mostly a function of the mass of the apparatus 40 and the elasticity of the mounts 148, is selected so that the system natural frequency is less than most of the frequency components of ground vibration. The system natural frequency may be less than 60% of the frequency components of ground vibration, preferably less than 80%, more preferably less than 90%, most preferably less than 95%. Such a system natural frequency can significantly reduce the amount of ground vibration transmitted to the scales 50. The system damping ratio, which is a function of the mass of the apparatus 40 and the elasticity and damping characteristics of the mounts 148, is preferably about 0.1 to 2.0, more preferably about 0.4 to 1.2, most preferably about 0.6 to 1.0.

The above-described stent-weighing apparatus 40 can be operated in several ways. According to one way of operating the stent-weighing apparatus 40, the first step is to use the robotic arm 44 to move a stent 10 to be weighed from the buffer 42 to the stent support gripper assembly 70. The robotic arm 44 is placed in its first position next to the buffer 42 to pick up the stent 10 to be weighed. At this point, the robotic arm 44 is at the lower vertical position. The robotic arm 44 grips the stent support 20 on which the stent 10 is mounted, with the stent support griper 56 of the robotic arm 44 gripping the first support element 22 of the stent support 20 and the core element holder 58 holding the core element 24 of the stent support 20. At this point, the stent support 20 is still in a receptacle 54 of the buffer 42. Then the robotic arm 44 is raised to its higher vertical position, as shown in FIG. 6, to lift the stent support 20 out of the receptacle 54. Next the first member 64 of the robotic arm 44 is rotated 180° relative to the second member 66 to move the stent support 20 from the vertical position as shown in FIG. 6 to a horizontal position just above the stent support gripper assembly 70.

In the next step, the stent support gripper assembly 70 receives the stent support 20 from the robotic arm 44 and removes the stent 10 from the stent support 20. To receive the stent support 20 from the robotic arm 44, the first and second support element grippers 80, 82 of the stent support gripper assembly 70 are positioned below the first and second support elements 22, 26 of the stent support 20, respectively. And the fingers 86, 92 of the first and second support element grippers 80, 82 are positioned apart to receive the first and second support elements 22, 26 of the stent support 20, respectively. The robotic arm 44 is then lowered from its higher vertical position to its lower vertical position to place the first and second support elements 22, 26 of the stent support 20 between the fingers 86, 92 of the first and second support element grippers 80, 82, respectively. At this point, the fingers 86 of the first support element gripper 80 are preferably aligned with the groove 30 of the first support element 22, and the fingers 92 of the second support element gripper 82 are aligned with the groove 34 of the second support element 26. Next the fingers 86 of the first support element gripper 80 move towards each other to grip the first support element 22 at its groove 30, and the fingers 92 of the second support element gripper 82 also move towards each other to grip the second support element 26 at its groove 34. The stent support gripper assembly 70 then moves longitudinally to align the stent 10 with the stent gripper 104 of the stent gripper assembly 72 so that the stent gripper 104 can grip the stent 10 for dismounting.

At this time, the stent gripper 104 of the stent gripper assembly 72 preferably is aligned with the scale 50 that is to be used to weigh the stent 10. Once the stent 10 is aligned with the stent gripper 104, the stent gripper 104 moves from its second position (the retracted position) to its first position (the middle position) with its fingers 106a, 106b open to grip the stent 10. After reaching its first position, the stent gripper 104 closes its fingers 106a, 106b to grip the stent 10. Then the first and second support element grippers 80, 82 of the stent support gripper assembly 70 move away from each other in the longitudinal direction 76. This movement removes the second support element 26 of the stent support 20 from the core element 24 of the stent support 20. The movement also extracts the core element 24 of the stent support 20 from the hollow center of the stent 10. As a result, the stent 10 is removed from the stent support 20.

At this point, the stent gripper 104 may extend further to its third position to place the stent 10 on the scale 50. Alternatively, the stent gripper 104 may move back to the retracted position. And the stent support gripper assembly 70 may mount the second support element 26 of the stent support 20 on the core element 24 of the stent support 20, and move the stent support 20 to one side of the stent gripper 104 before the stent gripper 104 extends from the retracted position to its third position to place the stent 10 on the scale 50. Mounting the second support element 26 on the core element 24 may require that the first and second core element guides 110, 112 move into their first positions to guide the core element 24 before the first and second support element grippers 80, 82 move the first and second support elements 22, 26 of the stent support 20 towards each other to mount the second support element 26 on the core element 24.

To place the stent 10 on the stent nest 136 on top of the scale 50, the stent gripper 104 extends its lower fingers 106b into the respective spaces 146 between two adjacent vertical members 140 of the stent nest 136 to place the stent 10 into the notches 144 of the vertical members 140. The upper and lower fingers 106a, 106b of the stent gripper 104 then move apart to release the stent 10.

After the stent 10 has been placed on the stent nest 136, the door of the scale assembly's housing 134 is closed, and the scale 50 begins to measure stent weight. The signal measured by the scale 50 generally includes a constant stent weight and disturbances that vary with time. Because the stent weight is small, the disturbances may sometimes constitute a significant portion of the measured signal. To minimize the effects of disturbances, the scale 50 does not measure stent weight until the disturbances (oscillations) in the measured signal is below a certain value for a given period of time.

After a reading of the stent weight has been obtained, the stent 10 is removed from the scale 50 and is again mounted on the stent support 20. The procedure for mounting the stent 10 on the stent support 20 may vary depending on whether, as described previously, the second support element 26 has been mounted on the core element 24 and moved to one side of the stent gripper 104. If this is the case, the stent gripper 104 may move the stent 10 from the scale 50 to the retracted position so that the stent support gripper assembly 70 can remove the second support element 26 from the core element 24 and place the second support element 26 and the core element 24 on different sides of the stent gripper 104. Then the stent gripper 104 can move the stent 10 from the retracted position to the middle position so that the stent 10 can be mounted on the stent support 20. If this is not the case (i.e., the second support element 26 and the core element 24 are already on different sides of the stent gripper 104), the stent gripper 104 may move the stent 10 from the scale 50 directly to the middle position so that the stent 10 can be mounted on the stent support 20.

After the stent gripper 104 has moved the stent 10 to the first (middle) position, the first and second core element guides 110, 112 also move into their first positions to guide the core element 24 of the stent support so that the core element 24 can be threaded through the stent 10 and the second support element 26. At this point, the stent 10 and the bores 114, 116 of the core element guides 110, 112 are substantially coaxially arranged. The first support element gripper 80 may then move the first support element 22 and core element 24 towards the stent 10 and the second support element 26. This movement causes the core element 24 to be threaded in sequence through the bore 114 of the first core element guide 110, the stent 10, the bore 116 of the second core element guide 112, and the second support element 26. As the first support element gripper 80 moves the first support element 22 towards the second support element 26, the second support element gripper 82 may also move the second support element 26 toward the first support element 22. After the stent 10 and second support element 26 have been mounted on the core element 24, the fingers 110a, 110b, 112a, 112b of the core element guides 110, 112 are opened to disengage the core element guides 110, 112 from the core element 24 of the stent support 20.

After the stent 10 has been mounted on the stent support 20, the robotic arm 44 may move the stent support 20 from the stent support gripper assembly 70 to the buffer 42. To this end, the robotic arm 44 is placed in its position to pick up the stent support 20 from the stent support gripper assembly 70. The stent support gripper assembly 70 preferably moves the stent support 20 in a position where the first support element 22 of the stent support 20 is aligned with the stent support griper 56 of the robotic arm 44 and the core element 24 of the stent support 20 is aligned the core element holder 58 of the robotic arm 44. Next the fingers 86 of the first support element gripper 80 move away from each other to release the first support element 22, and the fingers 92 of the second support element gripper 82 also move away from each other to release the second support element 26. Then the robotic arm 44 is lowered to grip the stent support 20, with the stent support griper 56 of the robotic arm 44 gripping the first support element 22 of the stent support 20 and the core element holder 58 holding the core element 24 of the stent support 20. Next the robotic arm 44 is raised to lift the stent support 20 from the stent support gripper assembly 70. The first member 64 of the robotic arm 44 is rotated 180° relative to the second member 66 to move the stent support 20 from this horizontal position to the vertical position as shown in FIG. 6. Then the robotic arm 44 is lowered to place the stent support 20 in a receptacle 54 of the buffer 42.

Apparatus for Aligning a Stent with a Stent Support

Spray coating is commonly used to apply a layer of coating to a stent. A spray coating apparatus typically includes a spray nozzle and a pump that supplies a coating substance from a reservoir to the spray nozzle. The coating substance is ejected through the nozzle to create a plume of coating substance.

During coating operation the stent support axially or linearly translates the stent through the plume of coating substance. The nozzle may be translated along the axis of the stent as an alternative to or in addition to axially translating the stent. The coating substance is deposited on the stent as the stent is translated through the plume of the spray nozzle from one end of the stent to the other end. After a selected number of passes through the plume, the deposited coating substance is allowed to dry or subjected to a drying process prior to further spraying of coating substance. The spraying and drying steps are repeated until a desired amount of coating substance is deposited on the stent.

The coating substance ejected by the nozzle is not uniformly distributed in the plume of the spray nozzle. The concentration of coating substance is highest in the areas along or near the longitudinal axis of the nozzle. As the distance from the axis of the nozzle increases, the concentration of coating substance decreases.

To increase the efficiency of coating operation, it is desirable to place the stent in an area of the plume that has a high concentration of coating substance, i.e., an area along or near the axis of the nozzle. To ensure that the stent remains in the desired area of the plume, it is important for the axis of the stent to be aligned with the axis of the stent support. If the stent support and stent are not coaxial, the stent will oscillate about the axis of the stent support during rotation, causing the stent to move in and out of the area of the plume with a high coating substance concentration. This will not only decrease the efficiency of coating operation but also produce an uneven coating pattern on the stent surface.

Additionally, misalignment between the stent axis and the stent support axis may cause inconsistent application of coating substance to the stents, with stents placed near the axis of the nozzle receiving more coating substance than stents placed relatively far from the axis of the nozzle. This variation in the amount of stent coating may increase the number of stents having coating weights outside of the acceptable range, thereby increasing the stent defective rate. These variations are difficult to compensate by adjusting the rate or duration of spray, because the misalignment is unpredictable.

Currently there are no efficient and reliable methods to ensure a proper alignment of a stent with a stent support.

Figure 18:
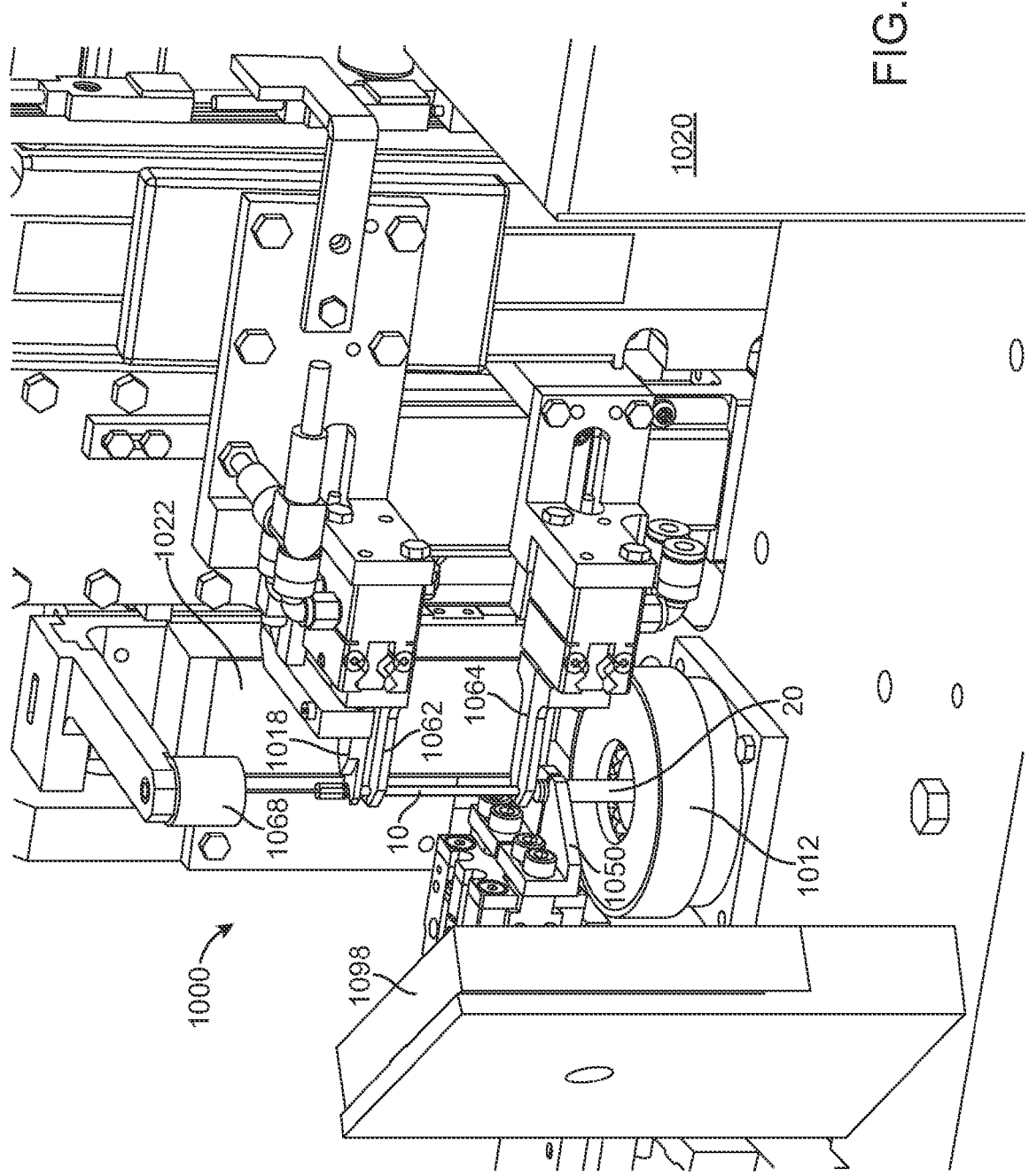
FIG. 18 is a perspective view of an exemplary device of the present invention for mounting a stent on a stent support in a way that reduces stent runout.

The device for aligning a stent with a stent support of the present invention can reliably, efficiently and precisely mount a stent on a stent support with a proper alignment of the axes of the stent and stent support. FIG. 18 illustrates an exemplary device 1000 of the present invention. The device 1000 includes a stent support receptacle 1012 for receiving a stent support 20 to position the stent support 20 in a vertical position; a digital imaging device 1020, such as a digital camera; a computer 1014 (FIG. 27); and a positioning device 1018. The device 1000 may include additional components, as shown in FIG. 18, which will be described hereinafter.

Figure 19:
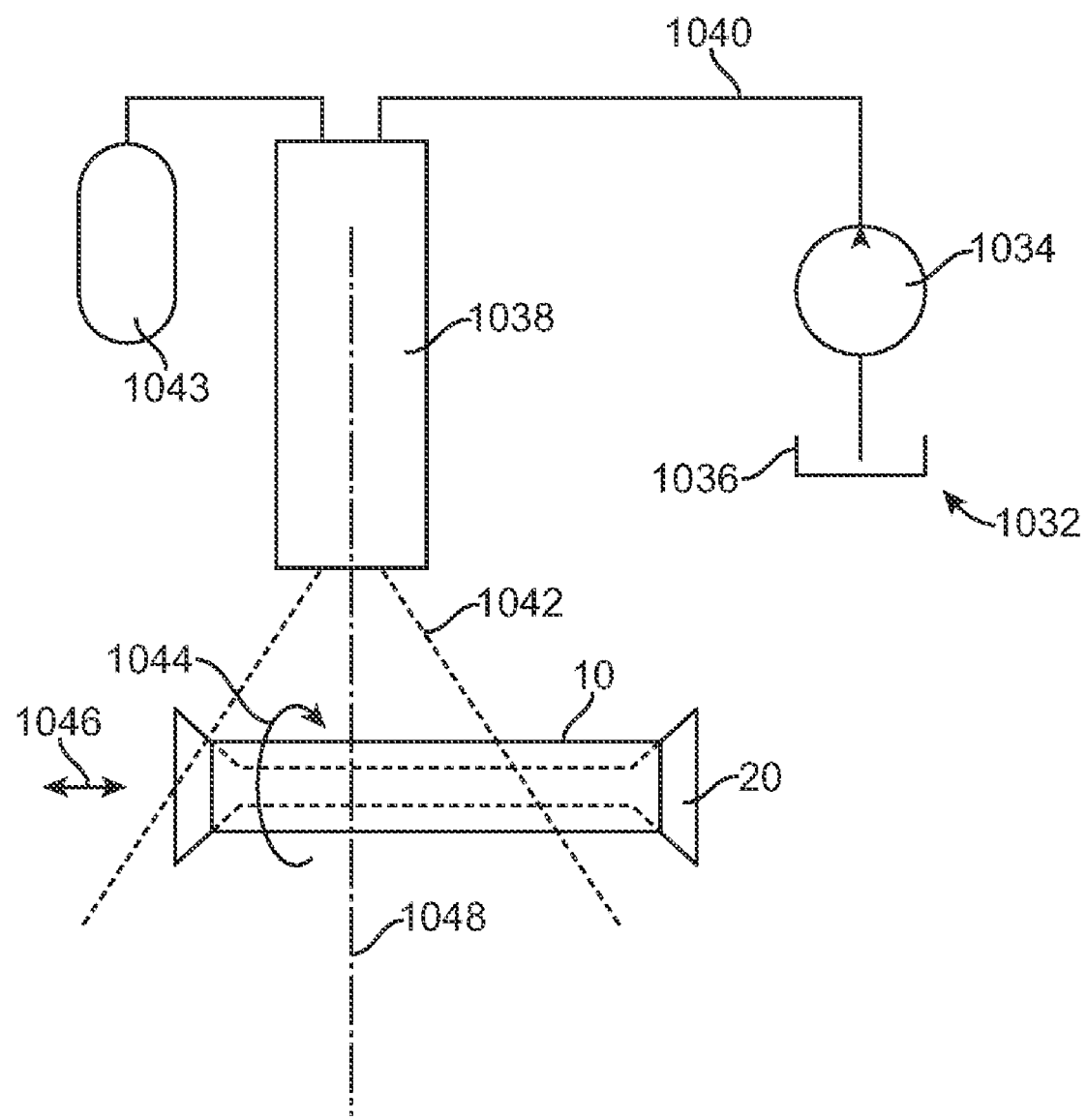
FIG. 19 is a schematic diagram for a spray coating apparatus.

Spray coating is commonly used to apply a coating layer to a stent. Spray coating a stent typically involves mounting a stent on a stent support, followed by spraying a coating substance from a nozzle onto the mounted stent. FIG. 19 depicts a spray coating apparatus 1032 for coating a stent 10. In this apparatus, a pump 1034 supplies a coating substance from a reservoir 1036 to a spray nozzle 1038 through a hose 1040. The coating substance is ejected through the nozzle 1038 to create a plume 1042 of coating substance. The nozzle 1038 preferably is a gas-assisted external mixing atomizer, which atomizes the coating substance with gas supplied by a gas supply 1043.

The coating substance is not uniformly distributed in the plume 1042 of the spray nozzle 1038. The concentration of coating substance is highest in the areas along or near the axis 1048 of the nozzle 1038. As the distance from the axis 1048 of the nozzle 1038 increases, the concentration of coating substance decreases. In other words, there are more coating substance droplets per unit of volume in the areas along or near the axis 1048 of the nozzle 1038 than in the areas near the periphery of the plume 1042.

During coating operation the stent 10 is supported on a stent support 20, and the stent support 20 and stent 10 rotate about the axis of the first support element 22 (FIG. 19), as shown by an arrow 1044. The speed of rotation can be from about 0.1 rpm to about 300 rpm, more narrowly from about 30 rpm to about 200 rpm. By way of example, the speed of rotation can be about 150 rpm.

Preferably, the stent support 20 and stent 10 are axially or linearly translated through the plume 1042, as shown by an arrow 1046. Alternatively or additionally, the nozzle 1038 can be translated along the axis of the stent 10. The coating substance is deposited on the stent 10 as the stent 10 is translated through the plume 1042 of the spray nozzle 1038 from one end to the other end of the stent 10. After a selected number of passes through the plume 1042, the deposited coating substance is allowed to dry or subjected to a drying process prior to further spraying of coating substance. The spraying and drying steps can be repeated until a desired amount of coating substance is deposited on the stent 10. The nozzle or the stent can be moved at about 1 mm/second to about 12 mm/second, for example about 6 mm/second.

To reduce stent runout, the opposing forces exerted by the first and second support elements 22, 26 to secure the stent 10 preferably are sufficient but not excessive. First, the opposing forces preferably are sufficient to prevent any significant movement of the stent 10 on the stent support 20. If the stent 10 moves relative to the stent support 20 during coating operation, the stent 10 will not remain in a desired area of the plume with a high coating substance concentration. Instead the stent 10 will oscillate about the axis of rotation (i.e., the axis of the first support element 22), causing the stent 10 to move in and out of the area of the plume with a high coating substance concentration.

Additionally, to ensure that the coating is evenly applied to the stent surface, it is preferable that the stent 10 is rotationally secured to, and rotates together with, the stent support 20 during coating operation. If the stent 10 slips rotationally relative to the stent support 20, the stent 10 will not be rotating at a constant speed. As a result, some areas of the stent surface may be exposed to the coating spray for a longer period of time than other areas, resulting in an even coating on the stent surface. The stent 10 is rotationally secured to the stent support 20 by the frictional forces between the stent ends and the support elements 22, 26 of the stent support 20, and the frictional forces are a function of the opposing forces. Thus, the opposing forces preferably are sufficient to ensure that the stent 10 is rotationally secured to the stent support 20 during coating operation.

Second, the opposing forces preferably are not excessive. Excessive forces applied to the ends of the stent 10 may cause the stent 10 to bend and the middle section of the stent 10 to bow out. When the stent support 20 is rotated, the bowed out middle section of the stent 10 may move in and out of the area of the plume with a high coating substance concentration. Since the opposing forces are largely a function of the position of the second support element 26, the desired stent support forces can be achieved by adjusting the position of the second support element 26.

Figure 29:
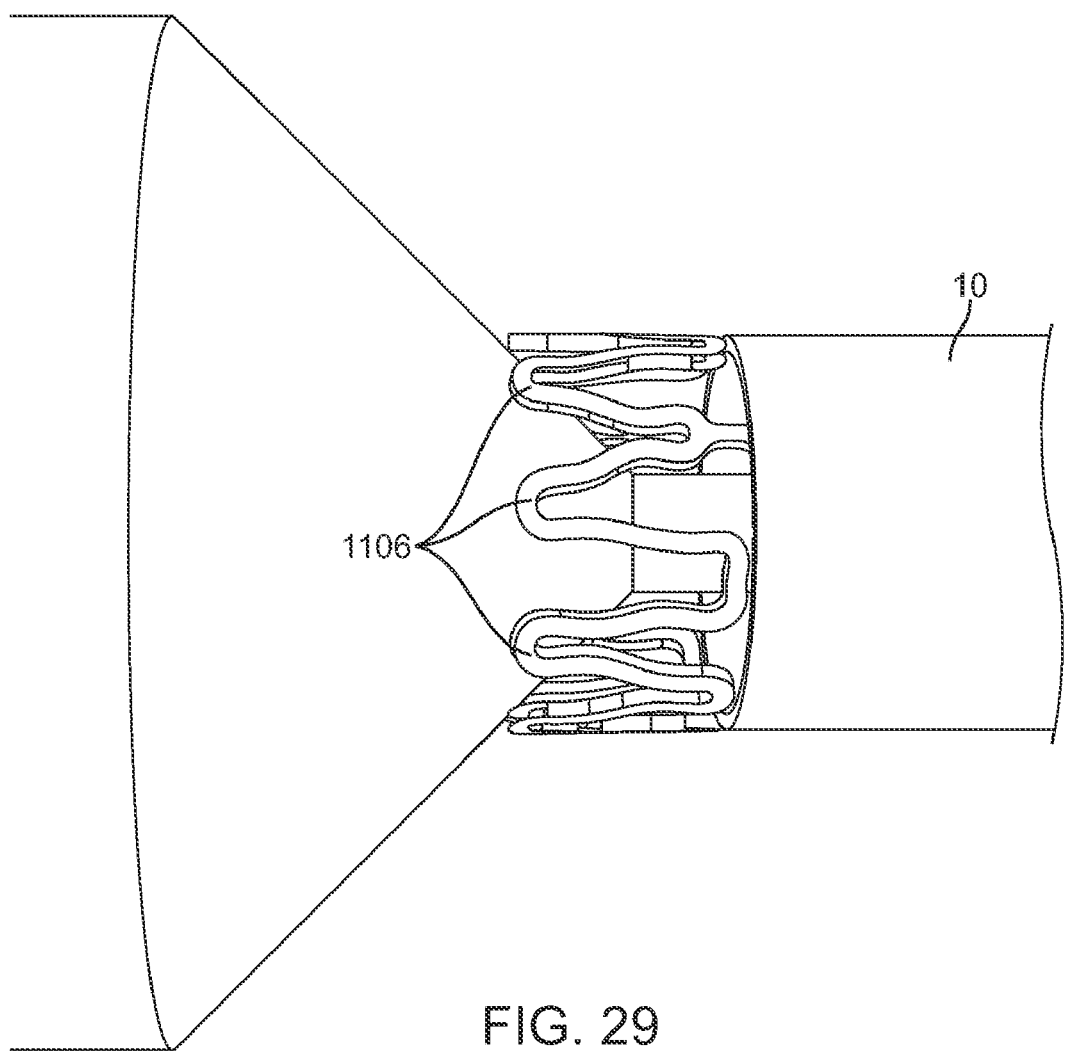
FIGS. 29 and 30 are perspective views of crowns at a stent end.
Figure 30:
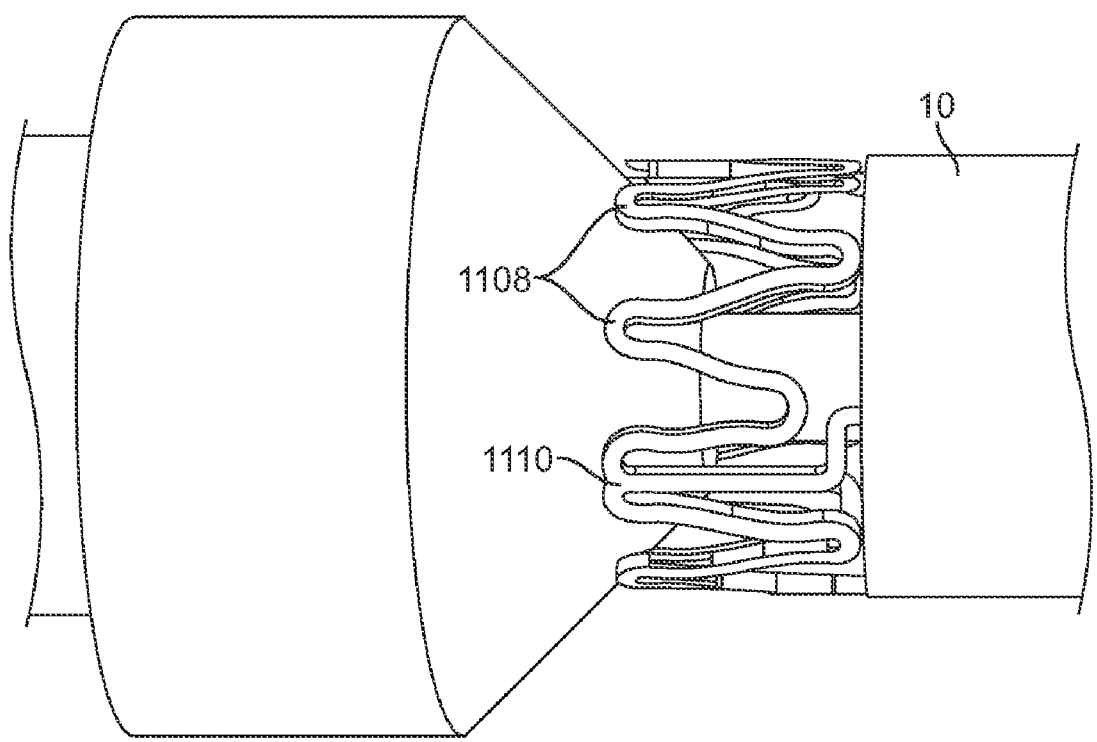

Additionally, insufficient or excessive opposing forces may increase the number or severity of coating defects on the stent's end crowns 1106 (FIGS. 29 and 30). If the opposing forces are insufficient, there may be a gap between an end crown 1106 of the stent 10 and the conical portion 28, 32 of a support element 22, 26, and coating material may accumulate in the gap. When the stent 10 is moved relative to the conical portion 28, 32, the dry coating material in the gap may stick to the end crown 1106, causing excessive coating material on the crown 1106. Alternatively, the dry coating material in the gap may stick to the conical surface 28, 32, causing insufficient coating material on the crown 1106. Excessive opposing forces may also lead to excessive coating material between an end crown 1106 and the conical portion 28, 32, because they may increase the contact area between the end crown 1106 and the conical portion 28, 32. An increased contact area may increase the coating material accumulated between the end crown 1106 and the conical portion 28, 32. The increased accumulation of coating material, as described above, are more likely to cause stent coating defects.

It should be noted that, in some embodiments of the present invention, the conical portion 28, 32 of each support element 22, 26 may include one or more features that reduce the contact between the conical portion 28, 32 and the end crowns 1106 of the stent 10. For example, each conical portion 28, 32 may include ridges that extend from the base of the conical portion 28, 32 to its apex. Preferably, the ridges are dimensioned and spaced so that when a stent end engages the conical portion 28, 32, the crest of each crown 1106 engages the crest of a ridge. This further reduces the contact between the conical portion 28, 32 and the end crowns 1106 of the stent 10.

Figure 20:
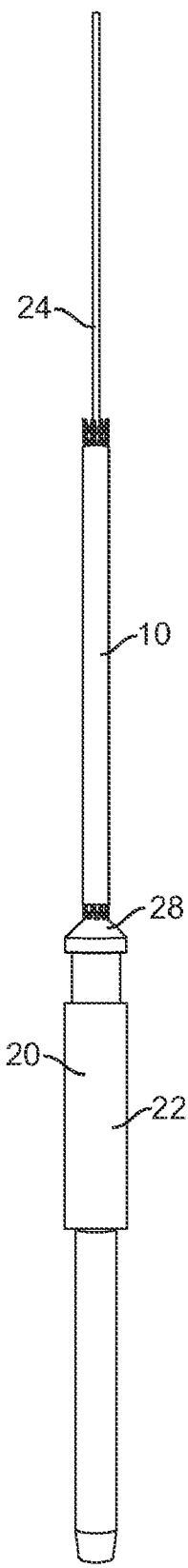
FIG. 20 is a perspective view of a stent mounted on the core element of a stent support without the second support element of the stent support.
Figure 21:
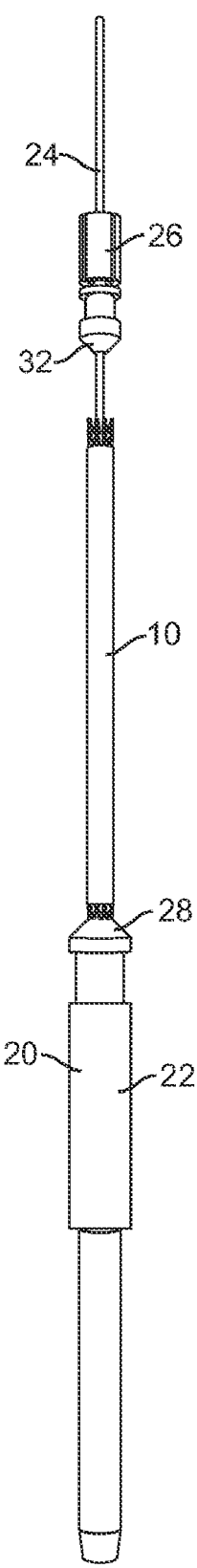
FIG. 21 is a perspective view of a stent mounted on the core element of a stent support with the second support element of the stent support.

Another aspect of the present invention relates to a method for mounting a stent on a stent support to achieve optimum opposing forces and to reliably and efficiently reduce stent runout. In a preferred embodiment of this method, as shown in FIG. 20, the stent 10 is first mounted on the core element 24 of the stent support 20 by extending the core element 24 through the hollow center of the stent 10. Then the second support element 26 is also mounted on the core element 24, as shown in FIG. 21. At this point, the stent 10 is placed between the first and second support elements 22, 26, but the second support element 26 is not advanced far enough to pinch the stent 10 between the first and second support elements 22, 26. The distance between the first and second support elements 22, 26 is greater than the length of the stent 10, and the stent 10 is free to move along the core element 24 between the first and second support elements 22, 26.

Figure 22:
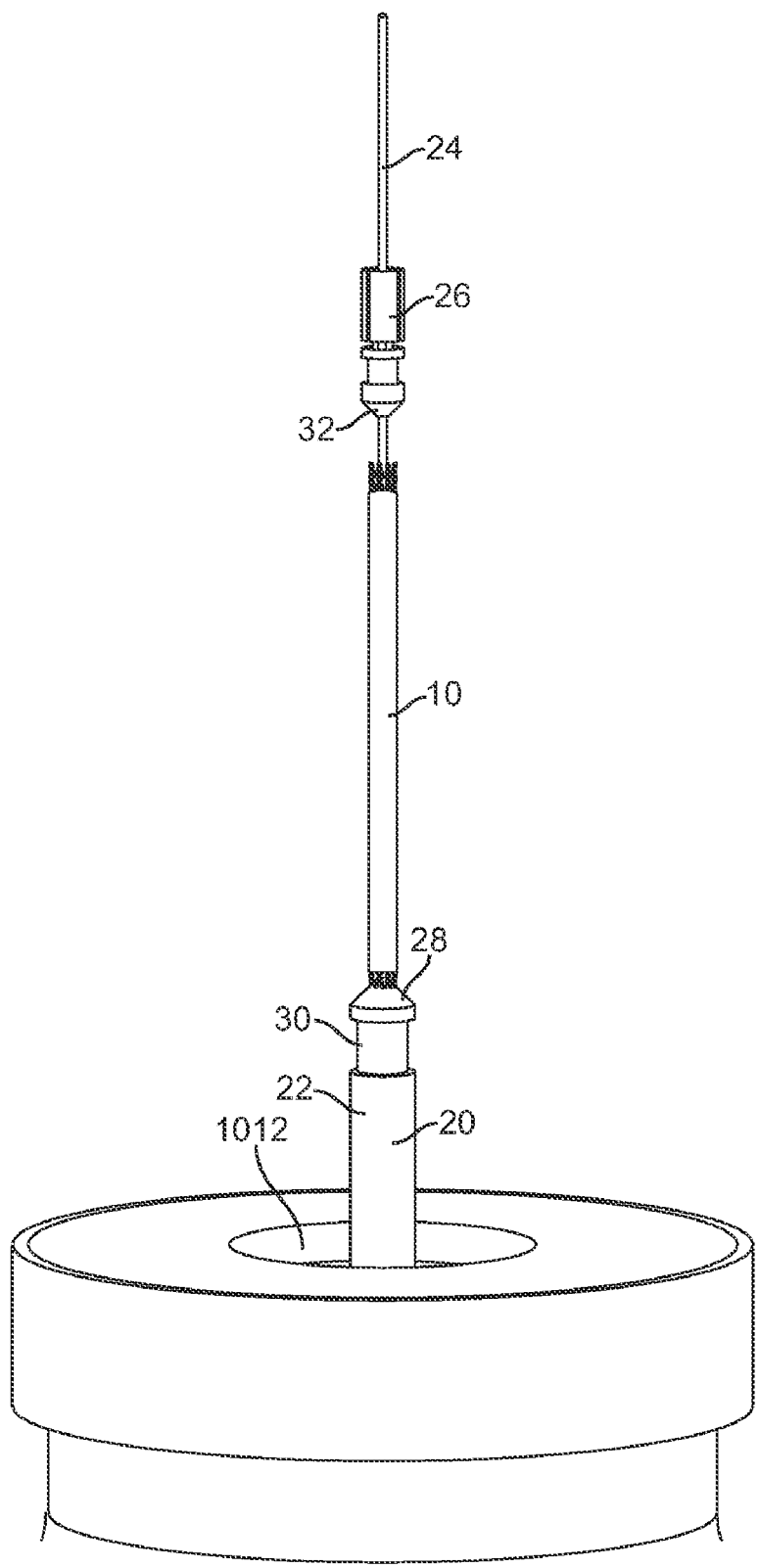
FIG. 22 is a perspective view of a stent and a stent support mounted vertically in a stent support receptacle.

Next the stent support 20 with the stent 10 mounted thereon is placed in a vertical position with the first support element 22 at a lower position and the second support element 26 at an upper position, as shown in FIG. 22. To hold the stent support 20 and stent 10 in the vertical position, the first support element 22 is placed in the stent support receptacle 1012, and then a stent support holder 1050 (FIG. 23) is used to hold the stent support 20 in a vertical position. The stent support holder 1050 preferably includes a pair of grippers (FIG. 18) that are pivotably connected like a pair of scissors, each of the grippers having a V-shaped groove (FIG. 18) for receiving the stent support 20. The grippers can pivot open to receive the stent support 20 and pivot close to hold the stent support 20 in an opening formed by the V-shaped grooves. In this position, the lower end of the stent 10 rests on the conical portion 28 of the first support element 22 under the weight of the stent 10. The weight of the stent 10, acting on the conical portion 28 of the first support element 22, tends to center the lower end of the stent 10 around the core element 24.

At this point, the stent 10 may be re-seated to ensure that the stent 10 is properly seated on the conical portion 28 of the first support element 22. The stent 10 may be re-seated in several ways. For example, the stent 10 may be re-seated by vibrating the first support element 22 or lightly striking the first support element 22 to cause it to vibrate. Vibration of the first support element 22 tends to cause the stent 10 to be properly seated on the conical portion 28 of the first support element 22. Alternatively, the stent 10 may be re-seated by lifting the stent 10 off the first support element 22 and releasing the stent 10. Furthermore, the stent 10 may be re-seated by manipulating the stent 10, such as lightly tapping on the stent 10.

Figure 23:
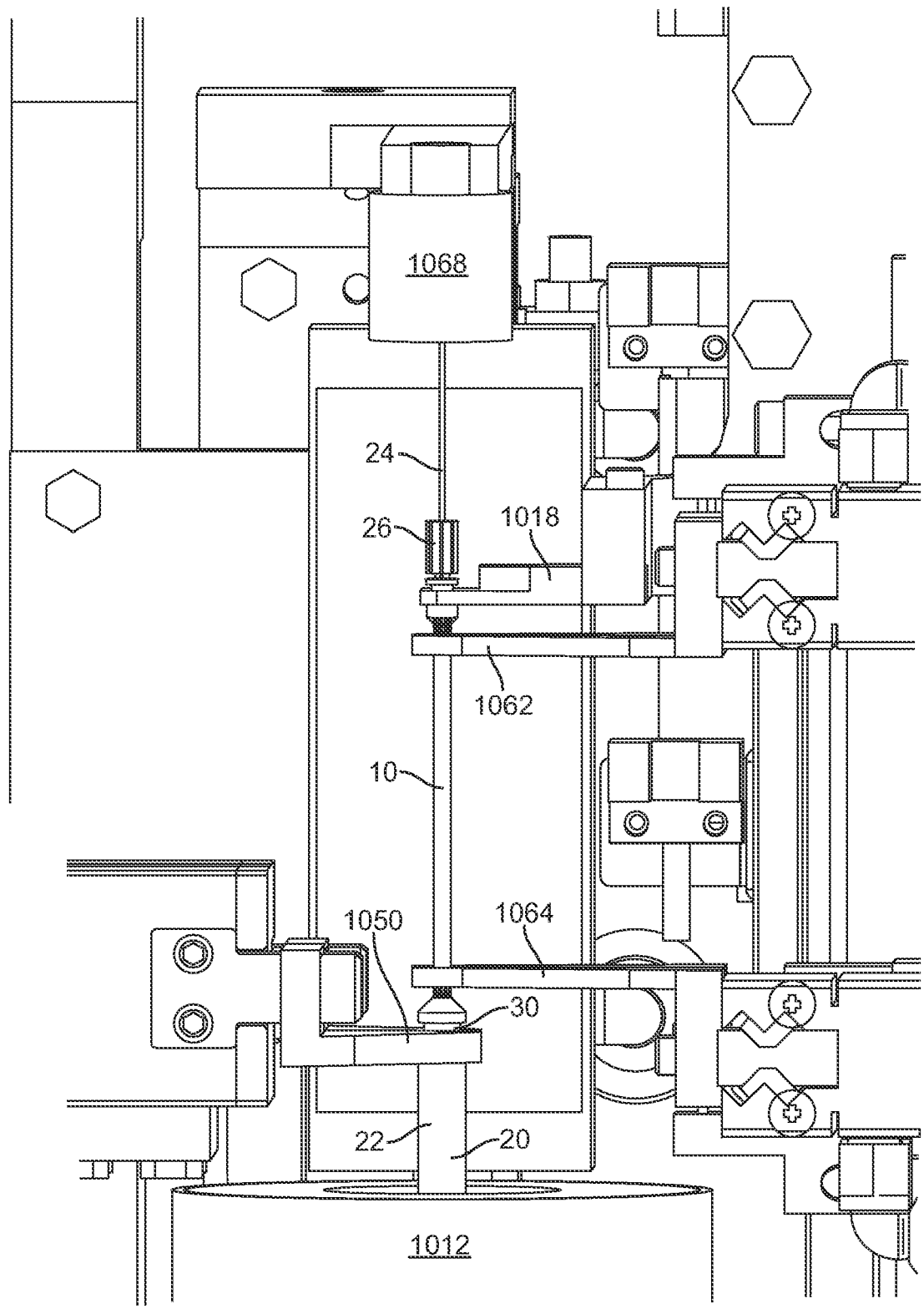
FIG. 23 is a perspective view of the free end of a core element being supported by a first core element support.

In addition, as shown in FIGS. 18 and 23, the device 1000 may have two stent holders 1062, 1064 that can be used to hold and center the stent 10 around the core element 24 of the stent support 20. Preferably, one of the stent holders 1062, 1064 holds and centers the top portion of the stent 10, and the other holder holds and centers the bottom portion of the stent 10. Each stent holder 1062, 1064 preferably includes a pair of grippers (FIG. 18) that are pivotably connected like a pair of scissors, each of the grippers having a V-shaped groove (FIG. 18) for holding the stent 10. The grippers can pivot open to receive the stent 10 and pivot close to hold the stent 10 in an opening formed by the V-shaped grooves.

When the stent support 20 and stent 10 are placed in a vertical position, the free end of the core element 24 preferably is centered and fixed to a point on the axis of the first support element 22 to ensure that the core element 24 is straight and coincides with the axis of the first support element 22. When its free end is not centered, the core element 24, due to its flexibility, may not always be straight and coincide with the axis of the first support element 22. This makes it difficult to measure stent runout as the position of the stent 10 is caused by both stent runout and the position of the core element 24. Separating the effects of stent runout and core element position may be difficult. Additionally, when the first support element 22 is rotated to produce a 360° digital image of the stent's outer surface, the core element 24 and the stent 10 may oscillate about the axis of the first support element 22. This oscillation makes it difficult to produce a high-quality digital image of the stent's outer surface.

Figure 24:
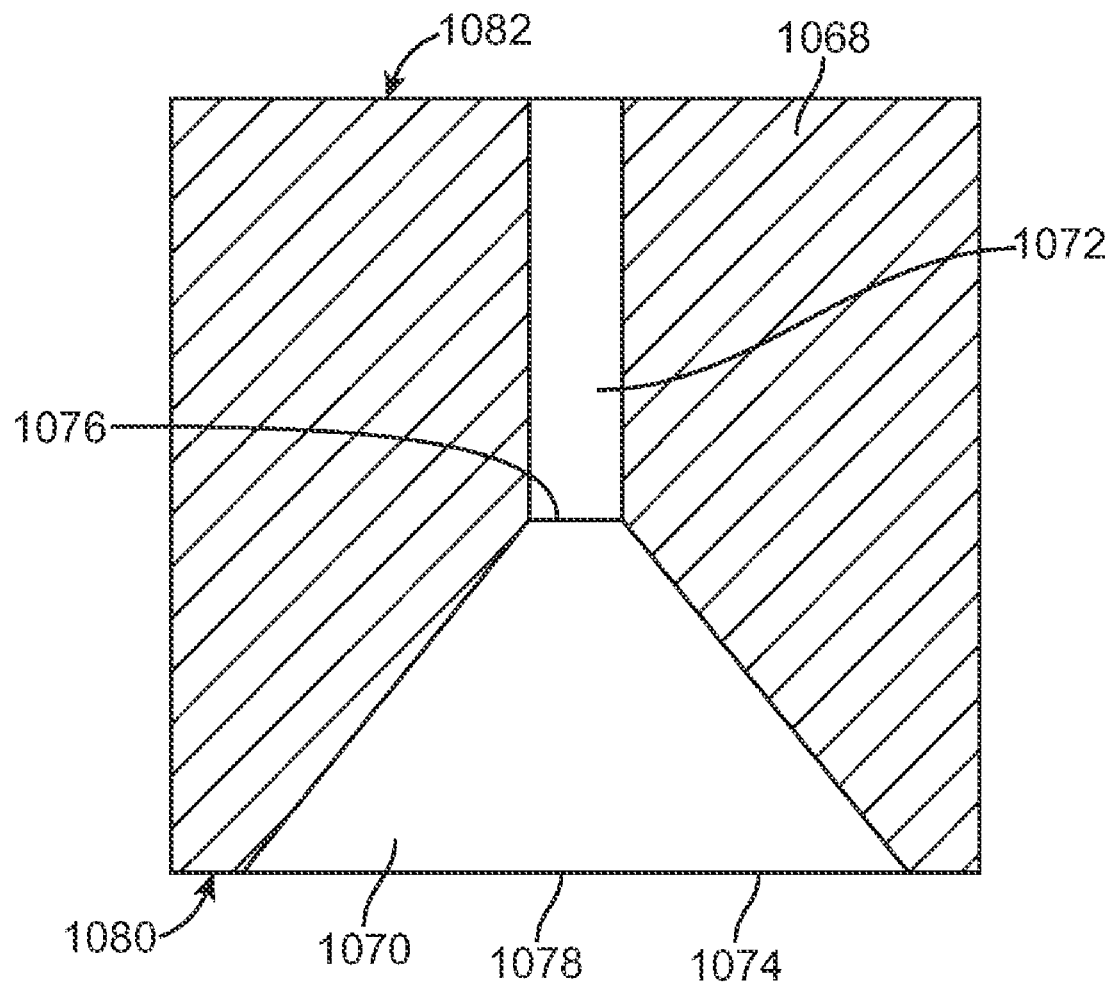
FIG. 24 is a cross-sectional view of the first core element support.

The centering of the free end of the core element 24 may be accomplished in any suitable way. For example, a core element support 1068, as shown in FIG. 23, can be used to center the free end of the core element 24. The core element support 1068 preferably has a cylindrical configuration and includes a conical inner cavity 1070 and a bore 1072, as shown in FIG. 24. The conical cavity 1070 has a base 1074 and an apex 1076, wherein the base 1074 defines an opening 78 on the bottom end surface 1080 of the cylindrical support 1068. Preferably, the bore 1072 extends coaxially from the apex 1076 of the conical cavity 1070 to the top end surface 1082 of the cylindrical support 1068.

In the device 1000, as shown in FIG. 23, the core element support 1068 preferably is positioned so that the axis of the conical cavity 1070 and bore 1072 coincides with the axis of the first support element 22. Additionally, the core element support 1068 preferably is able to move along the axis of the first support element 22.

During operation, after the stent support 20 and stent 10 are placed in a vertical position, the core element support 1068 starts moving from a position above the free end of the core element 24 towards to the free end of the core element 24 with the opening 1078 facing the free end of the core element 24. This movement of the support 1068 allows the opening 1078 of the support 1068 to capture the free end of the core element 24 and allows the conical cavity 1070 to guide the free end into the bore 1072. Preferably, the bore 1072 is sufficiently small such that the free end of the core element 24 preferably is centered and fixed to a point on the axis of the first support element 22 and such that the core element 24 is straight and coincides with the axis of the first support element 22. The opening 1078 preferably is sufficiently large that it can always capture the free end of the core element 24.

Figure 25:
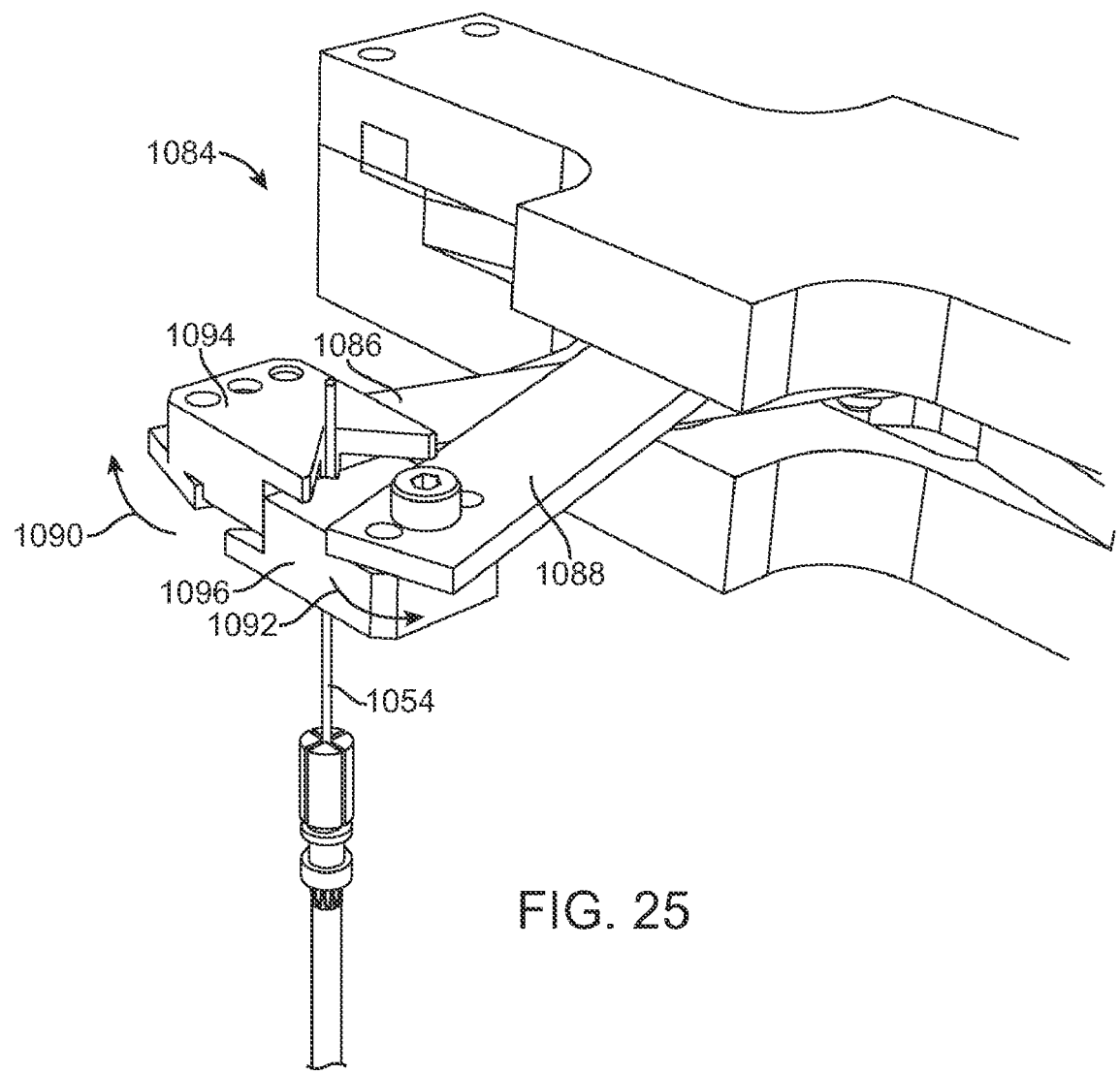
FIG. 25 is a perspective view of a second core element support.

Alternatively, as shown in FIG. 25, the free end of the core element 24 may be supported by a different core element support 1084. The core element support 1084 includes a scissor-like mechanism with two pivotable flat bars 1086, 1088 that can pivot as shown by arrows 1090, 1092, respectively. Clamps 1094, 1096 with opposing wedge-shaped cutout sections are coupled to the distal ends of the pivotable flat bars 1086, 1088, respectively. The free end of the core element 24 is clamped at the apices of the opposing wedge-shaped cutout sections but can still rotate. With this arrangement, the stent support 20 can rotate without much oscillation of the core element 24.

After the stent support 20 and stent 10 have been properly positioned, a digital image of the vertically-positioned stent support 20 and stent 10 is taken with the digital imaging device 1020. The device 1000 shown in FIG. 18 may include a backlight 1022 (FIG. 18) for illuminating the stent support 20 and stent 10 in silhouette to improve the quality of the digital image. The device 1000 may also include one or more reflecting members 1098 such as mirrors that reflect the image of the stent support 20 and stent 10 into the lens of the imaging device 1020, so that the imaging device 1020 does not need to directly face the stent support 20 and stent 10. The digital image of the stent support 20 and stent 10 is then analyzed by the computer 1014 to compute the vertical position of the stent's upper end. Based on the computed vertical position of the stent's upper end, the computer 1014 can compute a desired position of the second support element 26.

The relationship between the position of the stent's upper end and the desired position of the second support element 26 may be determined experimentally. For example, for a given position of the stent's upper end, the second support element 26 may be placed at various positions, and the stent runout is computed by the computer 1014 for each of these positions. Each position of the second support element that produces an acceptable stent runout can be designated as an acceptable position. The position that produces the smallest stent runout may be designated as the desired position. This process, repeated for all positions of the stent's upper end, establishes a relationship between the position of the stent's upper end and the desired position of the second support element 26. This relationship can be used to compute the desired position of the second support element 26 based on the vertical position of the stent's upper end. Preferably, the positioning device 1018 used to position the second support element 26 at the desired position is sufficiently precise that the second support element 26 is consistently positioned at the desired position or at least at an acceptable position.

After the desired position of the second support element 26 has been obtained, the positioning device 1018 is used to move the second support element 26 from its original position to the desired position. As the second support element 26 is advanced towards the stent 10, the conical sections 28, 32 of the first and second support elements 22, 26 engage the respective ends of the stent 10 to center the stent 10 around the core element 24 and to secure the stent 10 in the longitudinal direction of the stent support 20. The interference fit between the second support element 26 and the core element 24 ensures that the second support element 26 and stent 10 remain assembled and properly aligned during subsequent handling, processing and coating.

Figure 26:
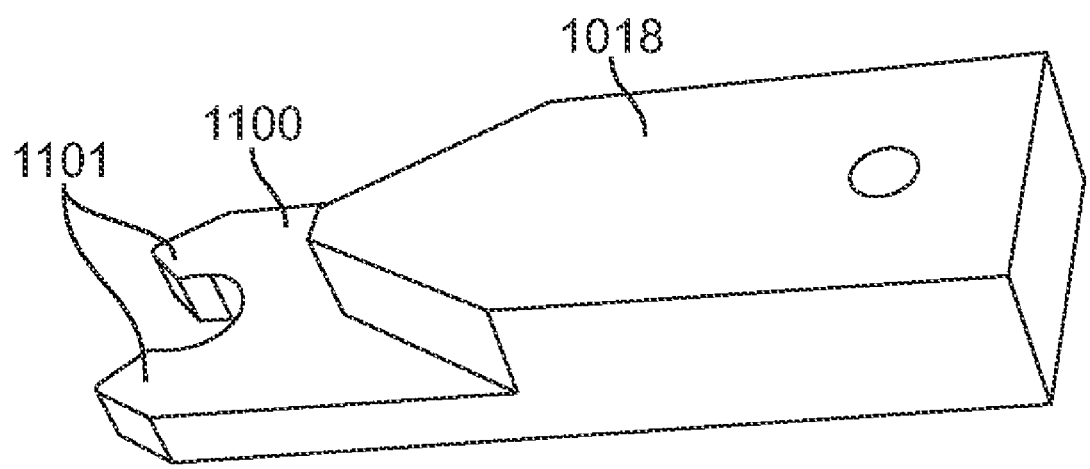
FIG. 26 is a perspective view of a positioning device.

In the preferred embodiment, the positioning device 1018 includes a fork member 1100, as shown in FIG. 26. When the positioning device 1018 is used to move the second support element 26, the fork member 1100 extends into a circumferential groove 30 of the second support element 26. Preferably, the distance between the legs 1101 of the fork member 1100 is greater than the diameter of the groove 30, so that the fork member 1100 is free to move up and down in the groove 30. However, the distance between the legs 1101 of the fork member 1100 preferably is less than the diameter of the second support element 26.

To move the second support element 26 downwards, the fork member 1100 engages the lower side surface of the groove 30. And to move the second support element 26 upwards, the fork member 1100 engages the upper side surface of the groove 30. This arrangement is advantageous because, as long as the position and dimensions of the groove 30 and the dimensions of the fork member 1100 are given, the relative position between the second support element 26 and the positioning device 1018 can be precisely determined. As a result, the position of the second support element 26 can be calculated from the position of the positioning device 1018 and can be controlled by controlling the position of the positioning device 1018.

Figure 27:
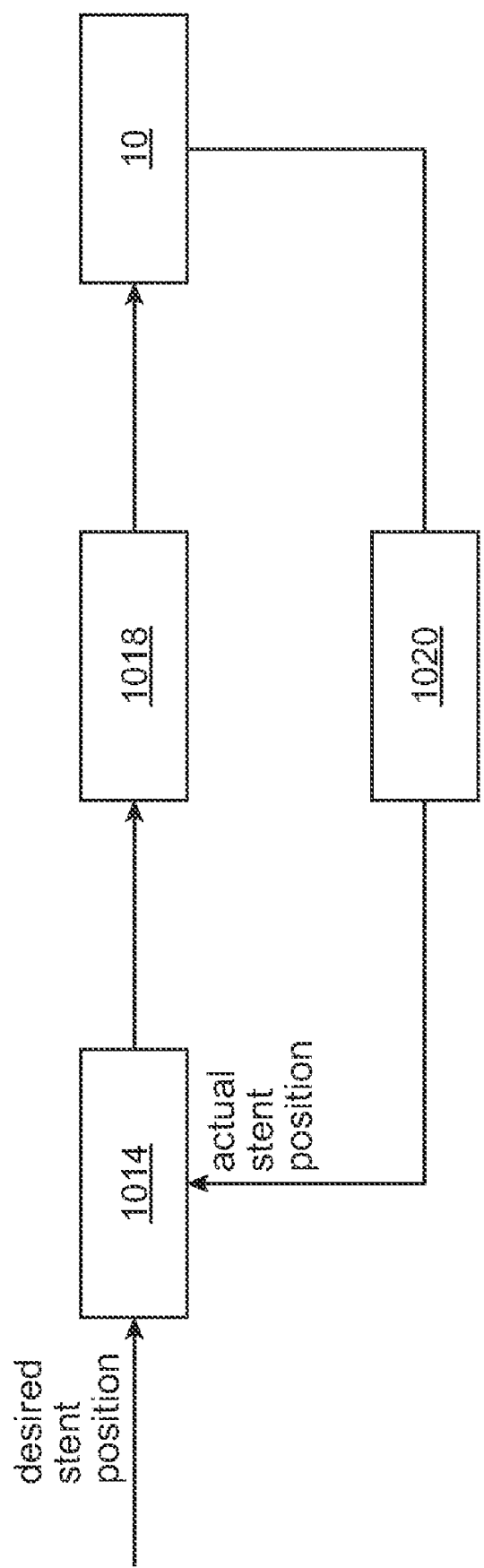
FIG. 27 is a schematic diagram showing a feedback control loop for controlling the position of the second support element of the stent support.

After the stent 10 has been mounted on the stent support 20, a second digital image of the stent support 20 and stent 10 may be taken to determine whether the second support element 26 is sufficiently close to the desired position. The computer 1014 can compute the actual position of the second support element 26 from the second digital image and compare with the desired position. If the difference between the actual and desired positions exceeds an acceptable limit, the second support element 26 can be re-positioned. This process forms a feedback control loop, as shown in FIG. 27, and can be repeated until the difference is within the acceptable limit. Alternatively, after several unsuccessful attempts the stent 10 and stent support 20 can be discarded as defective.

Alternatively or additionally, stent runout may be used to determine whether the second support element 26 is properly positioned. If the stent runout is above an acceptable limit, the second support element 26 is considered to be improperly positioned, and the stent 10 may be remounted or discarded as defective.

Figure 28:
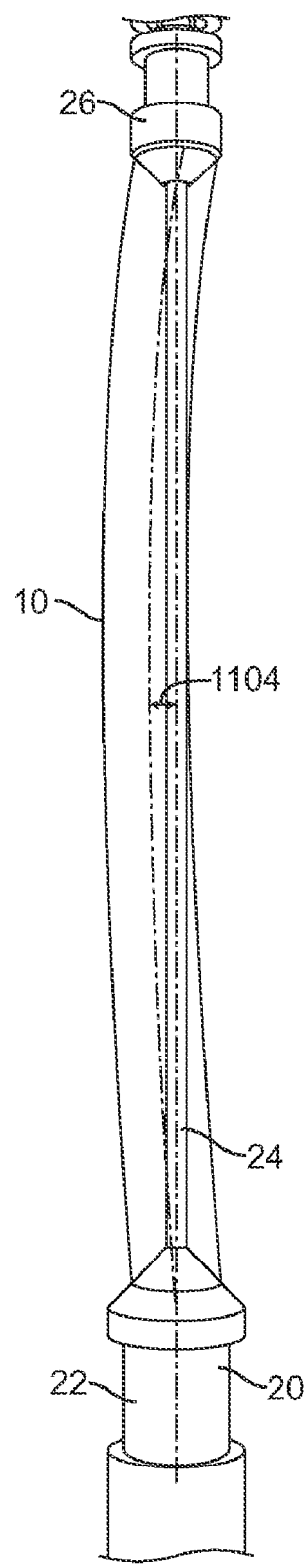
FIG. 28 is a view of a stent mounted on a stent support with stent runout.

Stent runout can be variously defined. As shown in FIG. 28, the stent runout can be defined as the radial distance 1104 between the axis of the stent 10 and the axis of the core element 24. Since this distance 1104 may vary along the axis of the core element 24, stent runout can be defined as the average or mean radial distance along the axis of the core element 24 or the maximum radial distance.

Stent runout may be determined in various manners. For example, stent runout can be determined from one or more digital images of the stent support 20 and stent 10. Often, however, stent runout cannot be accurately determined by taking a single digital image of the stent support 20 and stent 10. For example, if the direction of the stent runout happens to be perpendicular to the digital image, the runout cannot be detected at all from the digital image. Only when the direction of the stent runout is parallel to the digital image, stent runout cannot be accurately determined from the single digital image. Therefore, it is desirable to use two or more images of the stent support 20 and stent 10 to determine stent runout. In a preferred embodiment, a digital image of the stent support 20 and stent 10 is taken every 1° to 90° stent rotation for at least 180° of stent rotation, and stent runout is determined from the digital images. For example, a digital image of the stent support 20 and stent 10 may be taken every 5° of stent rotation for 180° or 360°. In many cases, the true stent runout is the maximum stent runout detected from the digital images.

Since a stent manufacturer often makes more than one type of stents, it may be desirable in some cases to verify that the proper type of stent is mounted on the stent support 20. The stent type may be determined from a digital image of the stent 10 in various manners. For example, if the different types of stents have different lengths, the length of a stent 10 can be computed from the digital image and can be used to determine the type of stent mounted on the stent support 20. The length of the stent 10 can be determined by measuring the distance between the two ends of the stent 10. Alternatively, if one end of the stent 10 is always at the same position, the stent length can be computed from the position of the other end. If the different types of stents have different end crowns 1106 (FIG. 29), the stent type can be determined from the number of end crowns 1106 at a stent end. The number of end crowns 1106 can be determined from a 360° digital image of the stent's outer surface. If the different types of stents have different types of end crowns, the stent type can also be determined from the types of end crowns at a stent end. For example, an end of one type of stent may have four U-shaped end crowns 1108 (FIG. 30) and five W-shaped end crowns 1110 (FIG. 30), and an end of another type of stent may have six U-shaped end crowns 1108 and three W-shaped end crowns 1110. In some cases, two or more of these stent features may be used together to determine stent types.

The different types of end crowns 1108, 1110 may also be used to determine the orientation of the stent 10. For example, a first end of a stent may have all U-shaped end crowns 1108, and a second end may have four U-shaped end crowns 1108 and five W-shaped end crowns 1110. If the second end of the stent should be the upper end of the stent 10 facing the second support element 26, the types of end crowns 1108, 1110 at a stent end can be inspected to ensure that the stent 10 is properly oriented.

Device for Coating a Stent

A spray apparatus, such as EFD 780S spray device with VALVEMATE 7040 control system (manufactured by EFD Inc., East Providence, R.I.) can be used to apply a composition to a stent. An EFD 780S spray device is an air-assisted external mixing atomizer. The composition is atomized into small droplets by air and uniformly applied to the stent surfaces. Other types of coating applicators, including air-assisted internal mixing atomizers (such as IVEK SonicAir nozzle), ultrasonic applicators (such as Accu-Mist nozzle or MicroMist nozzle from SonoTek Co. in Milton, N.Y.), or drop dispensing device can also be used for the application of the composition.

To facilitate uniform and complete coverage of the stent during the application of the composition, the stent can be rotated about the stent's central longitudinal axis. Rotation of the stent can be from about 0.1 rpm to about 300 rpm, more narrowly from about 30 rpm to about 200 rpm. By way of example, the stent can rotate at about 150 rpm. The stent can also be moved in a linear direction along the same axis. The stent can be moved at about 1 mm/second to about 30 mm/second, for example about 6 mm/second, or for a minimum of at least two passes (i.e., back and forth past the spray nozzle). In other applications, the spray nozzle can be devised to translate over the stent. The stent is rotated at a desired speed underneath the nozzle.

A nozzle can deposit coating material onto a stent in the form of fine droplets. An atomization pressure of a sprayer can be maintained at a range of about 5 psi to about 30 psi. The droplet size depends on factors such as viscosity of the solution, surface tension of the solvent, solution feed rate, and atomization pressure. The flow rate of the composition from the spray nozzle can be from about 0.01 mg/second to about 1.0 mg/second, for example about 0.1 mg/second. Only a small percentage of the composition that is delivered from the spray nozzle is ultimately deposited on the stent depending on the transfer efficiency of the spray setup. By way of example, when a composition is sprayed to deliver about 1 mg of solids, only about 100 micrograms or about 10% of the solids sprayed will likely be deposited on the stent. The solid percent in the composition typically can range from 0.1 wt % to 15 wt %, for example about 5 wt %.

To reduce or eliminate coating defects in coated stents, excessive solvent is removed from applied coating material through an in-process drying cycle. Excessive application of the polymer or excessive solvent left in the coating can cause coating defects such as pool web (excessive material accumulated between stent struts) due to the lack of good wettability of the coating droplets over a stent with a tight geometry.

To avoid excessive application of coating material, the coating process can involve multiple repetitions of spraying forming a plurality of layers. A repetition can involve a single pass or multiple passes of moving a spray nozzle (or moving the stent), a pass being from one end (e.g., proximal end) to the other end (e.g., distal end) of a stent. Each repetition can be, for example, about 0.5 second to about 20 seconds, for example about 10 seconds in duration. The amount of dry coating applied by each repetition can be about 1 microgram/$cm^2$ (of stent surface) to about 75 micrograms/$cm^2$, for example, less than about 20 micrograms/$cm^2$.

As indicated above, the coating composition can include a polymer and a drug dissolved in a solvent. Each repetition can be followed by in-process drying involving removal of a significant amount of the solvent(s). In an embodiment, there may be less than 5%, 3%, or more narrowly, less than 1% of solvent remaining in the coating after in-process drying between repetitions. When the coating process is completed, all or substantially all of the solvent may be removed from the coating material on the stent. Any suitable number of repetitions of applying the composition followed by removing the solvent(s) can be performed to form a coating of a desired thickness or weight. Excessive application of the polymer can, however, cause coating defects.

A stent coated with coating material can be dried by allowing the solvent to evaporate at room or ambient temperature. Depending on the volatility of the particular solvent employed, the solvent can evaporate essentially upon contact with the stent. Alternatively, the solvent can be removed by subjecting the coated stent to various drying processes. Drying time can be decreased to increase manufacturing throughput by heating the coated stent. For example, removal of the solvent can be induced by baking the stent in an oven at a mild temperature (e.g., 60° C.) for a suitable duration of time (e.g., 2-4 hours) or by the application of warm air. There can be some residual solvent left in the coating after the in-process drying depending on the solvent used and in-process drying time. The higher the boiling point of the solvent, the harder it is to remove solvent in the in-process drying process. The coated stent is typically dried in an oven as the final drying step when the multiple deposition stages are completed to remove residual solvent. The residual solvent can have harmful biological effects and plasticizing effects which can alter the release rate and coating properties. The energy source of the oven can range from a conventional oven to an infrared oven or UV.

Evaporation of the solvent(s) can be induced by application of a warm gas between each repetition which can prevent coating defects and minimize interaction between the active agent and the solvent. The stent may be positioned below a nozzle blowing a warm gas. A warm gas may be particularly suitable for embodiments in which the solvent employed in the coating composition is of a low volatility (e.g., dimethylsulfoxide (DMSO), dimethylformamide (DMF), and dimethylacetamide (DMAC)). The temperature of the warm gas can be from about 25° C. to about 200° C., more narrowly from about 40° C. to about 90° C. By way of example, warm gas applications can be performed at a temperature of about 60° C., at a flow speed of about 5,000 feet/minute, and for about 10 seconds.

The gas can be directed onto the stent following a curing period of about 3 seconds to about 60 seconds, more narrowly for about 10 seconds to about 20 seconds, so as to allow the residual solvent(s) to be removed to form a coating. The curing period is particularly short if the coating composition contains a volatile solvent since such solvents are typically removed quickly. As used herein "volatile solvent" means a solvent that has a vapor pressure greater than 17.54 Torr at ambient temperature, and "non-volatile solvent" means a solvent that has a vapor pressure less than or equal to 17.54 Torr at ambient temperature.

Any suitable gas can be employed, examples of which include air, argon, or nitrogen. The flow rate of the warm gas can be from about 20 cubic feet/minute (CFM) (0.57 cubic meters/minute (CMM)) to about 80 CFM (2.27 CMM), more narrowly about 30 CFM (0.85 CMM) to about 40 CFM (1.13 CMM). The warm gas can be applied for about 3 seconds to about 60 seconds. By way of example, warm air applications can be performed at a temperature of about 50° C., at a flow rate of about 40 CFM, and for about 10 seconds.

Figure 31:
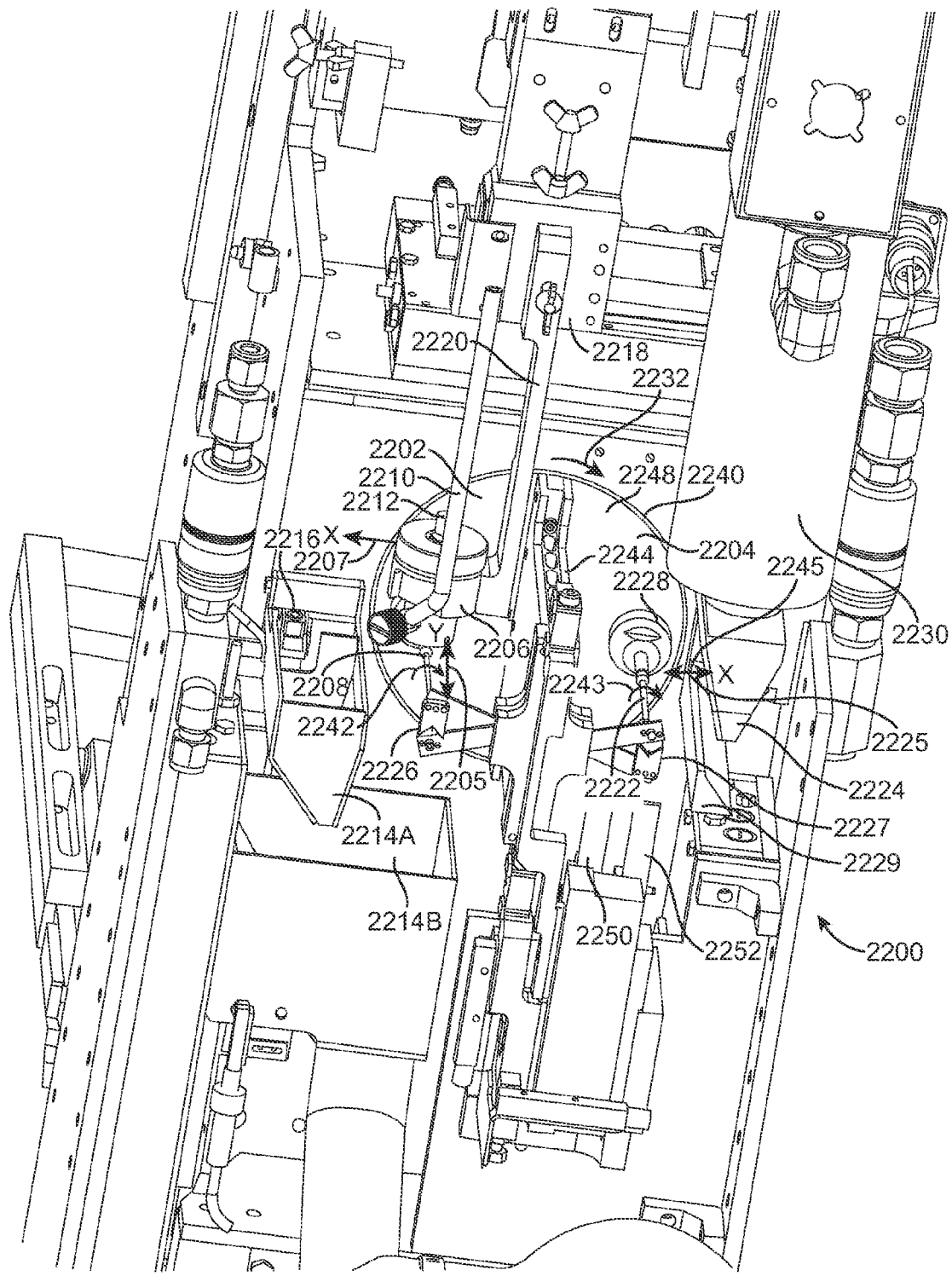
FIG. 31 depicts an exemplary stent coating and drying device.

Embodiments of the present invention may be illustrated by the exemplary spray coating device 2200 depicted in FIG. 31, which shows a front view. Device 2200 is configured to process two stents simultaneously. However, device 2200 can process only one stent if desired. Device 2200 has a spraying zone 2202 and a drying zone 2204, which enable coating of one stent and drying of another stent simultaneously. Stent support assemblies 2208 and 2222 can be moved between spraying zone 2202 and drying zone 2204 via a rotating drum to allow simultaneous spraying of a stent on one stent support assembly and drying of another stent on another stent support assembly.

Spraying zone 2202 has a spray nozzle 2206 that is mounted above movable stent support assembly 2208. Stent support assembly 2208 is inserted into a spindle which is connected to a gear system that is powered by a motor (not shown) which provides rotational motion to the stent support assembly 2208, as depicted by an arrow 2242, during the coating process. Hose 2210 feeds gas to spray nozzle 2206 and liquid coating material is fed to spray nozzle 2206 via port 2212. A tubing or line (not shown) can connect port 2212 to a liquid coating material source. Spray nozzle 2206 is translatable along a y-direction, as shown by double-headed arrow 2205, along the axis of stent support assembly 2208. Spray nozzle 2206 is also movable along an x-direction as shown by an arrow 2207.

Spraying zone 2202 includes upper funnel 2214A and lower funnel 2214B. Lower funnel 2214B is connected to an evacuation system that creates a vacuum at funnel 2214A and 2214B to collect excess coating material generated from the overspray. The evacuation system can be on during all or part of the coating process. A wetcap device 2216, described in more detail below, adjacent to upper funnel 2214A is for cleaning the tip of spray nozzle 2206.

Spray nozzle 2206 is dwelled in a nozzle holder 2220 which is attached to a mounting bracket block 2218. Mounting bracket block 2218 is coupled to a linear slide that can control movement of nozzle holder 2220 and spray nozzle 2206 back and forth in the x-direction during the application of the coating material over the stent. Mounting bracket block 2218 is also coupled to a sliding stage to enable nozzle holder 2220 along with spray nozzle 2206 to side shift back and forth in the y-direction to a position over upper funnel 2214A after a spray cycle is complete. The side-shifting of nozzle holder 2220 along with spray nozzle 2206 clears the path in the spray zone to allow the drum to rotate to advance the stent at the drying zone 2204 to the spraying zone 2202 to receive coating material. The side shift motion clears the path in the spray zone to allow the drum to rotate, advancing the stent at the drying zone to the spray zone to receive to more coating material.

Drying zone 2204 includes a drying nozzle 2224 that can be positioned over a movable stent support assembly 2222 for supporting a coated stent during drying. Stent support assembly 2222 is inserted into a spindle which is connected to a gear system that is powered by a motor (not shown) which provides rotational motion to the stent support assembly 2222, as depicted by an arrow 2243, during the drying process. In some embodiments, the same motor provides rotational motion to stent support assemblies 2208 and 2222. Drying nozzle 2224 includes an electrical heater 2230 to generate heated air for drying nozzle 2224. Drying nozzle 2224 is movable and can shift in an x-direction, as shown by a double-headed arrow 2245, from its position shown in FIG. 31 to a drying position over stent support assembly 2222. Drying nozzle 2224 can be positioned above stent support assembly 2222 so that it can dry a stent coated in spraying zone 2202 by blowing warm gas over a freshly coated stent. Stent grippers 2250 and 2252 for clocking a stent, as described in detail below, are disposed below stent support assembly 2222.

Movement of mounting bracket 2220, and thus, nozzle 2206, is accomplished by motors (not shown). Shifting of drying nozzle 2224 is performed by motors (not shown). The motors can be controlled by a controller that has pre-programmed instructions on the movement of nozzles 2206 and 2224.

The side shift of drying nozzle 2224 and spray nozzle 2206 may be accomplished with pneumatic slides or motor driven linear slides. The side-shift of the drying nozzle allows the indexing drum to rotate, but also accommodates differences in the drying time and the spraying time. The side-shift of drying nozzle 2224 results in a deflection of the drying air away from the stent to prevent over-drying while the other stent is finishing its spray cycle. Thus, the spray cycle and dry cycle are not limited to the same duration for process flexibility.

Stent support assemblies 2208 and 2222 are supported at their distal ends by clamps 2226 and 2227, respectively. The proximal end of stent support assembly 2222 is shown to be supported by a spindle or end cap 2228. The distal end of stent support assembly 2208 is supported in the same manner, but is hidden by spray nozzle 2206. End cap 2228 is mounted or coupled on a rotatable drum 2240 which rotates as shown by arrow 2232. Rotatable drum 2240 can rotate to reverse the position of stent support assemblies 2208 and 2222 so that stent support assembly 2208 is in drying zone 2204 and stent support assembly 2222 is in the spray zone 2202.

The scissor-type end supports facilitate automatic loading/unloading of parts to the spindles. Since the supports are mounted to a baffle 2244, ends of the mandrels are supported during the indexing of the drum. This prevents oscillation of the core wires with collets which could damage the coating. Such oscillation would limit the acceleration/deceleration of indexing of the drum.

In some embodiments, device 2200 can be used as part of an automated process. Robotic arms (not shown) can position a shaft of stent support assemblies 2208 and 2222 that include an uncoated stent within holes in endcaps or spindles. After coating is completed, the robotic arm can remove the stent support assemblies from the endcaps or spindles. Gripping collets inside the spindles can be opened and closed automatically to allow automated loading/unloading of parts.

Spray zone 2202 and drying zone 2204 are separated by baffle 2244 which is mounted on a back plate 2248 of rotatable drum 2240. Baffle 2244 is configured to reduce or eliminate heat and mass transfer between spray zone 2202 and drying zone 2204. In particular, baffle 2244 reduces or prevents coating material sprayed from nozzle 2206 from contacting a stent that is being dried in drying zone 2202. Additionally, baffle 2244 acts as a thermal barrier that reduces or prevents conductive or convective heat transfer between spray zone 2202 and drying zone 2204. In particular, baffle 2244 reduces or prevents conductive heat transfer to spraying zone 2202 due to heated gas from drying nozzle 2224. Baffle 2244 also blocks air currents that may carry coating material to drying zone 2204 or heated air to spraying zone 2202.

Figure 32:
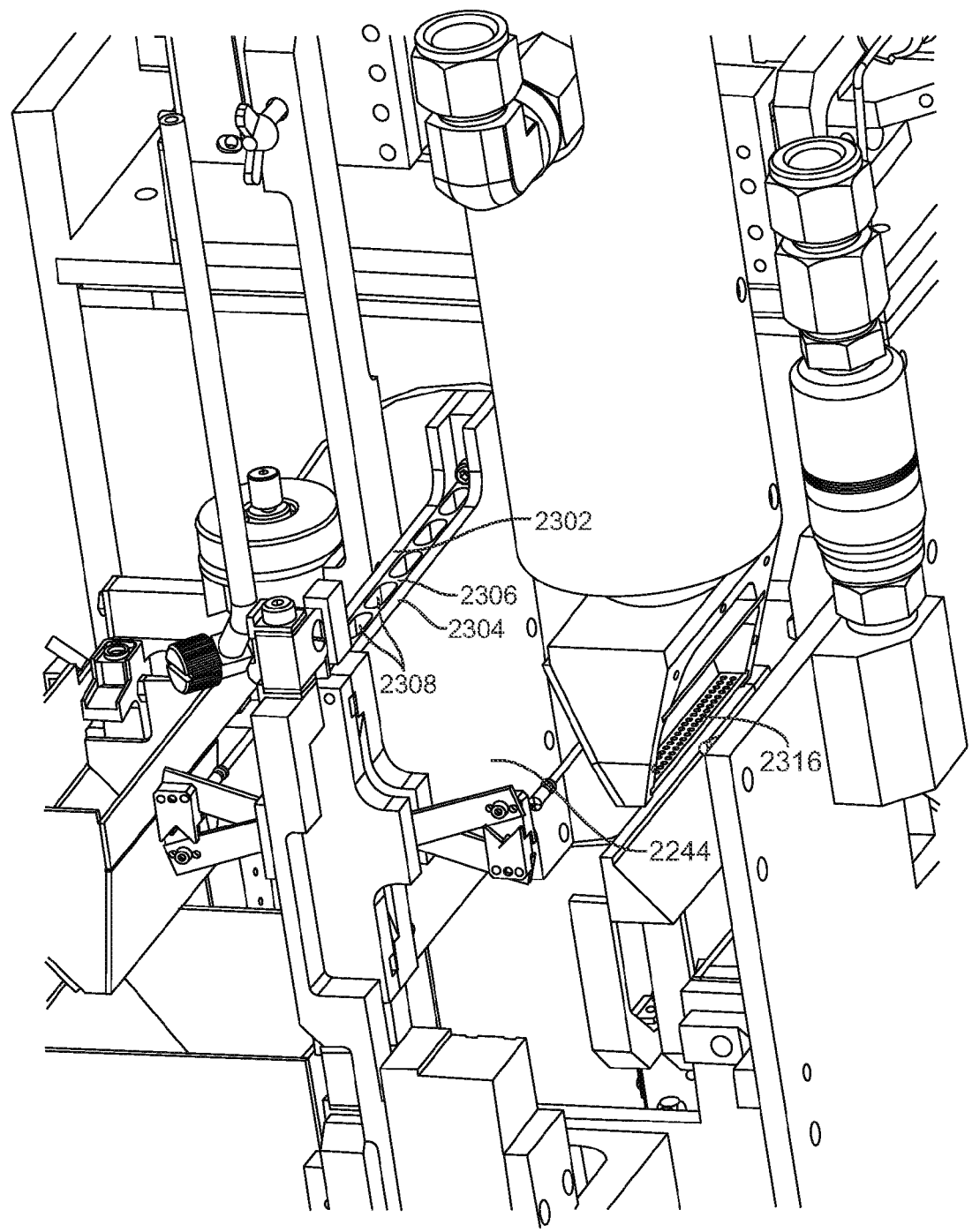
FIG. 32 depicts a close-up view of a baffle separating a spraying zone and a drying zone in the device depicted in FIG. 31.

Baffle 2244 can be fabricated of materials that provide thermal insulation between spraying zone 2202 and drying zone 2204. In addition, such materials should also maintain thermal and mechanical properties during the spraying and coating process. For example, the materials should be insoluble in the solvent(s) used in the coating material and should be resistant to significant changes in properties caused by the heat from drying nozzle 2224. For example, baffle 2244 can be fabricated at least in part of a polymeric or plastic material. A close-up view of baffle 2244 is provided in FIG. 32. Baffle 2244 is a composite structure having two outer polymer plates 2302 and 2304 that provide thermal insulation. Baffle 2244 has an inner metallic support 2306 to provide a rigid structural support to baffle 2246. Metallic layer 2306 has channels or voids 2308 to reduce the heat conduction through baffle 2244 and which also provides the required space to accommodate an end support mechanism to the stent support assemblies to improve the alignment of the assemblies to the nozzles as illustrated in FIG. 1C. In an exemplary embodiment, baffle 2244 has outer layers fabricated from polyetheretherketone (PEEK) and an inner layer of stainless steel. The structure of baffle 2244 is not limited to that depicted in FIG. 32.

As indicated above, it is desirable to coat stents with multiple spray/dry cycles Device 2200 is designed to allow spraying of stent in spray zone 2202 while a coating layer previously applied at spray zone 2202 is dried at drying zone 2204. Simultaneous spraying and drying reduces or eliminates idle time of sequential spraying and drying operation, thus increasing the throughput of a coating operation.

Specifically, a layer of coating material is applied to a first stent mounted on stent support assembly 2208 by spray nozzle 2206. At the same time, a second stent mounted on stent support assembly 2222 with coating material already applied in spray zone 2202 is dried by drying nozzle 2224. When both the spray coating on the first stent and drying of the second stent are completed, rotatable drum 2240 rotates and positions the second stent (dried) at spray zone 2202 and the first stent (freshly coated) at drying zone 2204. The first stent may then be dried at drying zone 2204 and a layer of coating material can be applied to the second stent at spray zone 2202. The spraying and drying can be repeated a selected number of times necessary to obtain a desired coating mass on each of the stents. Rotatable drum 2240 can rotate clockwise or counterclockwise to change the position of the first stent and second stent between spray zone 2202 and drying zone 2204. The motion of rotatable drum 2240 can be controlled by a belt driven gear assembly (not shown) which is powered by a motor (not shown). Stent support assembly 2208 and stent support assembly 2222 are rotated in each spraying and drying cycle. As shown by arrow 2232, the first stent is rotated to spray zone 2202 and the second stent is rotated to drying zone 2204, and after the spraying/drying cycle is complete the first stent is rotated back to drying zone 2204 for drying the stent and the second stent is rotated to spray zone 2202 to receive coating material.

To allow rotation of rotatable drum 2240 when both the spray coating of a first stent and drying of a second stent are completed, spray nozzle 2206 shifts away from stent support assembly 2208. In addition, drying nozzle 2224 can also shifts away from stent support assembly 2222 to allow rotation of rotatable drum 2240.

Figure 33:
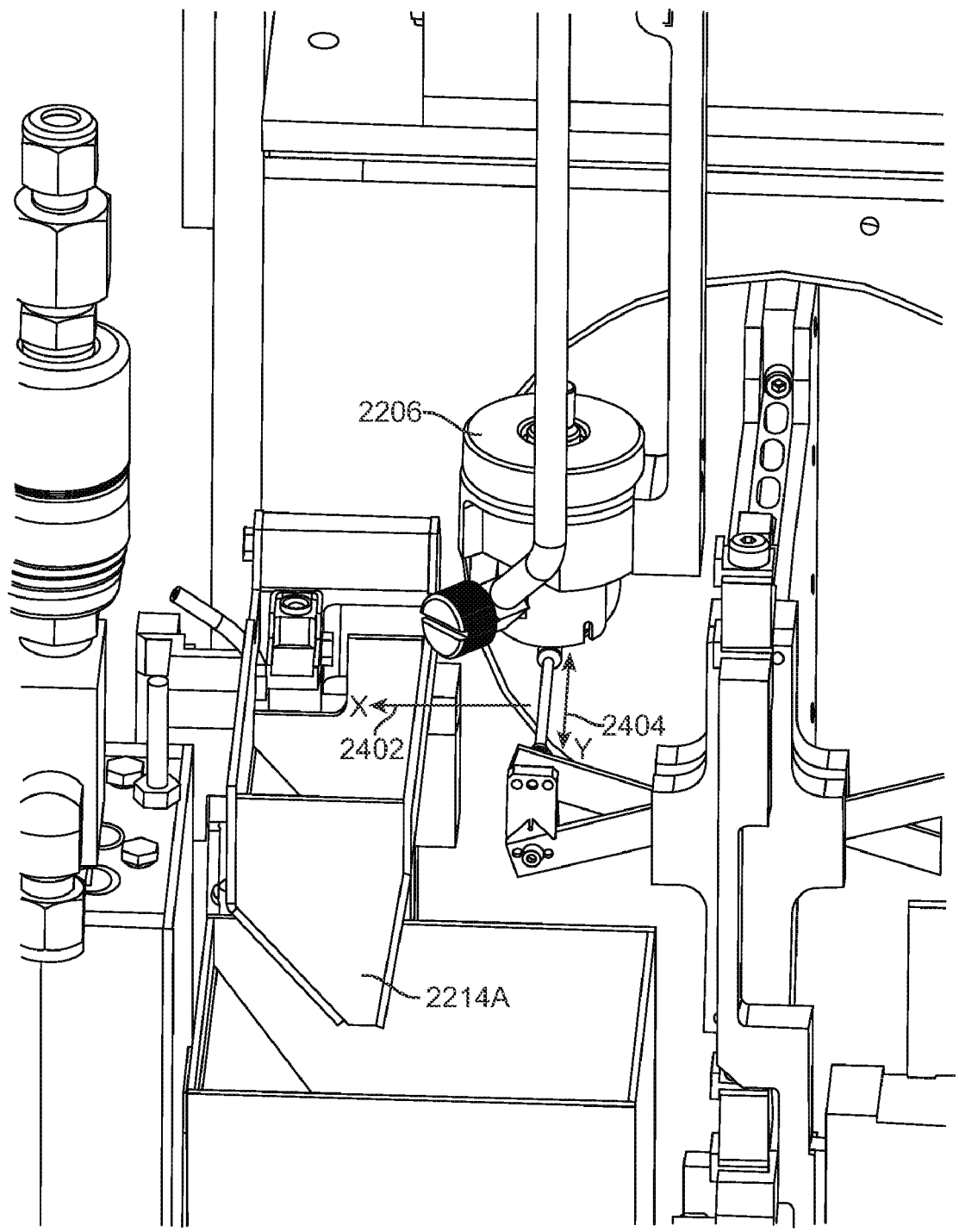
FIG. 33 depicts a close-up view of a spray zone of the device depicted in FIG. 31.

A close-up view of spray zone 2202 is shown in FIG. 33. Spray nozzle 2206 can shift in an x-direction to a position over upper funnel 2214A, as shown by an arrow 2402. As indicated above, spray nozzle 2206 translates linearly along the y-axis, as shown by an arrow 2404, of stent support assembly 2208 during application of coating material to a stent mounted on stent support assembly 2208. Spray nozzle 2206 can side shift in the x-direction to be positioned over upper funnel 2214A after the spray cycle is complete and spray nozzle 2206 can rest at any position along the y-axis over funnel 2214A to await the next spray cycle. Spray nozzle 2206 can continue spraying or turn off while it is waiting, or it can advance to the wetcap device 2216 for wet-capping to clean the nozzle tip.

Figure 34A:
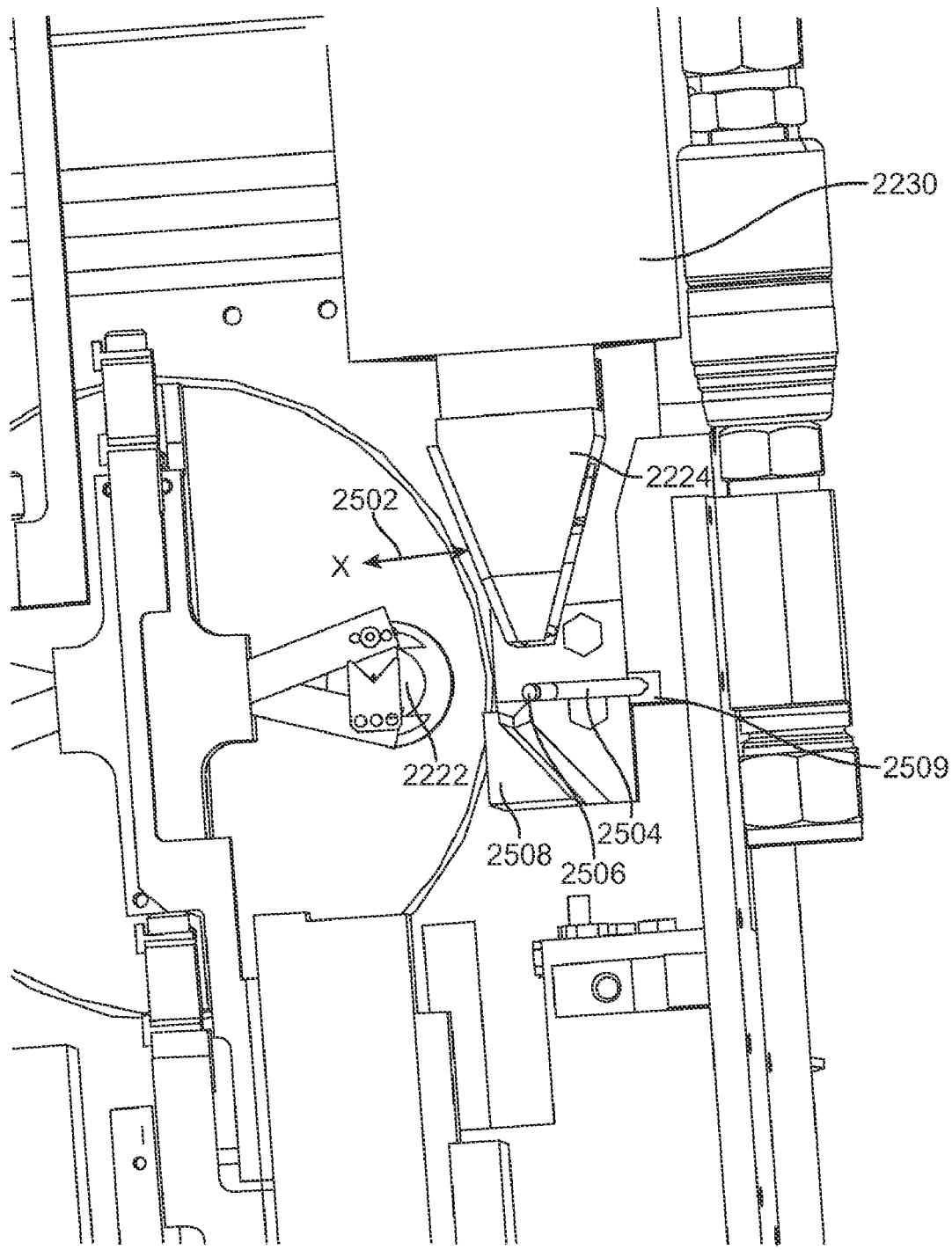
FIGS. 34A-B depict a close-up view of a drying zone of the device depicted in FIG. 31.
Figure 34B:
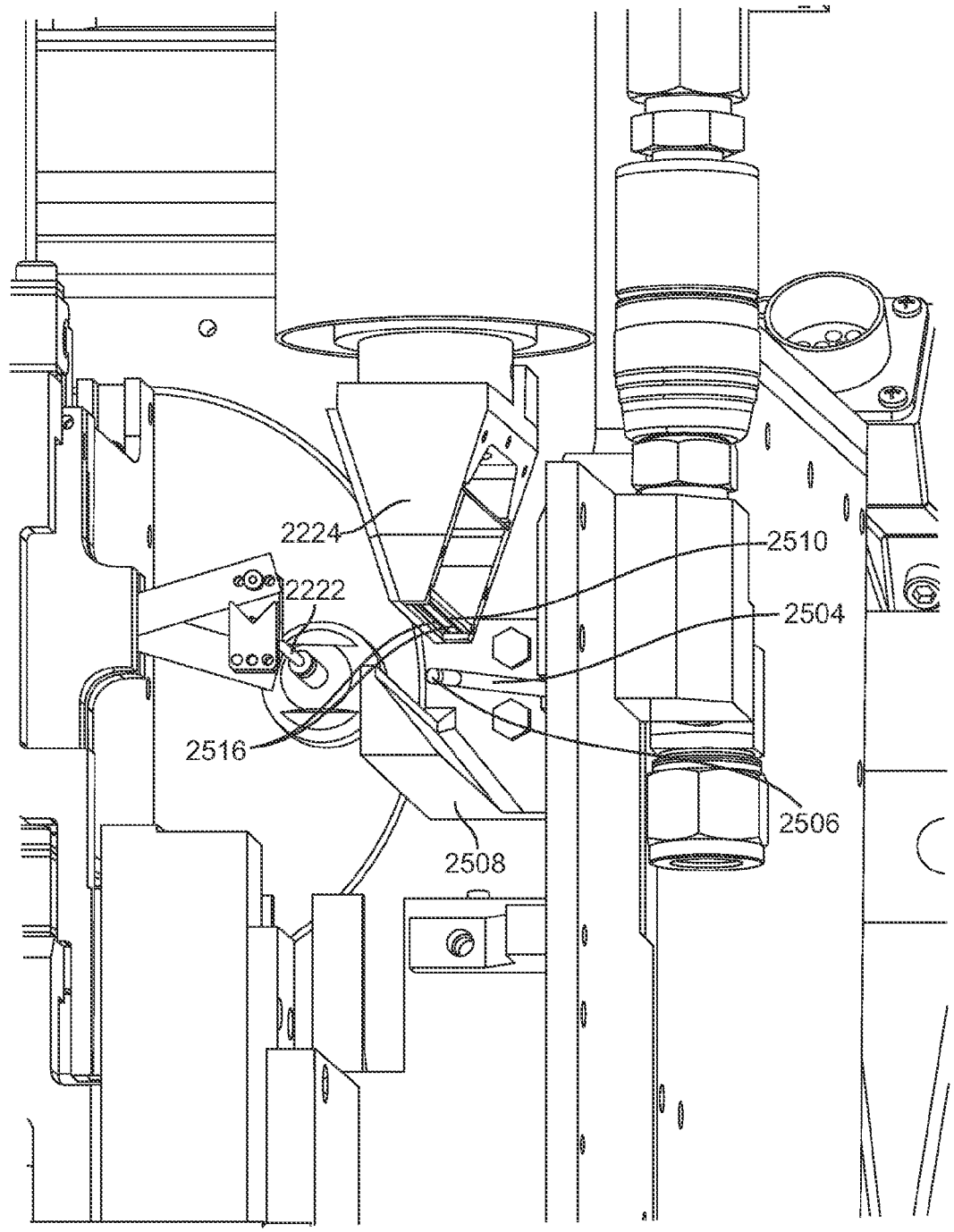

FIGS. 34A-B depict a close-up view of drying zone 2204. Drying nozzle 2224 is shown shifted away from a position above stent support assembly 2222, as shown by an arrow 2502, to a position as shown. A temperature probe 2504 with a sensing zone 2506 at its tip extends outward toward drying nozzle 2224. Temperature probe 2504 monitors the temperature of warm gas stream exiting from drying nozzle 2224. Temperature probe 2504 is coupled to a housing 2509. The housing 2509 and drying nozzle 2224 are both attached to a linear stage which enables and maintains the alignment of drying nozzle 2224 to temperature probe 2504. Temperature probe 2504 and drying nozzle 2224 move back and forth along the x-direction so that temperature probe 2504 remains a fixed distance from drying nozzle 2224 and can continue to monitor the temperature of the warm gas stream.

FIG. 34B shows a slotted opening 2510 through which warm gas passes for drying a coated stent mounted on stent support assembly 2222. A deflector shield 2508 is positioned below drying nozzle 2224 in its right-most shifted position. Deflector shield 2508 deflects the warm gas stream exiting drying nozzle 2224 to the downstream evacuation when drying nozzle 2224 is shifted away from stent support assembly 2222 when the drying cycle is complete. Perforated plates or screens 2516 can be incorporated into drying nozzle 2224 to improve the mixing of the hot gas exiting from the heating element (not shown) located at the upper portion of drying nozzle 2224 to provide an air stream with a uniform temperature distribution.

The time for drying a stent with drying nozzle 2224 can be different from the time for spraying a layer of coating material on a stent with spray nozzle 2206. In some embodiments, spraying nozzle 2206 can finish a coating layer on a stent mounted on a stent support assembly prior to a stent mounted on a stent support assembly is finished drying. In one embodiment, the flow of coating material from spray nozzle 2206 can be stopped after completing the deposition of a layer on a first stent in spraying zone 2202. The spraying and drying can be started again after rotatable drum 2240 has rotated and positioned the stent from the drying zone in spraying zone 2202 and the freshly coated stent in drying zone 2204.

A potential disadvantage of stopping the flow of coating material is nozzle fouling which refers to residual coating material in the nozzle drying up and reducing or preventing flow of coating material through the nozzle. Nozzle fouling can degrade the nozzle performance and it can reduce the coating weight consistency and coating quality. In an alternative embodiment, spray nozzle 2206 can continue to spray coating material even after completing deposition of a coating layer on a stent in spraying zone 2204 to minimize nozzle fouling. Spray nozzle 2206 can shift in the x-direction to a position away from the coated stent so that no additional coating material is applied to the stent. Spray nozzle 2206 can be positioned adjacent to or above funnel 2214 after completing deposition to prevent further deposition of coating material on the stent. The evacuation system (not shown) creates a vacuum at upper funnel 2214A and removes all or a substantial portion of the coating material that continues to be sprayed from spray nozzle 2206.

Figure 35:
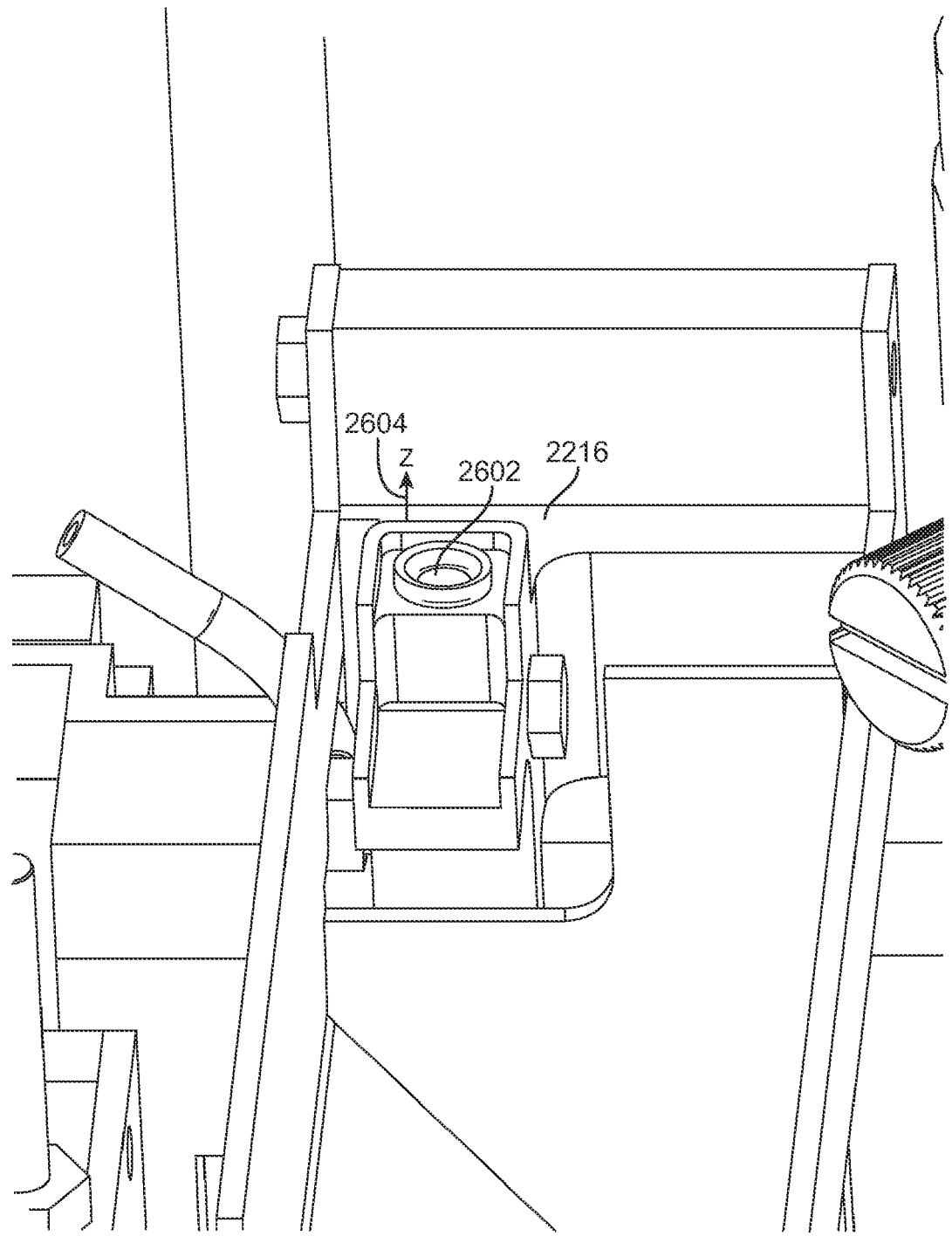
FIG. 35 depicts a close-up view of a cap fixture.

As described above, a wetcap device 2216 shown in FIG. 31 is provided for cleaning the tip of spray nozzle 2206. Wetcap device 2216 can remove coating material that may have accumulated at the tip of spray nozzle 2206 by using a solvent that can soften or dissolve the build-up of coating material at the nozzle tip. FIG. 35 depicts a close-up view of wetcap device 2216. Wetcap device 2216 has an opening or solvent well 2602 to allow the solvent, supplied from an external solvent supply system (not shown) to form a meniscus to allow the material build up at the nozzle tip to be dissolved or to be softened. In one embodiment, the solvent is the same as the solvent used in the coating material. To clean the tip of spray nozzle 2206 with wetcap device 2216, spray nozzle 2206 is shifted in the x-direction, y-direction, or a combination of both so that it is positioned above opening 2602 of cap fixture 2216. Cap fixture 2216 is configured to move upward in the z-direction, as shown by an arrow 2604. Cap fixture 2216 is moved upward an amount sufficient for the tip of spray nozzle 2206 is immersed in solvent well 2602 in the chamber.

Figure 36:
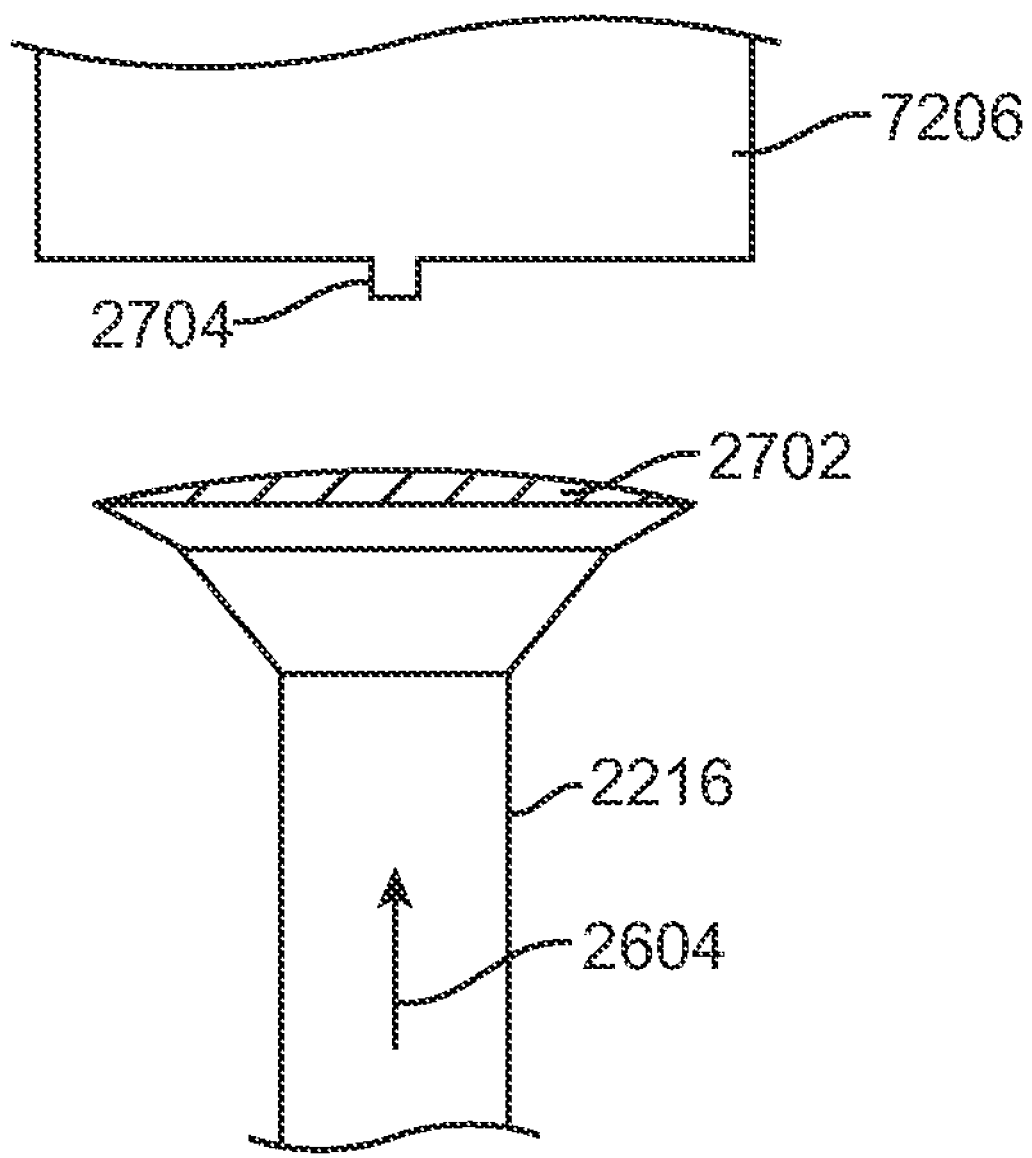
FIG. 36 shows a schematic side view of spray nozzle positioned above the cap fixture of FIG. 35.

FIG. 36 shows a schematic side view of spray nozzle 2206 positioned above cap fixture 2216 that contains a solvent 2702. As shown by arrow 2604, cap fixture 2216 can shift upward so that tip 2704 of spray nozzle 2206 is immersed in solvent 2702. Nozzle tip 2604 remains immersed in the solvent a sufficient period of time to remove coating material from the tip. After cleaning of nozzle tip 2704, cap fixture 2216 is lowered and spray nozzle 2206 is shifted back into a position for spraying a stent.

Nozzle tip 2704 can be cleaned with cap fixture 2216 at any time there is a lapse in spraying, i.e., between applications of a coating layer or a repetition. Specifically, nozzle tip 2704 can be cleaned at cap fixture 2216 to prior and/or during reversing the positions of stent support assemblies 2208 and 2222 with rotation drum 2240. Nozzle tip 2704 can be cleaned after every coating layer/repetition or at any frequency of coating layers. In one embodiment, nozzle tip 2704 is cleaned when the coating of the two stents is completed. Nozzle tip 2704 can be cleaned while the coated stents are removed from stent support assemblies 2208 and 2222 and uncoated stents are mounted on the stent support assemblies.

It is important for the solvent well 2602 in cap fixture 2216 to be filled with enough solvent enough so that nozzle tip 2704 is immersed in the solvent when cap fixture 2216 shifts upward. The level of solvent in cap fixture 2216 can change with time due to evaporation of the solvent. It may be necessary to continuously or periodically monitor the level of solvent in cap fixture 2216 to maintain the level of solvent so the nozzle tip is immersed when cap fixture 2216 is raised.

Figure 37A:
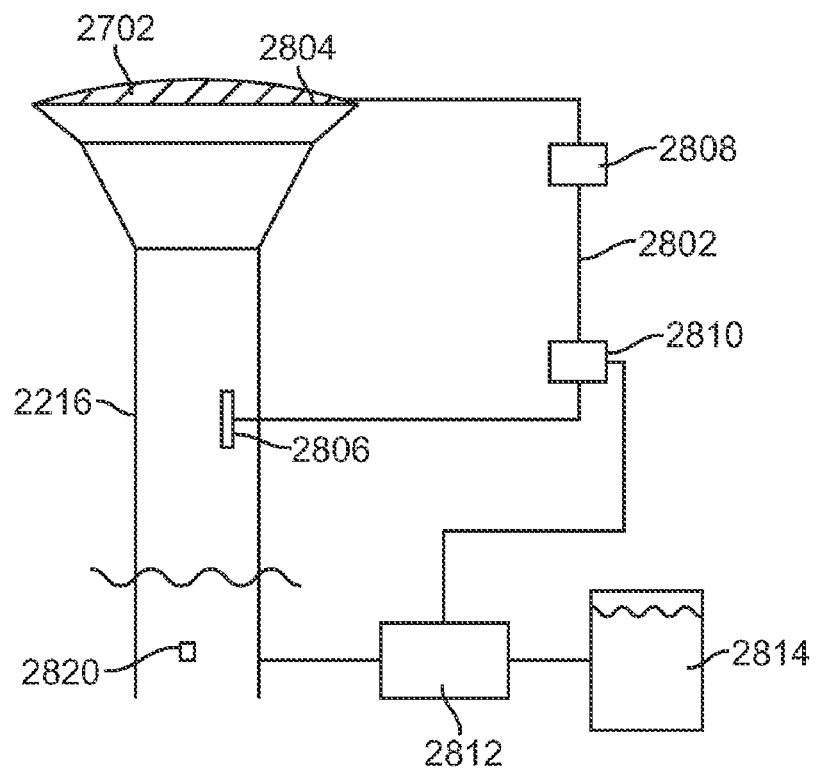
FIGS. 37A-B depict embodiments for controlling the level of solvent in a cap fixture.
Figure 37B:
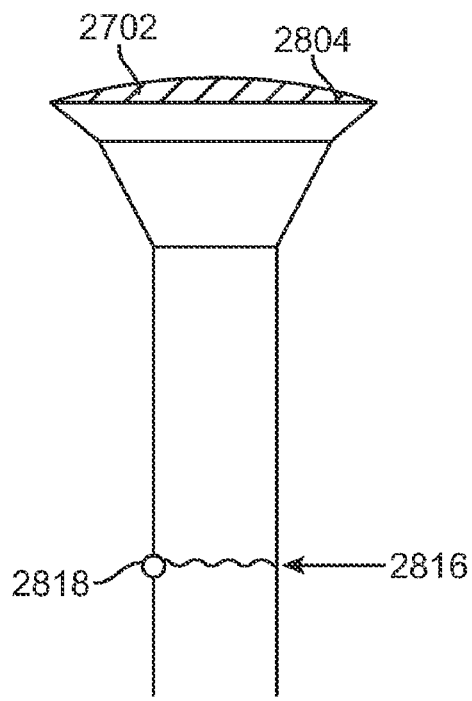

Various methods can be used to control the level of solvent in cap fixture 2216 so that nozzle tip 2704 is immersed when cap fixture 2216 is shifted upwards. Exemplary embodiments are depicted in FIGS. 37A-B. The embodiment in FIG. 37A includes a conductivity loop 2802. Conductivity loop 2802 has at one end an electrical lead 2804 positioned at a desired level of solvent in cap fixture 2216. At another end of conductivity loop 2802, an electrical lead 2806 is positioned in cap fixture 2216 below electrical lead 2804. An electrical current is passed through conductivity loop 2802 from current source 2808. A resistometer 2810 monitors changes in resistance in conductivity loop 2802. Conductivity loop 2802 remains closed as long as the level of solvent remains at or above the position of electrical lead 2804. When the level of solvent in cap fixture 2216 goes below the position of electrical lead 2804, resistometer 2810 detects an open loop due to an increase in resistance. Resistometer 2810 is in communication with a pump 2812. Pump 2812 can receive a signal from resistometer 2810 which causes pumping of solvent from a solvent reservoir 2814 into cap fixture 2216 until the level of solvent in cap fixture 2216 is restored to the level of electrical lead 2804. Pump 2812 can be configured to stop pumping solvent when it receives a signal from resistometer 2810 of a decrease in resistance due to closing of conductivity loop 2802.

In a similar manner, a conductivity loop can be between electrical lead 2804 and nozzle tip 2704. The continuity of this conductivity loop detects whether the tip of the nozzle is in the solvent. Such a loop accounts for a low solvent level as well whether the nozzle tip is mis-aligned nozzle to the solvent pool.

Another method of controlling the level of solvent in cap fixture 2216, illustrated in FIG. 37B, includes reducing the level of solvent from a desired level 2804 to a level 2816. The level can be reduced by pulling solvent to an external reservoir. Reducing the level of solvent to level 2816 can be determined by a detector 2818 positioned at level 2816 that detects a meniscus. Detector 2818 can be an ultrasonic detector manufactured by Cosense, Inc. of Hauppauge, N.Y. The amount of solvent removed can be measured, and, therefore, is known. Prior to another nozzle tip cleaning, the known amount of fluid can be metered and pumped back into cap fixture 2216 to restore the level of solvent to level 2804.

Additionally, the presence of bubbles in the solvent anywhere in the device is undesirable, including within cap fixture 2216. An ultrasonic sensor 2820 positioned within cap fixture 2216 can be used to detect the presence of bubbles. If the bubble volume is larger than a selected value, then the wet cap system can be purged by removing the solvent and replaced with fresh solvent.

After the spray nozzle shifts aways from wetcap device 2216 to funnel 2214A, spray nozzle 2206 can be programmed to be purged over funnel 2214A at selected times and rates prior to the restart of the coating process.

A number of parameters influence the magnitude and consistency of the mass per pass of coating material applied by a spray nozzle and coating quality, in general. These parameters include the mass flow rate of gas and liquid feed to spray nozzle 2206 shown in FIG. 31, the liquid/gas ratio fed to spray nozzle 22206, the distance between the spray nozzle and a stent supported on a stent support assembly, the rotation rate of a stent support assembly, and the translation rate of spray nozzle 2206. The liquid/gas ratio is critical since it determines the size of droplets produced by the spray nozzle. As the liquid/gas ratio increases, the size of the droplets increases. Device 2200 allows adjustment of each of the parameters to obtain a desired mass per pass and coating quality.

In particular, it is important for the mass flow rate of liquid and gas to remain at selected levels throughout coating process so that the amount of coating material deposited per pass remains constant. As a result, the overall mass of coating material deposited on the stent is consistent and predictable from stent to stent.

In some embodiments, device 2200 controls the flow of gas and liquid with a closed loop continuously monitored system. Device 2200 can include integrated components for control of the mass flow rate of the liquid and gas delivered to spray nozzle 2206. As discussed above, liquid coating material and gas are fed into spray nozzle 2206. Liquid coating material is fed into port 2212 through a hose or tubing (not shown) and gas is fed through hose 2210.

Figure 38A:
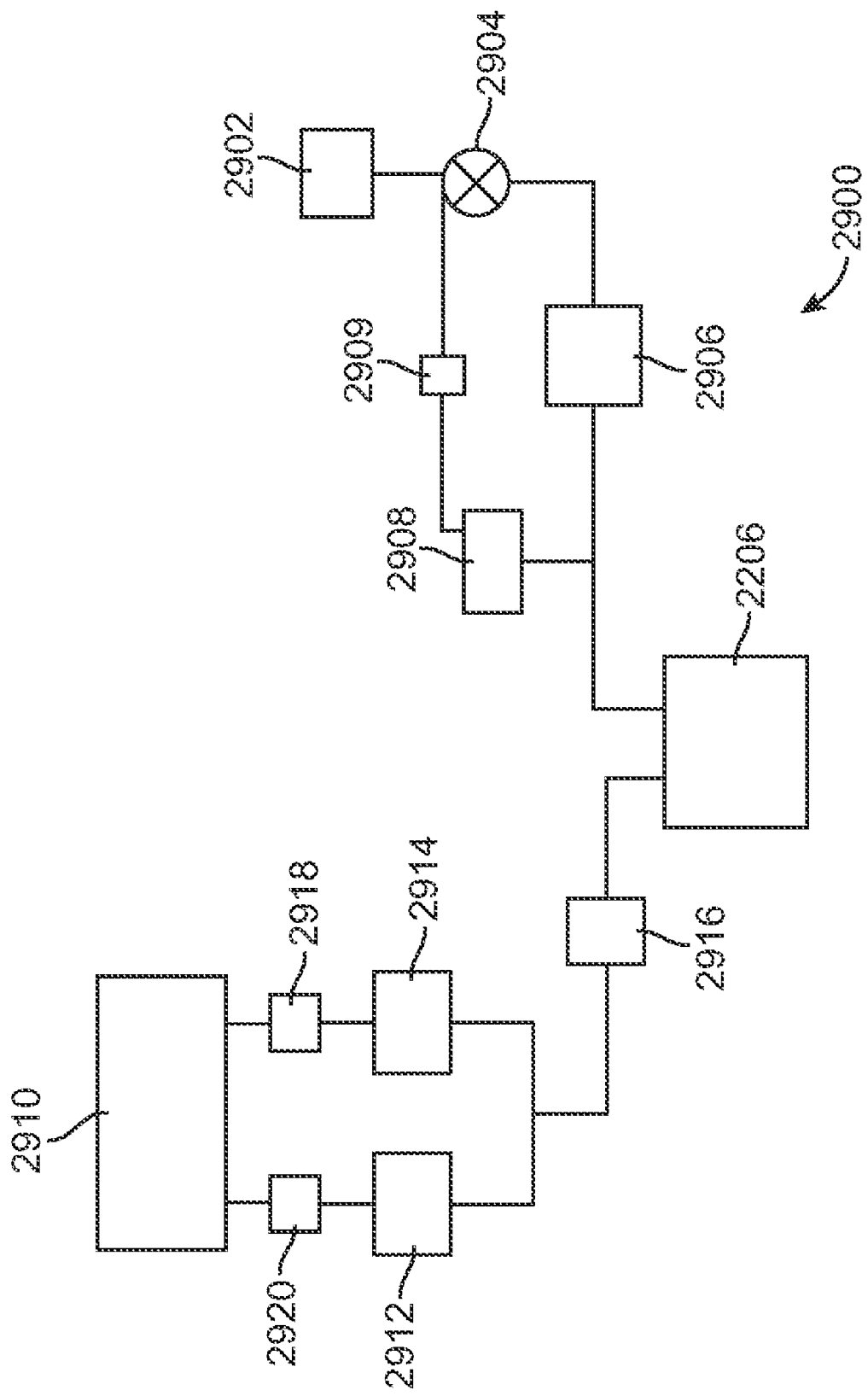
FIG. 38A depicts a schematic diagram of a system for controlling the liquid and gas flow delivered to a spray nozzle.
Figure 38B:
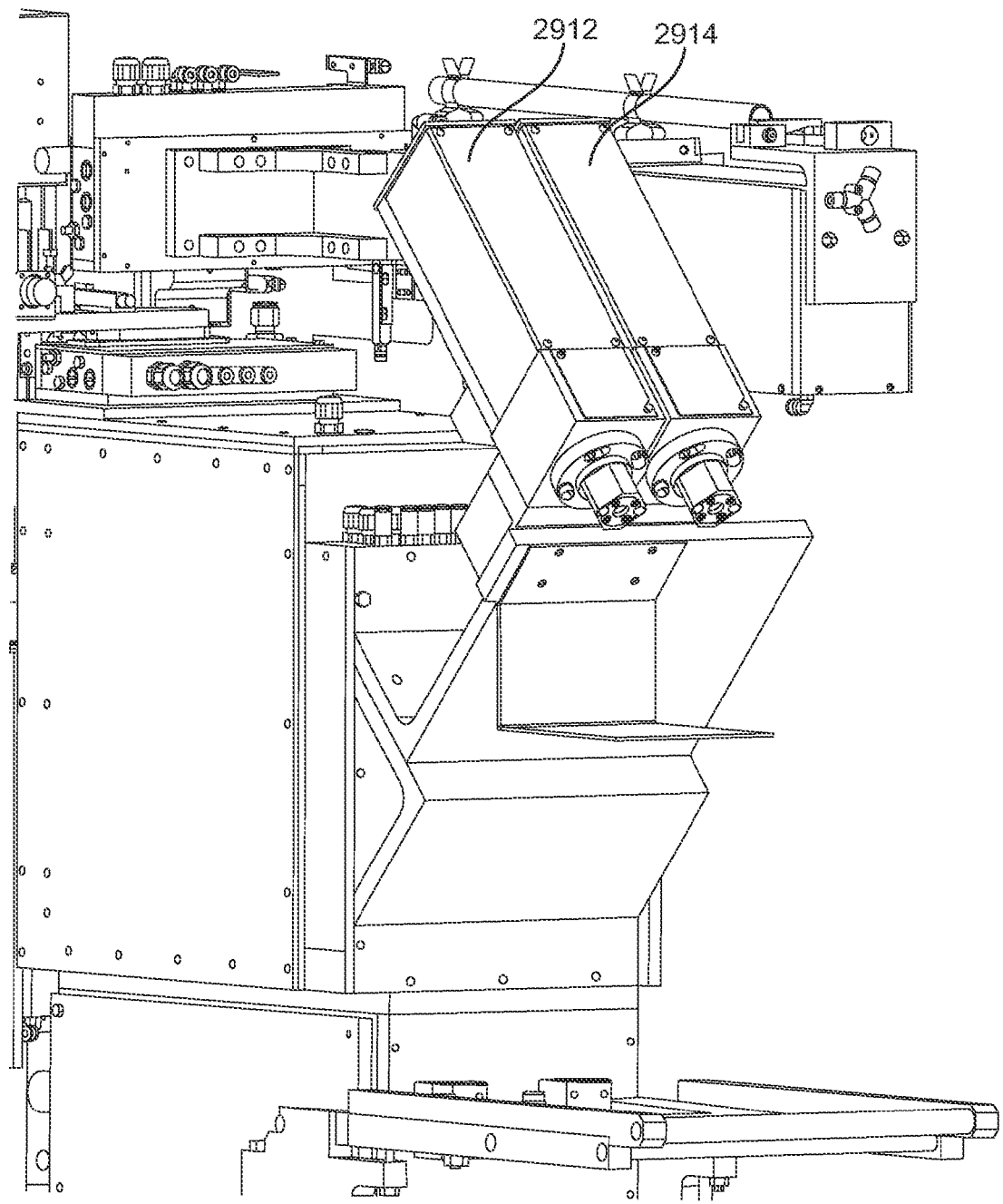
FIG. 38B depicts a view of the device in FIG. 31 showing metering pumps.

FIG. 38A depicts a schematic diagram of a system 2900 of components for controlling the liquid and gas flow delivered to spray nozzle 2206. The gas flow line of system 2900 includes a gas source 2902, pressure regulator 2904, mass flow controller 2906, and pressure transducer 2908. Liquid coating material is delivered from a liquid source 2910 by metering pumps 2912 and 2914 to spray nozzle 2206. The liquid and gas meet at the tip of nozzle 2206, and the liquid drop is broken up into smaller droplets by the gas (so-called atomization process). FIG. 38B depicts a close-up view of device 2200 showing metering pumps 2912 and 2914 for the liquid coating material.

Mass flow controller 2906 maintains a selected mass flow rate of gas and pressure transducer 2908 monitors the gas pressure in the gas line to spray nozzle 2206. Mass flow controller 2906 monitors and controls the mass flow rate of gas passed through mass flow controller 2906 to maintain the mass flow rate of gas delivered to spray nozzle 2206. Mass flow controller 2906 can compensate for an increase or decrease in mass flow rate of gas due to the pressure difference that occurs between valve 2904 and the location in the gas line of mass flow controller 2906. A decrease in mass flow rate can be caused, for example, by frictional losses. Mass flow controller 2906 can be any suitable commercially available gas mass flow controller, for example, a thermal mass flow controller. An example of a commercially available mass flow controller is MC20A high flow mass controller from MKS Instruments, Inc. Mass flow controller 2906 can include a valve which adjusts the flow rate based on detected changes in the flow rate of gas.

Pressure transducer 2908 is positioned in the gas line between mass flow controller 2906 and spray nozzle 2206. Positive departures in the pressure can be caused by, for example, blockage of the nozzle by coating material or blockage due to kinked hoses. Negative departures in the pressure may be due to leaks, for example, resulting from loose fittings. Pressure transducer 2908 monitors pressure in the gas line for changes in pressure and is in communication with valve 2904 through a controller 2909. A selected change in backpressure detected by pressure transducer 2908 is compensated for through a control signal from controller 2909 to pressure valve 2904.

Metering pumps 2912 and 2914 deliver a selected flow rate of liquid to spray nozzle 2206. Pumps 2912 and 2914 precisely meter liquid to spray nozzle 2206. Pumps 2912 and 2914 act in tandem to allow precise metering and to enable continuous spraying. As one pump is dispensing the liquid to nozzle 2206, the other pump is aspirating liquid from reservoir 2910. The use of two pumps in tandem is an advantage over a single larger pump since the smaller the pump, the more accurate the dispensing of a small amount of liquid to the nozzle.

Additionally, as indicated above, the presence of bubbles in the liquid line is generally undesirable. The presence of bubbles tends to cause a negative departure from the desired mass of coating material deposited on the stent by spray nozzle 2206. Bubbles in the pumps 2912 and 2914 also reduce the accuracy of the mass of liquid coating material dispensed by the pumps. Bubbles can be generated, for example, through the aspirating of pumps 2912 and 2914. The more volatile the solvent, the greater is the propensity of a pump to generate bubbles during aspirating. Bubble detectors can be positioned at any point along the liquid line as shown by bubble detectors 2916, 2918, and 2920. Bubble detectors 2916, 2918, and 2920 can monitor the volume of bubbles in the liquid coating material. If the detected volume is greater than a selected tolerance, a signal can be generated by a control system to communicate an alarm and/or take corrective action. Corrective action can include purging the liquid line, pumps, inspecting any leakage from the line, and/or reservoir of solvent.

Figure 39:
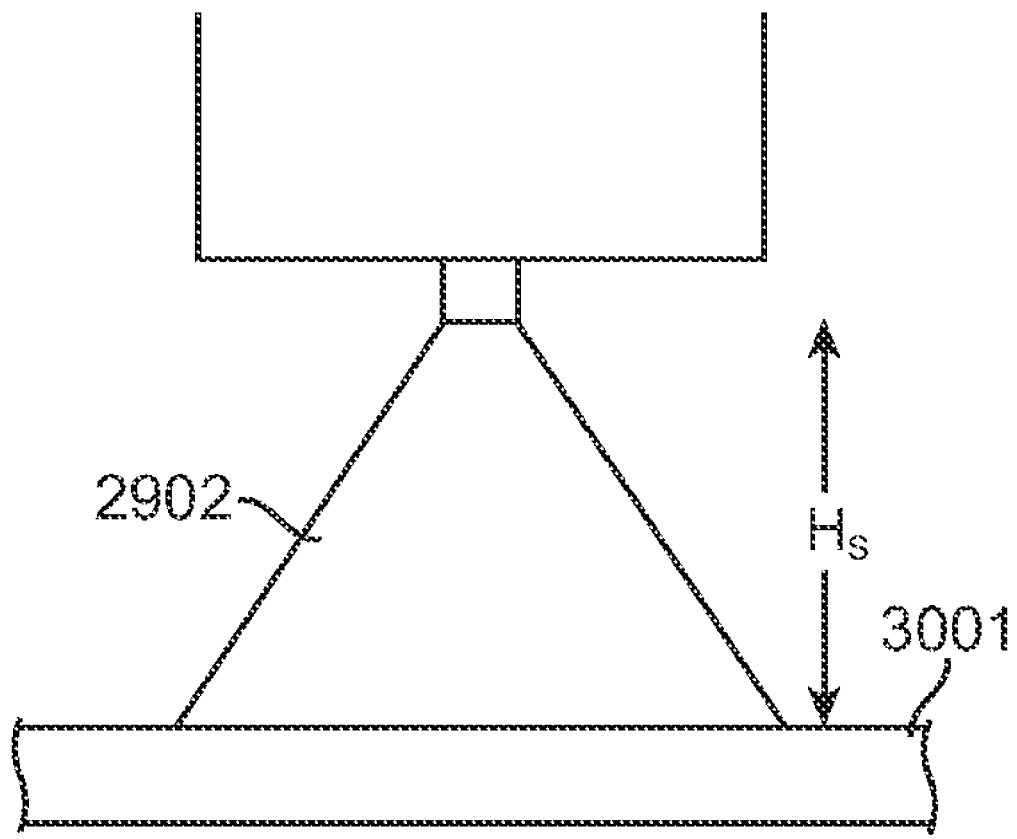
FIG. 39 depicts a schematic of a spray nozzle above a stent.

In some embodiments of device 2200 shown in FIG. 31, a distance between either or both spraying nozzle 2206 or drying nozzle 2224 and a stent support assembly can be adjustable. Spraying nozzle 2206 can be coupled to mounting bracket 2220 via a screw that allows the distance between the nozzle and the stent support assembly to be varied. Drying nozzle 2224 is mounted in a similar manner. Referring to FIG. 39, with respect to spraying, a height ($H_S$) above a stent 1001 is a process parameter that can be used to control the mass per mass deposited on stent 1001. The density and size of the droplets in a spray plume 2902 varies with $H_S$. Therefore, $H_S$ influences the characteristics of a resultant coating. Furthermore, the distance between the drying nozzle 2224 and a stent support assembly is an additional drying process parameter in addition to gas stream temperature and flow rate.

In further embodiments, either or both spray nozzle 2206 or drying nozzle 2224 are detachable from device 2200. Spraying nozzle 2206 is detachable from all connections with device 2200. Spraying nozzle 2206 can be releasably coupled to mounting bracket 2220 by various types of mounting mechanisms known in the art, for example, dovetail connectors, butterfly connectors, nuts and bolts, etc. Drying nozzle 2224 can also be releasably coupled in a similar manner to a mounting bracket (not shown). Gas feed hose 2210 and liquid feed line that feeds liquid coating material into port 2212 can also have quick-connect couplings to spray nozzle 2206.

Such known connection mechanisms can be configured to allow the mounting and positioning of a nozzle in a repeatable manner, i.e., a nozzle can be placed in the same position each time it is mounted. The releasable connections allow spray nozzle 2206 and drying nozzle 2224 to be lifted out and inserted back into device 2200 in to a designated position with respect to stent support assemblies 2208 and 2222.

A spray nozzle for coating a stent can be assembled and calibrated external to device 2200. For example, a spray plume from the nozzle can be calibrated so that it has selected properties. The selected properties can include, but are not limited to, a selected flow distribution that corresponds to a liquid and gas flow rate into the nozzle. The flow distribution can include the velocity or density of droplets as a function of distance from the nozzle tip. The calibrated spray nozzle can then be mounted in spray device 2200 such that a spray plume from the mounted nozzle has the selected properties.

The detachability and repeatability are particularly important when device 2200 is used in an automated fashion. Additionally, detachability and repeatability allows rapid replacement of spray or dry nozzles with clean nozzles or nozzles more appropriate for different applications. Detachability of a spray nozzle for cleaning away from device 2200 reduces idle time of device 2200.

It is important for the drying process to be performed in a consistent manner for each layer and each stent. The same or similar processing conditions or parameters should exist for each layer of coating material applied for each stent. Drying process parameters can influence the molecular structure and morphology of a dried polymer and drug coating. Drug release parameters depend upon on molecular structure and morphology of a coating. Therefore, drug release parameters depend upon parameters of the drying process. For example, generally, the rate of a drying process is directly proportional to the resultant drug release rate of a resultant coating.

Since the temperature of a drying process is directly related to the rate of drying, it is important to control the drying temperature to obtain coating consistency. In general, the more consistent the temperature during the drying process from layer to layer and stent to stent, the more consistent the resultant coating in a given stent and from stent to stent.

The temperature of a warm gas stream that is used to dry a stent may be adjusted by controlling the heat supplied by electrical heater 2230, depicted in FIG. 31. Temperature sensor 2506 shown in FIGS. 34A-B is positioned adjacent to a stent supported by a stent support assembly to measure the drying temperature of the applied coating. Temperature sensor 2506 is positioned as close as possible to stent without significantly disrupting the flow of heated fluid past the stent. In one embodiment, there is no or substantially no offset or difference in temperature between the drying temperature of the coating on the stent and the temperature measured by sensor 2506. In other embodiments, sensor 2506 is positioned far enough away so that there is an offset in the measured temperature and the drying temperature. Such an offset can be taken into account in a control system described below. Temperature sensor 2506 can be a thermistor, thermocouple, or any other temperature measuring device.

Temperature sensor 2506 measures the drying temperature to gather feedback ($T_F$) for controlling the drying temperature of a stent mounted on a stent support assembly. Sensor 2506 is coupled to a control system by a sensor wire. Any suitable control system, such as a closed loop system, can be used for maintaining the drying temperature of the coating at a desired temperature ($T_D$). A temperature, $T_F$, measured by sensor 2506 is transmitted to the control system. The control system compares $T_F$ to $T_D$ and then transmits a signal to electrical heater 2230. The signal carries instructions to heater 2230 to adjust the temperature of the warm gas stream supplied from drying nozzle 2224 if the difference in temperature is larger than a selected tolerance. In some embodiments, the desired temperature $T_D$ can be a function of drying time or coating thickness.

As described above, device 2200 includes stent support assemblies 2208 and 2222. In general, a stent can be supported on a mandrel or rod that supports the stent along its length by positioning the stent over the mandrel. A stent can also be supported at its ends with supports having a variety of geometries, such as supports with tapered or untapered ends. Thus, the present invention is not limited to the stent supports disclosed in the present application.

Figure 40A:
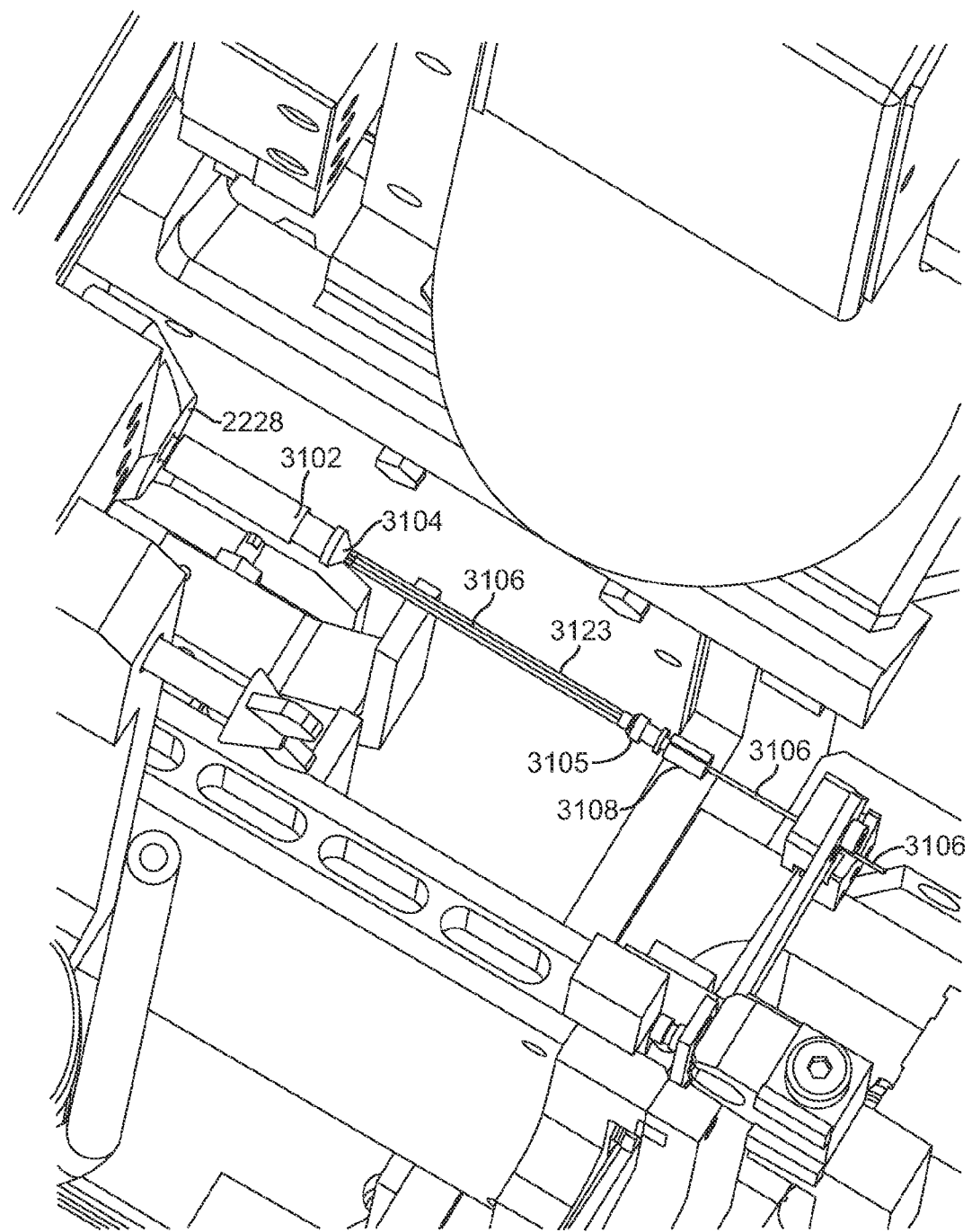
FIGS. 40A-C depict close-up views of a stent support assembly for supporting a stent during a spraying and drying process.
Figure 40B:
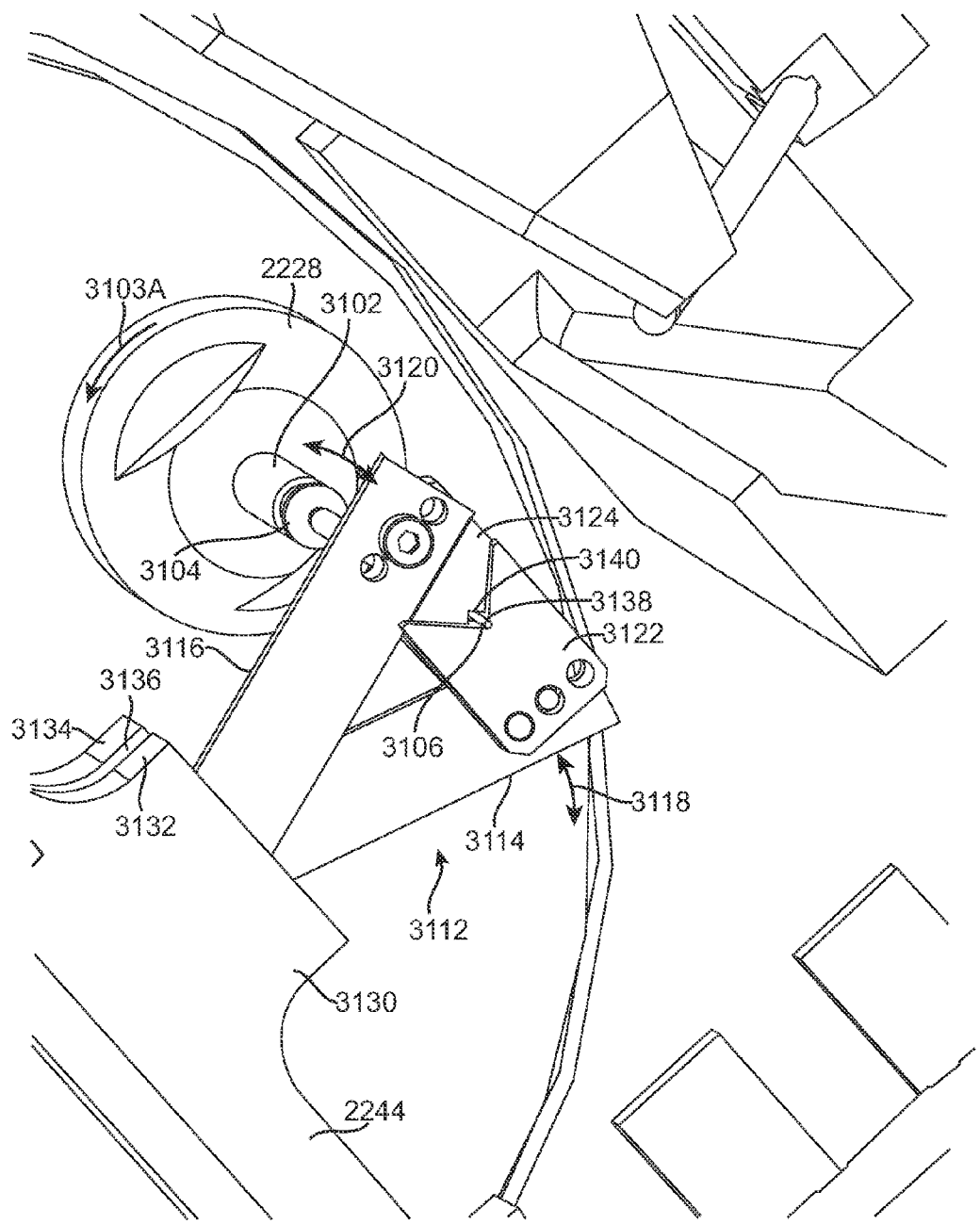
Figure 40C:
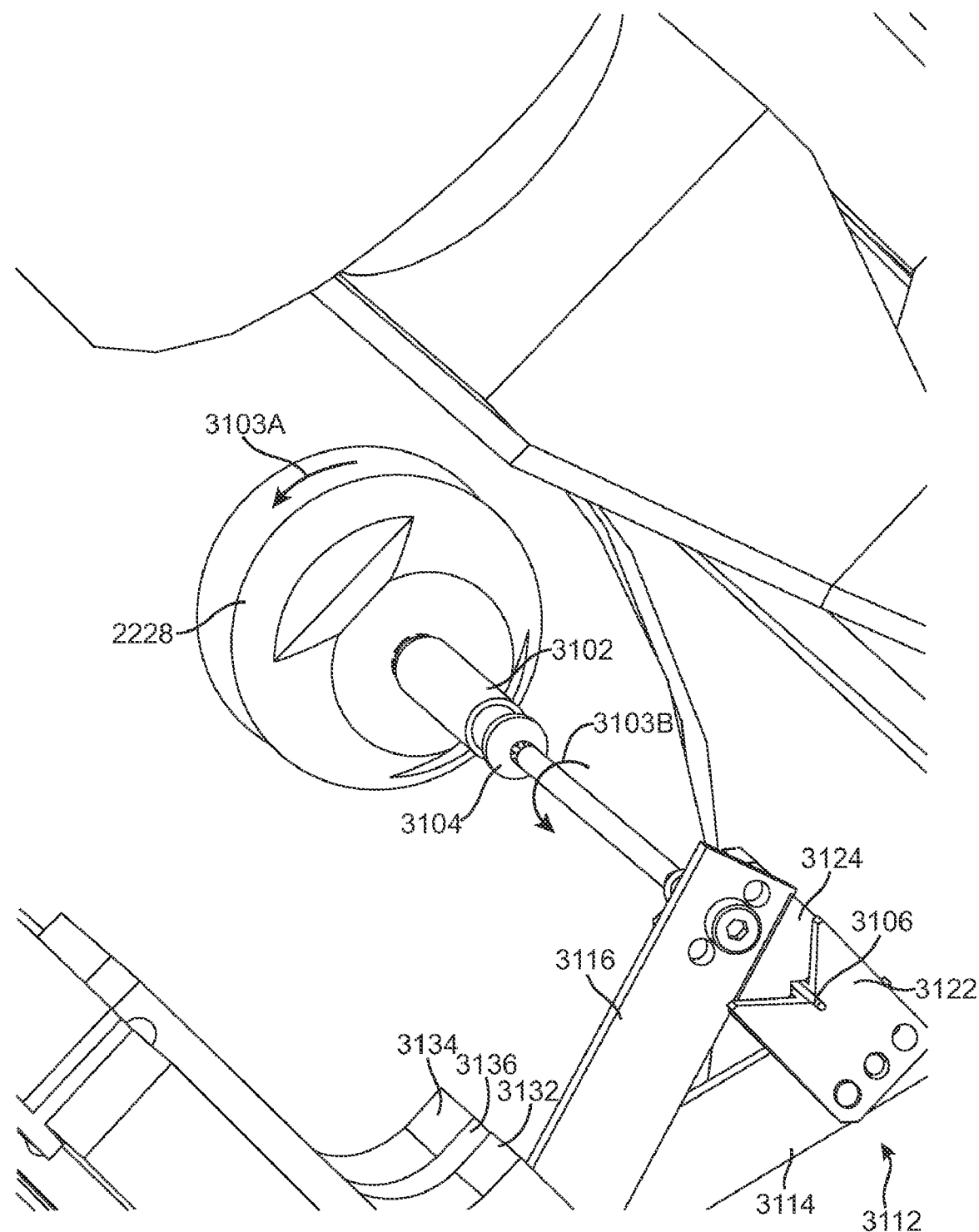

FIGS. 40A-C depict close-up views of a stent support assembly for supporting a stent during a spraying and drying process. The stent support assembly has a distal portion or shank 1102. A portion of shank 1102 is secured within a cylindrical hole in spindle or end cap 2228 which rotates, as shown by an arrow 1103A in FIG. 40B in FIG. 40C, to rotate the stent support assembly, as shown by an arrow 1103B, during coating and drying of a stent mounted on the stent support assembly. The stent support assembly further includes a mandrel cone 1104 for supporting a distal end of a stent and a mandrel cone 1105 for supporting a proximal end of the stent. As shown in FIG. 40A, a core wire 1106 extends from the tip of mandrel cone 1104 and through a collet 3108 with a mandrel cone space 3105. Mandrel cones 3104 and 3105 can have a roughened surface to absorb excess coating material. A stent 3123 is shown supported by mandrel cones 3104 and 3105 over core wire 3106.

Core wire 3106 has a diameter less than a stent. For example, core wire 3106 has a diameter between about 0.010" and 0.030". Core wire 3106 can be made of a metallic material such as Nitonol wire which can provide good dimensional stability and rigidity.

As shown in FIG. 40B, core wire 3106 is supported at a proximal end by a tailstock support 3112. Tailstock support 3112 is a scissor-like mechanism with two movable flat extension arms 3114 and 3116 that can open as shown by arrows 3118 and 3120, respectively. Flat extension arms 3122 and 3124 with opposing wedge- or v-shaped cut-out sections are coupled to distal ends of movable extended arms 3114 and 3116, respectively. Arms 3114 and 3116 are coupled to baffle 2244 by a support fixture 3130 that is coupled to baffle 2244. Support fixture 3130 is composed of two end plates 3132 (outer) and 3134 (inner) that are used to house and support flat extension arms 3114 and 3116. Proximal ends of extension arms 3114 and 3116 (one from drying zone 2204 and one from spray zone 2202) are connected to two bars (one at an upper location and one at a lower location) which are linked to an air cylinder to pull them up or down to close or open the tailstock support.

The proximal end of core wire 3106 is clamped at the apices 3138 and 3140 of the opposing wedge-shaped cut-out sections of plates 3122 and 3124. Therefore, the stent support assembly can be rotated with little or no deviation of core wire 3106 from the rotational axis. Tailstock support 3112 prevents any excessive movement at the distal end of core wire 3106 as it rotates about its axis and during rotation of rotatable drum 2240.

Figure 40D:
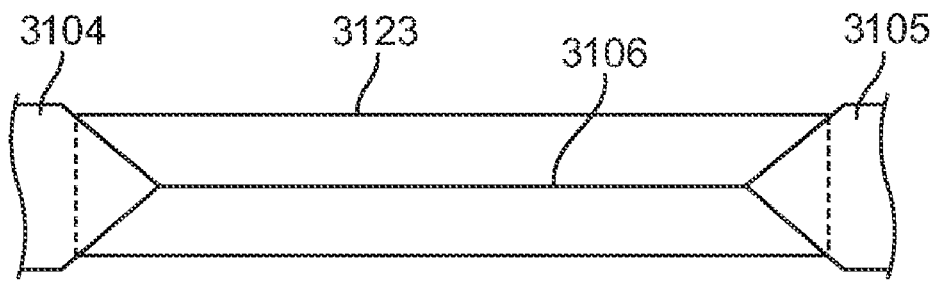
FIGS. 40D-E depicts an axial cross-section of a stents mounted on mandrels.

As shown in FIG. 40D, a stent 3123 can be mounted between mandrel cones 3104 and 3105 to obtain 1:1 rotation between stent 3123 and mandrel cones 3104 and 3105. The gap between the end rings of stent 3123 and mandrel cones 3104 and 3105 can be adjusted to provide an optimal contact force to assure that mandrel cones 3104 and 3105 and stent 3123 have the same or substantially the same axes of rotation.

However, the exerted force should not compress stent 3123 so as to distort the body of stent 3123. Over or under application of support force can lead to problems such as stent 3123 resting too loosely on the stent support assembly, stent 3123 bending, opposing ends of stent 3123 flaring on mandrel cones 3104 and 3105, and increased contact between stent 3123 and mandrel cones 3104 and 3105, all of which can lead to coating defects.

Figure 40E:
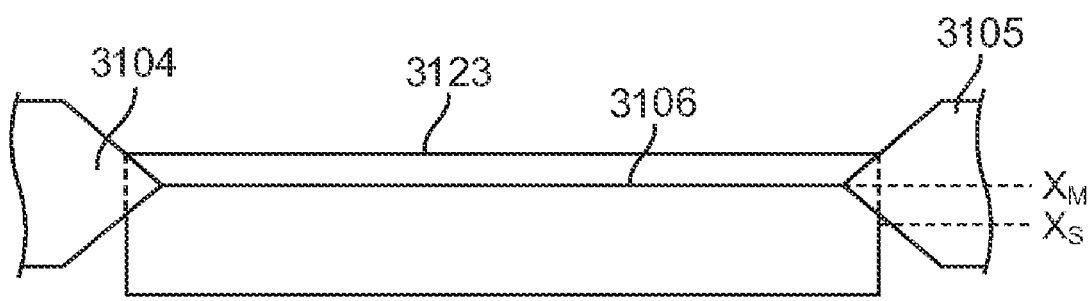

In other embodiments, a stent does not have a 1:1 rotation with supporting end elements such as mandrel cones 3104 and 3105. As shown in FIG. 40E, stent 3123 can be mounted on mandrel cones 3104 and 3105 so that stent 3123 and mandrel cones 3104 and 3105 have a different axis of rotation. Mandrel cones 3104 and 3105 have an axis of rotation $x_M$ and stent 3123 has an axis of rotation $x_S$ longitudinally through its center. Thus, the contact points or area between mandrel cones 3104 and 3105 and stent 3123 continuously change.

Another aspect of the present invention relates to reducing or eliminating coating defects that can result from stent contact with supports, such as mandrels, during coating. While some coating defects can be minimized by adjusting the coating parameters, other defects occur due to the nature of the interface between the stent and the apparatus on which the stent is supported during the coating process. Surface contact between the stent and the supporting apparatus can provide regions in which the liquid composition can flow, wick, and collect as the composition is applied. As the solvent evaporates, the excess composition hardens to form excess coating at and around the contact points between the stent and the supporting apparatus. Upon the removal of the coated stent from the supporting apparatus, the excess coating may stick to the apparatus, thereby removing some of the needed coating from the stent and leaving bare areas. Alternatively, the excess coating may stick to the stent, thereby leaving excess coating as clumps or pools on the struts or webbing between the struts.

Thus, it is desirable to minimize the influence of the interface between the stent and the supporting apparatus during the coating process to reduce or eliminate coating defects. As indicated above, the interface or contact points between a stent support and the stent can lead to defects. This is particularly the case where the support and the stent have 1:1 rotation, and thus, do not move relative to one another during the coating process. The lack of relative movement can lead to stationary contact points caused by the stent adhering to the support at a point of contact.

The contact area between a support and stent can be minimized when the support has a different axis of rotation than the stent. As described above, the ends of a stent can be supported loosely over tapered ends such as cones. Thus, as the mandrel rotates, the contact points continuously change. Even in this approach, the stent can stick to the support members, resulting in stationary contact points.

Figure 41A:
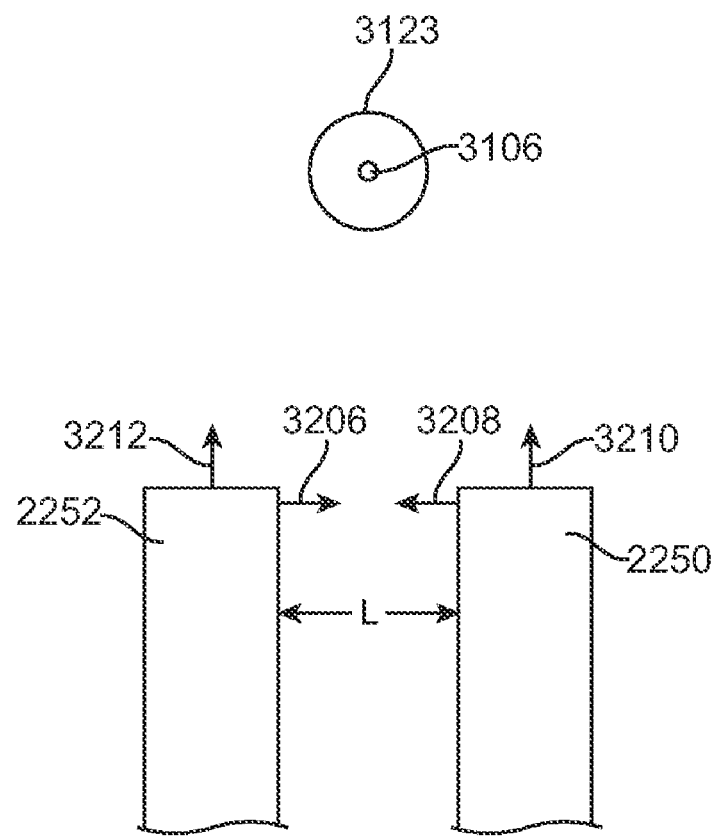
FIGS. 41A-C depicts a close-up view of the stent grippers from FIG. 31.

Embodiments of the present invention include shifting or changing the contact points of a stent during a coating process to minimize the coating defects at the contact points. As shown in FIG. 31, stent gripper plates 2250 and 2252 provide a mechanism to steadily hold the stent on stent support assembly 2222 to enable the stent support assembly to move the contact points of the stent with the stent support assembly. FIG. 41A depicts a close-up view of stent gripper plates 2250 and 2252 from FIG. 31 positioned below stent 3123 disposed over core wire 3106. Stent gripper plates 2250 and 2252 are disposed at a distance L from one another, the distance L being greater than the outside diameter of a stent that is being coated. Stent gripper plates 2250 and 2252 can be shifted toward each other as shown by arrows 3206 and 3208 and upwards towards a stent support assembly positioned above stent grippers 2250 and 2252.

Figure 41B:
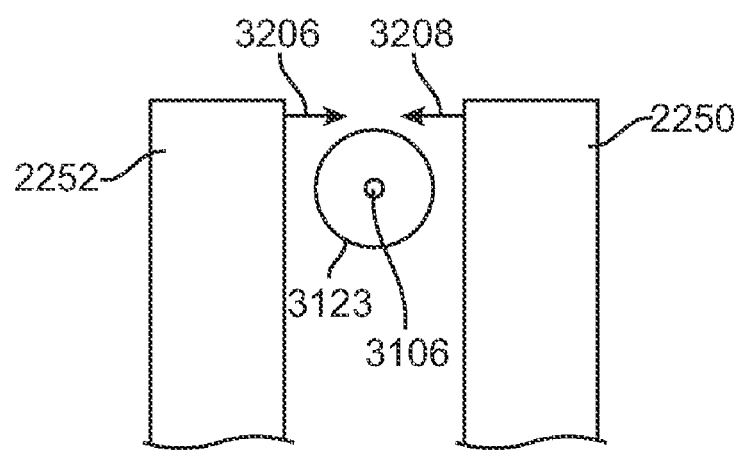
Figure 41C:
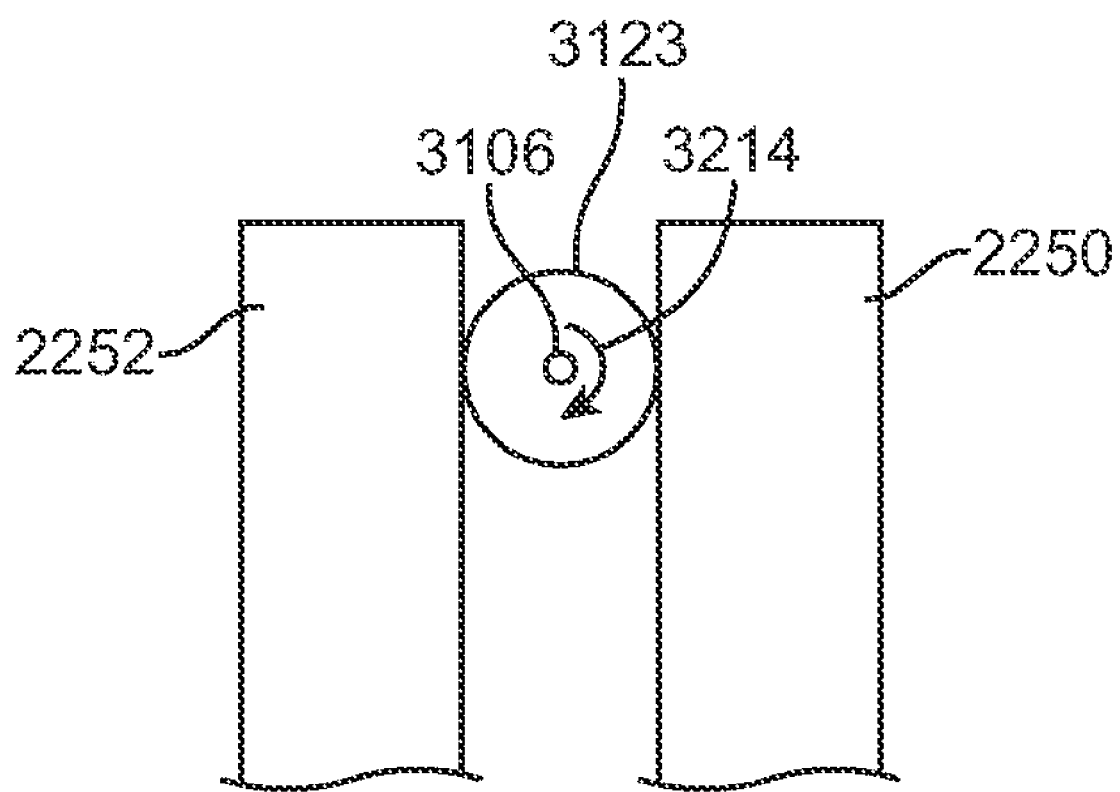

Upon drying of a stent, stent gripper plates 2250 and 2252 are first shifted upwards to the stent support assembly so that stent 3123 is between stent gripper plates 2250 and 2252, as depicted in FIG. 41B. The rotation of the stent support assembly is stopped so that stent 3123 is not rotating. Stent gripper plates 2250 and 2252 then move towards one another as shown by arrows 3206 and 3208. As depicted in FIG. 41C, stent grippers 2250 and 2252 move close to each other to a predetermined gap which will hold stent 3123 stationary while stent support assembly rotates with respect to stent 3123, as shown by an arrow 3214. The stent support assembly can be rotated or clocked just enough to move any contact points between stent 3123 and any part of the stent support assembly, for example, less than 5°. Alternatively, the stent support assembly can be rotated greater than 5°, 10°, 30°, 60°, 90°, 270°, or greater than 360°. In addition, the stent support assembly can be rotated clockwise or counter-clockwise. The rotating or clocking can be uni-directional or bi-directional. For example, the mandrel can be clocked back and forth one or more times.

There are alternative methods of moving contact points or breaking stationary contact points between a stent and a support. In one embodiment, a stent support can be vibrated to break stationary contact points. For example, an ultrasonic device such as a transducer can be used to vibrate a stent support or stent grippers. In another embodiment, a stream or puff of air can be directed at a stent mounted on a support to disturb stationary contact points.

EXAMPLES

The examples and experimental data set forth below are for illustrative purposes only and are in no way meant to limit the invention. The following examples are given to aid in understanding the invention, but it is to be understood that the invention is not limited to the particular materials or procedures of examples.

Tables 1a-d and 2a-d include spray-coating results for a coated stent using an exemplary spray coating device 200. Tables 1a-d provide coating results for an exemplary device referred to as machine 1 and Tables 2a-d provide coating results for an exemplary device referred to as machine 2. Each table represents data for a set of stents. Tables 1a-b and 2a-b are coating results of a poly(butyl methacrylate) (PBMA) primer and 1c-d and 2c-d are coating results for the poly (vinylidene fluoride-co-hexafluoropropene) (PVDF-HFP) drug coating over the primer layer. The coating weight is in μg. The relative standard deviation (RSD) is used to gauge the applied coating weight consistency per spray repetition.

TABLE 1a

Spraying results for 8 mm stent for machine 1.
Machine 1 (8 mm Medium)

| Back Sprayer | Actual Coating Weight | Actual Mass Per Pass |
|---|---|---|
| Average | 273.2 | 4.6 |
| STDev | 6.6 | 0.1 |
| Minimum | 262 | 4.4 |
| Maximum | 290 | 4.8 |
| RSD | 2.4% | 2.4% |
| Coating Integrity Yield |  | 100% |

TABLE 1b

Spraying results for 8 mm stent for machine 1.
Machine 1 (8 mm Medium)

| Back Sprayer | Actual Coating Weight | Actual Mass Per Pass |
|---|---|---|
| Average | 272.7 | 4.5 |
| STDev | 7.2 | 0.1 |
| Minimum | 260 | 4.3 |
| Maximum | 288 | 4.8 |
| RSD | 2.6% | 2.6% |
| Coating Integrity Yield |  | 95.83% |

TABLE 1c

Spraying results for 8 mm stent for machine 1.
Machine 1 (8 mm Medium)

| Back Sprayer | Actual Coating Weight | Actual Mass Per Pass |
|---|---|---|
| Average | 1132.9 | 18.9 |
| STDev | 18.7 | 0.3 |
| Minimum | 1082 | 18.0 |
| Maximum | 1166 | 19.4 |
| RSD | 1.7% | 1.7% |
| Coating Integrity Yield |  | 90.63% |

TABLE 1d

Spraying results for 8 mm stent for machine 1.
Machine 1 (8 mm Medium)

| Back Sprayer | Actual Coating Weight | Actual Mass Per Pass |
|---|---|---|
| Average | 1116.3 | 18.6 |
| STDev | 24.3 | 0.4 |
| Minimum | 1076 | 17.9 |
| Maximum | 1162 | 19.4 |
| RSD | 2.2% | 2.2% |
| Coating Integrity Yield |  | 100.00% |

TABLE 2a

Spraying results for 8 mm stent for machine 2.
Machine 2 (8 mm Medium)

| Back Sprayer | Actual Coating Weight | Actual Mass Per Pass |
|---|---|---|
| Average | 275.2 | 4.59 |
| STDev | 4.9 | 0.08 |
| Minimum | 263.0 | 4.38 |
| Maximum | 284.0 | 4.73 |
| RSD | 1.8% | 1.8% |
| Coating Integrity Yield |  | 96.15% |

TABLE 2b

Spraying results for 8 mm stent for machine 2.
Machine 2 (8 mm Medium)

| Back Sprayer | Actual Coating Weight | Actual Mass Per Pass |
|---|---|---|
| Average | 273.2 | 4.6 |
| STDev | 5.3 | 0.1 |
| Minimum | 261 | 4.35 |
| Maximum | 284 | 4.73 |
| RSD | 1.9% | 1.9% |
| Coating Integrity Yield |  | 96.15% |

TABLE 2c

Spraying results for 8 mm stent for machine 2.
Machine 2 (8 mm Medium)

| Back Sprayer | Actual Coating Weight | Actual Mass Per Pass |
|---|---|---|
| Average | 1113.7 | 18.56 |
| STDev | 23.9 | 0.40 |
| Minimum | 1082.0 | 18.03 |
| Maximum | 1167.0 | 19.45 |
| RSD | 2.1% | 2.1% |
| Coating Integrity Yield |  | 100.00% |

TABLE 2d

Spraying results for 8 mm stent for machine 2.
Machine 2 (8 mm Medium)

| Back Sprayer | Actual Coating Weight | Actual Mass Per Pass |
|---|---|---|
| Average | 1098.0 | 18.3 |
| STDev | 17.2 | 0.3 |
| Minimum | 1071 | 17.85 |
| Maximum | 1133 | 18.88 |
| RSD | 1.6% | 1.6% |
| Coating Integrity Yield |  | 96.43% |

Tables 3a-b include spraying and drying parameters used to obtain the above coating results. Table 3a provides examples showing the spraying process parameters for applying primer and drug coating. Table 3b shows an example of some common process parameters used in applying the primer and drug coating.

TABLE 3a

Coating parameters used in coating device.

| Parameter Description | Primer Coat | Drug coat polymer |
|---|---|---|
| IVEK Pump rate, ml/hr | 5 | 7.5 |
| Atomization air flow, LPM | 12 | 12 |
| Drying gas flow, LPM | 110 | 110 |
| Number of passes | 15 | 40 |
| # of spray passes per dry cycle | 3 | 3 |

TABLE 3b

Coating parameters used in coating device.

| Parameter Description | Parameter Value |
|---|---|
| Spindle Rotation Speed, rpm | 150 |
| Spray translation speed, mm/s | 16 |
| Drying Time, second | 10 |
| Drying Temp, ° C. | 45 |
| Nozzle Start Position, mm | 10 |
| Nozzle End Position, mm | 10 |

Figure 42:
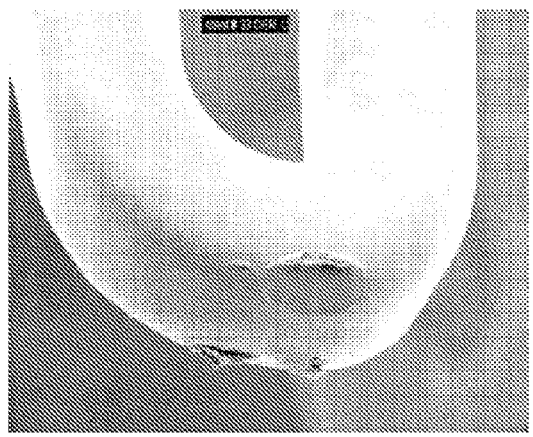
FIGS. 42-46 depict Scanning Electron Microscope images of a coated stent.
Figure 43:
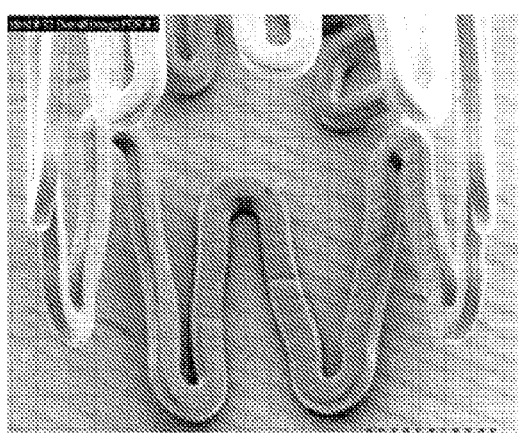
Figure 44:
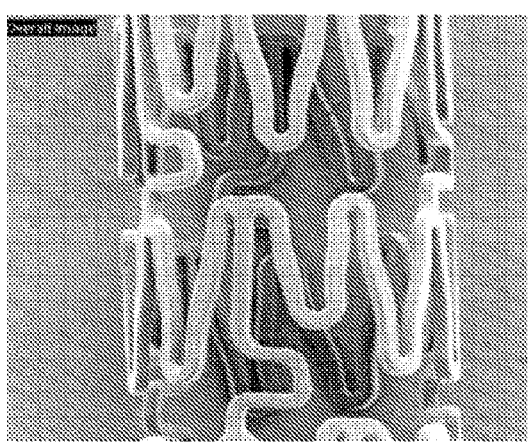
Figure 45:
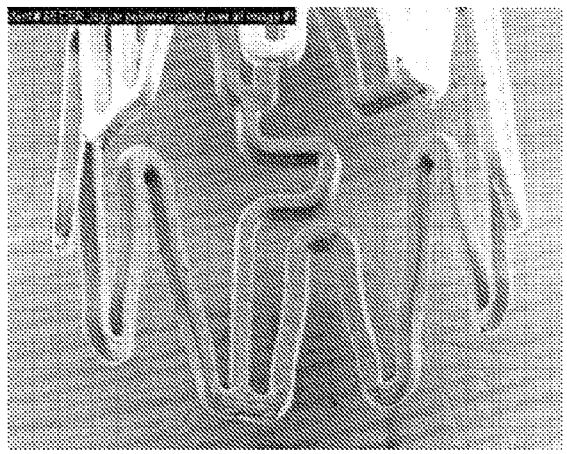
Figure 46:

FIGS. 42-46 are Scanning Electron Microscope images of a stent coated with an exemplary coating device 1200. As above, the stent was coated with PBMA primer and PVDF-HFP. FIG. 42 depicts the U-crown of the coated stent. FIG. 43 depicts the proximal end of the coated stent. FIG. 44 depicts the overall coating quality of the coated stent. FIG. 45 depicts the distal end of the coated stent. FIG. 46 depicts a close-up view (400× high magnification) of the end ring.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

Device for Drying a Coated Stent

The coating composition can include a polymer dissolved in a solvent. Each repetition can be followed by in-process drying involving removal of a significant amount of the solvent(s). In an embodiment, there may be less than 5%, 3%, or more narrowly, less than 1% of solvent remaining in the coating after drying between repetitions. Between repetitions, some or all of the solvent can be removed from the coating material on the stent by subjecting the stent to an in-process drying process. Any suitable number of repetitions of applying the composition followed by removing the solvent(s) can be performed to form a coating of a desired thickness or weight.

A stent coated with coating material can be dried by allowing the solvent to evaporate at room or ambient temperature. Depending on the volatility of the particular solvent employed, the solvent can evaporate essentially upon contact with the stent. Alternatively, the solvent can be removed by subjecting the coated stent to various drying processes. Between repetitions, for instance, room temperature or a warm gas can be blown onto the coated stent to remove solvent. Solvent can also be removed by baking the stent in an oven at a mild temperature (e.g., 60° C.) for a suitable duration of time (e.g., 2-4 hours) or by the application of warm air. There can be some residual solvent left in the coating after the in-process drying depending on the solvent used and in-process drying time. The higher the boiling point of the solvent, the harder it is to remove solvent in the in-process drying process. The coated stent is typically dried in an oven as the final drying step when the multiple deposition stages are completed to remove residual solvent. The residual solvent can have harmful biological effects and plasticizing effects which can alter the release rate and coating properties. The energy source of the oven can range from a convection oven to an infrared oven or UV.

Various embodiments of the present invention are directed to a device and methods for drying and/or curing the coating material applied to a stent. In particular, these embodiments of the invention are intended to improve the oven drying or curing process repeatability for drug-eluting stent manufacturing. In a conventional manufacturing process, stents are spray coated with a drug-polymer solution and manually placed into clean room ovens for the final drying or curing of the coating. The bake time is typically 30 to 60 minutes. The spray coating process produces one stent at a time, and the stents are individually loaded into the ovens by operators where stents are queued into batches for baking.

There are several drawbacks to the conventional process. One drawback is that the operator must repeatedly open the oven door to add and remove stents from the oven which can prevent the temperature profile in the oven from reaching a steady state. This can cause temperature fluctuations that can adversely affect other stents in the batch. The door opening may not be controlled, and may occur at varying time intervals. Variations in door opening times can result in inconsistencies in temperature exposure of drying stents.

Another drawback of a conventional process is that the operator typically manually keeps track of the drying time for each stent in the oven and must take care not to mix up the order of stent addition or removal from the oven. Thus, control of drying time depends upon the operator which can lead to small and, potentially, large inconsistencies in drying time.

Still a further drawback of the conventional process is that stents may be placed in different locations within the oven, leading to differences in baking temperature and/or differences in convection air exposure. Thus, the temperature history of a stent depends on its location in the oven. An additional drawback of the conventional process is that each time the oven door is opened, the stents in the oven are exposed to possible particulate contamination.

Various embodiments of the present invention described below reduce or eliminate the drawbacks of a conventional drying process. The variation in temperature due to door opening is reduced or eliminated. In addition, embodiments eliminate the need for an operator to track stents and baking times. Furthermore, each stent is exposed to the same temperature profile in the oven.

Figure 47:
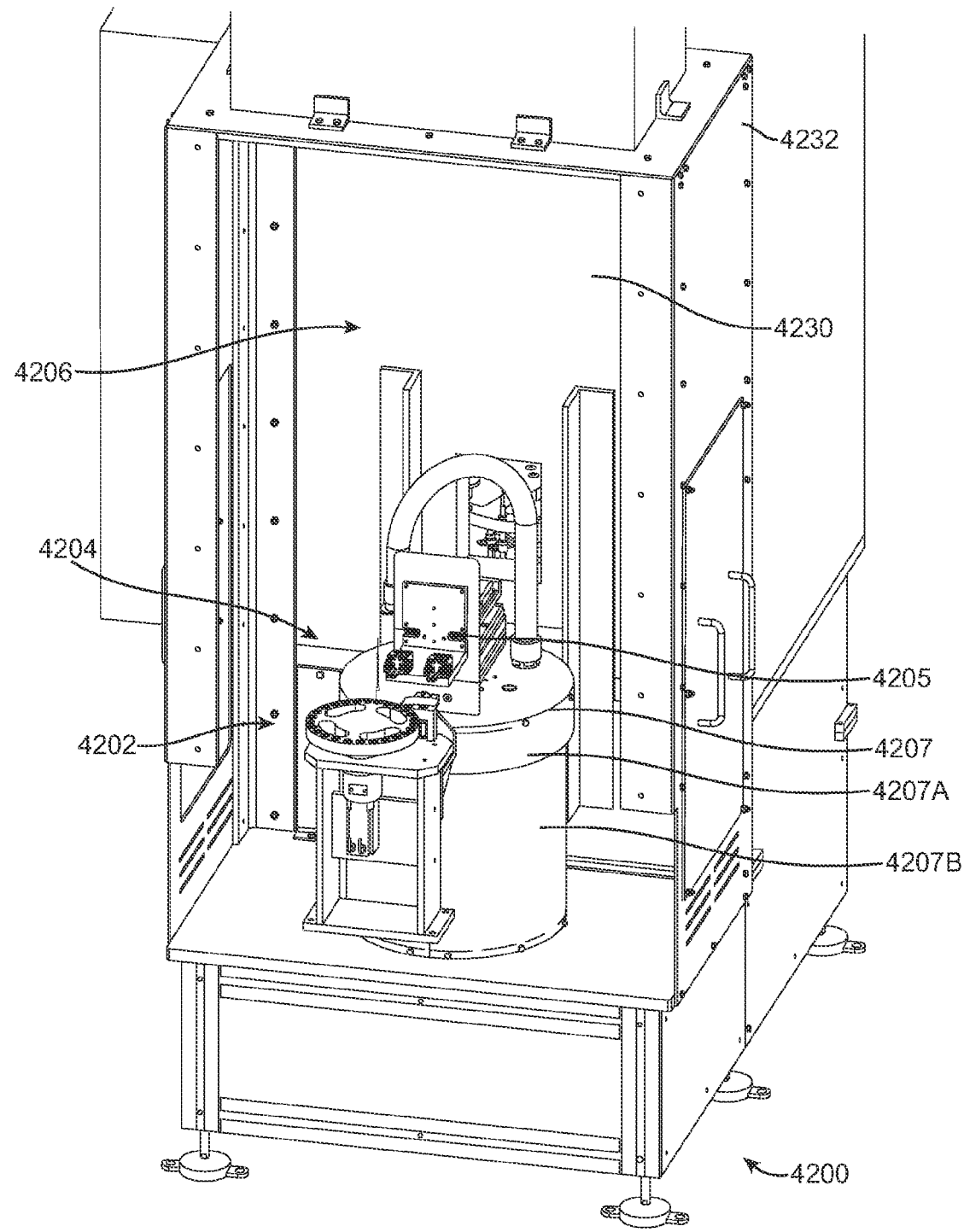
FIG. 47 depicts an exemplary drying device.

Embodiments of the present invention may be illustrated by the exemplary drying device 4200 depicted in FIG. 47. Device 4200 includes a buffer mechanism 4202, a transfer mechanism 4204, and a drying mechanism or oven 4206. Oven 4206 is defined by an enclosure composed of a front wall 4230, side walls 4232, and a back wall (not shown).

Device 4200 can be used in conjunction with any spray coating process. Coated stents can be manually positioned into buffer mechanism 4202 for drying. Alternatively, device 4200 can be a module of an automated process which includes two or more modules designed to coat stents. For example, in an automated system, a robotic arm with grippers can place a stent in buffer mechanism 4202 and a robotic arm with grippers can remove a dried stent from buffer mechanism 4202.

Figure 48:
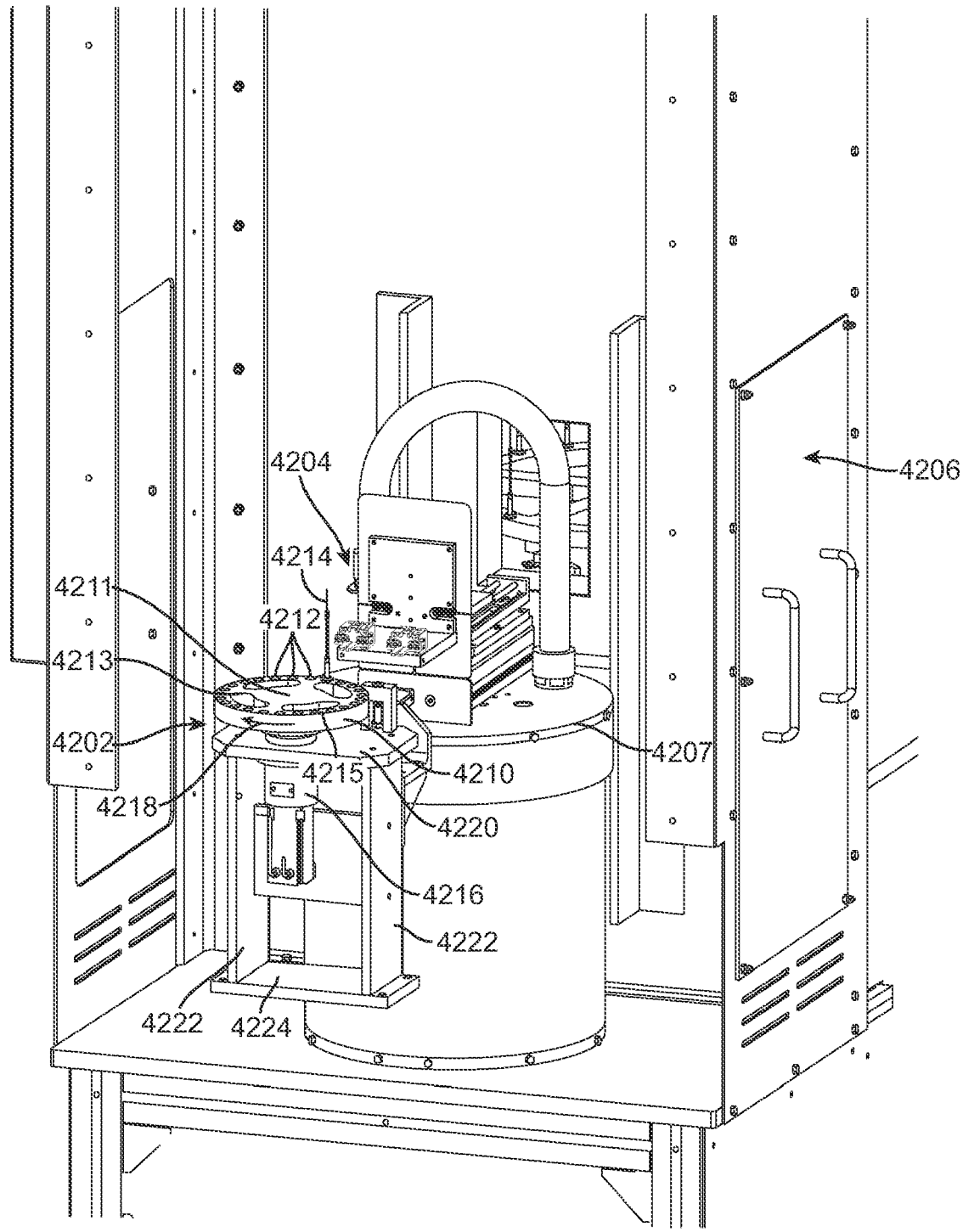
FIG. 48 depicts a close-up view of a drying device.

FIG. 48 depicts a close-up view of device 4200. Buffer mechanism 4202 includes a buffer dial 4210. Stents for drying are loaded onto buffer dial 4210 to await transfer to drying mechanism 4206 for drying and are transferred via transfer mechanism 4204. In a case in which the coating process is faster than the drying process, buffer dial 4210 acts as a buffer between a coating process prior to drying and the drying process. Stents are stored on buffer dial 4210, since stents are generally supplied to the drying process faster than the stents can be dried. Stents that have been dried in drying mechanism 4206 are transferred to buffer mechanism 4202, where they await to be transferred out from device 4200.

Buffer dial 4210 includes a center 4211 with spokes 4213 radiating outward to a peripheral region 4215. Peripheral region 4215 includes a plurality of holes or nests 4212 for holding stent supports, such as stent support 4214, on which stents are mounted. Buffer dial 4210 is coupled to a rotary spindle 4216 that rotates buffer dial 4210 as shown by arrow 4218. Rotary spindle 4216 can be configured to rotate buffer dial 4210 in an indexing or discrete fashion or continuously. The storage capacity of stents in buffer mechanism 4202 can be increased by replacing buffer dial 4210 with one with a greater circumference and having a larger number of holes for storing stents. Buffer dial 4210 can be releasable coupled to rotary spindle 4216, e.g., with screws, etc., to enable switching out of one buffer dial for another. Buffer dial 4210 is mounted on a housing including a mounting plate 4220, two side plates 4222, and a bottom plate 4224.

Figure 49:
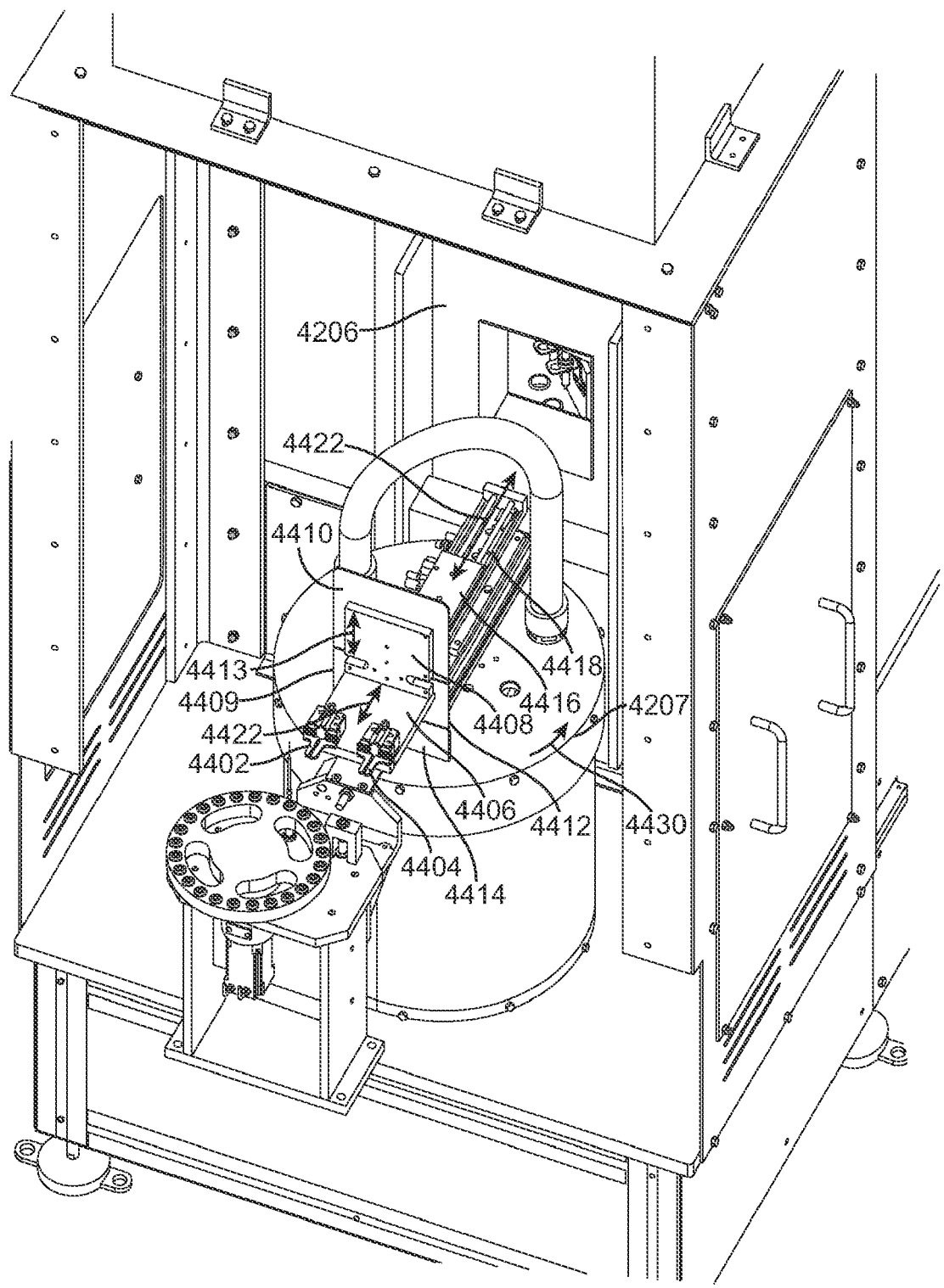
FIG. 49 depicts a close-up view of a transfer mechanism of a drying device.

As noted above, stents are transferred from buffer mechanism 4202 to drying mechanism 4206 via transfer mechanism 4204. As shown in FIG. 47, transfer mechanism 4204 includes a transfer unit 4205 mounted on a rotatable mounting plate 4207. Mounting plate 4207 is supported by cylindrical shields 4207A and 4207B. FIG. 49 depicts a close-up view of transfer mechanism 4204. Transfer mechanism 4204 includes grippers 4402 and 4404. Gripper 4402 grips a stent support disposed in buffer dial 4210, removes the gripped stent support from buffer dial 4210, and carries the gripped stent support to drying mechanism 4206. Gripper 4404 carries a gripped stent from drying mechanism 4206 and places it in buffer dial 4210 to await removal from device 4200 by a gripping device controlled by a robotic arm or that is manually directed. Gripper devices such as those depicted in FIG. 49 are well known to those of skill in the art of automated processing of parts.

Grippers 4402 and 4404 are mounted on gripper plate 4406. Gripper plate 4406 is mounted perpendicular relative to vertical wall 4408 which is mounted on a shield 4409. Shield 4409 is in four parts: a baffle top 4410, a baffle bottom 4412, and two lower shields 4414. Gripper plate 4406 is coupled to an actuator which can move gripper plate 4406 up and down, as shown by an arrow 4413, along with grippers 4402 and 4404 to allow the grippers to remove and place stent supports on and from buffer dial 4210 and oven dial 4702 (described below). The distal end of gripper plate 4406 is coupled to a slider plate 4416 which is mounted on an actuator 4418 that moves slider plate 4416 and gripper plate 4406 as shown by arrows 4420 and 4422, respectively.

Figure 50:
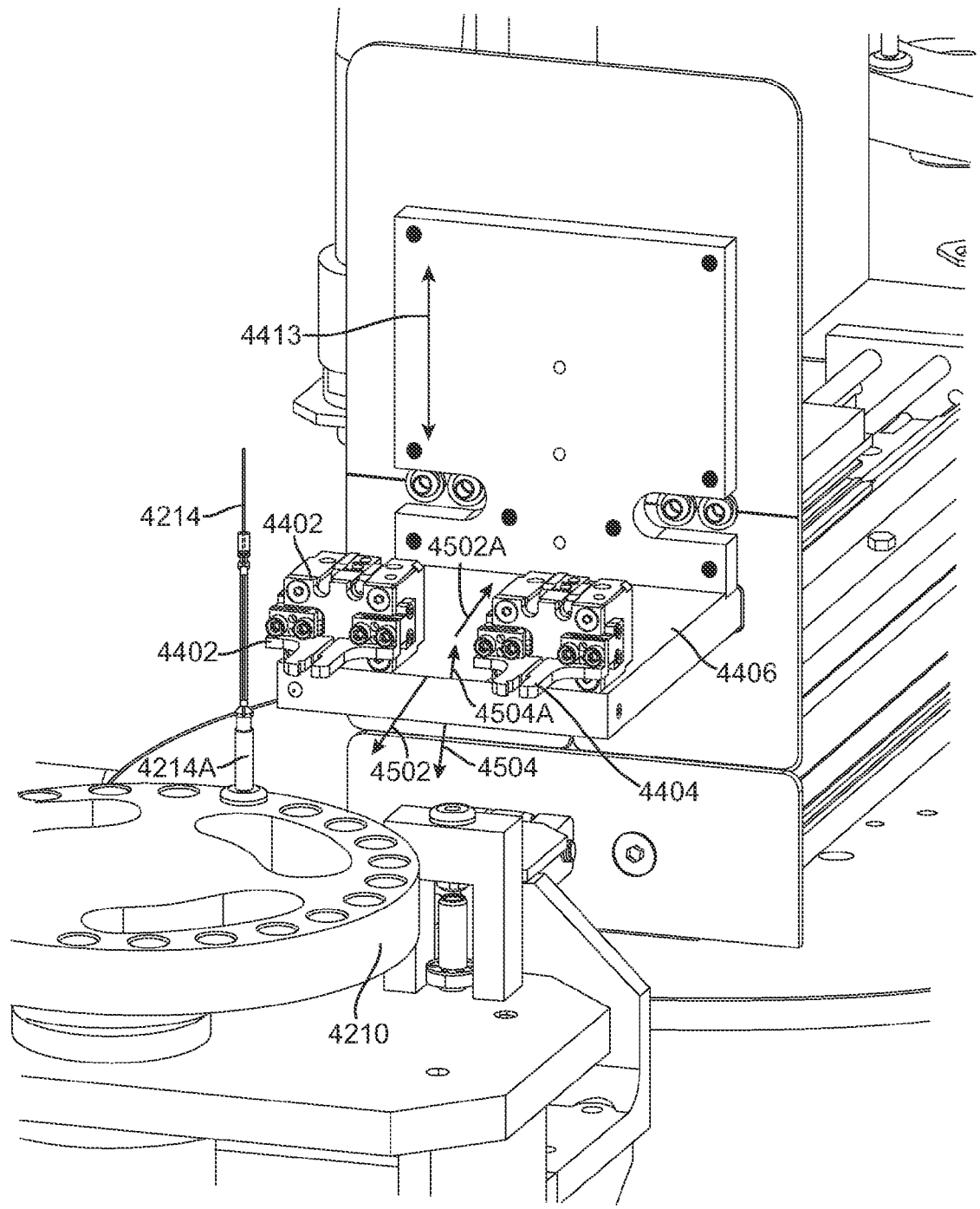
FIG. 50 depicts a close-up view of the transfer mechanism of FIG. 49 in the proximity of stent grippers.

FIG. 50 depicts a close-up view of FIG. 49 focused in the proximity of grippers 4402 and 4404. To grip and remove stent support 4214, gripper plate 4406 moves toward buffer dial 4210 and downward, as shown by arrows 4502 and 4504, respectively, so that gripper 4402 can grip and remove a stent support 4214 which is carrying a stent ready for drying. Gripper plate 4406 moves to position gripper 4402 so that it can grip stent support 4214 at its distal end 4214A.

Gripper plate 4406 can also be moved so that gripper 4404 can deposit a stent support (not shown) with a dried stent in one of holes 4212. After gripping stent support 4214 with gripper 4404, gripper plate 4406 actuates upwards, as shown by an arrow 4504A, to remove stent support 4214 from buffer dial 4210. Gripper plate 4406 is then actuated in the direction of an arrow 4502A.

Figure 51:
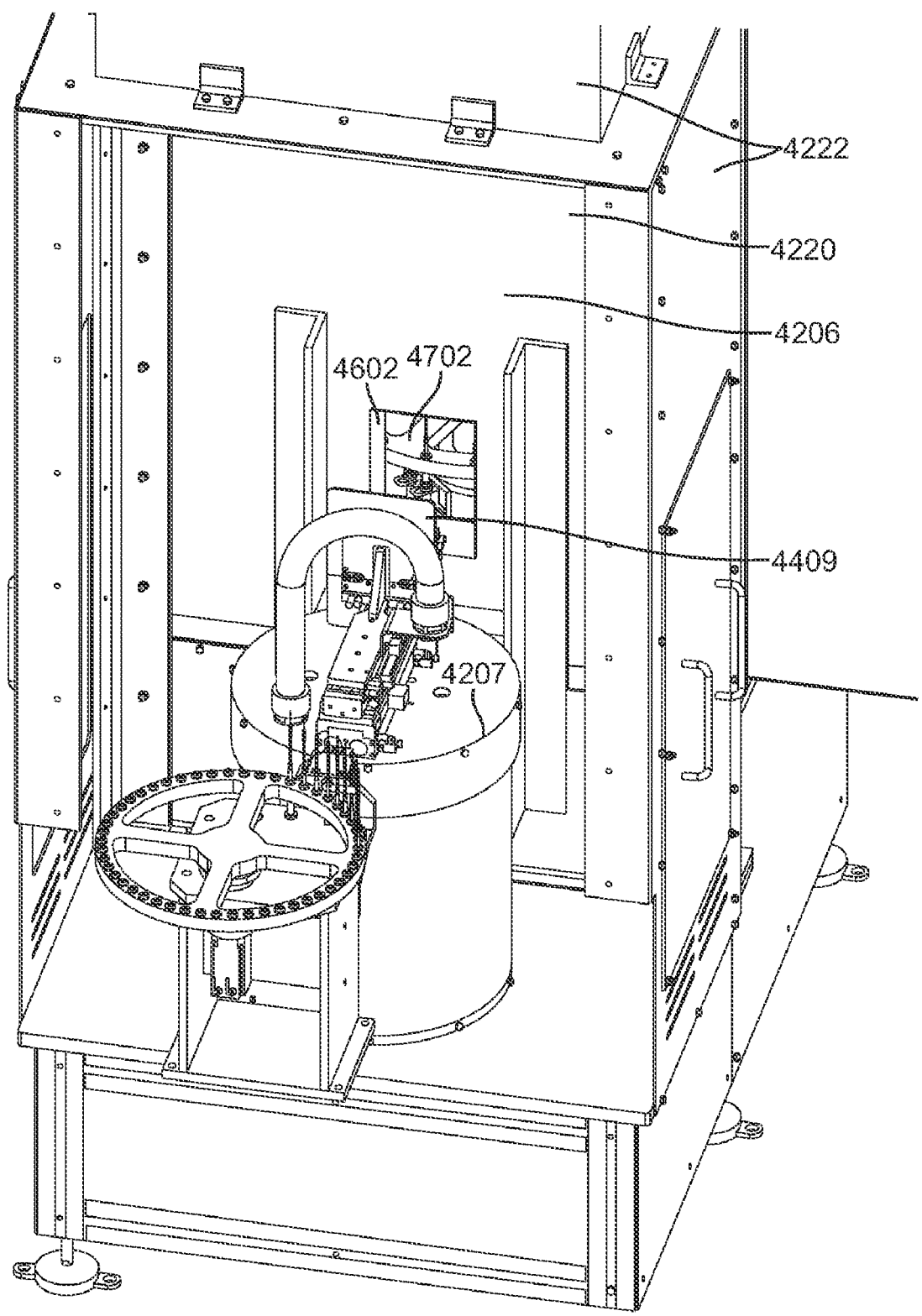
FIG. 51 depicts a view of the transfer mechanism of FIG. 4 with 9 mounting plate rotated 180° from the position shown in FIGS. 47-50.

As shown by arrow 4430 in FIG. 49, rotatable mounting plate 4207 can rotate to position grippers 4402 and 4404 so that gripper 4402 can place a stent support in oven 4206 and gripper 4404 can remove a dried stent from oven 4206. Gripper 4402 can also remove stents from the oven. For example, if a processing sequence is aborted, gripper 4402 can be used to remove all stents from oven 4206. FIG. 51 depicts a view of transfer mechanism 4204 with mounting plate 4207 rotated 180° from the position shown in FIGS. 47-50 showing the back face of shield 4409. In this position, grippers 4402 and 4404 (not shown) are facing oven 4206. Oven 4206 includes a window 4602 through which the interior of oven 4206 is accessible by grippers 4402 and 4404.

Figure 52:
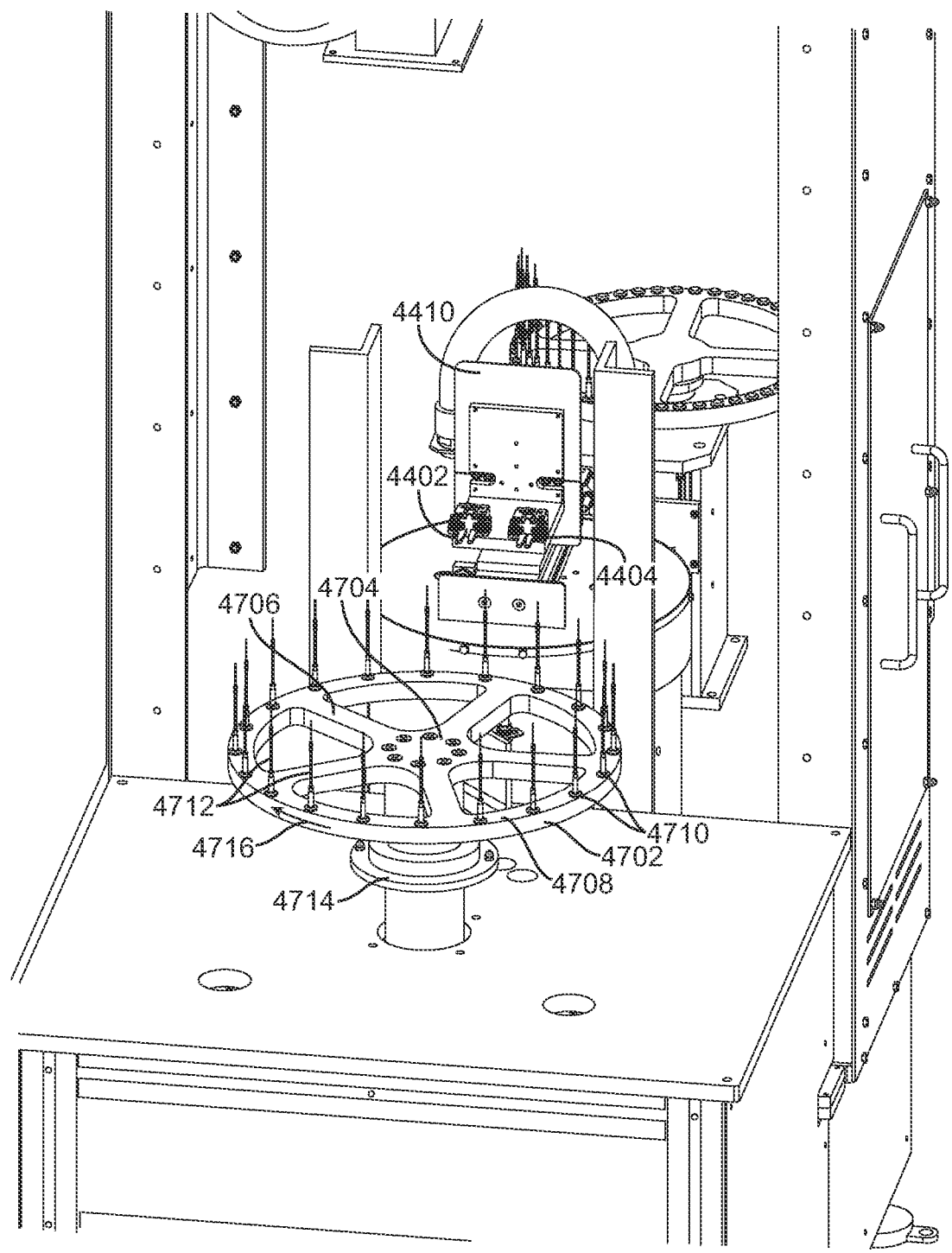
FIG. 52 depicts of view looking through the back of device 200 shown in FIG. 51 with the back and side walls removed.

As indicated in FIG. 47, oven 4206 is defined by an enclosure composed of a front wall 4230, side walls 4232, and a back wall (not shown). FIG. 52 depicts of view looking through the back of device 4200 shown in FIG. 51 with the back and side walls removed. Oven 4206 can be a modified commercially available oven suitable for drying a coated medical device such as a stent. For example, a commercially available or specially modified forced-air convection oven can be used. An exemplary oven is a Despatch LAC1-10 forced-air convection oven, from Despatch Industries, Lakeville, Minn. The modifications are described below.

Device 4200 includes a door (not shown) for covering window 4602. The door can cover or seal window 4602 during the periods between placement and removal of stents from oven 4206. Device 4200 includes a "guillotine" door that closes from bottom to top of window 4602 or opens from top to bottom. The opening and closing of the door in this manner reduces or prevents generation of particles due to the movement of the door. Such particles can contaminate the coated stents. Alternatively, the door can open from bottom to top or the door can swing open and close from the sides, top, or bottom of the opening. The door acts as a thermal barrier to reduce or prevent thermal energy from escaping from the oven. Heat transferred through window 4602 can adversely affect the coating quality of stents stored in device 4200 or coating quality of stents or coating operation adjacent to device 4200. Reducing or preventing heat transfer through window 4602 also provides for a more uniform temperature within oven 4206 and less variability of temperature within oven 4206.

Referring to FIG. 52, device 4200 includes an oven dial 4702 for holding stents during drying within oven 4206. Oven dial 4702 includes a center 4704 with spokes 4706 radiating outward to a peripheral region 4708. Peripheral region 4708 includes a plurality of holes or nests 4710 for holding stent supports 4712 on which stents are mounted. Oven dial 4702 is mounted on a rotary spindle 4714 which rotates oven dial 4702 as shown by an arrow 4716. Rotary spindle 4714 can rotate oven dial 4702 in an indexing fashion, i.e., a discrete step-wise movement.

Figure 53:
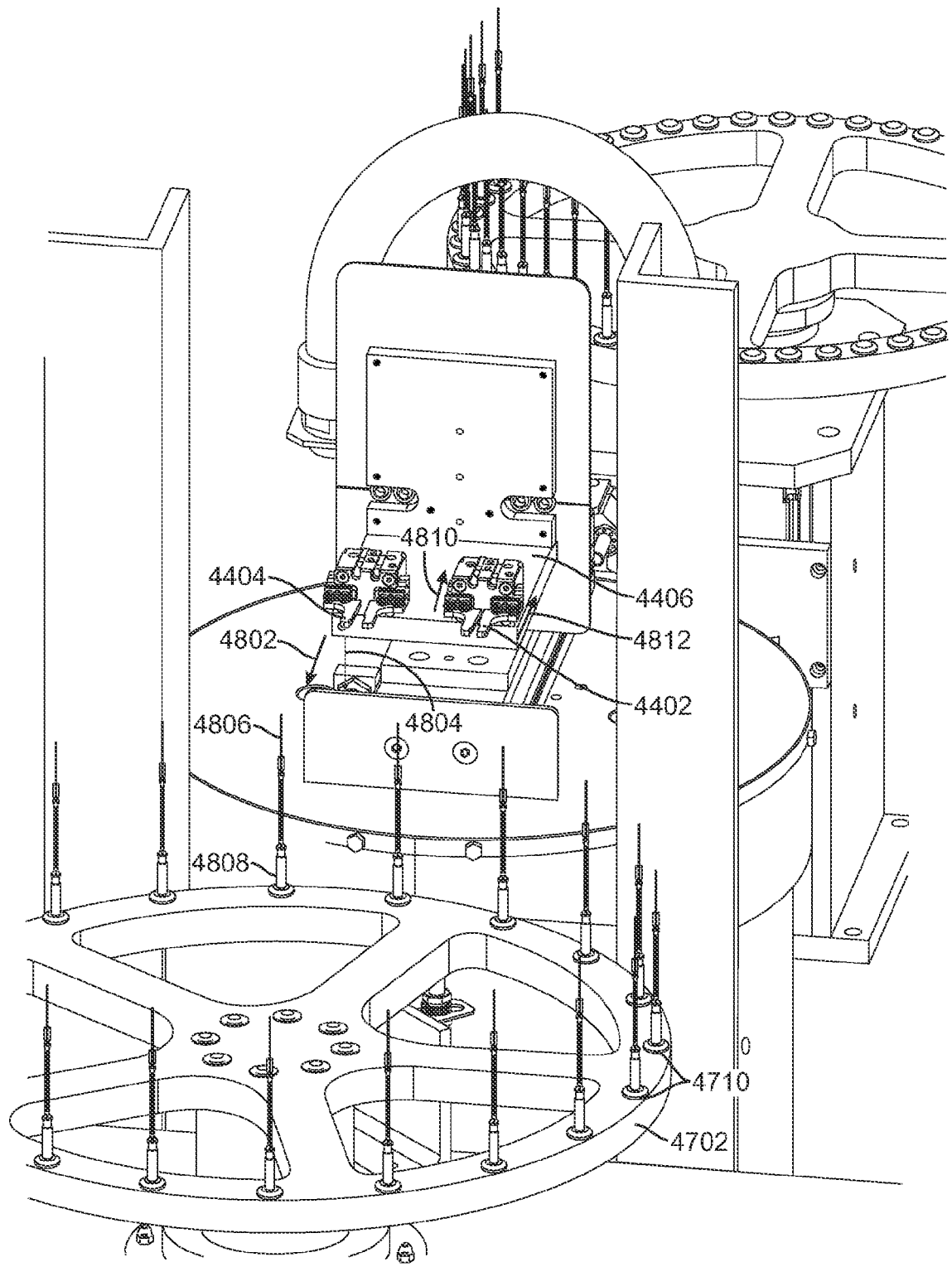
FIG. 53 depicts a close-up view of the oven dial in the proximity of stent grippers.

Dual grippers 4402 and 4404 allow removal of a dried stent from oven dial 4702 and placement of a stent in oven dial 4702. FIG. 53 depicts a close-up view of oven dial 4702 in the proximity of grippers 4402 and 4404. Gripper plate 4406 can move toward oven dial 4702 and downward, as shown by arrows 4802 and 4804, so that gripper 4402 can grip and remove a stent support carrying a dried stent. Gripper plate 4406 is moved to position gripper 4402 so that it can grip a stent support 4806 at its distal end 4808. Gripper plate 4406 is also moved so that gripper 4404 can deposit a stent support with an undried stent in one of holes 4710. After gripping a stent support with gripper 4402, gripper plate 4406 is actuated upwards as shown by arrow 4810, to remove the stent support from oven dial 4702. Gripper plate 4406 is then actuated in the direction of arrow 4812.

Transfer mechanism 4204 can be operated in such a way that one of gripper 4404 or 4402 is carrying a stent either to or from oven 4206, respectively. When operating in this fashion, each time gripper 4404 deposits a stent support in oven dial 4702, gripper 4402 removes a stent support from oven dial 4702, if a stent support is available to remove. In addition, each time gripper 4402 deposits a stent support in buffer dial 4210, gripper 4404 removes a stent support from buffer dial 4210, if a stent support is available to remove.

The residence time of a stent support on oven dial 4702 depends on the size or circumference of oven dial 4702 and the indexing rate of oven dial 4702. The larger the circumference of oven dial 4702, the longer is the residence time of a stent on a stent support on oven dial 4702. Oven dial 4702 can be releasably coupled to rotary spindle 4714, e.g., with screws, etc., to enable switching out of one oven dial for another. In addition, the slower the indexing rate of oven dial 4702, the longer is the residence time. The residence time can be programmable and adjustable.

The polymer and drug in the stent coating can be very sensitive to temperature. Both the polymer and the drug can degrade in an undesirable manner. Additionally, it is important for drying conditions to be consistent from stent to stent since such variability in temperature can affect the properties of the coating.

Several features of oven 4206 described herein reduce variations in temperature that can degrade the coating and that provide for consistent drying of stents. The guillotine door reduces or eliminates temperature variations in oven 4206 between the stent placement and removal steps. In addition, the motion of the rotary oven dial 4702 results in the same temperature exposure of each stent. This results in consistency in temperature exposure from stent to stent. Additionally, oven 4206 includes numerous temperature probes (not shown) that continuously or discretely monitor the temperature. Temperature controllers (not shown) control the temperature based on the monitored temperature and desired temperature. A desired temperature in the oven can be at least 40° C., 50° C., 60° C., or at least 80° C.

Furthermore, the temperature can be recorded and stored at any time or during regular or irregular intervals. The temperature at such intervals can be associated with individual stents in oven 4206 so that there is a temperature history for individual stents. For example, the temperature can be recorded for a stent when it is placed in an oven and when it is removed from an oven.

Figure 54:
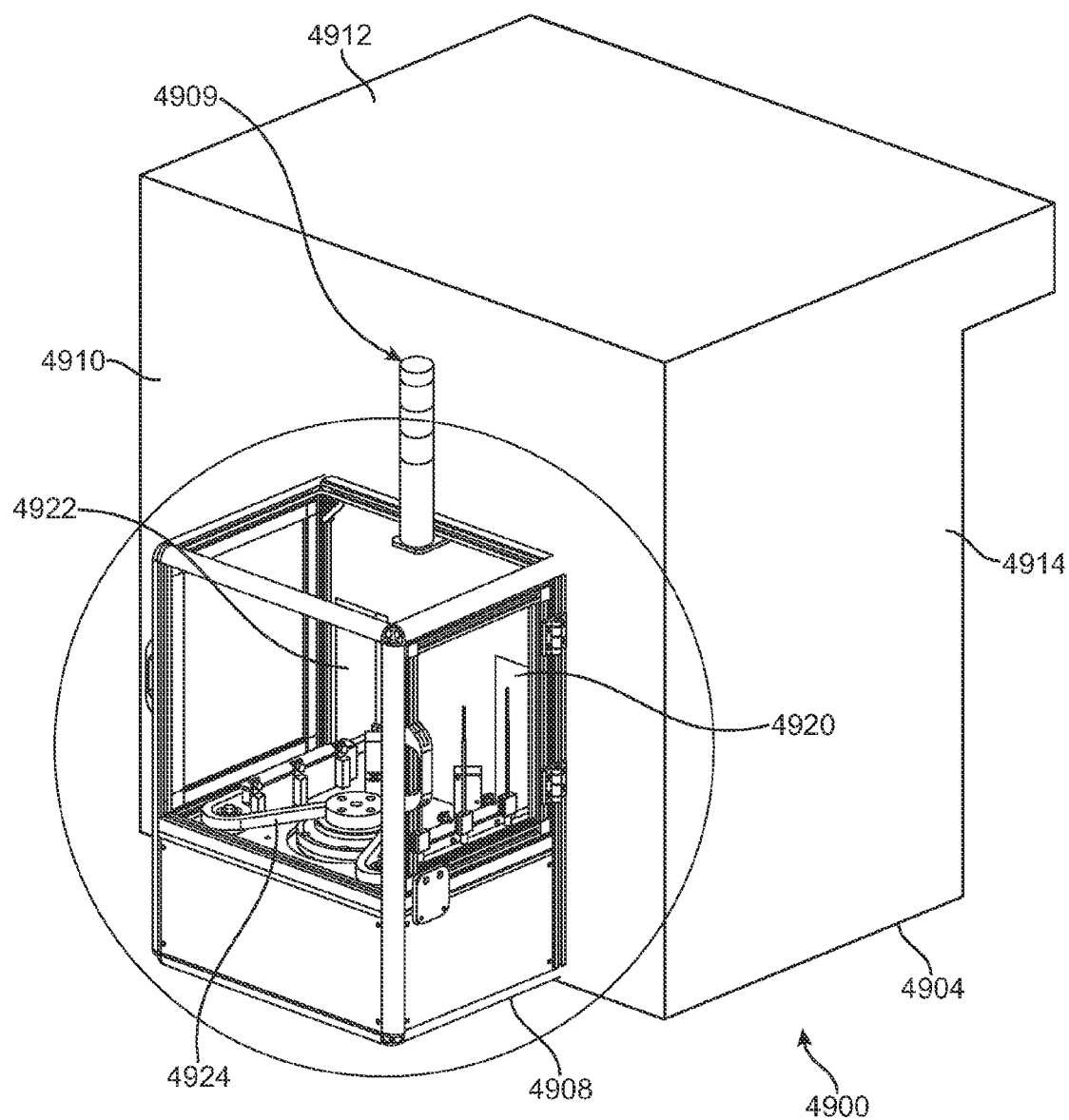
FIG. 54 depicts another exemplary drying device.
Figure 55:
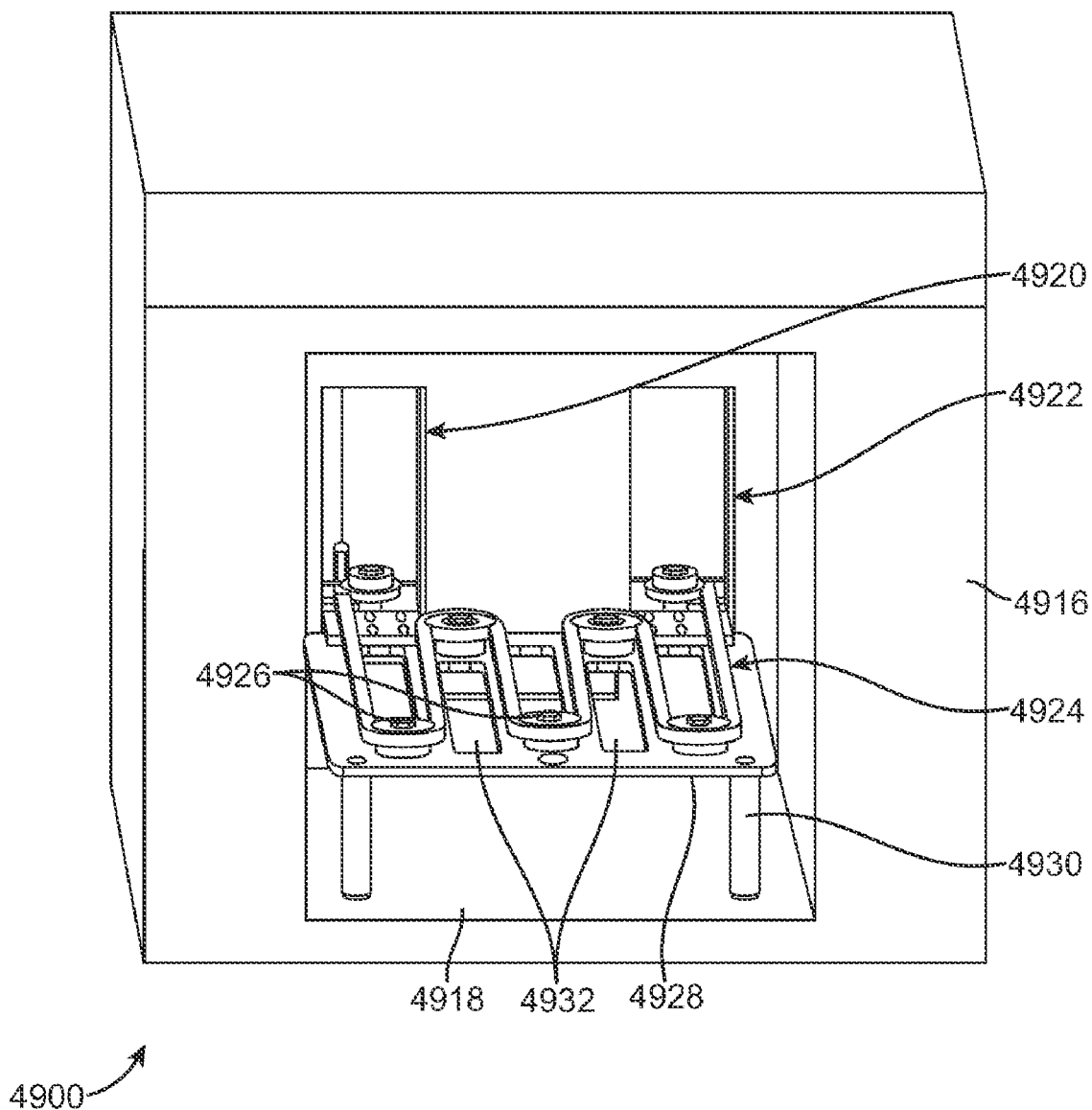
FIG. 55 depicts a rear view of the exemplary drying device shown in FIG. 54 showing the interior of an oven enclosure.
Figure 56:
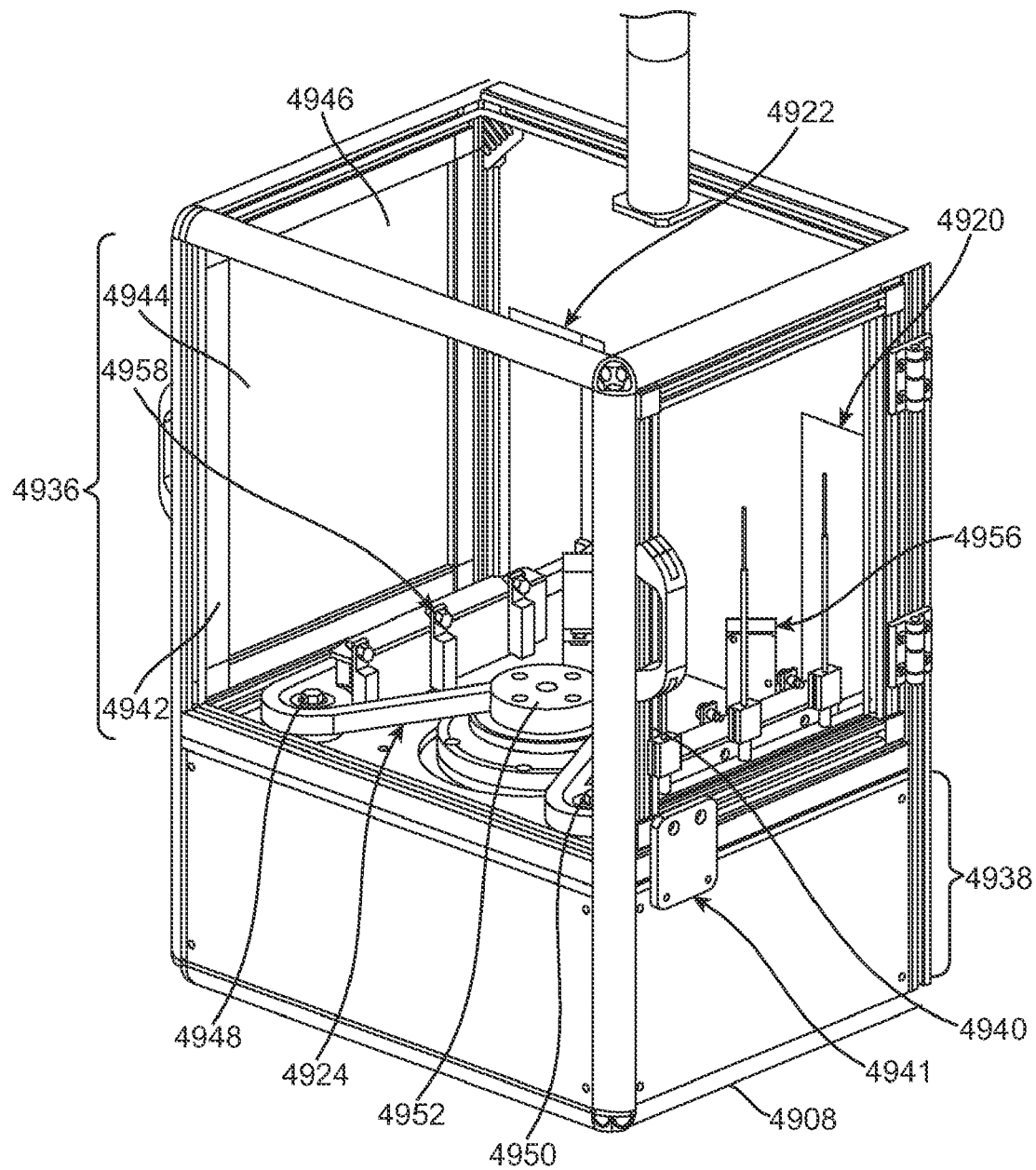
FIG. 56 depicts a close-up view of a loading enclosure of the stent drying device shown in FIG. 54.
Figure 57:
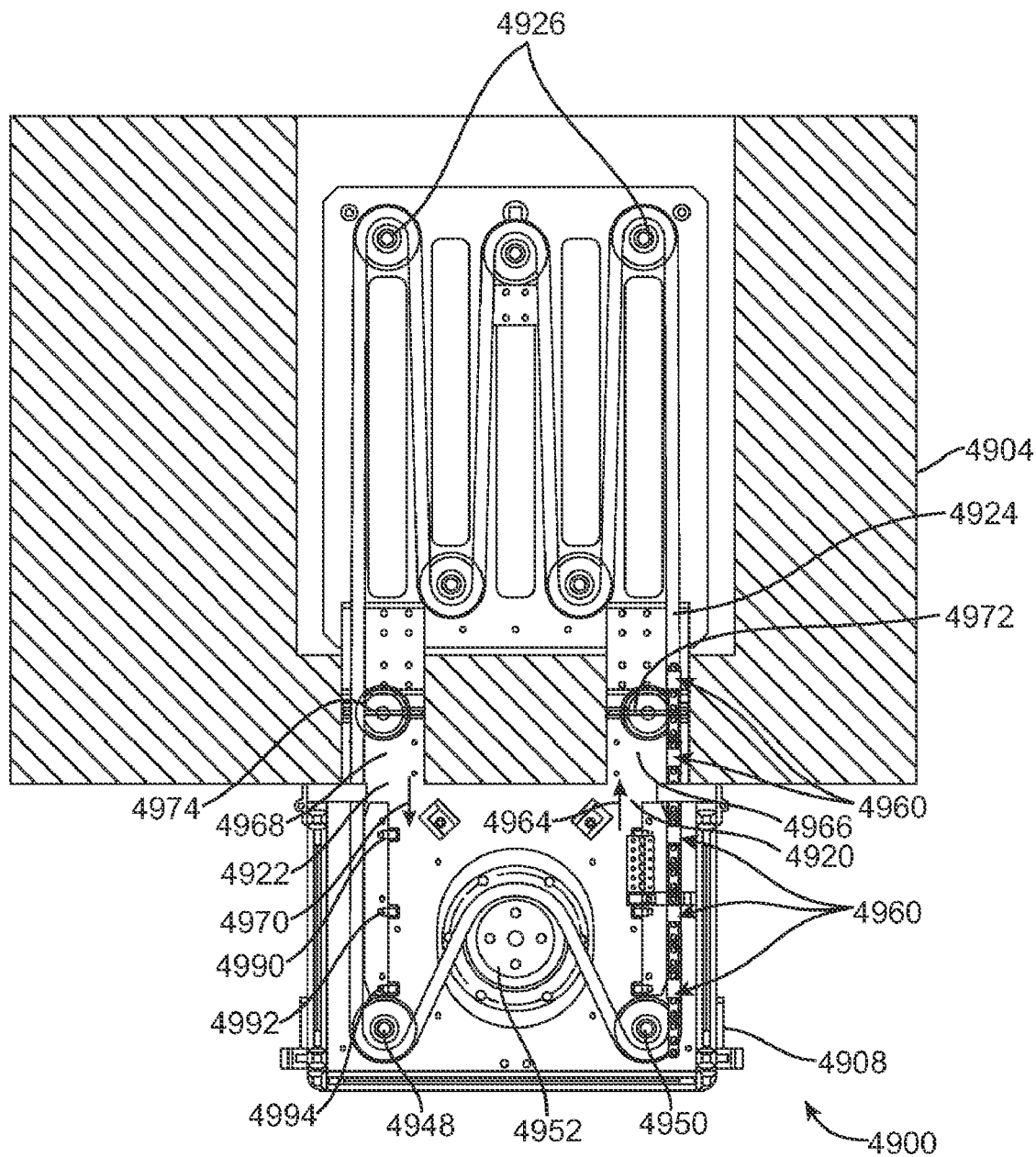
FIG. 57 depicts a top view of the drying device shown in FIG. 54.

FIGS. 54-57 depict another exemplary embodiment of a drying device 4900. As shown in FIG. 54, device 4900 includes two sections or portions, an oven 4904 and a loading enclosure 4908. FIG. 55 depicts a rear view of device 4900 showing the interior of oven 4904. FIG. 56 depicts a close-up view of loading enclosure 4908. FIG. 57 depicts a top-sectional view of device 4900 shown in FIG. 54.

Oven 4904 can be a modified commercially available oven suitable for drying a coated medical device. For example, a model CR1 clean room oven, manufactured by Sheldon Manufacturing Inc. of Cornelius, Oreg., can be modified in the manner described below. Oven 4904 includes an oven enclosure with a front wall 4910, top wall 4912, a bottom wall (not shown), side walls 4914, and a rear wall 4916. Rear wall 4916 has an opening 4918 and a door that seals the opening. The door has been removed to show the interior of the oven enclosure. Oven 4904 also includes two rectangular front openings 4920 and 4922 in front wall 4910 which are visible in FIG. 54 and through the interior of the oven enclosure in FIG. 55.

As shown in FIG. 55, device 4900 includes a conveyor belt or chain 4924 for transporting stents into oven 4904 from loading enclosure 4908, through oven 4904, and out of oven 4904 back into loading enclosure 4908. Conveyor belt 4924 follows a zig-zag pattern in the oven interior. Other paths can be used, for example, round oval, rectangular, combinations thereof, etc.

Conveyor belt or chain 4924 can be made up of links or perforations so that it can be directed or driven through the oven enclosure using gears 4926 with teeth which are supported on a plate 4928. Plate 4928 is supported on the floor of oven 4904 by elongate members 4930. Plate 4928 includes openings 4932 that allow for circulation of air within the oven enclosure. Conveyer belt 4924 can also be "featureless", possessing no perforations. Featureless gears can be driven and guided by gears without teeth. Exemplary belts can be obtained from Belt Technologies, Inc. in Agawam, Mass.

Referring to FIG. 56, stents can be loaded onto device 4900 into loading enclosure 4908. Loading enclosure 4908 has a top section 4936 supported by a bottom section 4938. Loading enclosure 4908 has an access door 4940 that allows access to the interior of loading enclosure 4908 to load stents on conveyor belt 4924. Access door 4942 allows access for unloading of stents that have passed through oven 4904. When the access doors are closed, the enclosure provides for operator safety from moving conveyor belt 4924. As shown, doors 4940 and 4942 can include plates made from transparent material such as plastic or glass to allow viewing of the interior of loading enclosure 4908. Front panel 4944 and top panel 4946 can also be made from a transparent material to allow viewing.

Conveyor belt 4924 is directed or driven through the interior of loading enclosure 4908 by gears 4948, 4950, and 4952. One or more of the gears are drive gears which are coupled to a motor that rotates the gears and drives conveyor belt 4924. In some embodiments, stents can be loaded onto barcode-labeled tracking mandrels before placement into loading enclosure 4908 which can include barcode readers 4956. Barcode readers 4956 are in communication with a control system that keeps track of stents. Photosensors 4958 are included in loading enclosure 4908 near the exit of oven 4904 to confirm the presence of tracking mandrels. Loading enclosure 4908 can be supplied with filtered air at a positive pressure, to reduce or prevent particulate contamination from entering as access doors are opened.

FIG. 57 shows a top sectional view of device 4900. Stents mounted on tracking mandrels are loaded into recesses 4960 in conveyor belt 4924. Conveyor belt 4924 moves the mounted stents into oven 4904 as shown by an arrow 4964 though opening 4920 and into a access tunnel 4966. Conveyor belt 4924 then moves the stents into the oven enclosure through the zig-zag pattern. Stents exit oven 4904 through an access tunnel 4968 and opening 4922 into loading enclosure 4908, as shown by an arrow 4970.

Access tunnels 4966 and 4968 include revolving doors 4972 and 4974, respectively, to reduce temperature fluctuations within the oven enclosure. Revolving doors 4972 and 4974 can be coupled to idler sprockets that rotate as the chain moves to provide synchronized motion of the doors relative to the tracking mandrels. Conveyor belt 4924 can move in preselected increments (e.g., one, two, or three inches), and dwell for a pre-selected time after each movement. The movements of conveyor belt 4924 can be servo-controlled with programmable acceleration/deceleration and velocity. The movements can be between 0.5 and 1.5 seconds in duration, so that revolving doors 4972 and 4974 are open for very brief times to minimize exposure of the oven interior. In an incrementally moving conveyor belt 4924, FIG. 57 depicts a first unloading position 4990, a second unloading position 4992, and a third unloading position 4994.

As shown in FIG. 56, door interlocking mechanisms 4941 on doors 4940 and 4942 prevent undesired opening of the doors while conveyor belt 4924 is moving. In one embodiment, interlocking mechanisms 4941 are synchronized to chain movement so that conveyor belt 4924 does not move while doors 4940 or 4942 are open.

Figure 58:
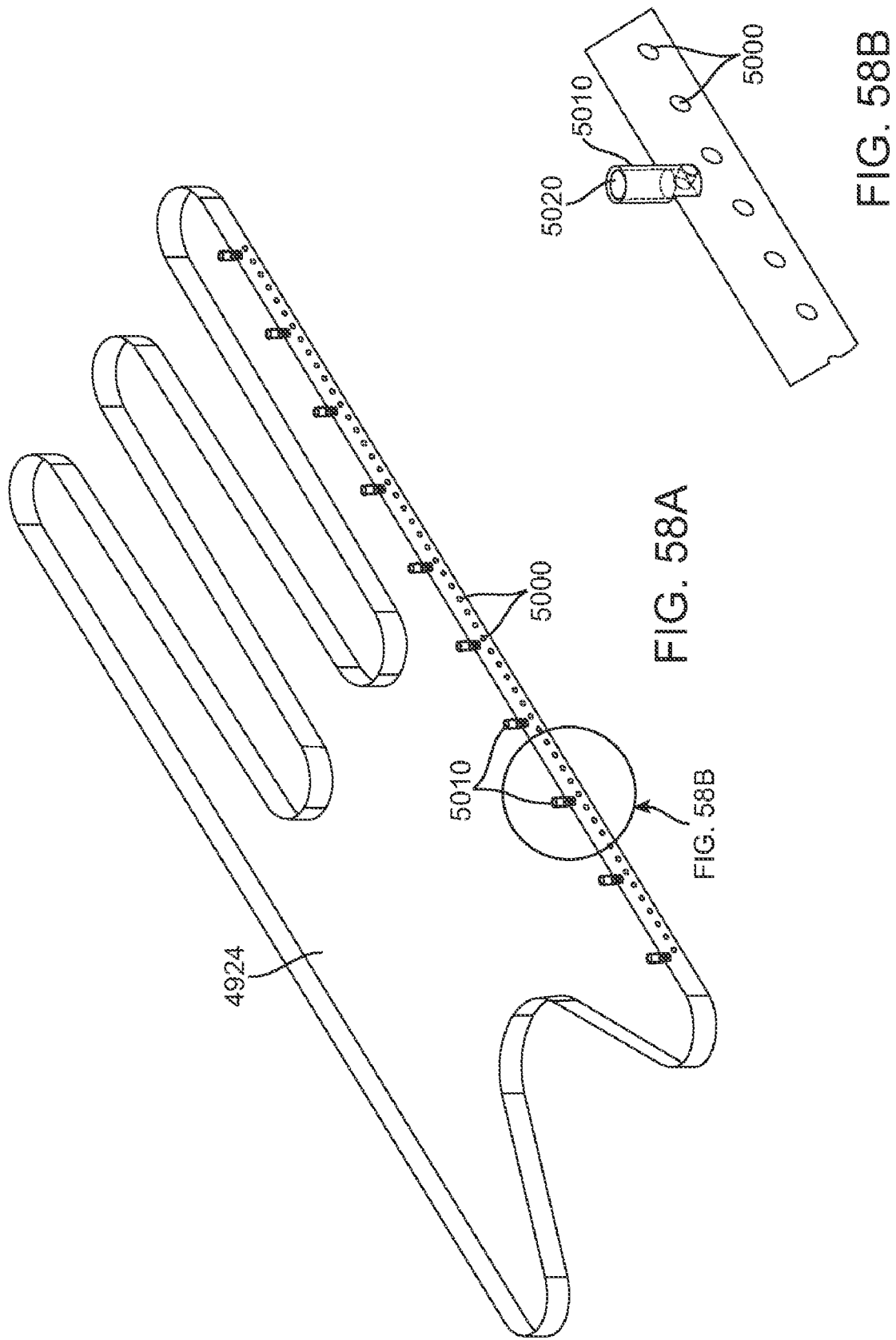
FIG. 58A depicts a close-up view of a conveyor belt.
FIG. 58B depicts stent mandrel supports in the conveyer belt of FIG. 58A.

FIG. 58A depicts a close-up view of conveyor belt 4924 which includes a plurality of holes 5000 for engaging gears. Conveyor belt 4924 includes a plurality of mandrel supports 5010 for supporting mandrels supporting stents. As shown in FIG. 58B, mandrel supports 5010 have a cylindrical recess 5020 in which a proximal end of a mandrel can engage.

Referring to FIG. 54, loading enclosure 4908 can also include a light tower 4909 that displays the status of the stents on conveyor belt 4924. Light tower 4909 can be in communication with sensor 4958. For example, a green light can blink when a stent enters first unloading position 4990. A yellow light can blink when the stent reaches second unloading position 4992, and a red light can blink when the stent reaches third unloading position 4994. All lights can blink if the stent is not unloaded from third unloading position 4994. Sensor 4958 can be in communication with a control system which can lock device 4900 if a stent moves beyond third unloading station 4994.

In some embodiments, sensors can be provided that detect whether and how long doors 4940 and 4942 are open. The sensors can be in communication with a control system that can signal an alarm system. An alarm can sound if doors 4940 or 4942 are left open more than a selected amount of time, e.g., 10 seconds. In addition, device 4900 can lock up if doors 4940 or 4942 are open at indexing time or are open more than one dwell or index cycle. Additionally, the rear door can also be monitored. A dry cycle time can be adjusted for a door open time interruption. A control system can be adapted to modify the cycle time to account for interruptions due to open doors.

Figure 59:
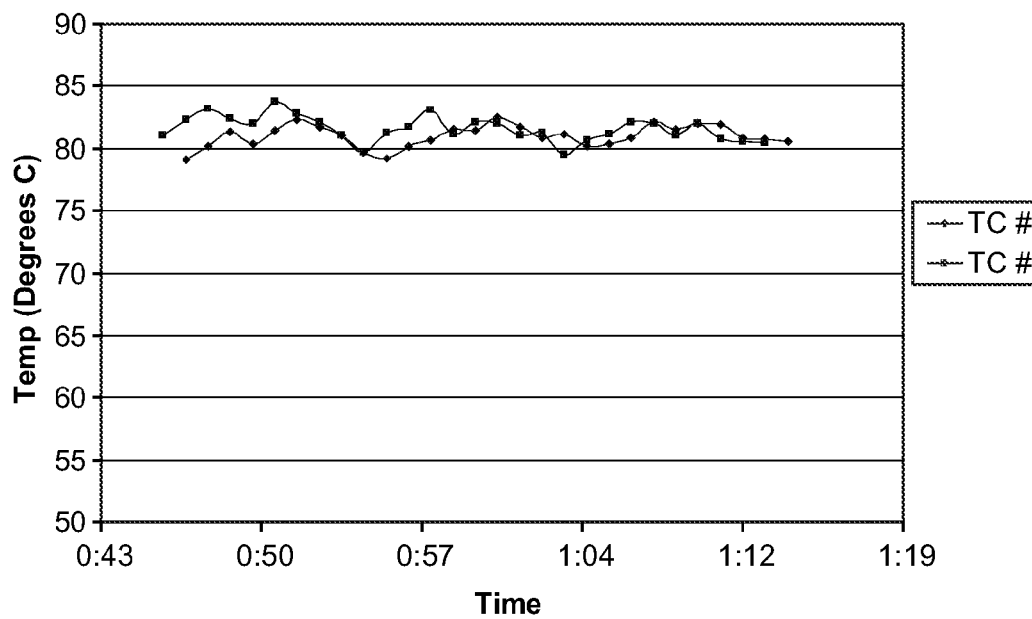
FIG. 59 depicts a plot of the temperature as a function of time within a conveyor oven.
Figure 60:
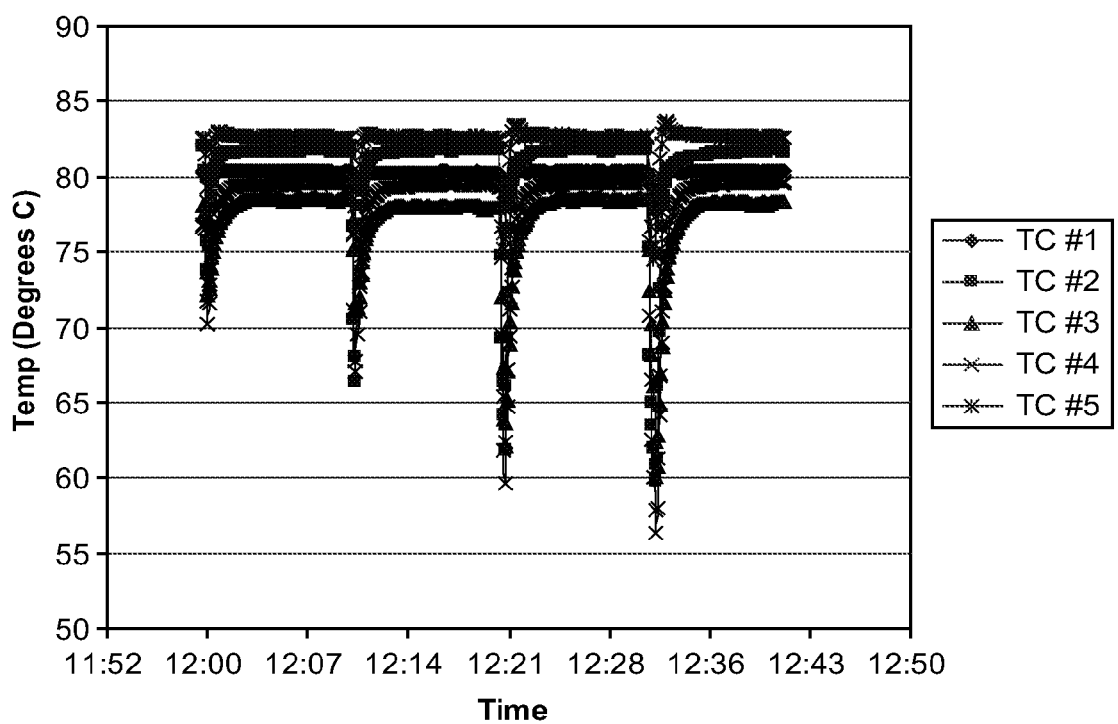
FIG. 60 depicts a plot of the temperature as a function of time within a conventional batch oven.

FIG. 59 and FIG. 60 are plots of the temperature as a function of time within a conveyor oven and a conventional batch oven, respectively. FIG. 59 includes data for two different sensors positioned within the conveyor oven. FIG. 60 includes data for five different sensors positioned within the conventional oven. In FIG. 60, the dips in the temperature correspond to openings of the door. FIG. 59 shows that the temperature in conveyor oven is relatively consistent over the time frame measured.

The baking duration of the stents can be a function of the dwell time and the length of a chain within the oven. In one exemplary embodiment, conveyor belt 4924 is 105 inches with 36 stents in the oven. A dwell time of 100 seconds between chain movements provides a total baking time of 60 minutes for each stent.

Device for Inspecting a Stent

The ability to quickly and accurately inspect stents for defects is an important part of the process of manufacturing stents. In some applications, the required tolerances and/or regulations may be extremely demanding. Additionally, the small dimension of stents can make visual inspection extremely challenging and time consuming. Furthermore, in addition to manufacturing defects, drug coating on stents introduces the possibility for other defects. For example, the coating may pool between gaps in the lattice structure, or may allow a foreign object (such as dust or a polymer strand) to adhere to the stent. The embodiments of the present invention address these as well as other needs.

Figure 61:
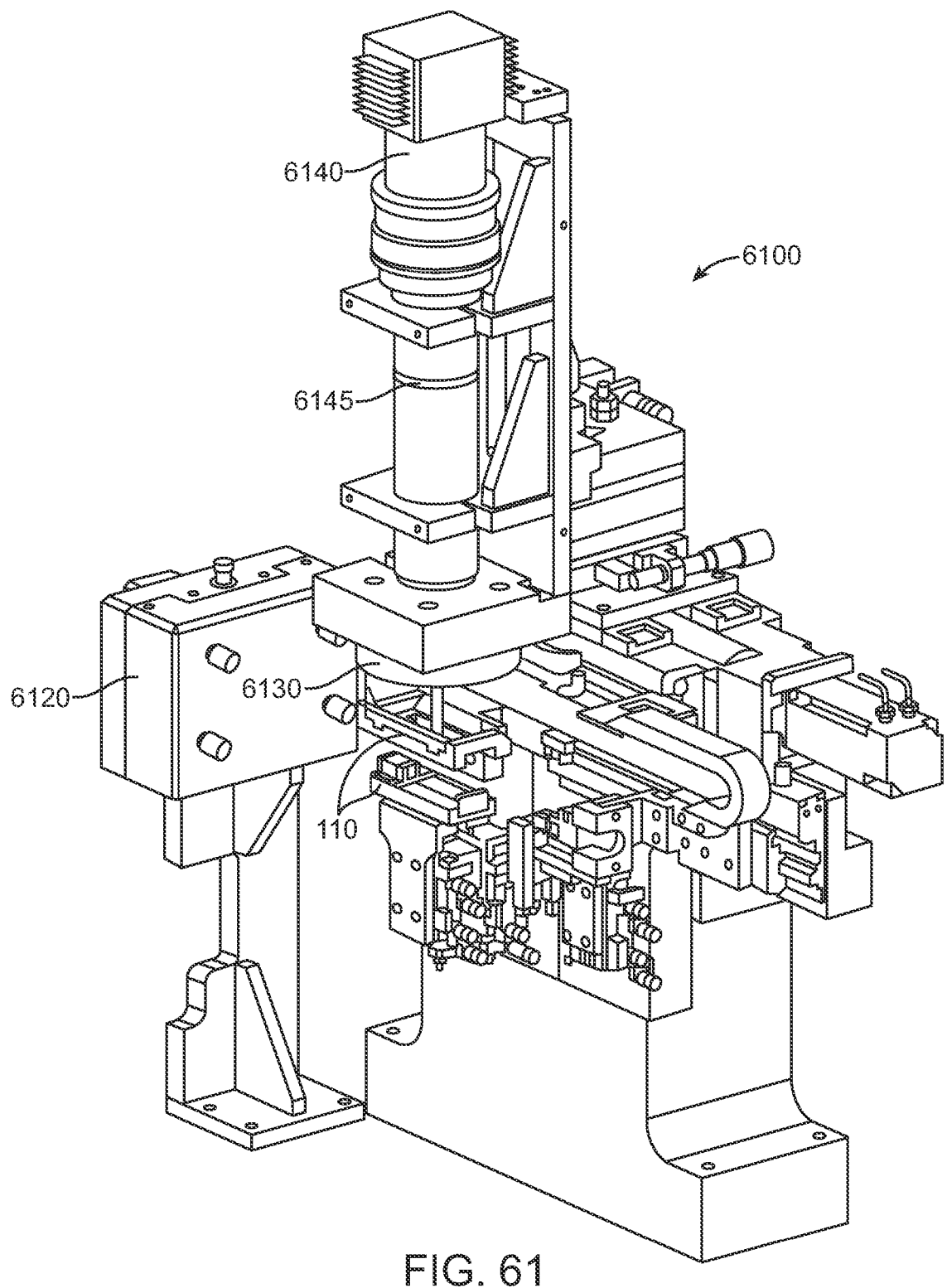
FIG. 61 is a three-dimensional design schematic depicting an exemplary system for inspecting a stent according to various aspects of the present invention.

Referring to FIG. 61, an inspection system 6100 may be configured to inspect stents 10 to determine whether proper manufacturing tolerances have been met, as well as to identify defects. The inspection system 6100 may include a roller assembly 6110, a drive system 6120, a light 6130, and a camera 6140. The inspection system 6100 may interface with any other appropriate systems and devices, such as a computer control system.

Figure 62:
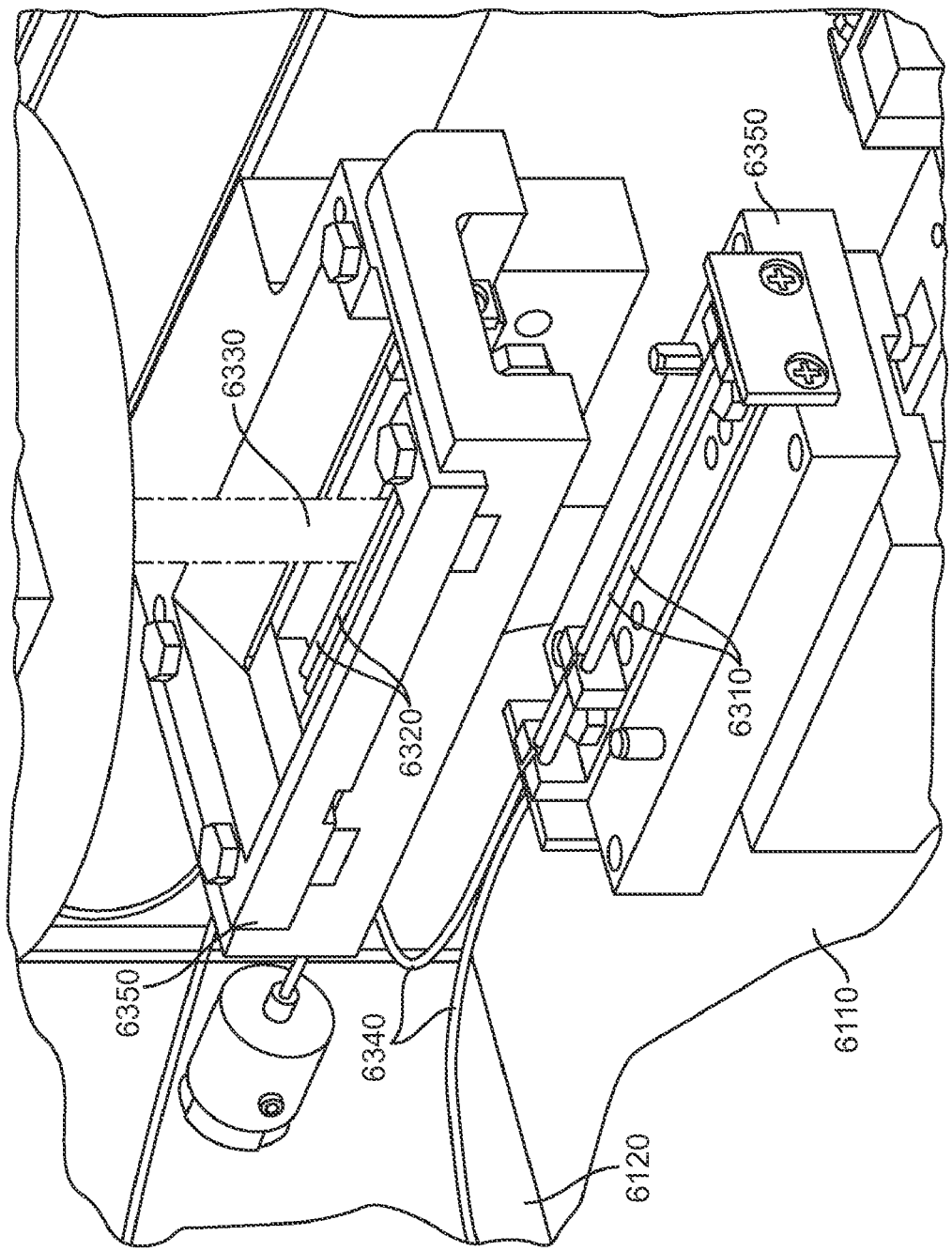
FIGS. 62 and 63 are three-dimensional design schematics depicting details of the system in FIG. 61.

The roller assembly 6110 holds the stent 10 in place and rotates the stent 10 about its longitudinal axis to allow the stent 10 to be imaged. The roller assembly 6110 may be configured to handle any cylinder of any configuration and dimension. Referring now to FIG. 62, a roller assembly 6110 according to various aspects of the present invention may include a lower pair of rollers 6310 and an upper pair of rollers 6320. The roller assembly 6110 may be configured to allow the upper rollers 6320 to rise to allow a stent 10 to be placed between the two lower rollers 6310, then drop down to cradle the stent 10 between the four rollers 6310, 6320. Similarly, the lower rollers 6310 may be configured to drop down to allow the loading and unloading of the stent 10, then rise up to allow the stent 10 to be cradled by the four rollers 6310, 6320. The rollers 6310, 6320 may interface with any suitable structure or device. For example, the rollers 6310, 6320 may be supported by bearing blocks 6350 that may be configured to move up and down to allow loading and unloading of the stent 10. The rollers 6310, 6320 may be configured to move in any direction and in any manner to achieve any other desired result.

Figure 63:
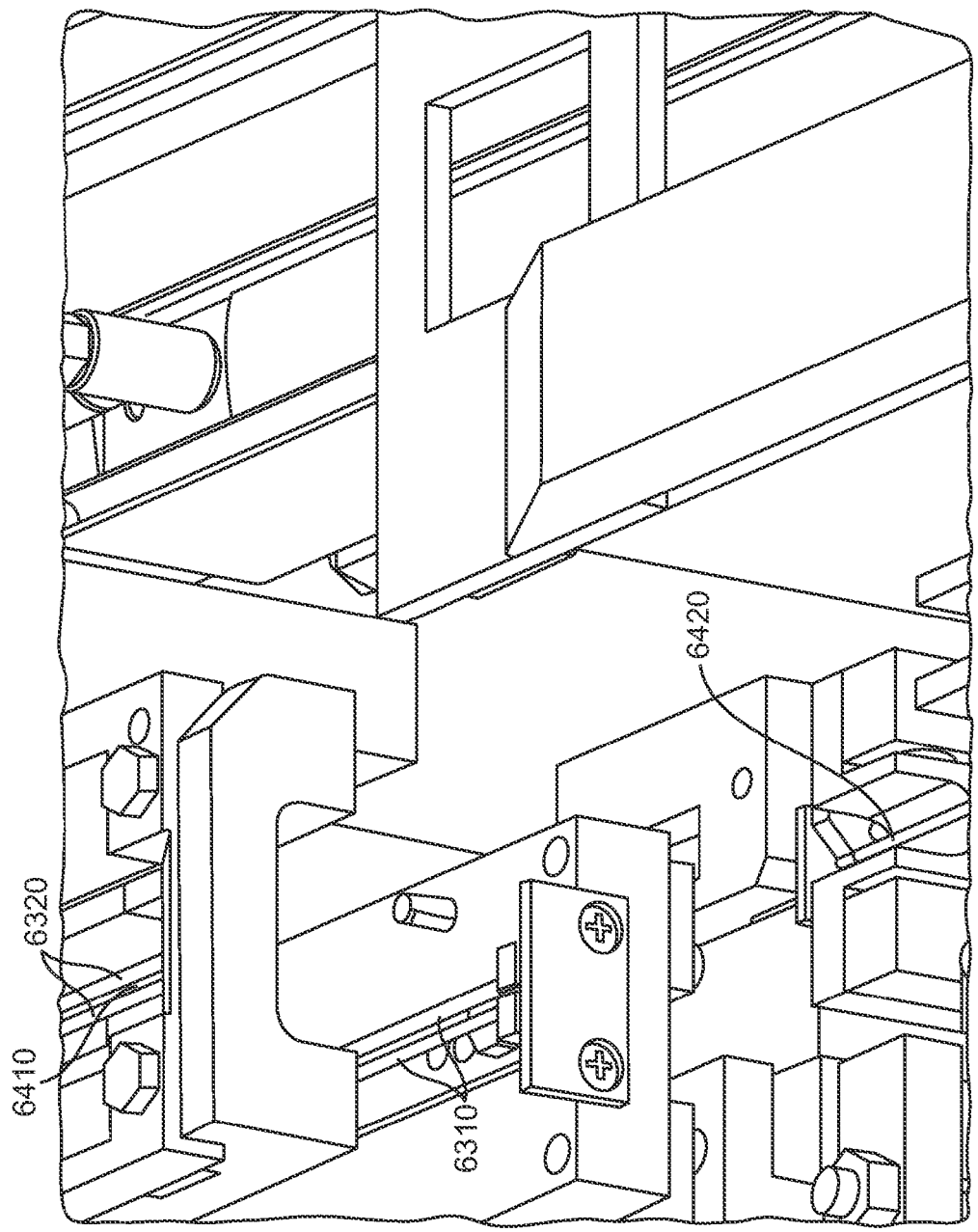

The rollers 6310, 6320 may be of any suitable dimension, and may be positioned in any manner. For example, referring to FIGS. 62 and 63, the roller pairs 6310, 6320 may be of suitable length and width to hold a stent 10 for imaging, and may include a gap 6410 between two pairs of rollers 6310, 6320 to allow a camera 6140 to view the stent 10. As depicted in FIGS. 62 and 63, the camera's 6140 field of view 6330 passes between the gap 6410 between the two top rollers 6320 to view a stent 10 held by the roller assembly 6110.

The rollers 6310, 6320 are configured to avoid damaging the stent 10 while providing a stable surface to rotate the stent 10 upon. The rollers 6310, 6320 may comprise any suitable material and may include any structural property. For example, the rollers 6310, 6320 may comprise a rubberized coating to allow the stent 10 to be cradled between the rollers 6310, 6320 without deforming or compressing the stent 10, and/or without damaging a drug coated on the stent 10 and/or the structure of the stent 10. Those skilled in the art will recognize that aspects of the present invention may be practiced with minor deformations of the stent 10 that do not significantly affect the structure of the stent 10 or any coating thereon. Furthermore, the rollers 6310, 6320 may be configured to rigidly support the stent 10 and rotate without distorting, which could cause the rollers 6310, 6320 to slip against the surface of the stent 10. The rollers 6310, 6320 may interface with any suitable system or device, such as a drive system 6120.

The roller assembly 6110 may be connected to a drive system 6120 configured to cause the rollers 6310, 6320 to rotate. The drive system 6120 may comprise any suitable number of systems and/or devices to control the rotation of the rollers. In one embodiment of the present invention, for example, the drive system 6120 may comprise a set of four electric motors that are independently controlled by software operating on a computer system, with each electric motor controlling a separate roller. The drive system 6120 may be configured in any manner to achieve any suitable result, such as to rotate the rollers 6310, 6320 in a synchronous manner, and/or to rotate one or more rollers 6310, 6320 independently from each other. The drive system 6120 may rotate the rollers 6310, 6320 in any direction, for any duration, and at any appropriate speed. The drive system 6120 may be controlled by the computer system to rotate the stent 10 a predetermined amount in order to image different portions of the stent 10 with the camera 6140. The drive system 6120 may be controlled by a computer system that interfaces with the camera 6140 and/or any other component of the inspection system 6100, allowing the computer system to coordinate the rotation of the stent 10 with the imaging of the stent 10.

The drive system 6120 may be connected to the roller assembly 6110 in any suitable manner, such as through flexible drive shafts 6340 configured to move with the roller pairs 6310, 6320 to allow the stent 10 to be loaded and unloaded from the roller assembly 6110. The flexible drive shafts 6340 may comprise any suitable material and may be of any appropriate dimension. The flexible drive shafts 6340 may be configured to dissipate ancillary forces that may otherwise be transferred from the drive system 6120, causing the rollers 6310, 6320 to distort.

Figure 64:
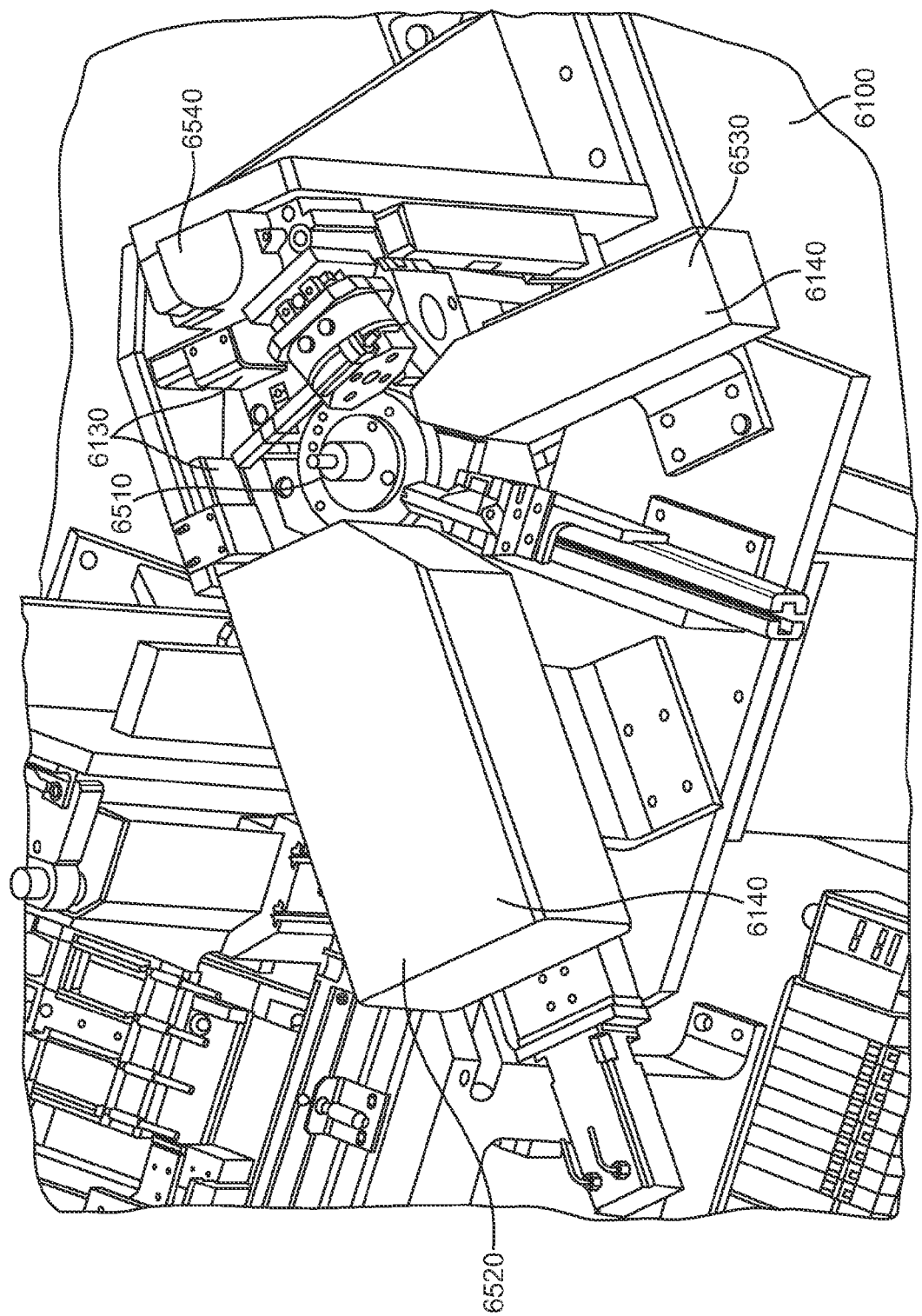
FIG. 64 is a three-dimensional design schematic depicting an exemplary system for inspecting a stent according to various aspects of the present invention.
Figure 65:
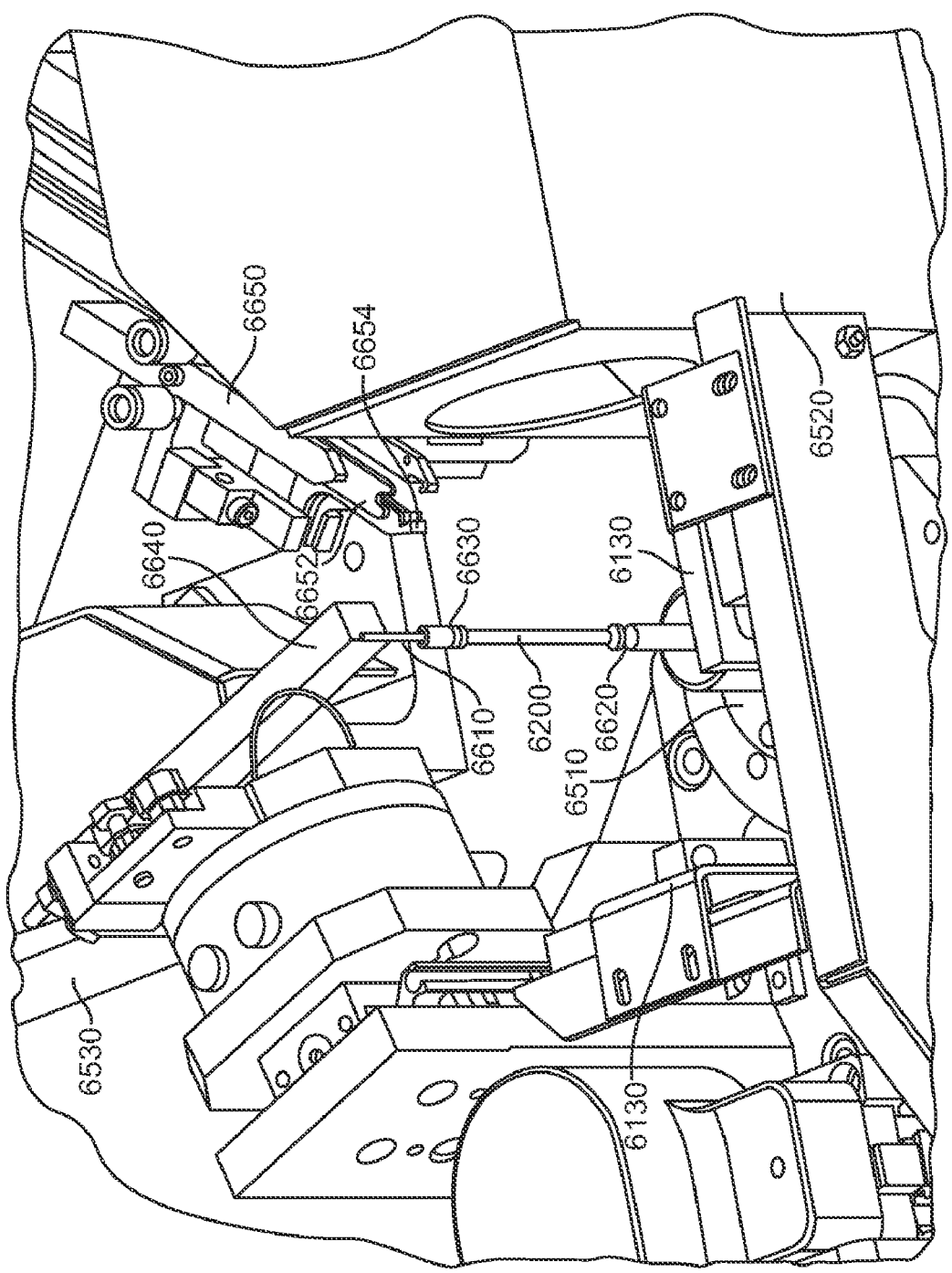
FIG. 65 is a three-dimensional design schematic depicting details of the system in FIG. 64.

The stent 10 may be held in place in any appropriate manner to achieve any desired result. In one embodiment of the present invention as shown in FIG. 64, for example, the stent 10 may be held by a rotating base 6510 to allow defects protruding from the stent 10 to be detected. The base 6510 holds the stent 10 in the field of view of two cameras 6520, 6530. The base 6510 may be raised and lowered using a positioning system 6540 to allow the cameras 6520, 6530 to image the full length of the stent 10. The stent 10 is located between the cameras 6520, 6530 and light sources 6130 that illuminate the boundary edges of the stent 10. As depicted in FIG. 65, the base 6510 may hold the stent 10 in place using a mandrel 610 connected to a bottom collet 620. In this exemplary embodiment of the present invention, the mandrel 610 is placed through the interior of the stent 10 and a top collet 630 is brought down to capture the stent 10 concentrically around the mandrel 610 by a capture arm 640. The capture arm 640 may also aid in holding the stent 10 and mandrel 610 as the base 6510 rotates.

The mandrel 610 may interface with the stent 10 in any suitable manner. For example, the mandrel 610 may be configured to pass through the stent 10 without contacting its interior so as to avoid damaging the structure of the stent 10 and/or a drug coating the stent 10. The mandrel 610 may releasably connect to the top and bottom collets 620, 630 to aid in the transfer of the stent 10 to and from the base 6510.

The top and bottom collets 620, 630 engage the stent 10 to hold it in place while it is rotated by the base 6510 and imaged by the cameras 6520, 6530. The collets 620, 630 may engage the stent 10 in any suitable manner, such as by inserting a tapered and/or conical end of the collet 620, 630 into the interior of the stent 10 at each end of the stent 10. The base 6510 may rotate the stent 10 in any direction, at any speed, and for any duration. For example, the base 6510 may rotate the stent 10 in 5-degree increments to allow defects protruding from the stent 10 to be imaged by the cameras 6520, 6530.

Figure 66B:
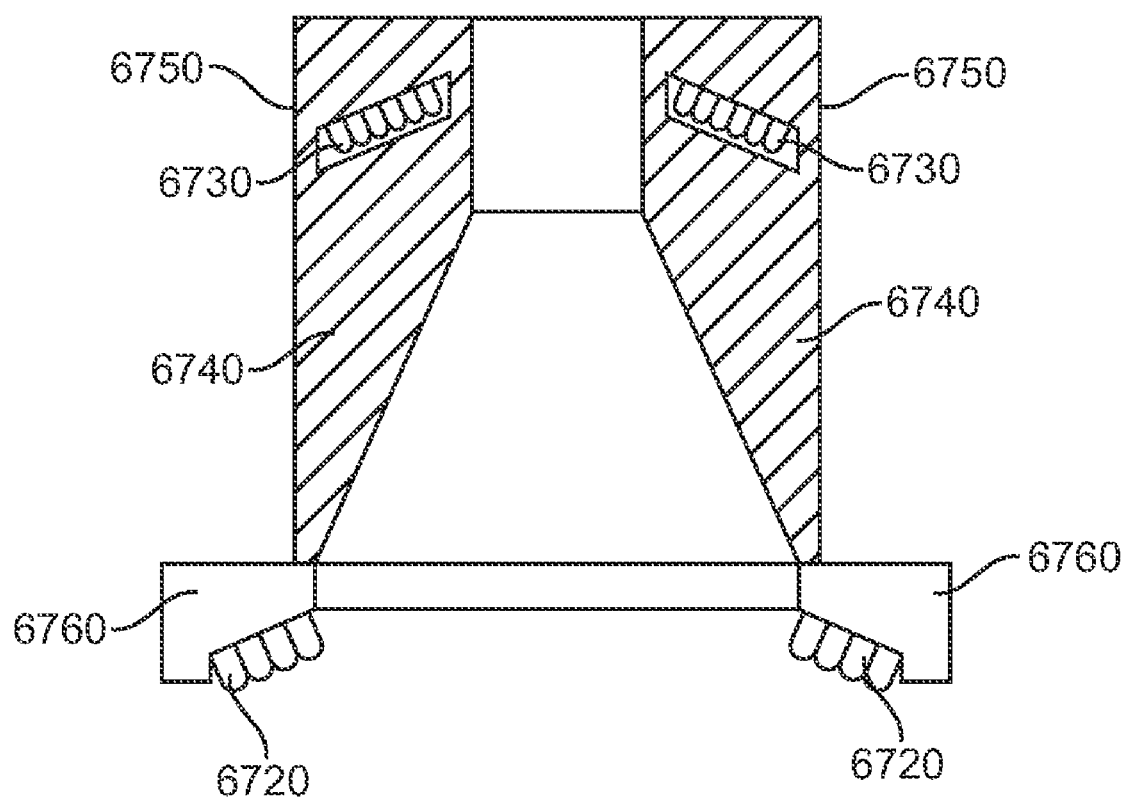
FIG. 66B is a side view of an exemplary light source according to various aspects of the present invention.

The stent 10 may be handled and moved by one or more robotic devices in order to automate the process of inspecting the stent 10. The stent 10 may be manipulated in any suitable manner by any appropriate device or system. For example, referring to FIG. 66A, the stent 10 may be moved to and from the roller assembly 6110 by a transfer arm 6710. The transfer arm 6710 may be configured to transfer the stent 10 to other systems and devices, such as other inspection stations. The transfer arm 6710 may be controlled in any manner, such as through software operating on a computer system. Any number of transfer arms 6710 may be employed in an inspection system 6100, each having any suitable configuration to manipulate and move the stent 10.

Other robotic devices may be employed to automate the inspection of cylinders in an inspection system 6100. In the exemplary embodiment of the present invention shown in FIG. 65, a stent 10 may be provided to the base 6510 by a robotic transfer arm 6710, and a capture arm 6640 may engage the top collet 6630 with the top of the stent 10. The capture arm 6640 may hold the collet 6630 in place to help keep the stent 10 from deforming or otherwise moving on the base 6510 as it rotates.

Additionally, a stabilizer arm 6650 may be used to automatically position the stent 10 on the base 6510. In the exemplary embodiment of the present invention depicted in FIG. 65, a stabilizer arm 6650 may comprise a collet interface 6652 and a set of jaws 6654. The stabilizer arm 6650 may be configured to pick the stent 10 up with the jaws 6654 while the stent 10 is on the base 6510 and maneuver the stent 10 such that the stent 10 properly interfaces with the bottom collet 6620. For example, in the case where a bottom collet 6620 comprises a conical surface that engages with the interior of the stent 10 at one end, the stabilizer arm 6650 may pick up the stent 10 and drop it over the conical surface of the bottom collet 6620 such that the stent 10 properly settles over the bottom collet 6620. Similarly, the collet interface 6652 may be configured to engage the top collet 6630, such as by interfacing with a groove in the top collet 6630. The collet interface 6652 may lift the top collet 6630 up and down to allow a conical surface to engage inside the stent 10. The stabilizer arm 6650 may comprise any other suitable structures and devices for manipulating the positioning of a cylinder.

The inspection system 6100 includes a light source 6130 configured to illuminate a cylinder for inspection. The light source 6130 may comprise any suitable number of devices and may have any appropriate structure. For example, referring to FIG. 66B, an exemplary light source 6130 according to various aspects of the present invention may comprise a ring light 6720 concentrically placed around a dome light 6730. Any desired configuration of ring light and dome light may be used in conjunction with the present invention, such as an LDR2-90 ring light and an LDM-50 dome light, both from CCS, Inc. In this exemplary embodiment of the present invention, the ring light 6720 may surround the stent 10 to provide light to the stent 10 at steep angles, i.e.—nearly parallel to the stent 10, in order to create shadows on the surface of the stent 10 to allow a camera 6140 viewing the stent 10 to detect surface imperfections of the stent 10. The ring light 6720 may be supported by a light can 6760. The dome light 6730 may be employed to provide lighting to portions of the stent 10 that otherwise would be left dark by the ring light 6720. The dome light 6730 may be supported by a light can 6750 that includes a translucent material 6740 to provide diffuse light from the dome light 6730 to the cylinder being inspected. In another exemplary embodiment, referring now to FIG. 64, the light sources 6130 may comprise substantially rectangular lights to provide backlighting for an inspection camera 6520 and a focus feedback camera 6530.

The light source 6130 may comprise any other appropriate systems and devices, such as a light source positioning system configured to adjust the position of various elements of the light source 6130 to illuminate the stent 10 from various angles relative to the camera 6140. For example, the light source positioning system may be configured to allow the dome light 6730 to be positioned independently of the ring light 6720. The ring light 6720 and dome light 6730 may be oriented in any appropriate manner to achieve any result. For example, the dome light 6730 may be positioned within the ring light 6720 to allow the camera 6140 to view the stent 10 between a gap between the ring light 6720 and dome light 6730.

The light source 6130 may provide lighting having any desired characteristics, such as wavelength, intensity, and the like. For example, the light source 6130 may be configured to provide lighting that is diffuse, that is, light that scatters over a large angular range, in order to avoid glare and/or non-uniform areas of brightness to be viewed by the camera 6140 as well as to compensate for a tendency of non-uniform and highly-reflective surfaces on a cylinder to scatter light away from the camera 6140. Additionally, the light source 6130 may provide light in a specific spectrum in order to avoid affecting a drug or other substance coating a stent 10. In one exemplary embodiment of the present invention, the light source 6130 may be configured to provide lighting having a wavelength of about 600 nm to about 6700 nm in order to avoid activating a drug coating the stent 10.

The light source 6130 may interface with any suitable system, and device to achieve any desired purpose. For example, the light source 6130 may be in communication with a computer system configured to control the intensity, wavelength, and position of the light source 6130. Any characteristic of the lighting provided by elements of the light source 6130, such as wavelength, intensity, and the like, may be controlled individually or in concert with other elements as appropriate. For example, in one exemplary embodiment of the present invention, the ring light 6720 and dome light 6730 may be independently turned off or on. The ring light 6720 may be turned off and the dome light 6730 turned on in order to aid in the inspection of the interior of a stent 10. Alternatively, the ring light 6720 may be turned on and the dome light 6730 turned off in order to aid in the inspection the roughness of the surface of a stent 10 or other cylinder.

The light source 6130 may interact with any structure in the inspection system 6100 in any appropriate manner. For example, the light source may utilize the structure of the bearing blocks 6350 holding the rollers 6310, 6320 to help contain the illumination provided by the light source 6130 and/or to prevent external light from interfering with the imaging of a cylinder. The light source 6130 may be positioned in any manner, such as between the camera 6140 and the stent 10 as described previously. Alternatively, referring now to FIG. 64, an inspection system 6100 according to various aspects of the present invention may be configured such that the stent 10 is between a light source 6130 and an inspection camera 6520, and between another light source 6130 and a focus feedback camera 6530.

The camera 6140 takes an image of a portion of a cylinder for analysis. Any appropriate type of camera 6140 may be utilized in an inspection system 6100. In one exemplary embodiment of the present invention, the camera 6140 may comprise a linescan camera 6140 configured to image a single row of pixels at a time. A linescan camera 6140 having any appropriate characteristics may be utilized, such as a Dalsa digital line scan camera with a 1×6000 aperture. The camera 6140 may image any part of the stent 10, as well as any features and/or defects protruding from the stent 10. Additionally, the camera 6140 may image features such as apertures in the surface of a stent 10. Any other portion and feature of a cylinder may be imaged as well. For example, the interior of a stent 10 or other hollow cylinder having apertures in its surface may be imaged by the inspection system 6100 by moving the camera close to the stent 10, allowing the camera 6140 to focus beyond the apertures to view the interior. The camera 6140 may be positioned at any suitable distance to allow the camera 6140 to focus on the interior of the stent 10. An image created by the camera 6140 may be generated in any format and in any medium, such as a digitized image stored in the memory of a computer system.

Figure 67:
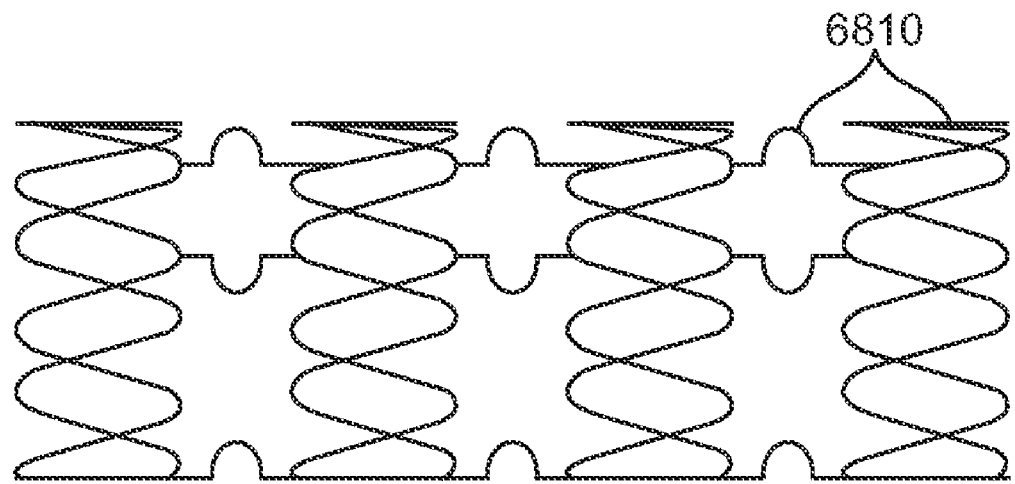
FIGS. 67 and 68 depict exemplary images of defects protruding from a stent.
Figure 68:
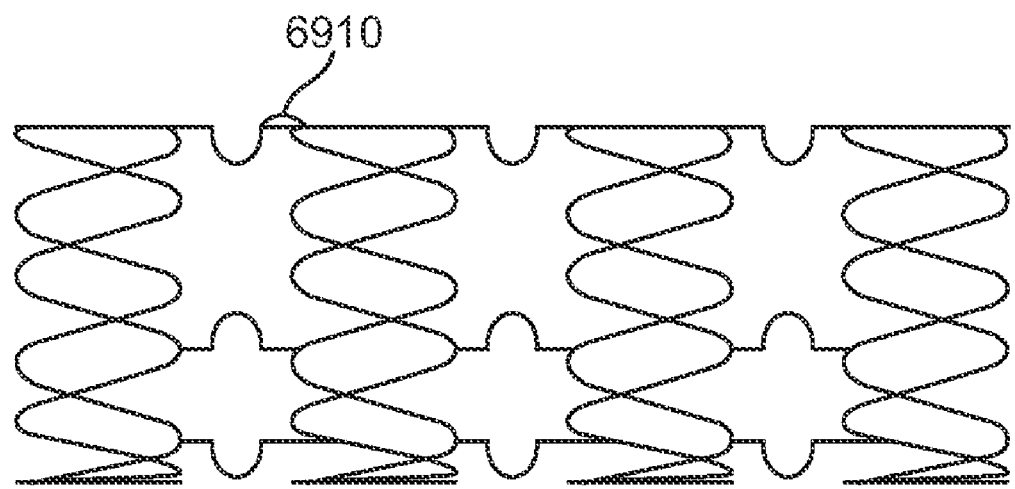

Any number of cameras 6140 of any type may be employed in an inspection system 6100. For example, referring to FIG. 64, an inspection system 6100 according to various aspects of the present invention may comprise two field of view cameras 6520, 6530 positioned such that their facings are ninety degrees relative to each other. In this exemplary embodiment of the present invention, the inspection camera 6520 captures an image of a stent 10 of a portion of the stent 10. The stent 10 is illuminated from behind by a light source 6130, creating a backlight effect that highlights the external boundaries defining the width/diameter of the stent 10 structure as well as any features protruding from the external boundaries. For example, the image depicted in FIG. 67 indicates a defect 6810 protruding from the stent 10. The inspection camera 6520 may be configured to image the stent 10 at any resolution in order to inspect any feature of any dimension on a stent 10. Referring to FIG. 68, a protruding defect 6910 may be identified even where the defect 6910 is very small relative to the structure of the stent 10. For example, in some embodiments of the present invention, defects of ten micrometers or smaller can be identified.

The inspection camera 6520 may create multiple images of the stent 10 in order to achieve any desired result. For example, the inspection camera 6520 may create a plurality of images along the full length of a stent 10 that is otherwise longer than the field of view of the inspection camera 6520. A positioning system 6540 may be used to move the base 6510 holding the stent 10 along the field of view of the inspection camera 6520. The base 6510 may rotate the stent 10 a predetermined amount, such as five degrees, to expose a new portion of the stent 10 to the inspection camera 6520, and the imaging process can be repeated to image entire stent. The degree of rotation may be increased or decreased depending on the size of the defects sought to be identified and/or to increase the speed of the inspection process. By simultaneously imaging both edges defining the width of the stent 10 at each position of rotation, the stent 10 can be rotated only 6180 degrees while still inspecting the full circumference of the stent 10.

An inspection system 6100 may include a focus feedback camera 6530 configured to detect any shifting of position by the stent 10 about the mandrel 6610, particularly as the stent 10 is rotated. When the stent 10 shifts toward or away from the inspection camera 6520, the stent 10 may move out of the focus of the inspection camera 6520. The focus feedback camera 6530 may be configured to detect a shift in position of the stent 10 and report the shift in position in order to cause the inspection camera 6520 to be refocused. The focus feedback camera 6530 may interact with any suitable system or device to identify and report a shift in position. For example, the focus feedback camera 6530 may interface with a computer system that analyzes an image generated by the focus feedback camera 6530, detects a shift in position of the stent 10, and causes the inspection camera 6520 to refocus accordingly.

A camera 6140 according to various aspects of the present invention may interact with any number of other systems and devices. For example, as shown in FIG. 61, a camera 6140 may be utilized in conjunction with one or more lenses 6145. A lens 6145 may be configured in any manner to achieve any desired result, such as to allow the camera 6140 to achieve a specific length of view to control the width of the linescan image being created. Similarly, the distance of one or more lenses 6145 from the stent 10 may be selected to affect any appropriate characteristic of the image. For example, the lens 6145 may be located closer to a stent 10 in order to create a higher-resolution image of a smaller portion of the stent 10, and farther away to create a lower-resolution image of a larger portion of the stent 10. Additionally, positioning the lens closer to a stent 10 may aid in preventing any movement of the stent from affecting the quality of the image.

A camera 6140 may also operate in conjunction with a camera positioning device, for example to allow the camera 6140 to be moved toward and away from the cylinder being inspected. Additionally, the camera positioning device may be configured to allow the camera 6140 to be moved laterally, such as along the length of a cylinder that is too long to fit in the view of the camera 6140 in a single image.

Referring to FIG. 63, an inspection system 6100 may include a background mandrel 6420. The background mandrel 6420 may be inserted within the inner diameter of a stent 10 to provide a background for imaging by the camera 6140. In order to prevent damage to the stent 10 or a coating on the stent 10, the background mandrel 6420 may be configured to dispose within the stent 10 without touching the interior of the stent 10. For example, in the exemplary embodiment of the present invention depicted in FIG. 62, the roller assembly 6110 fully supports and rotates the stent 10 to allow the background mandrel 6420 to be disposed within the stent 10 without touching its interior.

An inspection system 6100 according to various aspects of the present invention may be operated and controlled in any manner. For example, various systems and processes may be controlled by one or more software programs operating on one or more computer systems. The computer system may interface with any of the individual components of the inspection system 6100, such as the roller assembly 6110, light source 6130, camera 6140, etc., as well as any other systems and devices external to the inspection system 6100. Any process implemented and/or controlled by the computer system may be operated manually, such as by a human operator or other control system, and/or configured to operate automatically, such as under the control of a software program.

The computer system may control any function and aspect of the inspection system 6100 to achieve any desired result. For example, the computer system may control the rotation and positioning of a cylinder by the roller assembly 6110 and/or base 6140 during imaging. The computer system may also control one or more cameras 6140 in taking an image of the cylinder, including moving and focusing the camera 6140 to take images along the length of a stent 10 in order to image its full length. The computer system may use input from a focus feedback camera 6530 to control the focusing of an inspection camera 6520. The position, intensity, wavelength, and other characteristics of the light source 6130 may be controlled by the computer system. The computer system may also control any features of the inspection system 6100 for transferring and manipulating the stent 10, such as the wire capture arm 6640, stabilizer arm 6650, and transfer arm 6710. The computer system may interface with any suitable sensing systems or devices to achieve any purpose, such as to detect the pressure exerted on a cylinder, measure the position of a stent 10 with relation to other features in the inspection system 6100, and the like.

The computer system may be configured to process and/or analyze images of a cylinder. The computer system may be configured to perform any suitable analysis, such as to inspect a stent 10 for defects. The computer system may be configured to process images in any suitable manner. For example, the computer system may sequence and/or index images with reference to the position of the roller assembly 6110 or base 6140 when the image was taken so that the images can be related back to the part of the cylinder imaged.

Figure 69:
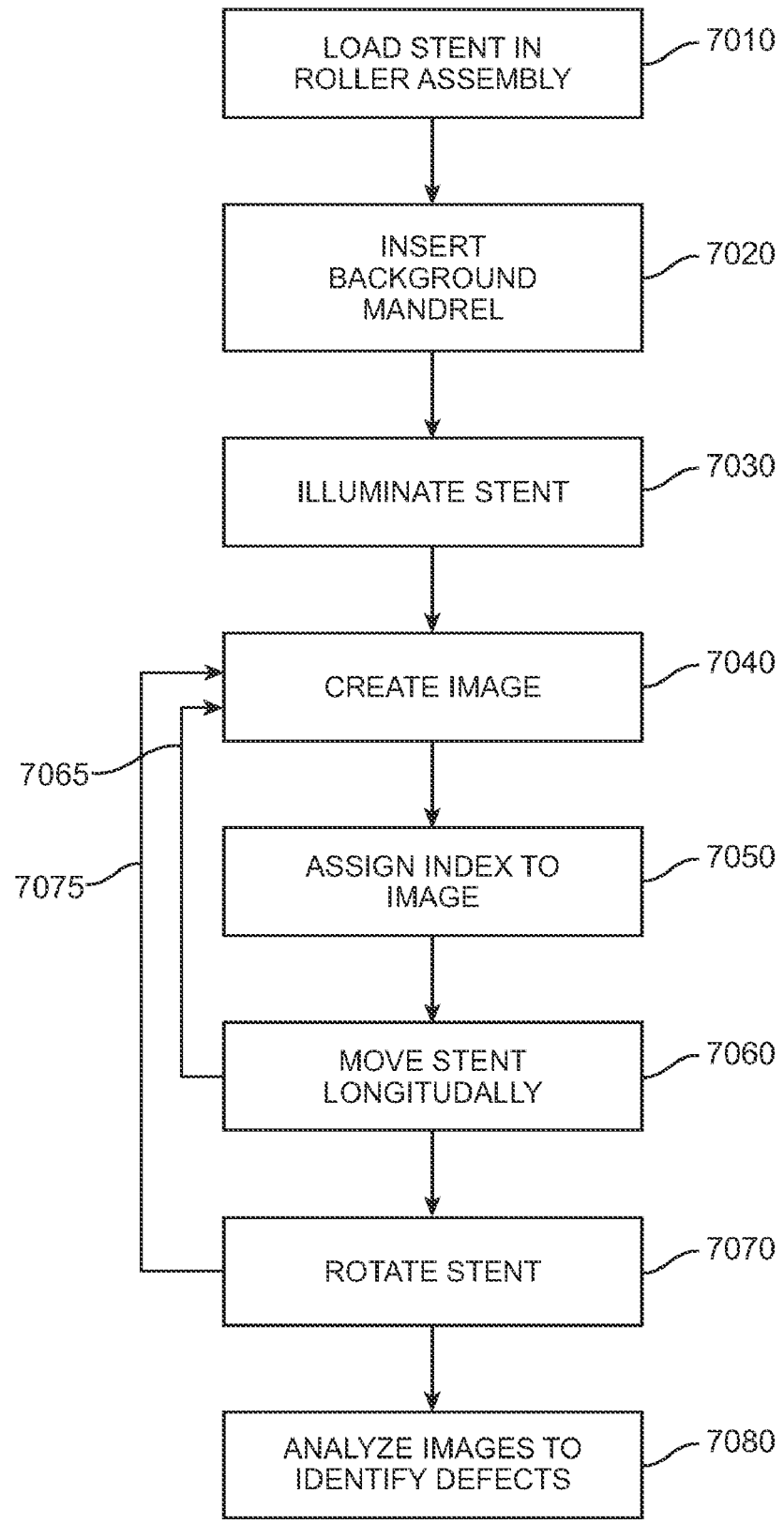
FIG. 69 is a process flow diagram illustrating an exemplary process for inspecting a stent according to various aspects of the present invention.

FIG. 69 illustrates an exemplary process that may be employed by an inspection system 6100 for inspecting stent 10s according to various aspects of the present invention. A stent 10 is automatically provided to a roller assembly 6110 by a transfer arm 6710 (7010). A background mandrel 6420 is inserted through the interior of the stent 10 to provide a background to for the image of the stent 10 (7020). The light source 6130 illuminates the stent 10 (7030) and the linescan camera 6140 creates an image of a portion of the stent 10 (7040), the image comprising a single row of pixels along a portion of the length of the stent 10. The images may be indexed to record their relation to the physical structure of the stent 10 (7050). If the length of the stent 10 is outside the field of view of the camera 6140, the camera 6140 and/or the stent 10 may be moved to allow the camera 6140 to image the full length of the stent 10 (7060). This longitudinal movement may be repeated in order to allow the full length of the stent to be imaged (7065). The stent 10 is rotated by the roller assembly 6110 to allow the next row of pixels to be imaged (7070) and the process is repeated (7075) until the entire stent 10 is imaged.

Figure 70:
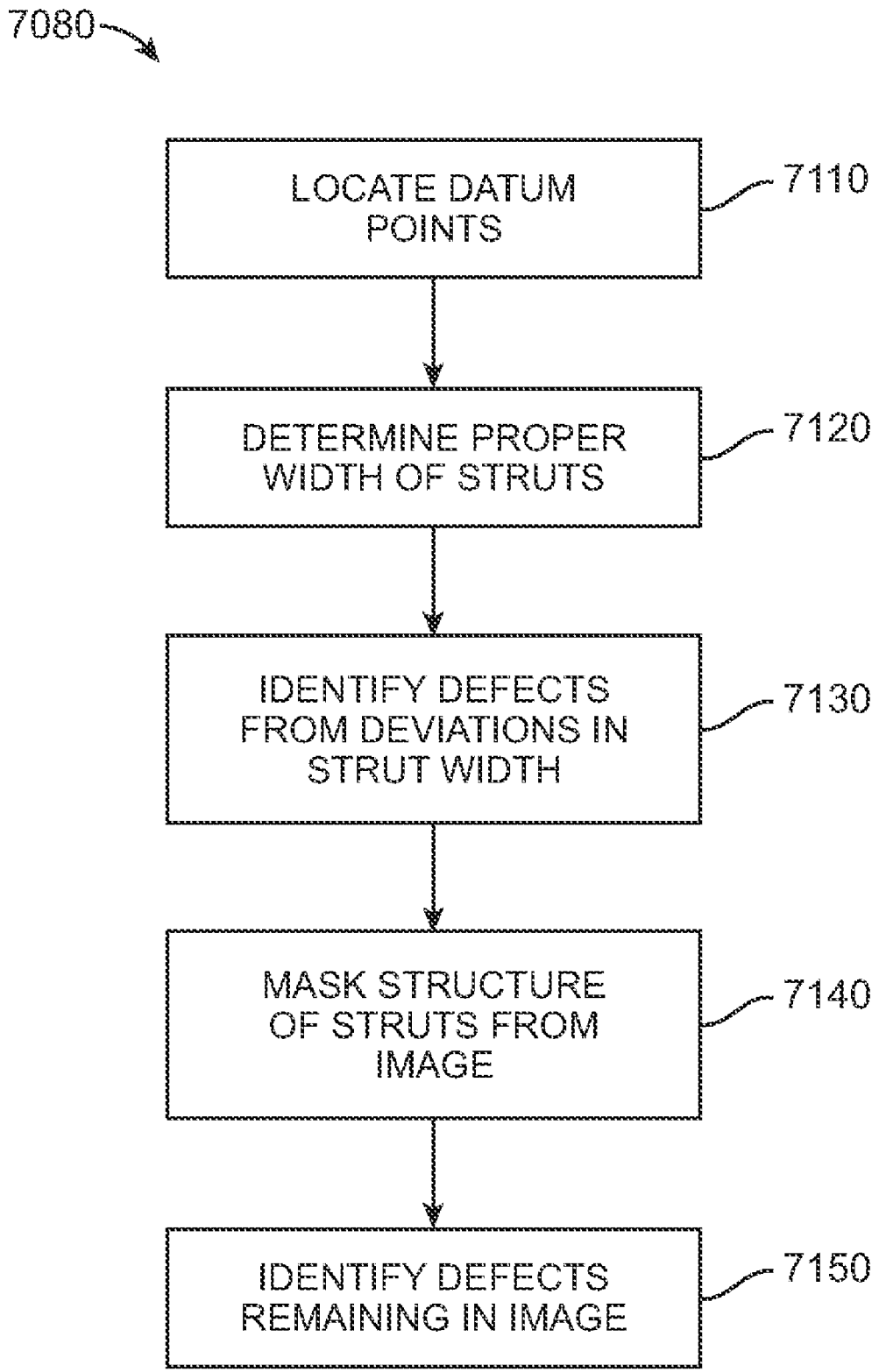
FIG. 70 is a process flow diagram illustrating an exemplary process for identifying defects associated with a stent according to various aspects of the present invention.
Figure 71:
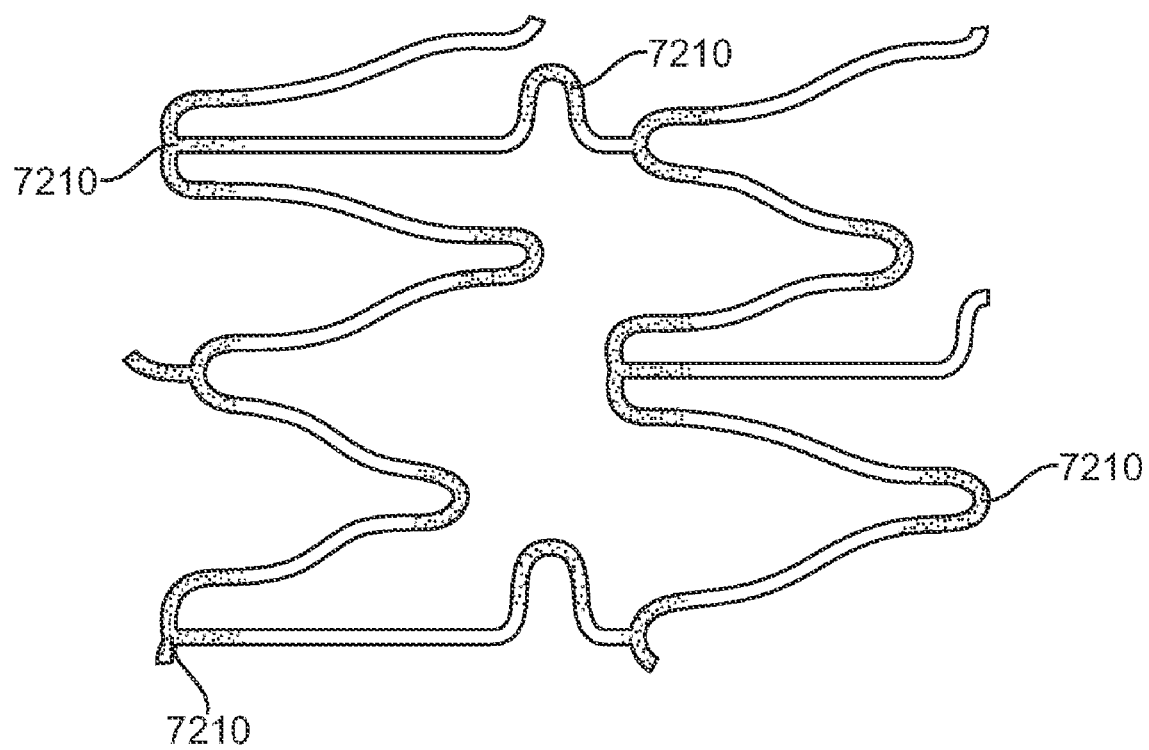
FIG. 71 depicts the location of datum points in an exemplary image according to various aspects of the present invention.
Figure 72:
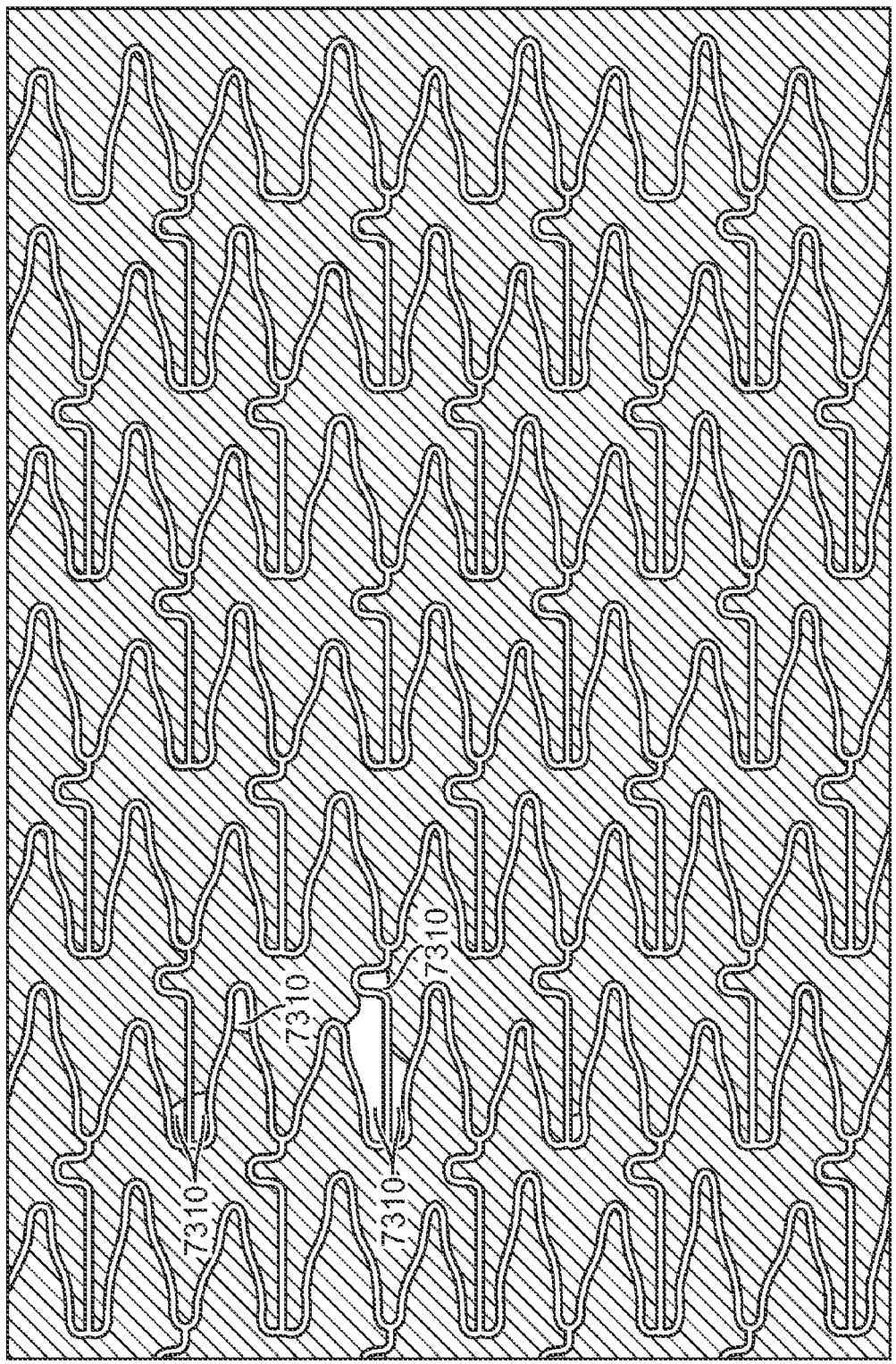
FIG. 72 depicts a two-dimensional image of the structure of a stent, wherein defects are present between the struts of the stent.
Figure 73:
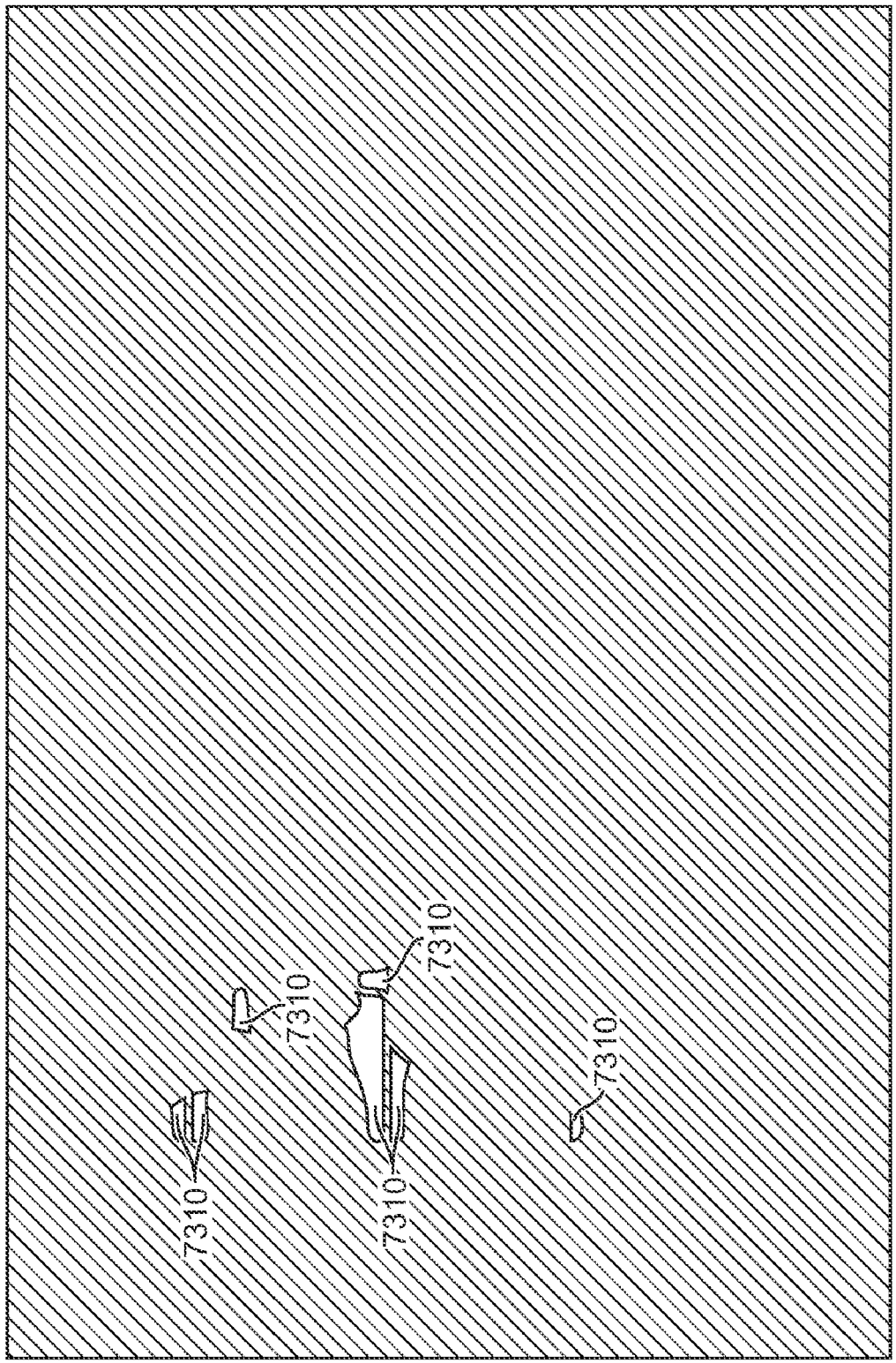
FIG. 73 depicts the two-dimensional image in FIG. 72 wherein the structure of the stent has been subtracted to aid in identifying defects.

The images are analyzed to identify any defects (7080). FIG. 70 depicts an exemplary process for analyzing images for defects (7080) according to various aspects of the present invention. Datum points corresponding to the structure of the stent 10 are located in the image (7110). The datum points correspond to any element of the stent 10 that may be used to identify the general structure of the stent 10, and may be selected according to any criteria. For example, referring to FIG. 71, the shaded portions of the struts 12 indicate datum points 7210 that are selected to correspond the beginning and ending points of struts 12 in the stent 10. The datum points are used to determine the proper width of struts 12 in the image (7120). Defects are determined by identifying deviations in the measured width of individual struts 12 in the image (7130). Any other suitable dimension of a feature of a strut 12 may be identified (7120) and analyzed to find defects (7130), such as a strut's height, length, etc. For example, defect analysis (7130) may be performed on a stent 10 to detect any distortion that might have occurred during the manufacturing process. Additionally, defects lying between the struts 12 in a stent 10 may be identified by masking the image of the struts 12 (7140) and analyzing the remaining features in the image to determine whether they are defects in the stent 10 (7150). FIG. 72, for example, depicts a representative image of a stent 10 prior to masking. In this image, the struts 12 forming the stent 10 are represented in two-dimensions by a light structure on a dark background. Defects 7310 between the struts 12 of the stent 10 show up as light shading. In order to aid in identifying the defects 7310, referring now to FIG. 73, the structure of the stent 10 is masked out, leaving the light-shaded defects 7310 in the image. The structure of the stent 10 may be masked out of an image in any suitable manner. For example, software running on a computer system may identify the structure of the stent 10 in a digitized image, and remove and/or fill that structure to match the background of the image.

Any type of defect may be identified by the process for analyzing images (7080), such as defects associated with the manufacture of a stent 10, or defects associated with a coating covering the stent 10. Defects associated with any suitable coating may be detected, such as a polymer coating, a drug coating, a combination of a drug and polymer coating, and/or any other form of coating. An analysis process may be performed using any number of images. For example, an inspection system 6100 may analyze single images of portions of a cylinder after each image is created, or process multiple images together. Any portion of a process for inspecting cylinders may be performed manually by a human being or automatically, such as by using software operating on a computer system.

Figure 74:
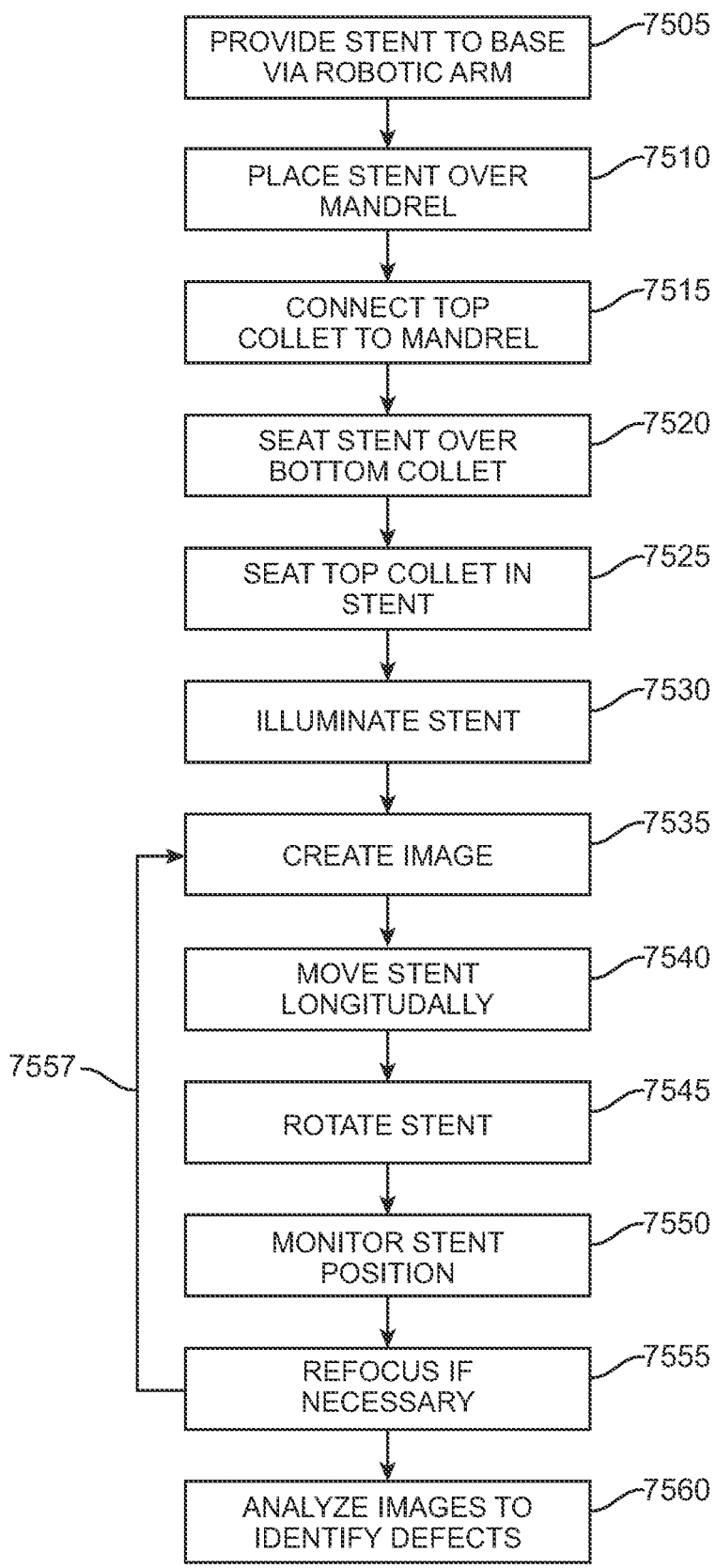
FIG. 74 is a process flow diagram illustrating an exemplary process for inspecting a stent according to various aspects of the present invention.

FIG. 74 illustrates another exemplary inspection process that may be employed by an inspection system 6100 according to various aspects of the present invention. A stent 10 is automatically provided to a base 6510 by a transfer arm 6710 (7505). The stent 10 is placed over a mandrel 6610 connected to a bottom collet 6620 (7510). A wire capture arm 6640 brings a top collet 6630 in connection with the mandrel 6610 (7515). A stabilizer arm 6650 grasps the stent 10, then lifts and releases the stent 10 to cause it to settle over a conical surface on the bottom collet 6620 (7520). When properly settled, the interior of the stent 10 engages the conical surface of the bottom collet 6620 without the stent 10 touching the mandrel 6610. The stabilizer arm 6650 interfaces with the top collet 6630, lifting and dropping the top collet 6630 to cause a conical surface on the top collet 6630 to settle into the interior of the stent 10 (7525).

With the stent 10 engaged by the top and bottom collets 6620, 6630, the stent 10 is positioned between two light sources 6130 and two cameras 6140, 6520, 6530, where each light source 6130 illuminates the stent 10 from behind each camera 6520, 6530 (7530). The inspection camera 6520 creates an image of the stent 10 that includes the full width of the stent 10 and features protruding from the edges of the stent 10 (7535). The base 6510 moves up and down to allow the inspection camera 6520 to create images along the full length of the stent 10 (7540). The base 6510 rotates the stent 10 a certain amount, such as 5 degrees, to expose a new portion of the stent 10 to the inspection camera 6520 (7545). The focus feedback camera 6530 monitors whether the stent 10 changes position on the mandrel 6610 at any point during the imaging process (7550). If a change in position is detected, the inspection camera 6520 is refocused accordingly (7555). The inspection camera 6520 may be refocused in any suitable manner, such as by adjusting a focus control in the camera 6520, physically moving the camera with relation to the stent 10, and the like. The process may be repeated (7557) in order to capture images of the full diameter of the stent 10. Since both edges of the stent 10 are being captured in a single image, the stent 10 need only be rotated 6180 degrees to image the full diameter of the stent 10.

Figure 75:
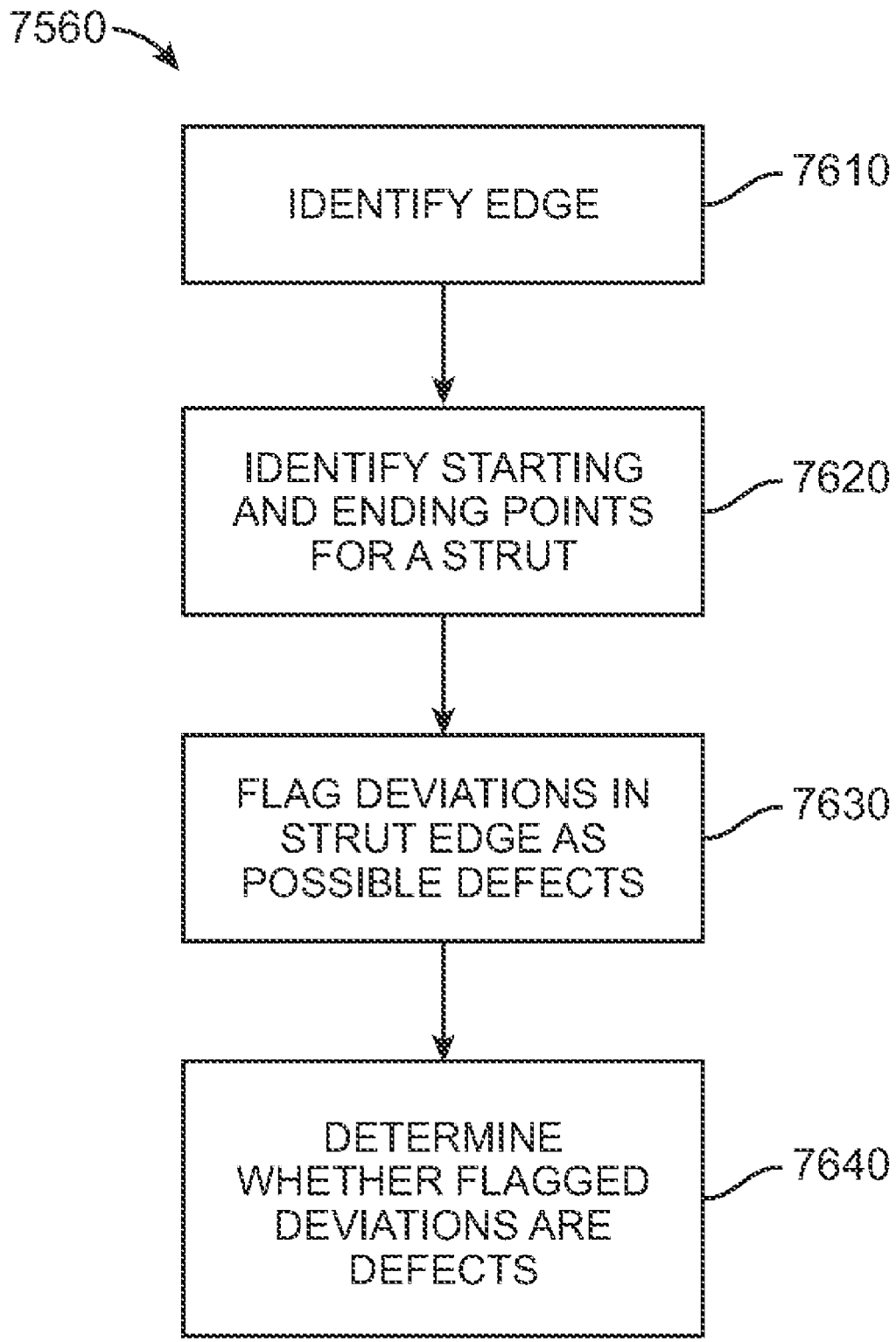
FIG. 75 is a process flow diagram illustrating an exemplary process for identifying defects associated with a stent according to various aspects of the present invention.
Figure 76:
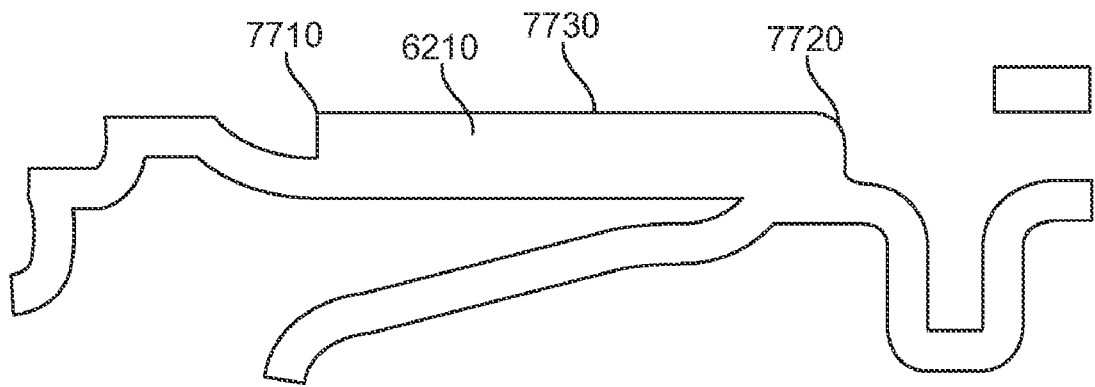
FIGS. 76, 77, 78, and 79 are exemplary images of portions of a stent that illustrate elements of the process described in FIG. 75.
Figure 77:
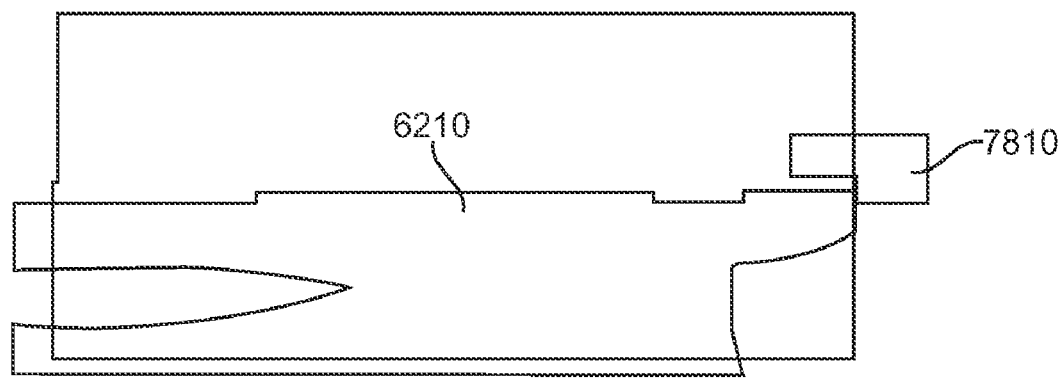
Figure 78:
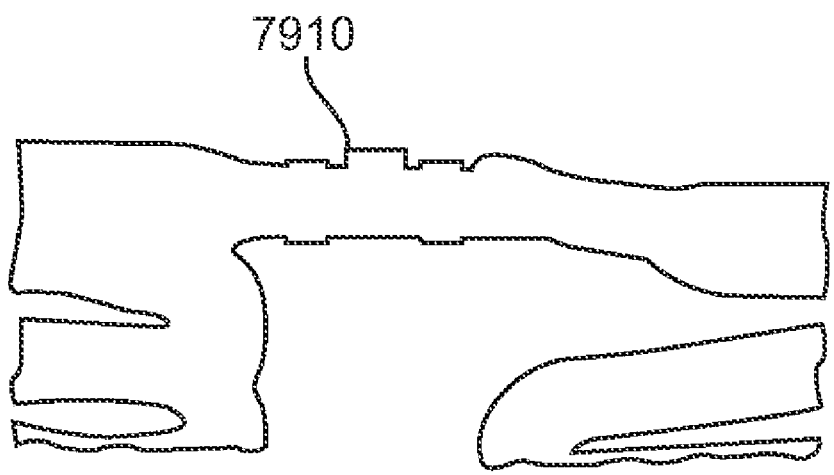
Figure 79:
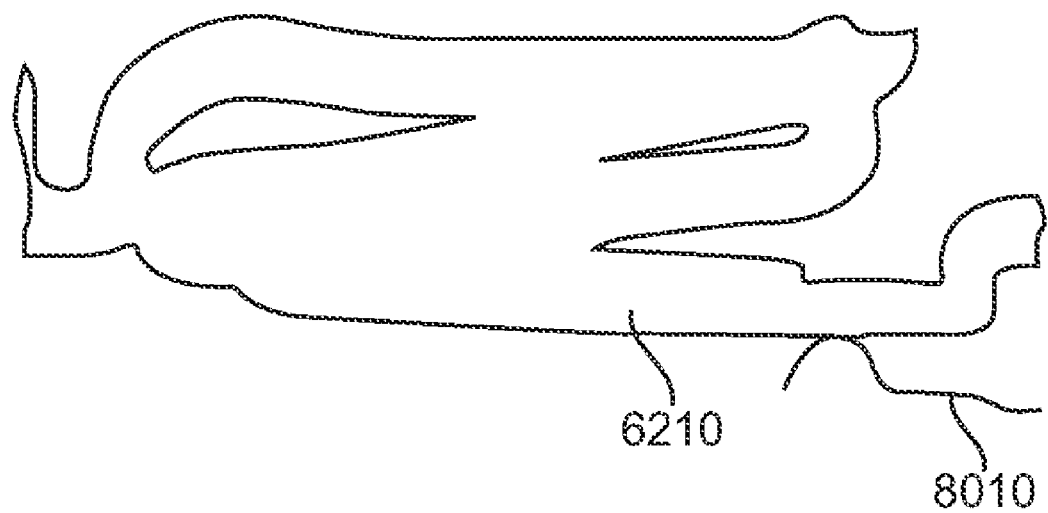

The images are analyzed to identify defects protruding from the stent 10 (7560). An exemplary process for analyzing an image for protruding defects (7560) is illustrated in FIG. 75. An approximate edge location is identified from the image (7610). For each strut 12 comprising a portion of the edge, referring now to FIG. 76, a starting position 7710 and an ending position 7720 of the strut is identified (7620). The line 7730 between the starting position 7710 and ending position 7720 defining the edge of the strut 12 is analyzed and any deviations from the line 7730 that are outside defined tolerances (i.e. height, length, and area) are flagged as potential defects (7630). For each deviation flagged as a potential defect, a determination is made as to whether the deviation is part of the structure of the stent 10 (7640). For example, a deviation found near the edge of the strut may be analyzed to determine the relative size of the deviation compared to other features in the image to determine whether it is a defect or part of the structure of the stent 10. Referring to FIG. 77, a non-linear link 7810 partially caught in the scan of the strut 12 can be identified as part of the structure of the stent 10 and is not considered a defect. Similarly, referring now to FIG. 78, a deviation caused by a non-linear link configuration 7910 having a substantially uniform thickness at the deviation as well as on either end of the deviation may be identified as part of the structure of the stent 10 as opposed to a defect. However, as shown in FIG. 79, a deviation 8010 that has a thickness less than the minimum normal strut 12 thickness can be identified as a defect. The process for defect analysis (7560) may be repeated for each strut in an image. A process for defect analysis (7560) may be performed for any number of images and for some or all of the edges of a stent 10 captured in an image.

The particular implementations shown and described above are illustrative of the invention and its best mode and are not intended to otherwise limit the scope of the present invention in any way. Indeed, for the sake of brevity, conventional data storage, data transmission, and other functional aspects of the systems may not be described in detail. Furthermore, the connecting lines shown in the various figures are intended to represent exemplary functional relationships and/or physical couplings between the various elements. Many alternative or additional functional relationships or physical connections may be present in a practical system.

The invention claimed is:

1. A system for coating a stent, comprising:
   a device for weighing a stent;
   a gripper configured to move the stent, from the device for weighing, onto a stent support;
   a device for aligning the stent with the stent support such that the stent is coaxial with the stent support;
   a device for coating the stent while the stent is on and coaxial with the stent support, the device for coating including a device configured to discharge a coating composition toward the stent and a device configured to rotate the stent support while the stent is on and coaxial with the stent support;
   a device for drying the stent; and
   a device for inspecting the stent wherein the device for aligning includes a camera configured to take an image of the stent, a computer configured to receive the image and to provide a signal based on the image, and a mechanism configured to move a first portion of the stent support relative to a second portion of the stent support based on the signal.

2. A method for coating a stent, comprising:
   weighing a stent using a device for weighing a stent;
   moving the stent, from the device for weighing, onto a stent support;
   aligning the stent with the stent support such that the stent is coaxial with the stent support;
   coating the stent while the stent is on and coaxial with the stent support, the coating of the stent including discharging a coating composition toward the stent and rotating the stent support during the discharging and while the stent is on and coaxial with the stent support;
   drying the stent; and
   inspecting the stent wherein the aligning of the stent includes taking an image of the stent, providing a signal based on the image, moving a first portion of the stent support relative to a second portion of the stent support based on the signal.

3. The system of claim 1, wherein the device for drying includes a heating device and a transfer mechanism configured to move the stent support with the stent toward the heating device.

4. The system of claim 1, wherein the device for inspecting includes a roller assembly configured to rotate the stent, a camera configured to take images of the stent, and a computer coupled to the roller assembly and the camera and configured to coordinate rotation of the stent by the roller assembly with imaging of the stent by the camera.

5. The method of claim 2, wherein the drying of the stent includes moving the stent support with the stent toward a heating device.

6. The method of claim 2, wherein the inspecting of the stent includes rotating the stent, taking images of the stent, and coordinating the rotating of the stent with the taking of the images.

* * * * *